US012655196B2

(12) United States Patent
Brix et al.

(10) Patent No.: US 12,655,196 B2
(45) Date of Patent: Jun. 16, 2026

(54) MHC MULTIMERS, METHODS FOR THEIR GENERATION, LABELING AND USE

(71) Applicant: Agilent Technologies, Inc., Santa Clara, CA (US)

(72) Inventors: Liselotte Brix, Bagsværd (DK); Henrik Pedersen, Lynge (DK); Tina Jakobsen, Ballerup (DK); Jørgen Schøller, Lyngby (DK); Jesper Lohse, Copenhagen NV (DK); Katja Brunstedt, Lyngby (DK); Kivin Jacobsen, Hvalså (DK)

(73) Assignee: Agilent Technologies, Inc., Santa Clara, CA (US)

( * ) Notice: Subject to any disclaimer, the term of this patent is extended or adjusted under 35 U.S.C. 154(b) by 0 days.

(21) Appl. No.: 18/516,130

(22) Filed: Nov. 21, 2023

(65) Prior Publication Data

US 2024/0150431 A1 May 9, 2024

Related U.S. Application Data

(63) Continuation of application No. 16/015,955, filed on Jun. 22, 2018, now abandoned, which is a continuation of application No. 12/644,554, filed on Dec. 22, 2009, now Pat. No. 10,030,065, which is a continuation of application No. PCT/DK2008/050167, filed on Jul. 3, 2008.

(60) Provisional application No. 60/929,583, filed on Jul. 3, 2007, provisional application No. 60/929,581, filed on Jul. 3, 2007, provisional application No. 60/929,586, filed on Jul. 3, 2007, provisional application No. 60/929,582, filed on Jul. 3, 2007.

(30) Foreign Application Priority Data

| Jul. 3, 2007 | (DK) | ............................ PA 2007 00972 |
| Jul. 3, 2007 | (DK) | ............................ PA 2007 00973 |
| Jul. 3, 2007 | (DK) | ............................ PA 2007 00974 |
| Jul. 3, 2007 | (DK) | ............................ PA 2007 00975 |

(51) Int. Cl.

| A61K 38/00 | (2006.01) |
| A61K 47/61 | (2017.01) |
| A61K 47/64 | (2017.01) |
| A61K 47/66 | (2017.01) |
| B82Y 5/00 | (2011.01) |
| C07K 14/705 | (2006.01) |
| C07K 14/74 | (2006.01) |
| C12N 5/0783 | (2010.01) |

(52) U.S. Cl.
CPC ........ *C07K 14/70539* (2013.01); *A61K 47/61* (2017.08); *A61K 47/6425* (2017.08); *A61K 47/665* (2017.08); *B82Y 5/00* (2013.01); *A61K 38/00* (2013.01)

(58) Field of Classification Search
None
See application file for complete search history.

(56) References Cited

U.S. PATENT DOCUMENTS

| 4,281,061 A | 7/1981 | Zuk et al. |
| 4,336,173 A | 6/1982 | Ugelstad |
| 4,387,164 A | 6/1983 | Hevey et al. |
| 4,459,378 A | 7/1984 | Ugelstad |
| 4,485,045 A | 11/1984 | Regen |
| 4,544,545 A | 10/1985 | Ryan et al. |
| 4,654,267 A | 3/1987 | Ugelstad et al. |
| 4,876,190 A | 10/1989 | Recktenwald |
| 4,994,373 A | 2/1991 | Stavrianopoulos et al. |
| 5,039,487 A | 8/1991 | Smith |
| 5,130,297 A | 7/1992 | Sharma et al. |
| 5,194,425 A | 3/1993 | Sharma et al. |
| 5,260,422 A | 11/1993 | Clark et al. |
| 5,284,935 A | 2/1994 | Clark et al. |
| 5,312,744 A | 5/1994 | Shibata |
| 5,468,481 A | 11/1995 | Sharma et al. |
| 5,543,332 A | 8/1996 | Lihme et al. |
| 5,583,031 A | 12/1996 | Stern |
| 5,627,037 A | 5/1997 | Ward et al. |
| 5,635,363 A | 6/1997 | Altman et al. |
| 5,652,342 A | 7/1997 | Zimmerman et al. |
| 5,807,552 A | 9/1998 | Stanton et al. |
| 5,869,270 A | 2/1999 | Rhode et al. |

(Continued)

FOREIGN PATENT DOCUMENTS

| DE | 19740735 A1 | 3/1999 |
| DE | 10247014 | 4/2004 |

(Continued)

OTHER PUBLICATIONS

HLA Nomenclature (2023, 2 pages) (Year: 2023).*

(Continued)

*Primary Examiner* — Michael Szperka
*Assistant Examiner* — Marianne DiBrino
(74) *Attorney, Agent, or Firm* — Adams & Reese, LLP

(57) ABSTRACT

The present invention describes novel methods to generate MHC multimers and methods to improve existing and new MHC multimers. The invention also describes improved methods for the use of MHC multimers in analysis of T-cells in samples including diagnostic and prognostic methods. Furthermore, the use of MHC multimers in therapy are described, e.g. anti-tumour and anti-virus therapy, including isolation of antigen specific T-cells capable of inactivation or elimination of undesirable targeT-cells or isolation of specific T-cells capable of regulation of other immune cells.

7 Claims, 31 Drawing Sheets

Specification includes a Sequence Listing.

(56) References Cited

U.S. PATENT DOCUMENTS

| | | | |
|---|---|---|---|
| 5,891,741 A | 4/1999 | Siiman et al. |
| 5,955,079 A | 9/1999 | Mond et al. |
| 5,994,089 A | 11/1999 | Siiman et al. |
| 5,998,204 A | 12/1999 | Tsien et al. |
| 6,015,884 A | 1/2000 | Schneck et al. |
| 6,074,645 A | 6/2000 | Diamond et al. |
| 6,090,587 A | 7/2000 | Rhode et al. |
| 6,096,315 A | 8/2000 | Zimmerman et al. |
| 6,106,840 A | 8/2000 | Clark et al. |
| 6,129,916 A | 10/2000 | Chang |
| 6,140,113 A | 10/2000 | Schneck et al. |
| 6,156,317 A | 12/2000 | Diamond et al. |
| 6,156,514 A | 12/2000 | Acevedo et al. |
| 6,197,302 B1 | 3/2001 | Hirsh et al. |
| 6,197,928 B1 | 3/2001 | Tsien et al. |
| 6,211,342 B1 | 4/2001 | Hirsh et al. |
| 6,232,445 B1 | 5/2001 | Rhode et al. |
| 6,248,564 B1 | 6/2001 | Walter et al. |
| 6,251,399 B1 | 6/2001 | Diamond et al. |
| 6,268,411 B1 | 7/2001 | Schneck et al. |
| 6,306,605 B1 | 10/2001 | Acevedo et al. |
| 6,309,645 B1 | 10/2001 | Rhode et al. |
| 6,335,173 B1 | 1/2002 | Kaplan |
| 6,387,622 B1 | 5/2002 | Siiman et al. |
| 6,413,934 B1 | 7/2002 | Stayton et al. |
| 6,448,071 B1 | 9/2002 | Schneck et al. |
| 6,451,314 B1 | 9/2002 | Clark et al. |
| 6,451,769 B1 | 9/2002 | Huebner et al. |
| 6,458,354 B1 | 10/2002 | Schneck et al. |
| 6,458,933 B1 | 10/2002 | Hansen |
| 6,486,130 B1 | 11/2002 | Livey et al. |
| 6,517,838 B1 | 2/2003 | Hook et al. |
| 6,534,633 B1 | 3/2003 | Weidanz et al. |
| 6,548,067 B1 | 4/2003 | Seeman et al. |
| 6,605,711 B1 | 8/2003 | Valmori et al. |
| 6,734,013 B2 | 5/2004 | Schneck et al. |
| 7,041,442 B1 | 5/2006 | Kern et al. |
| 7,060,869 B2 | 6/2006 | Tsien et al. |
| 7,064,190 B1 | 6/2006 | Endl et al. |
| 7,074,904 B2 | 7/2006 | Wong et al. |
| 7,094,555 B2 | 8/2006 | Kwok et al. |
| 7,116,407 B2 | 10/2006 | Hansen et al. |
| 7,141,656 B2 | 11/2006 | Rhode et al. |
| 7,202,349 B2 | 4/2007 | Davis et al. |
| 7,364,869 B2 | 4/2008 | Nixon et al. |
| 7,474,904 B1 | 1/2009 | Million-Rousseau et al. |
| 7,524,503 B2 | 4/2009 | Khanna et al. |
| 7,902,121 B2 | 3/2011 | Chen et al. |
| 8,114,669 B2 | 2/2012 | Choo |
| 8,268,964 B2 | 9/2012 | Scholler et al. |
| 8,298,782 B2 | 10/2012 | Busch et al. |
| 8,374,468 B2 | 2/2013 | Jiang |
| 10,336,808 B2 * | 7/2019 | Schøller ................. A61P 31/00 |
| 11,585,806 B2 | 2/2023 | Pedersen et al. |
| 2002/0006903 A1 | 1/2002 | Schneck et al. |
| 2002/0034513 A1 | 3/2002 | Rhode et al. |
| 2002/0058787 A1 | 5/2002 | Strominger |
| 2002/0082411 A1 | 6/2002 | Carter et al. |
| 2002/0091079 A1 | 7/2002 | Rhode et al. |
| 2002/0119149 A1 | 8/2002 | Jakobsen et al. |
| 2002/0119162 A1 | 8/2002 | Nielsen et al. |
| 2002/0127231 A1 | 9/2002 | Schneck et al. |
| 2002/0164340 A1 | 11/2002 | Brumeanu et al. |
| 2002/0165364 A1 | 11/2002 | Tsien et al. |
| 2002/0198144 A1 | 12/2002 | Wong et al. |
| 2003/0017447 A1 | 1/2003 | Bernardo et al. |
| 2003/0073102 A1 | 4/2003 | Kwok et al. |
| 2003/0096432 A1 | 5/2003 | Jakobsen |
| 2003/0104635 A1 | 6/2003 | Jakobsen |
| 2003/0118594 A1 | 6/2003 | Nag et al. |
| 2003/0171290 A1 | 9/2003 | Carr et al. |
| 2003/0199438 A1 | 10/2003 | Shaw et al. |
| 2003/0228258 A1 | 12/2003 | Scheinberg et al. |
| 2004/0068100 A1 | 4/2004 | Mach et al. |
| 2004/0072262 A1 | 4/2004 | Montero-Julian et al. |
| 2004/0082012 A1 | 4/2004 | Busch et al. |
| 2004/0086520 A1 | 5/2004 | Diamond |
| 2004/0137642 A1 | 7/2004 | Erfle et al. |
| 2004/0141958 A1 | 7/2004 | Steinaa et al. |
| 2004/0143094 A1 | 7/2004 | Donda et al. |
| 2004/0204565 A1 | 10/2004 | Schneck et al. |
| 2004/0209295 A1 | 10/2004 | Schwabe et al. |
| 2004/0209314 A1 | 10/2004 | Lang et al. |
| 2004/0223977 A1 | 11/2004 | Diamond |
| 2004/0253632 A1 | 12/2004 | Rhode et al. |
| 2005/0003431 A1 | 1/2005 | Wucherpfennig et al. |
| 2005/0019843 A1 | 1/2005 | Chen et al. |
| 2005/0074822 A1 | 4/2005 | Nixon et al. |
| 2005/0074848 A1 | 4/2005 | Schwabe |
| 2005/0079152 A1 | 4/2005 | Bot et al. |
| 2005/0095655 A1 | 5/2005 | Montero-Julian et al. |
| 2005/0208529 A1 | 9/2005 | Winther et al. |
| 2005/0214284 A1 | 9/2005 | Price-Schiavi |
| 2005/0214852 A1 | 9/2005 | Gaynor et al. |
| 2005/0239160 A1 | 10/2005 | Shaw et al. |
| 2006/0018878 A1 | 1/2006 | Cooper et al. |
| 2006/0018929 A1 | 1/2006 | Zaia et al. |
| 2006/0073159 A1 | 4/2006 | Vonderheide et al. |
| 2006/0078563 A1 | 4/2006 | Srivastava |
| 2006/0084116 A1 | 4/2006 | Muchhal |
| 2006/0112440 A1 | 5/2006 | Tsien et al. |
| 2006/0141540 A1 | 6/2006 | Miltenyi et al. |
| 2006/0155115 A1 | 7/2006 | Jakobsen et al. |
| 2006/0166214 A1 | 7/2006 | Kato et al. |
| 2006/0166875 A1 | 7/2006 | Jakobsen et al. |
| 2006/0171954 A1 | 8/2006 | Endl et al. |
| 2006/0228758 A1 | 10/2006 | Muchhal et al. |
| 2006/0228759 A1 | 10/2006 | Muchhal et al. |
| 2006/0234309 A1 | 10/2006 | Shankar et al. |
| 2006/0234310 A1 | 10/2006 | Cai et al. |
| 2006/0240482 A1 | 10/2006 | Kwok et al. |
| 2007/0026503 A1 | 2/2007 | Lacey |
| 2007/0134814 A1 | 6/2007 | Kajander et al. |
| 2007/0154953 A1 | 7/2007 | Brunner et al. |
| 2007/0178532 A1 | 8/2007 | Jacobson et al. |
| 2007/0184022 A1 | 8/2007 | Wang et al. |
| 2007/0280957 A1 | 12/2007 | Falk et al. |
| 2008/0219947 A1 | 9/2008 | Linette et al. |
| 2008/0269068 A1 | 10/2008 | Church et al. |
| 2009/0004213 A1 | 1/2009 | Singh et al. |
| 2009/0061478 A1 | 3/2009 | Poulsen et al. |
| 2009/0232766 A1 | 9/2009 | Wang et al. |
| 2009/0324630 A1 | 12/2009 | Jensen |
| 2010/0159594 A1 | 6/2010 | Hansen et al. |
| 2010/0226854 A1 | 9/2010 | Scholler et al. |
| 2011/0236411 A1 | 9/2011 | Scholler et al. |
| 2012/0020998 A1 | 1/2012 | Plumas et al. |

FOREIGN PATENT DOCUMENTS

| | | | |
|---|---|---|---|
| EP | 0106873 B1 | 5/1984 |
| EP | 0516953 A1 | 12/1992 |
| EP | 0633028 B1 | 1/1995 |
| EP | 0636696 A1 | 2/1995 |
| EP | 0420913 A1 | 11/1995 |
| EP | 0420913 B1 | 11/1995 |
| EP | 0423201 B1 | 6/1996 |
| EP | 0594772 B1 | 8/1996 |
| EP | 0742014 A1 | 11/1996 |
| EP | 0946592 | 10/1999 |
| EP | 0949508 A1 | 10/1999 |
| EP | 1023319 | 8/2000 |
| EP | 0776339 B1 | 10/2000 |
| EP | 1181313 | 2/2002 |
| EP | 0981747 B1 | 7/2002 |
| EP | 1227321 | 7/2002 |
| EP | 0630255 B1 | 12/2002 |
| EP | 0812331 B1 | 5/2004 |
| EP | 0935607 B1 | 7/2004 |
| EP | 1437366 | 7/2004 |
| EP | 0877760 B1 | 9/2004 |
| EP | 1526141 | 8/2005 |
| EP | 0525821 B1 | 3/2006 |
| EP | 0997477 B1 | 3/2006 |

(56)        References Cited

FOREIGN PATENT DOCUMENTS

| | | |
|---|---|---|
| EP | 1017799 | 3/2006 |
| EP | 1349569 | 4/2007 |
| EP | 1012320 | 10/2007 |
| JP | 2001158800 A | 6/2001 |
| RU | 2260047 | 4/2004 |
| RU | 2260047 C2 | 4/2005 |
| WO | 1989012458 | 12/1989 |
| WO | 1989012459 | 12/1989 |
| WO | 1990004411 | 5/1990 |
| WO | 1991008307 A1 | 6/1991 |
| WO | 1991009870 | 7/1991 |
| WO | 199115766 A1 | 10/1991 |
| WO | 1991157766 | 10/1991 |
| WO | 1992000055 | 1/1992 |
| WO | 1992008983 A1 | 5/1992 |
| WO | 1992018150 | 10/1992 |
| WO | 1992021972 | 12/1992 |
| WO | 1993001498 | 1/1993 |
| WO | 1993001498 A1 | 1/1993 |
| WO | 1993004175 | 3/1993 |
| WO | 1993008306 | 4/1993 |
| WO | 1993010220 | 5/1993 |
| WO | 1994011078 | 5/1994 |
| WO | 1994012196 | 6/1994 |
| WO | 1995011998 | 5/1995 |
| WO | 1995012676 | 5/1995 |
| WO | 1995014781 | 6/1995 |
| WO | 1996004314 | 2/1996 |
| WO | 1996026962 | 9/1996 |
| WO | 1996026962 A1 | 9/1996 |
| WO | 1997005239 | 2/1997 |
| WO | 1997028191 | 8/1997 |
| WO | 1997035991 | 10/1997 |
| WO | 1997042221 | 11/1997 |
| WO | 1997044667 | 11/1997 |
| WO | 1998003552 | 1/1998 |
| WO | 1998005965 | 2/1998 |
| WO | 1998006749 | 2/1998 |
| WO | 1998005684 | 5/1998 |
| WO | 1999002183 A2 | 1/1999 |
| WO | 1999011661 | 3/1999 |
| WO | 1999011775 | 3/1999 |
| WO | 1999014236 | 3/1999 |
| WO | 1999021572 | 5/1999 |
| WO | 1999024577 A1 | 5/1999 |
| WO | 1999013095 | 7/1999 |
| WO | 1999036568 A2 | 7/1999 |
| WO | 1999042597 | 8/1999 |
| WO | 1999050637 | 10/1999 |
| WO | 1999058557 | 11/1999 |
| WO | 1999060119 | 11/1999 |
| WO | 2000006745 | 2/2000 |
| WO | 2000015665 | 3/2000 |
| WO | 200021989 A1 | 4/2000 |
| WO | 2000023053 | 4/2000 |
| WO | 2000057183 A1 | 9/2000 |
| WO | 2000075180 A2 | 12/2000 |
| WO | 2000078966 | 12/2000 |
| WO | 2001027625 A1 | 4/2001 |
| WO | 2001063286 A2 | 8/2001 |
| WO | 200173443 A2 | 10/2001 |
| WO | 200173443 A3 | 10/2001 |
| WO | 2001072782 | 10/2001 |
| WO | 2001072782 A2 | 10/2001 |
| WO | 2001070245 | 11/2001 |
| WO | 2001080833 | 11/2001 |
| WO | 2001090198 | 11/2001 |
| WO | 2001090747 | 11/2001 |
| WO | 2002016422 | 2/2002 |
| WO | 2002055992 | 3/2002 |
| WO | 2002054065 | 7/2002 |
| WO | 2002072631 | 9/2002 |
| WO | 2002083903 A2 | 10/2002 |
| WO | 2002089837 | 11/2002 |
| WO | 2003000720 A1 | 1/2003 |
| WO | 2003016905 A2 | 2/2003 |
| WO | 2003031591 A2 | 4/2003 |
| WO | 2003072753 A2 | 9/2003 |
| WO | 2003073097 | 9/2003 |
| WO | 2003073097 A2 | 9/2003 |
| WO | 2002083906 | 10/2003 |
| WO | 2003101473 | 12/2003 |
| WO | 2004000873 A2 | 12/2003 |
| WO | 2004014957 A1 | 2/2004 |
| WO | 2004018520 | 3/2004 |
| WO | 2004033497 | 4/2004 |
| WO | 2004093905 A1 | 11/2004 |
| WO | 2005002621 | 1/2005 |
| WO | 2005003394 A2 | 1/2005 |
| WO | 2005007689 A1 | 1/2005 |
| WO | 2005035567 | 4/2005 |
| WO | 2005049073 | 6/2005 |
| WO | 2005054860 A1 | 6/2005 |
| WO | 2005111624 A2 | 11/2005 |
| WO | 2005116051 A2 | 12/2005 |
| WO | 2006009838 | 1/2006 |
| WO | 2006009838 A2 | 1/2006 |
| WO | 2006014292 | 2/2006 |
| WO | 2006056027 A1 | 6/2006 |
| WO | 2006071990 A2 | 7/2006 |
| WO | 2006081826 | 8/2006 |
| WO | 2006082387 | 8/2006 |
| WO | 2006082387 A1 | 8/2006 |
| WO | 2006090283 A2 | 8/2006 |
| WO | 2006113622 A2 | 10/2006 |
| WO | 2006130347 A2 | 12/2006 |
| WO | 2007015168 A2 | 2/2007 |
| WO | 2007065098 | 6/2007 |
| WO | 2007085266 A2 | 8/2007 |
| WO | 2007136778 A2 | 11/2007 |
| WO | 2008015425 A2 | 2/2008 |
| WO | 2008016680 A1 | 2/2008 |
| WO | 2008019366 A2 | 2/2008 |
| WO | 2008031133 | 3/2008 |
| WO | 2008116468 A2 | 10/2008 |
| WO | 2008121836 A1 | 10/2008 |
| WO | 2009003492 | 1/2009 |
| WO | 2009003492 A1 | 1/2009 |
| WO | 2009003493 | 1/2009 |
| WO | 2009003493 A2 | 1/2009 |
| WO | 2009039854 A2 | 4/2009 |
| WO | 2009077173 A2 | 6/2009 |
| WO | 2009106073 A2 | 9/2009 |
| WO | 2009114207 | 9/2009 |
| WO | 2009125231 A2 | 10/2009 |
| WO | 2009126816 | 10/2009 |
| WO | 2009126828 A2 | 10/2009 |
| WO | 2009155535 A2 | 11/2009 |
| WO | 2010009735 A2 | 1/2010 |
| WO | 2010032022 A2 | 3/2010 |
| WO | 2010037395 A2 | 4/2010 |
| WO | 2010037397 | 4/2010 |
| WO | 2010037402 A1 | 4/2010 |
| WO | 2012044999 A2 | 4/2012 |
| WO | 2012094492 A2 | 7/2012 |
| WO | 2015185067 A1 | 12/2015 |

OTHER PUBLICATIONS

Liu et al (MHC Complex: Interaction with Peptides. IN: eLS. John Wiley & Sons, Ltd: Chichester, DOI: 10.1002/9780470015902. a0000922.pub2, 2011, pp. 1-12) (Year: 2011).*
Ali-Khan et al (Curr. Prot. Prot. Sci. 2002, 22.1.1-22.1.19, Suppl. 30, John Wiley & Sons, Inc.) (Year: 2002).*
Woolhouse et al (Phil. Trans. R. Soc. B, 2012, 367: 2864-2871) (Year: 2012).*
Schumacher and Schreiber (Science, 2015, 348(6230): 69-74) (Year: 2015).*
Buonaguro et al (Clin. Vacc. Immunol. 2011, 18(1): 23-34) (Year: 2011).*
Wieczorek et al (Front. Immunol. 2017, vol. 8, article 292: 1-16) (Year: 2017).*

(56) References Cited

OTHER PUBLICATIONS

Reche and Reinherz (G. Nicosia et al., Eds. ICARIS 2004, LNCS 3239: 189-196) (Year: 2004).*

Nishioka et al (Front. Immunol. 2018, vol. 9, article 548, pp. 1-6, doi: 10.3389/fimmu.2018.005448) (Year: 2018).*

Girardi et al (JBC, 2016, 291(20): 10677-10683) (Year: 2016).*

Kraemer et al (Stem Cell Int. 2015, pp. 1-12, article ID 346714) (Year: 2015).*

Britannica Online Encyclopedia (Britannica.com/print/article/114462, 2021, 2 pages) (Year: 2021).*

Denkberg et al (Eur. J. Immunol., 2000, 30: 3522-3532) (Year: 2000).*

Newell et al (Nature Methods, Jul. 2009, 6(7): 497-500 plus supplementary material, 20 pages) (Year: 2009).*

Repana et al (Genome Biol. 2019 20: 1-12) (Year: 2019).*

Wintzingerode et al. Peptide nucleic acid-mediated PCR clamping as a useful supplement in the determination of microbial diversity. Applied and Environmental Microbiology, vol. 66 No. 2, Feb. 2000, pp. 549-557.

June, Adoptive T cell therapy for cancer in the clinic. J Clin Invest. 2007, 117(6), pp. 1466-1476.

Demaria et al. Combining radiotherapy and immunotherapy: a revived partnership. Int. J. Radiation Oncology Biol. 63, 3,2005, pp. 655-666.

Kozlov, I. et al. Efficient strategies for the conjugation of oligonucleotides to antibodies enabling highly sensitive protein detection. Biopolymers, vol. 73, No. 5, pp. 621-630, 2004.

Timmerman et al. Immunogenicity of a plasmid DNA vaccine encoding chimeric idiotype in patients with B-cell lymphoma. Cancer Research 62, 5845-5852, 2002.

Hendrickson et al., "High sensitivity multianalyte immunoassay using covalent DNA-labeled antibiodies and polymerase chain reaction", Nucleic Acid Res. 1995, vol. 23, No. 3, pp. 522-529.

Joerger et al., "Analyte detection with DNA-labeled antibodies and polymerase chain reaction", Clin. Chem. 41/9, 1371-1377 (1995).

Xu et al., "Design of 240,000 orthogonal 25mer DNA barcode probes". PNAS, Feb. 17, 2009, vol. 106, No. 7, 2289-2294.

Altman JD et al. Phenotypic analysis of antigen-specific T lymphocytes. Science, 1996; 274:94-96.

Davis MM et al. T-cell antigen receptor genes and T-cell recognition. Nature. 1988;334:395-402.

Eppstein et al., Biological activity of liposome-encapsulated murine interferon gamma is mediated by a cell membrane receptor. Proc. Natl. Acad. Sci. USA 82: pp. 3688-3692 (1985).

Hansen et al. Phage display of peptide/major histocompatibility class I complexes. European Journal of Immunology, vol. 31, pp. 32-38, 2001.

Hwang et al. Hepatic uptake and degradation of unilamellar sphingomyelin/cholesterol liposomes: A kinetic study. Proc. Natl. Acad. Sci. USA 77: pp. 4030-4304 (1980).

Khurana A. et al. A Method for Production of Recombinant mCD1d Protein in Insect Cells. J Vis Exp. 2007; (10): pp. 1-2.

Manz R. et al. Analysis and sorting of live cells according to secreted molecules, relocated to a cell-surface affinity matrix. Proc. Natl. Acad. Sci. USA vol. 92:1921-1925 (1995).

Morgan RA et al. Cancer Regression in Patients After Transfer of Genetically Engineered Lymphocytes. Science, Oct. 6, 2006 314(5796): 126-129.

Pannetier C et al. T-cell repertoire diversity and clonal expansions in normal and clinical samples. Immunol Today. 1995;16:176-181.

Robins HS et al. Comprehensive assessment of T-cell receptor beta-chain diversity in alphabeta T cells. Blood. 2009;114:4099-4107.

Soen Y et al. Detection and characterization of cellular immune responses using peptide-MHC microarrays. PLoSBiol. 2003; 1:429-438.

Stone JD et al. HLA-restricted epitope identification and detection of functional T cell responses by using MHC-peptide and costimulatory microarrays. ProcNatlAcadSciUSA. 2005; 102:3744-3749.

Xu et al., "Preparation and Characterization of HLA-A0201 Tretamer Loaded with IE-1 316-324 Antigenic Peptide of Human Cytomegalovirus" Cellular & Molecular Immunology, vol. 3, No. 5, pp. 367-371 (2006).

Andersen et al., "Spontaneous cytotoxic T-cell responses against Survivin-derived MHC class I-restricted T-cell epitopes in situ as well as ex vivo in cancer patients," Cancer Res., vol. 61, pp. 5964-5968, Aug. 15, 2001.

Bogers et al., "CCR5 targeted SIV vaccination strategy preventing or inhibiting SIV infection," Vaccine, Butterworth Scientific, pp. 2974-2984, Aug. 13, 2004 (Aug. 13, 2004), vol. 22, No. 23-24. Guildford, GB.

Reznik et al., "A Streptavidin Mutant Useful for Directed Immobilization on Solid Surfaces", Bioconjugate Chemistry 2001, 12, 1000-1004.

Day et al., "Ex vivo analysis of human memory CD4 T cells specific for hepatitis C virus using MHC class II tetramers", J Clin Invest. 112: 831-842 (2003).

Moon et al., "Naive CD4+ T Cell Frequency Varies for Different Epitopes and Predicts Repertoire Diversity and Response Magnitude", Immunity, 27, 203-213 (2007).

Scriba et al., "Ultrasensitive Detection and Phenotyping of CD4+ T Cells with Optimized HLA Class II Tetramer Staining", Journal of Immunology, 2005, 175: 6334-6343.

Davis et al., "Interrogating the repertoire: broadening the scope of peptide-MHC multimer analysis", Nature Reviews Immunology, vol. 11, (2011), pp. 551-558.

Donolato et al., "On-Chip Manipulation of Protein-Coated Magnetic Beads via Domain-Wall Conduits", Adv. Mater. 2010, 22, 2706-2710.

Degauque et al., "Characterization of Antigen-Specific B Cells Using Nominal Antigen-Coated Flow-Beads", PLoS One, (2013) vol. 8, Issue 12, pp. 1-10.

Drouin et al., Searching for borrelial T-cell epitopes associated with antibiotic-refractory Lyme arthritis,: Molecular Immunology, pp. 2323-2332, Jan. 11, 2008 (Jan. 11, 2008), vol. 45, No. 8, GB.

Ed. Charron, "HLA: Genetic diversity of HLA. Functional and Medical Implication," EDK Press, pages corresponding to Tables 1A and 1B, 1997.

Erout et al., "Preparation of Conjugates between Oligonucleotides and N-Vinylpyrrolidone/N-Acryloxysuccinimide Copolymers and Applications in Nucleic Acid Assays to Improve Sensitivity," Bioconjugate Chem. 1996, pp. 568-575, vol. 7.

Fields, et al., "Solid phase peptide synthesis utilizing 9—fluorenylmethoxycarbonyl amino acids," Int. J. Peptide Res., 353:161-214, 1990 (Abstract Only).

Frayser et al., "Empty and peptide-loaded class II major histocompatibility complex proteins produced by expression in *Escherichia coli* and folding in vitro," Protein Expression and Purification, pp. 105-114, Feb. 1999, vol. 15 (Abstract Only).

Garboczi et al., HLA-A2. peptide complexes: Refolding and crystallization of molecules expressed in *Escherichia coli* and complexed with single antigenic peptides,: Proc. Natl. Acad. Sci., 89:3429-3433, 1992.

Gordon et al., "Applications of Combinatorial Technologies to Drug Discovery. 2. Combinatorial Organic Synthesis, Library Screening Strategies, and Future Directions," Journal of Medicinal Chemistry, 37 (10):1385-1401, 1994 (Abstract Only).

Haanen et al., "In situ detection of virus-and-tumor-specific T-cell Immunity," Nature Medicine, Sep. 2000, pp. 1056-1060, vol. 6 (Abastract Only).

Hadrup et al., "Persistence of surviving specific T cells for seven years in a melanoma patient during complete remission," Cancer Biol. Ther., pp. 480-482, May 2006, vol. 5.

Houghten et al., "Generation and use of synthetic peptide combinatorial libraries for basic research and drug discovery," Nature, 354:84-86, 1991 (Abstract Only).

Hughes et al. "Generation and use of alternative multimers of peptide-MHC complexes, " Journal of Immunological Methods, 268:83-92, 2002.

Jung et al., "Multiple Peptide Synthesis Methods and their Applications," Angewandte Chemie, 31 (4):367-486, 1992 (Abstract Only).

(56)        References Cited

OTHER PUBLICATIONS

Kalandadze et al., "Expression of Recombinant HLA-DR2 molecules," J. Biol. Chem., pp. 20156-20162, Aug. 16, 1996, vol. 271.
Knabel et al., "Reversible MHC multimer staining for functional isolation of T-cell populations and effective adoptive transfer," Nature Medicine, Nature Publishing Group, pp. 631-637, Jun. 1, 2002 (Jun. 1, 2002), vol. 8, No. 6.
König, "Interactions between MHC molecules and co-receptors of the TCR," Current Opinion in Immunology, pp. 75.83, 2002, vol. 14.
Kozono et al., "Production of soluble MHC class II proteins with covalently bound single peptides," Nature, pp. 151-154, May 12, 1994, vol. 369 (Abstract Only).
Kuroda et al., "Analysis of Gas-specific Cytotoxix T Lympocytes in Simian Immunodeficiency Virus-infected Rhesus Monkeys by Cell Staining with Tetrameric Major Histocompatibility Complex Class I-Peptide Complex," J.Exp.Med., May 4, 1998, 1373-1381, vol. 187, No. 9.
Kuttler et al., "An algorithm for the Prediction of Proteasomal Cleavages," J. Miol. Biol., 298:417-429, 2000.
Larsson, "Immunocytochemical detection systems," in Immunocytochemistry: Theory and Practice, pp. 77-145, CRC Press, 1988.
Lee et al., "Characterization of circulating T cells specific for tumor-associated antigens in melanoma patients," Nature Medicine, Jun. 1999, pp. 677-685, vol. 5, No. 6.
Lehner, "Allomicrovac: A combined microbicidal -immunising strategy against SIV and HIV infection," Vaccines for Humans, pp. 64-65, Dec. 5, 2008 (Dec. 5, 2008), XP0025629223, URL biblioteca. porto.ucp.pt-docweb-MULTIMEDIA-ASSOCIA-PDF-VAC.PDF.
Ljunggren et al., "Empty MHC class I molecules come out in the cold," Nature 346:476-480, 1990.
Mallone et al., "MHC class II tetramers and the pursuit of antigen-specific T cells: Define, deviate, delete," Clin. Immunol., pp. 232-242, 2004, vol. 110.
Marchand et al., "Tumor regression responses in melanoma patients treated with a peptide encoded by gene MAGE-3," Int. J. Cancer, 63:883-885, 1995.
Matsumura et al., "Emerging Principles for the Recognitions of Peptide Antigen by MHC class I Molecules," Science 257:927-934, 1992.
Matsumura et al., "In vitro peptide binding to soluble empty class I major histocompatibility complex molecules isolated from tranfected *Drosophila melanogaster* cells," J. Biol. Chem., pp. 25389-23595, Nov. 25, 1992, vol. 267.
McCluskey et al., :T-cell activation by purified, soluble, class I MHC molecules: Requiremet for polyvalency, J. Immunol. 141(5): 1451-55, 1988.
Mcheyzer-Williams et al., "Tracking antigen-specific helper T cell responses," Current Opinion in Immunology, pp. 278-284, 1996, vol. 8.
Merrifield, et al., "Instrument for Automated Synthesis of peptides," Analytical Chemistry, 38 (13):1905-1914, 1966 (Abstract Only).
Merrifield, "Solid Phase Synthesis," Science 232:341-347, 1986 (Abstract Only).
Meyer et al., "Direct enumeration of Borrelia-reactive CD4 T-cell ex vivo by using MHC class II tetramer," Proceedings of the National Academy of Sciences of USA. (PNAS), National Academy of Science, pp. 11433-11438, Oct. 10, 2000 (Oct. 10, 2000), vol. 97, No. 21, Washington D.C., US.
Mutis et al., "Tetramic HLA class I-minor histocompatibility antigen peptide complexes demonstrate minor histocompatibility antigen-specific cytoxic T lymphocytes in patients with graft-visus-host disease," Nature Medicine, Jul. 1999, pp. 839-842, vol. 5, No. 7.
Neudorfer et al., "Reversible HLA multimers (streptamers) for the isolation of human cytoxic T lymphocytes functionally active tumor- and virus-derived antigens," Journal of Immunolgical Methods, 320:119-131, 2007.
O'Herrin et al., "Analysis of the Expression of Peptide-Major Histocompatibility Complexes using high affinity Soluble Divalent T-Cell Receptors," The Journal of Biological Chemistry, Oct. 20, 1997, pp. 1333-1345, vol. 186, No. 8.
Reich et al., "Stability of empty and peptide-loaded class II major histocompatibility complex molecules at neutral and enosomal pH: Comparison to class I proteins," Proc. Natl. Acad. Sci. USA, pp. 2495-2500, Mar. 1997, vol. 94.
Reijonen et al., "Use of HLA class II tetramers in tracking antigen-specific T cell and mapping T-call epitopes," pp. 282-288, 2003, vol. 29.
Scheirle et al., "Peptide binding to soluble HLA-DR4 molecules produced by insect cells," J. Immunol., pp. 1994-1999, Sep. 15, 1992, vol. 149 (Abstract Only).
Sengupta et al., "Heat shock protein-mediated cross-presentation of exogenous HIV antigen on HLA class I and class II," Journal of Immunology, American Association of Immunologists, pp. 1987-1993, Aug. 1, 2004 (Aug. 1, 2004), vol. 173, No. 3.
Shambrook, Fritsch and Maniatis, "Molecular Cloning," Cold Spring Harbor Press, 1989, Index and Table of Contents pp. xi to xxxviii and 1-1 to 1-47.
Shields et al., "The Effect of Human [32—Microglobulin on Major Histocompatibility Complex I Peptide Loading and the Engineering of a High Affinity Variant," The Journal of Biological Chemistry, Oct. 23, 1998, pp. 28010-28018, vol. 273, No. 43.
Skinner et al., "In situ tetramer staining," J. Immunol. Meth., pp. 29-34, 2002, vol. 268.
Sorensen et al., "Efficient tumor cell lysis mediated by a bcl-X(L) specific T cell clone isolated from a breast cancer patient," Cancer Immunology, Immunotherapy, Springer, pp. 527-533, Jul. 19, 2006 (Jul. 19, 2006), vol. 56, No. 4.
Stern et al., "The human class II MHC protein HLA-DR1 assembles as empty alpha beta heterodimers in the absence of antigenic peptide," Cell, pp. 465-477, Feb. 7, 1992, vol. 68 (Abstract Only).
Stratmann et al., "Susceptible MHC Alleles, not background genes, select an autoimmune T cell reactivity," The Journal of Clinical Investigation, pp. 902-914, Sep. 2003, vol. 112, No. 6.
Stockel et al., "Refolding of human class II major histocompatibility complex molecules isolated from *Escherichia coli*", J. Biol. Chem., pp. 29571-29578, Nov. 25, 1994, vol. 269.
Sun et al., "MHC class I multimers," Arthritis Res., pp. 265-269, Jul. 2001, vol. 3.
Ugolini et al., "Regulation of T cell function by NK cell receptors for classical MHC class I molecules," Current Opinion in Immunology 12:295-300, 2000.
Valmori et al., "Enhanced generation of specific tumor-reactive CTL in vitro by selected Melan-A-MART-1 immunodominant peptide analogues," J. Immunol., pp. 1750-1758, Feb. 15, 1998, vol. 160.
Jain et al., "The Principles and Applications of Avidin-Based Nanoparticles in Drug Delivery and Diagnosis", J. Control Release, 2017, 245: 36 pages.
Liu et al., "Major Histocompatibility Complex: Interaction with Peptides", In: eLS. John Wiley & Sons, Ltd: (2011) Chichester, pp. 1-12.
Wieczorek et al., "Major Histocompatibility Complex (MHC) Class I and Class II Proteins: Conformational Plasticity in Antigen Presentation", Frontiers in Immunology, 2017, vol. 8, article 292: pp. 1-16.
Reche et al., "Definition of MHC Supertypes Through Clustering of MHC Peptide Binding Repertoires", G. Nicosia et al. (Eds.) ICARIS 2004, LNCS 3239, pp. 189-196 (2004).
Ali-Khan et al., "Overview of Peoteome Analysis", Current Protocols in Protein Science (2002), 22.1.1-22.1.19, Suppl. 30, John Wiley & Sons, Inc.) (Year: 2002) 19 pages.
Buonaguro et al., "Translating Tumor Antigens into Cancer Vaccines", Clin. Vacc. Immunol. 2011, 18(1): pp. 23-34.
Girardi et al., "Structure of an a-Helical Peptide and Lipopeptide Bound to the Nonclassical Major Histocompatibility Complex (MHC) Class I Molecule CD1d", JBC, 2016, 291(20): pp. 10677-10683.
Nishioka et al., "CD1d-Restricted Type II NKT Cells Reactive With Endogenous Hydrophobic Peptides", Frontiers in Immunology, 2018, vol. 9, article 548, pp. 1-6.
Nikolich-Zugich et al., "The many important facets of T-cell repertoire diversity", Nature Reviews, 2004, vol. 4: pp. 123-132.

(56)                    References Cited

OTHER PUBLICATIONS

Schumacher et al., "Neoantigens in cancer immunotherapy", Science, 2015, vol. 348, pp. 69-74.
Kraemer et al., "HLA-E: Presentation of a Broader Peptide Repertoire Impacts the Cellular Immune Response—Implications on HSCT Outcome", Stem Cells International, 2015, pp. 1-12.
Pullen et al., "Recognition of a single amino acid change on the surface of a major transplantation antigen is in the context of self peptide", Journal of Immunology, (1994), 152, pp. 3445-3452.
Marrack et al., "Evolutionarily Conserved Amino Acids That Control TCR-MHC Interaction", Annual Review of Immunology, (2008), 26:pp. 171-203.
Singh et al., "Emerging Concepts in TCR Specificty: Rationalizing and (Maybe) Predicting Outcomes", Journal of Immunology, (2017), 199:pp. 2203-2213.
Woolhouse et al., "Human viruses: discovery and emergence", Phil. Trans. R. Soc. B., (2012), 367: pp. 2864-2871.
Viola et al., "T-cell activation and the dynamic world of rafts.," APMIS 107:615-623, 1999.
Vyth-Dreese et al., "In situ visualzation of antigen specific T cells in cryopreserved human tissues," J. Immunol. Meth., pp. 78-85, 2006, vol. 310.
White et al., "Soluble class I MHC with B2-microglobulin covalently linked peptides: specific binding to a T cell hybridoma," J. Immunol., pp. 2671-2676. Mar. 1, 1999, vol. 162.
Xu et al., "MHC-peptide tetramer-based studies of T cell function," J. Immunol Meth., pp. 21-28, 2002, vol. 268.
Zhang et al., "Essential role of LAT in T cell development," Immunity 10:323-332, 1999.
Akiyama et al. "Analysis of HLA-A24-restricted CMVpp65 peptide-specific CTL with HLA-A*2402-CMVpp65 tetramer," Immunology Letters, vol. 95, pp. 199-205, (2004).
Busch et al. "Detection of Borrelia burgdorferi—Specific CD8+ Cytotoxic T Cells in Patients with Lyme Arthritis," The Journal of Immunology, vol. 157, pp. 3534-3541, (1996).
Celis et al. "Identification of potential CTL epitopes of tumor-associated antigen mage-1 for five common HLA-A alleles," Molecular Immunology, vol. 31, No. 18, pp. 1423-1430 (1994).
Chen et al. "Modulation of CD1d-restricted NKT cell responses by CD4," Journal of Leukocyte Biology, vol. 82, pp. 1455-1465 (2007).
Denkberg et al. "Recombinant human single-chain MHC-peptide complexes made from E. coli by in vitro refolding: functional single-chain MHC-peptide complexes and tetramers with tumor associated antigens," Eur. J. Immunol., vol. 30, pp. 3522-3532 (2000).
Drake et al. "Cutting Edge: Lipid Raft Integrity Affects the Efficiency of MHC Class I Tetramer Binding and Cell Surface TCR Arrangement on CD8+ T Cells1," The Journal of Immunology, vol. 166, No. 12, pp. 7009-7013 (2001).
He et al. "Procedure for preparing peptide-major histocompatibility complex tetramers for direct quantification of antigen-specific cytotoxic T lymphocytes," World J Gastroenterol, vol. 11, No. 27, pp. 4180-4187 (2005).
Kao et al. "Loss of CD8 and TCR binding to Class I MHC ligands following T cell activation," International Immunology, vol. 17, No. 12, pp. 1607-1617 (2005).
Karin et al. "Reversal of Experimental Autoimmune Encephalomyelitis by a Soluble Peptide Variant of a Myelin Basic Protein Epitope: T Cell Receptor Antagonism and Reduction of Interferon γ and Tumor Necrosis Factor a Production," J. Exp. Med., vol. 180, pp. 2227-2237 (1994).
Kronenberg et al. "The unconventional lifestyle of NKT cells," Nature Reviews Immunology vol. 2 No. 8 pp. 557-568 (2002).
Nepom "MHC multimers: expanding the clinical toolkit," Clinical Immunology, vol. 106, pp. 1-4 (2003).
Ruan et al. "Preparation of HLA-A*0201 NLVPMVATV peptide tetramers and application to detect cytomegalovirus specific CTL," Chin J Microbiol Immunol., vol. 26., No. 9, pp. 855-858 (2006)—English Abstract Only.

Ruan et al. "Improved preparation of class I HLA tetramers and their use in detecting CMV-specific CTL," Journal of Immunological Methods, vol. 312, pp. 148-156 (2006).
Schueler-Furman et al. "Structure-based prediction of binding peptides to MHC class I molecules: Application to a broad range of MHC alleles," Protein Science, vol. 9, Issue 9, pp. 1838-1846 (2000).
Theisen et al. "Evolution of the borrelia burgdorferi outer surface protein OspC," Journal of Bacteriology, vol. 177, No. 11, pp. 3036-3044 (1995).
Weinberg "The Biology of Cancer," Garland Science, pp. 737-747 (2007).
Rognan et al. (PNAS USA, 1985, 92: 753-757).
Parker et al. (JBC, 1992, 267:5451-5459).
DiBrino et al. (PNAS USA, 1993, 90: 1508-1512).
IEBD Analysis Resource, 7/12, 3 pages, world wide web at tools.immuneeptiipr.org/tools/population/tutorial.jsp.
H.S. Reker et al., "Parallel detection of antigen-specific T-cell responses by multidimensional encoding of MHC multimers", Nature Methods (Nature Publishing Group), Basingstoke GB, vol. 6, No. 7, doi: 10.1038/NMETH.1345, ISSN 1548-7091, 20090701, (Jul. 1, 2009) pp. 520-528.
Takeshi-Sano et al., Immuno-PCR: Very sensitive antigen detection by means of specific antibodyODNA conjugates. Science American Association for the Advancement of Science, UA, vol. 258, No. 5079, Oct. 2, 1992, 120-122.
Alp, et al., "Fine specificity of cellular immune responses in humans to human cytomegalovirus immediate-early 1 protein", Journal of Virology, vol. 65, No. 9, 1991 pp. 4812-4820.
Bleesing, et al., "Cell Function-Based Flow Cytometry" Seminars in Hematology, Apr. 2001, pp. 169-178, vol. 38, No. 2.
Bross, et al., "Approval summary: Gemtuzumab ozogamicin in relapsed acute myeloid leukemia", Clin. Cancer Res., 2001, 7:1490-1496.
Cecconi, et al., "Use of MHC Class II Tetramers to Investigate CD4 + T Cell Responses: Problems and Solutions," Cytometry, 2008, Part A 73, No. 11, pp. 1010-1018.
Chattopadhyay, et al., "Techniques to improve the direct Ex Vivo detection of low frequency antigen-specific CD8 +T cells with peptide-major histocompatibility complex class I tetramers," Cytometry, 2008, Part A, vol. 73, pp. 1001-1009.
Drouin, et al., "Molecular Characterization of the OspA161-175 T cell epitope associated with the treatment-resistant Lyme Arthritis: differences among the three pathogenic species of Borrelia burgdorferi sensu lato", Journal of Autoimmunology, 2004, vol. 23, No. 3, pp. 281-292.
Ferre, et al., "Purification of correctly oxidized MHC class I heavy-chain molecules under denaturing conditions: A novel strategy exploiting disulfide assisted protein folding", Protein Science, 2003, 12, pp. 551-559.
Fornas, et al., Flow Cytometry Counting of CD34+ cells in whole blood, Nature Medicine, 6 (2000) 7:833-836.
Heijnen, et al., "Enumeration of Antigen-Specific CD8+ T Lymphocytes by Single-Platform, HLA Tetramer-Based Flow Cytometry: A European Multicenter Evaluation", Clinical Cytometry, 2004, pp. 1-13, vol. 62B.
Lissina, et al., "Protein Kinase Inhibitors Substantially Improve the Physical Detection of T-Cells with Peptide-MHC Tetramers," J. Immunol. Methods, 2009, vol. 340, pp. 11-24.
Maloney, et al., "IDEC-C2B8 (Rituximab) anti-CD20 monoclonal antibody therapy in patients with relapsed low-grade non-Hodgkin's lymphoma," Sep. 1997, Blood, 90 (6):2188-2195.
Melenhorst, et al.," Detection of Low Avidity CD8+ T Cell Populations with Coreceptor-Enhanced Peptide-Major Histocompatibility Complex Class I Tetramers," j. Immunol. Methods, 2008, vol. 338, No. 1-2, pp. 31-39.
Vollers, et al., "Class II Major Histocompatibility Complex Tetramer Staining: Progress, Problems, and Prospects," Immunology, 2008, vol. 123, pp. 305-313.
Weichsel, et al., "Profound Inhibition of Antigen-Specific T-Cell Effector Functions by Dasatinib," Clin. Cancer Res.2008, vol. 14, pp. 2484-2491.

(56) References Cited

OTHER PUBLICATIONS

Wolfl, et al., "Quantitation of MHC Tetramer-Positive Cells From Whole Blood: Evaluation of Single-Platform, Six-parameter Flow Cytometric Method", Cytometry Part A, 2004, pp. 120-130, vol. 57A.

Le Doussal et al., "Phage display of peptide/major histocompatibility complex", Journal of Immunological Methods, vol. 241, issues 1-2, 31, pp. 147-158, 2000.

Seneci, Pierfausto, "Encoding Techniques for Pool Libraries of Small Organic Molecules", Journal of Receptors and Signal Transduction, vol. 21, 2001—Issue 4. pp. 409-445. doi.org/10.1081/RRS-100107925.

Andersen et al., Parallel detection of antigen-specific T-cell responses by combinatorial encoding of MHC multimers. NatProtoc., vol. 7, No. 5, pp. 891-902 (2012).

HLA nomenclature—HLA allele numbers (hla.alleles.org/nomenclature/stats.html (2010).

Bauer et al., "Maximizing immune responses: the effects of covalent peptide linkage to beta-2-microglobulin"; Oncol Res. 17(5):205-16, (2008).

Celis et al., Induction of anti-tumor cytotoxic T lymphocytes in normal humans using primary cultures and synthetic peptide epitopes. Proc Natl Acad Sci USA, vol. 91, 2105-2109 (1994).

Cortez-Gonzales et al., Immunogenic HLA-B7-restricted peptides of hTRT. Intl Immunology vol. 18, No. 12 1707-1718 (2006).

DiBrino et al., "HLA-A1 and HLA-A3 T cell epitopes derived from influenza virus proteins predicted from peptide binding motifs." J Immunol., 151(11):5930-5 (1993).

Desrosiers, "Prospects for an AID vaccine", Nature Medicine 10, 221-223 (2004).

Greten et al., "Peptide-beta2-microglobulin-MHC fusion molecules bind antigen-specific T cells and can be used for multivalent MHC-Ig complexes", J Immunol Methods. 271(1-2):125-35 (2002).

Hackett and SHarma, "Frontiers in peptide-MHC class II multimer technology", Nature Immunology 3, 887-889 (2002).

Larsen MV (4/07 Prediction of T-cell epitopes for therapeutic and prophylactic vaccines, Ph.D. thesis, Center for Biological Sequence Analysis BioCentrum DTU—Denmark), (2007).

Lauritsen et al., Two distinct pathways exist for down-regulation of the TCR. J Immunology, 161:260-7 (1998).

Matthews et al., "Prospects for Development of a Vaccine Against HTLV-III-Related Disorders"; AIDS Research and Human Retroviruses, 3: 197-206 (1987).

Ochoa-Garay et al., The ability of peptides to induce cytotoxic T cells in vitro does not strongly correlate with their affinity for the H-2Ld molecule: Implications for vaccine design and immunotherapy. Molecular Immunology vol. 34, No. 3, 273-281 (1997).

Oka et al., Induction of WT1 (Wilms' tumor gene)—specific cytotoxic T lymphocytes by WT1 peptide vaccine and the resultant cancer regression. PNAS vol. 101, No. 38, 13885-13890 (2004).

Hadrup et al., "Parallel detection of antigen-specific T-cell responses by multidimensional encoding of MHC multimers", Nature Methods (Nature Publishing Group), Basinstoke GB, vol. 6, No. 7, doi: 10.1038/NMETH.1345, ISSN 1548-7091, pp. 520-528 (2009).

Schroers et al., Identification of HLA DR7-restricted epitopes from human telomerase reverse transcriptase recognized by CD4+ T-helper cells, Cancer Research 62, 2600-2605 (2002).

Speiser et al., In Vivo Activation of Melanoma-Specific CD8(+) T Cells by Endogenous Tumor Antigen and Peptide Vaccines. A Comparison to Virus-Specific T Cells. Eur J Immunol 32:731-741 (2002).

Stoeva et al., "Multiplexed Detection of Protein Cancer Markers with Biobarcoded Nanoparticle Probes", Journal of the American Chemical Society, American Chemical Society, US, vol. 128, No. 26, doi: 10.1021/JA0613106, ISSN 0002-7863, (2006), pp. 8378-8379 (2006).

Sano et al. Immuno-PCR: Very sensitive antigen detection by means of specific antibody-DNA conjugates. Science American Association for the Advancement of Science, UA, vol. 258, No. 5079, Oct. 2, 1992, 120-122.

Xu, "Preparation and Characterization of HLA-A 0201 Tretamer Loaded with IE-1 316-324 Antigenic Peptide of Human Cytomegalovirus," Cullular & Molecular Immunology, vol. 3, No. 5, pp. 367-371 (2006).

Yang et al. "Immunization with recombinant macaque major histocompatibility complex class I and II and human immunodeficiency virus gp140 inhibits simian-human immunodeficiency virus infection in macaques," Journal of General Virology, vol. 93, pp. 1506-1518 (2012).

Batard et al (J. Immunol. Methods, Jan. 17, 2006, 310: 136-148).

Rammensee et al (Immunogenetics, 1995, 41: 178-228).

Nikolich-Zugich et al (Nature Reviews/Immunology, 2004, 4: 123-132).

Altman et al., "Formation of functional peptide complexes of class II major histocompatibility complex proteins from subunits produced in *Escherichia coli*," Proc. Natl. Acad. Sci. USA, pp. 10330-10334, Nov. 1993, vol. 90.

Altman et al., "Phenotypic Analysis of Antigen-Specific T Lymphocytes," Science 274:97-97, 1996.

Appel et al., "Anergy induction by dimeric TCR ligands," J. Immunol., pp. 5279-5285, Apr. 15, 2001, vol. 166.

Appel et al., "Kinetics of T-cell receptor binding by bivalent HLA-DR-peptide complexes that activate antigen-specific human T-cells," J. Biol. Chem., pp. 312-321, Jan. 7, 2000, vol. 275.

Anderson et al., "Spontaneous cytotoxic T-cell responses against surviving MHC class I-restricted T-cell epottopes in situ as well as ex vivo in cancer patients," Cancer Res., vol. 61, pp. 5964-5968, Aug. 15, 2001.

Ausubel et al., "Characterization of in vivo expanded OspA-specific human T-cell clones," Clinical Immunology, Academic Press, pp. 313-322, Jun. 1, 2005 (Jun. 1, 2005), vol. 115, No. 3.

Bakker et al., "MHC multimer technology: Current status and future prospects," Current Opinion in Immunology, 17:428-433, 2005.

Barany et al., "Solid-phase peptide synthesis: A silver anniversary report," Int. J. Peptide Protein Res., 30:705-739, 1987 (Abstract Only).

Batard et al., "Dextramers: New generation of fluorescent MHC class I-peptide multimers for visualization of antigen-specific CD *< +> T cells," Journal of Immunological Methods, Elsevier Science Publishers, pp. 136-148, Mar. 20, 2006 (Mar. 20, 2006), vol. 310, No. 1-2.

Berger et al., "Circulation of hoimg of melanoma-reactive T cells to both cutaneous and visceral metastases after vaccination with monocyte-derived dendric cells," Int. J. Cancer, pp. 229-237, 2004, vol. 111.

Bergmeier et al., Innate and adoptive mucosal immunity in protection against HIV infection,: Advances in Dental Research 2006, pp. 21-28, 2006, vol. 19, No. 1, XP002562924.

Bill et al., "Use of soluble MHC class II-peptide multimers to detect antigen-specific T cells in human disease," Arthritis Res., pp. 261-265, Feb. 28, 2002, vol. 4.

Bjorkman et al., "The foreign antigen binding site and T cell recognition regions of class I histocompatibility antigen," Nature 329: 529-518, 1987.

Bogers, "CCR5 targeted VIV vaccination strategy preventing or inhibiting SIV infection," Vaccine, Butterworth Scientific, pp. 2974-2984, Aug. 13, 2004 (Aug. 13, 2004), vol. 22, No. 23-24. Guildford, GB.

Burlingham et al., :Soluble MHC, Immunoregulation, and tolerance: A progress report, Human Immunol., pp. 1316-1319, Dec. 2000, vol. 61.

Callan et al., "Direct Visualizing of Antigen-specific CD8+ T Cells during the primary Immune Response to Epstein-Barr Virus in Vivo," J. Exp. Med., May 1998, pp. 1395-1402, vol. 187, No. 9.

Cameron et al., Labeling antigen-specific DC4(+) T cells with class II MHC oligomers, J. Immunol. Methods, pp. 51-69, Oct. 1, 2002, vol. 268.

Carena et al., "Major Histocompatibility Complex Class I Molecules Modulate Activation Threshold and Early Signaling of T-Cell Antigen Receptor-γδ Stimulated by Nonpeptidic Ligands," J. Exp. Med., Nov. 17, 1997, pp. 1769-1774, 186 (10).

(56) References Cited

OTHER PUBLICATIONS

Casares et al., "Antigen-specific downregulation of T cells by doxorubicin delivered through a recombinant MHC II-peptide chimera," Nature Biotech., pp. 142-147, Feb. 2001, vol. 19 (Abstract Only).

Cochran, et al., "Receptor clustering and transmembrane signaling T cells," TIBS, pp. 304-310, May 2001, vol. 26.

Coles et al., Memory CD8 T lymphocytes express inhibitory MHC-specific Ly49 receptors, Eur. J. Immunol. 30:236-244, 2000.

Constantin et al., "Major histocompatibility complex (MHC) tetramer technolgt: An evaluation," Biol. Res. Nursing, pp. 115-127, Oct. 2002, vol. 4.

Dal Porto et al., "A soluble divalent class I major histocompatibility complex molecule inhibits alloreactive T cells at nanomolar concentrations," Porc. Natl. Acad. Sci. 90.6671-6675, 1993.

Devito-Haynes et al., "Soluble donor HLA class I and βm-free heavy chain in serum of lung transplant recipients: Steady-state levels and increases in patients with recurrent CMV infection, acute rejection episodes, and poor outcome," Human Immunol., pp. 1370-1382, Dec. 2000, vol. 61.

* cited by examiner

Figure 1. Reactive groups and the bonds formed upon their reaction.

Figure 1 continued.  Reactive groups and the bonds formed upon their reaction.

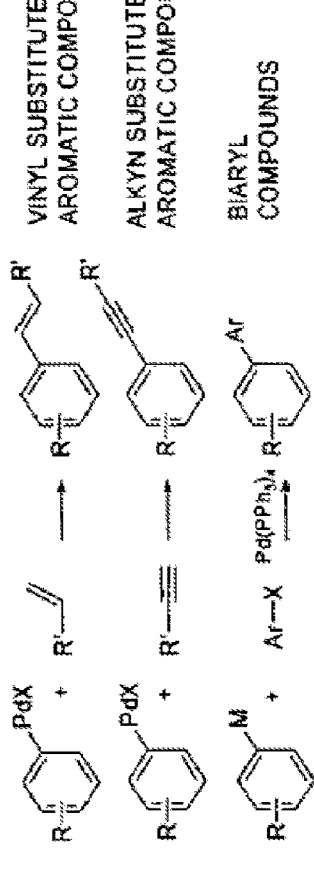

Aromatic nucleophilic substitution

SUBSTITUTED AROMATIC COMPOUNDS

Nu = Oxygen-, Nitrogen-, Sulfur- and Carbon Nucleophiles

X = F, Cl, Br, I, $OSO_2CH_3$, $OSO_2CF_3$, $OSO_2TOL$, , etc.

Z', Z = COOR, CHO, COR, $CONR^R{}_2$, $COO^-$, CN,
NO_2, SOR, SO_2R, SO_2NR'_2, . . ect.

Transition metal catalysed reactions

VINYL SUBSTITUTED AROMATIC COMPOUNDS

ALKYN SUBSTITUTED AROMATIC COMPOUNDS

BIARYL COMPOUNDS

Figure 1 continued.  Reactive groups and the bonds formed upon their reaction.

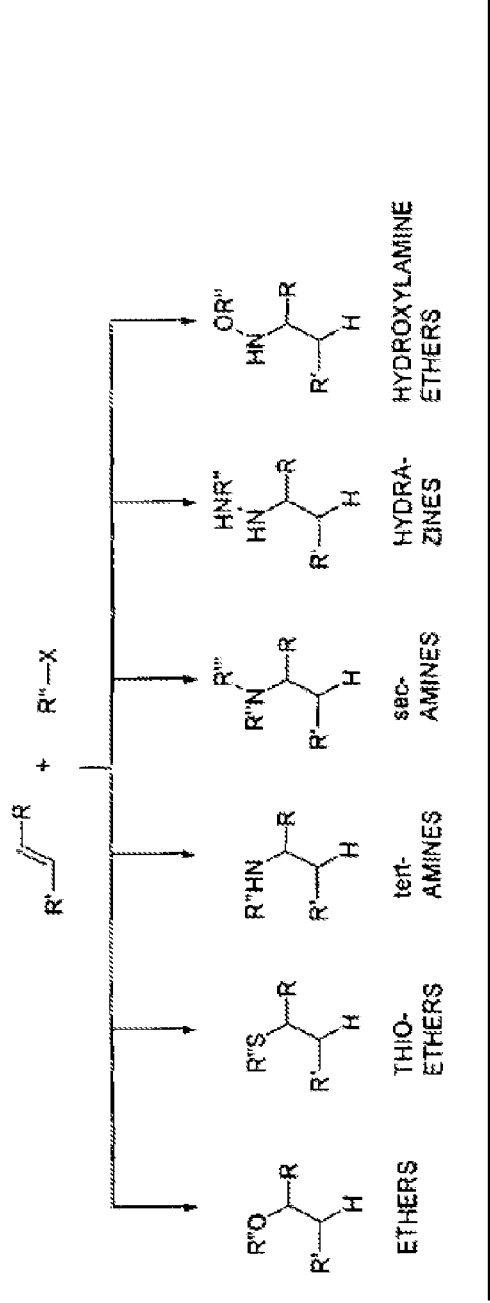
Figure 1 continued. Reactive groups and the bonds formed upon their reaction.

Figure 1:
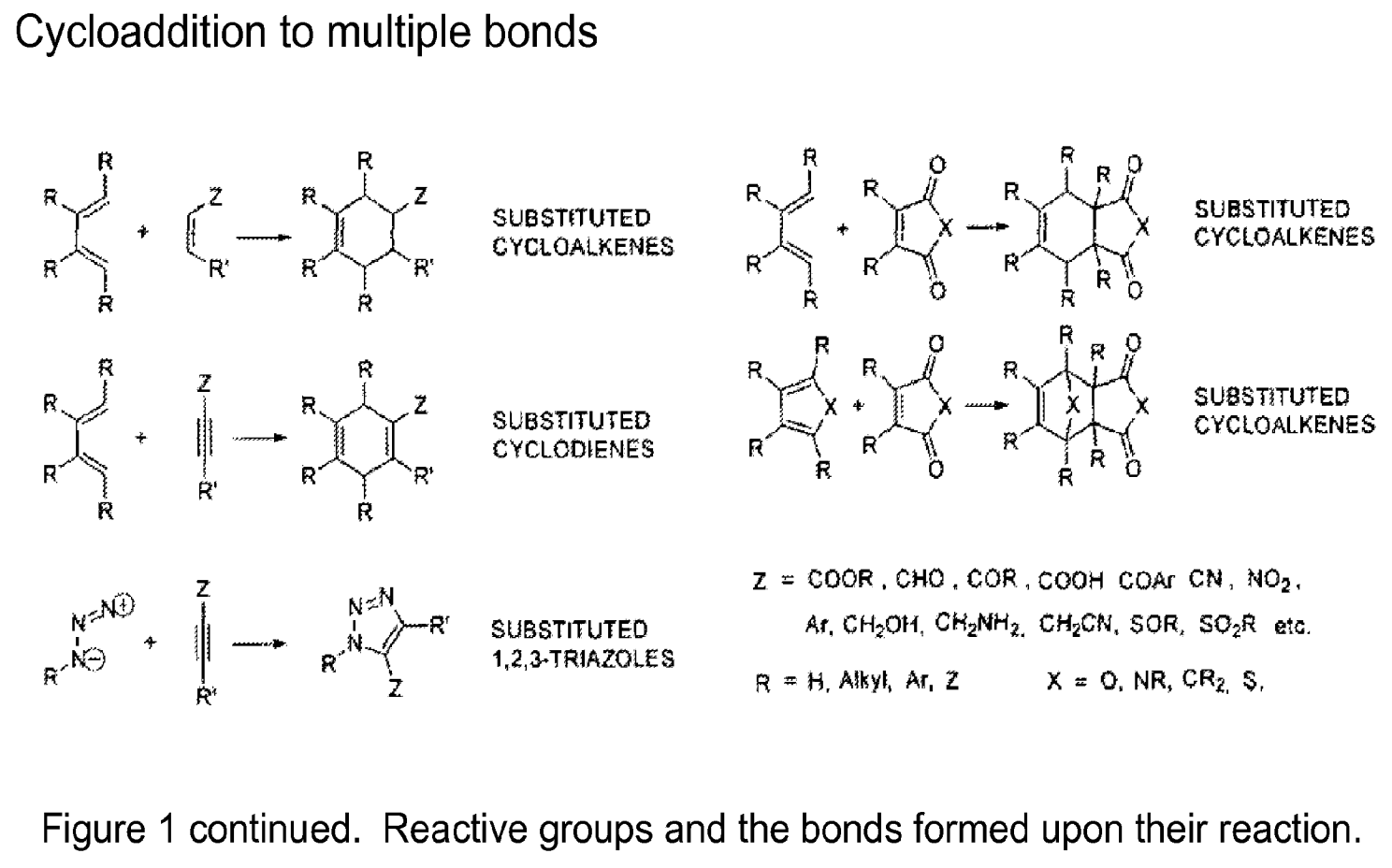

Cycloaddition to multiple bonds

SUBSTITUTED CYCLOALKENES

SUBSTITUTED CYCLOALKENES

SUBSTITUTED CYCLOALKENES

SUBSTITUTED CYCLODIENES

SUBSTITUTED 1,2,3-TRIAZOLES

Z = COOR, CHO, COR, COOH COAr CN, NO₂, Ar, CH₂OH, CH₂NH₂, CH₂CN, SOR, SO₂R etc.

X = O, NR, CR₂, S,

R = H, Alkyl, Ar, Z

Figure 1 continued.  Reactive groups and the bonds formed upon their reaction.

C) Addition to carbon-hetero multiple bonds

Figure 1 continued.  Reactive groups and the bonds formed upon their reaction.

Figure 2:
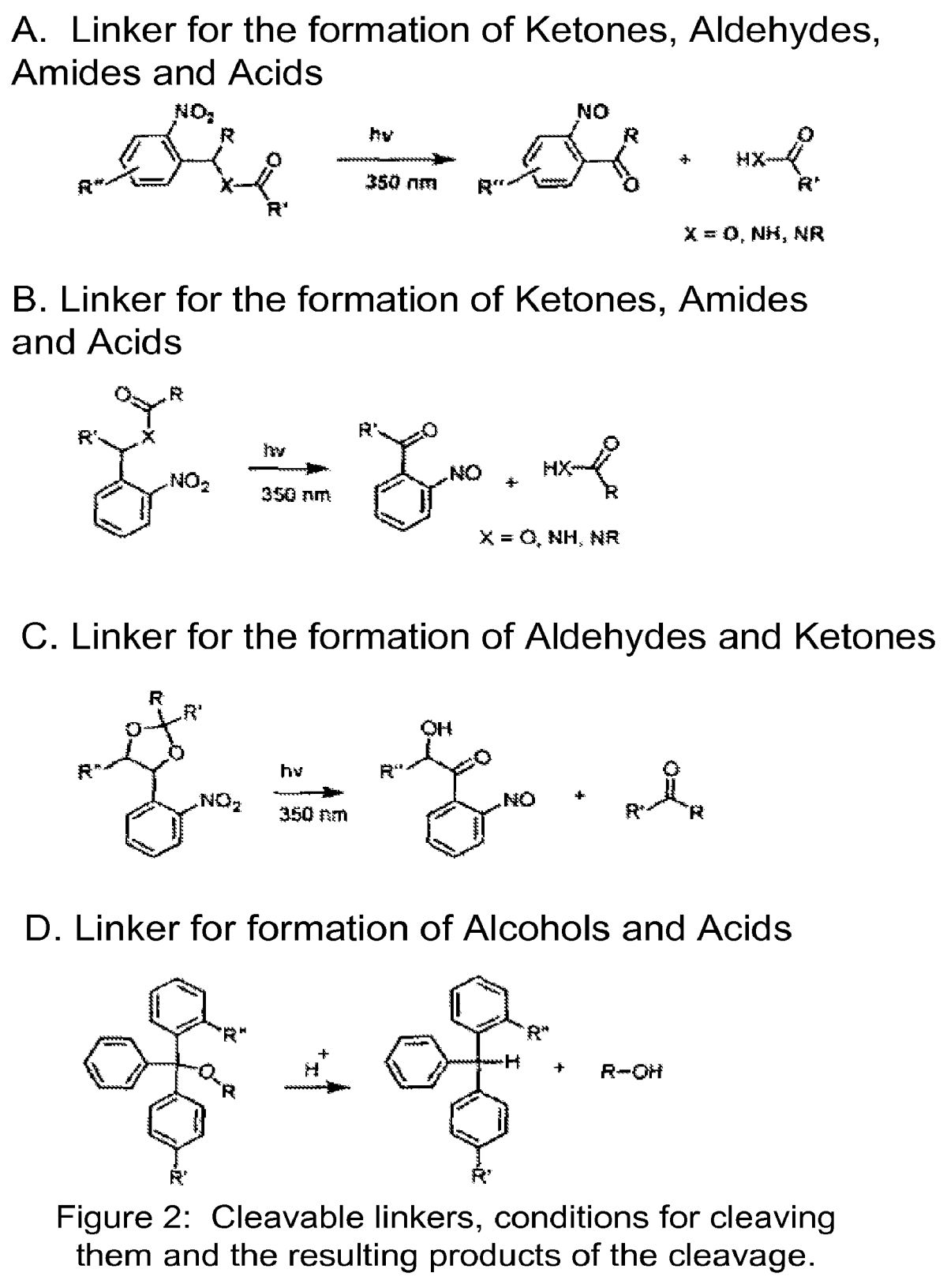

A. Linker for the formation of Ketones, Aldehydes, Amides and Acids

X = O, NH, NR

B. Linker for the formation of Ketones, Amides and Acids

X = O, NH, NR

C. Linker for the formation of Aldehydes and Ketones

D. Linker for formation of Alcohols and Acids

Figure 2: Cleavable linkers, conditions for cleaving them and the resulting products of the cleavage.

Figure 2:
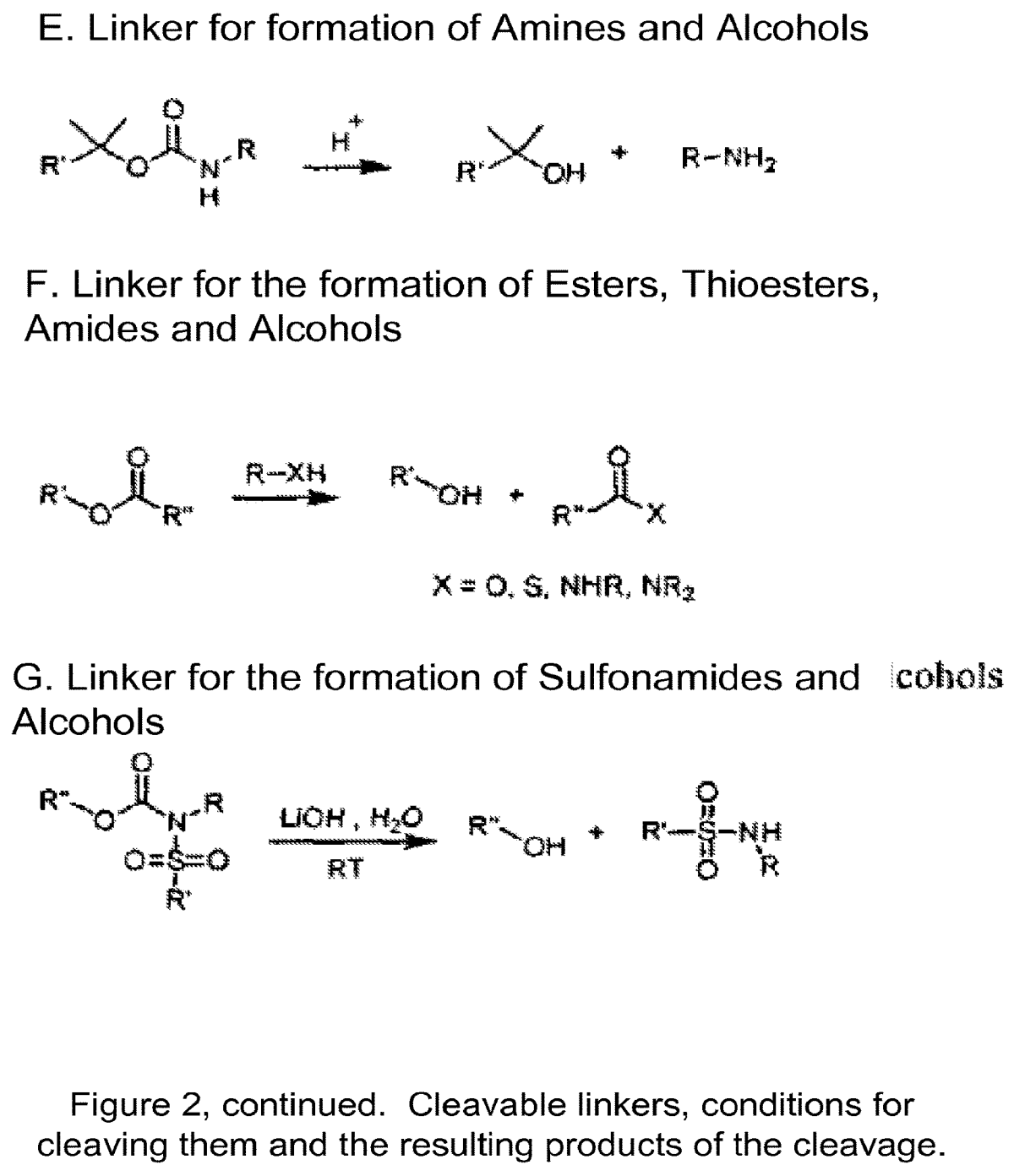

E. Linker for formation of Amines and Alcohols

F. Linker for the formation of Esters, Thioesters, Amides and Alcohols

X = O, S, NHR, NR$_2$

G. Linker for the formation of Sulfonamides and Alcohols Alcohols

Figure 2, continued.  Cleavable linkers, conditions for cleaving them and the resulting products of the cleavage.

Figure 2:
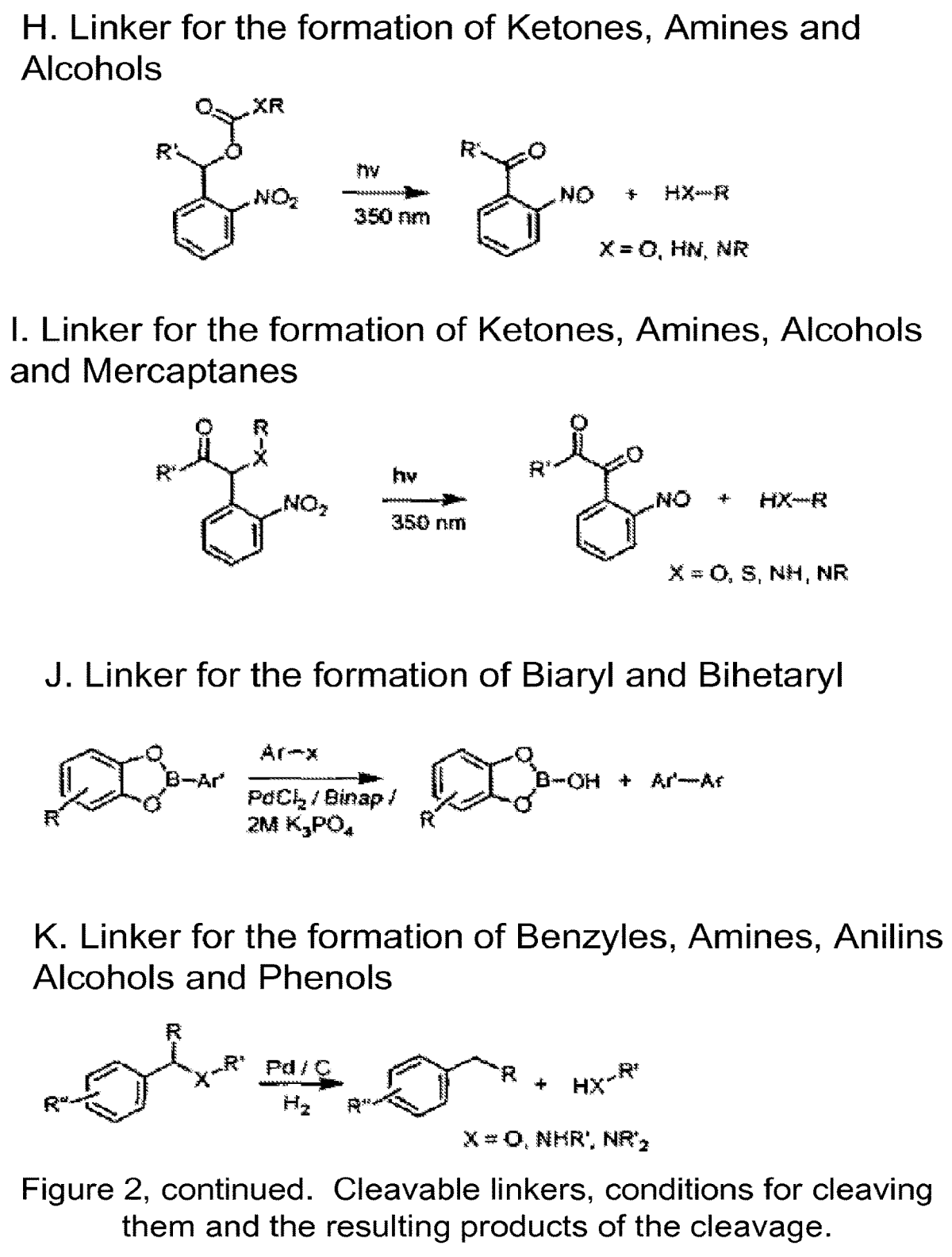

H. Linker for the formation of Ketones, Amines and Alcohols

I. Linker for the formation of Ketones, Amines, Alcohols and Mercaptanes

J. Linker for the formation of Biaryl and Bihetaryl

K. Linker for the formation of Benzyles, Amines, Anilins Alcohols and Phenols Figure 2, continued. Cleavable linkers, conditions for cleaving them and the resulting products of the cleavage.

Figure 2:
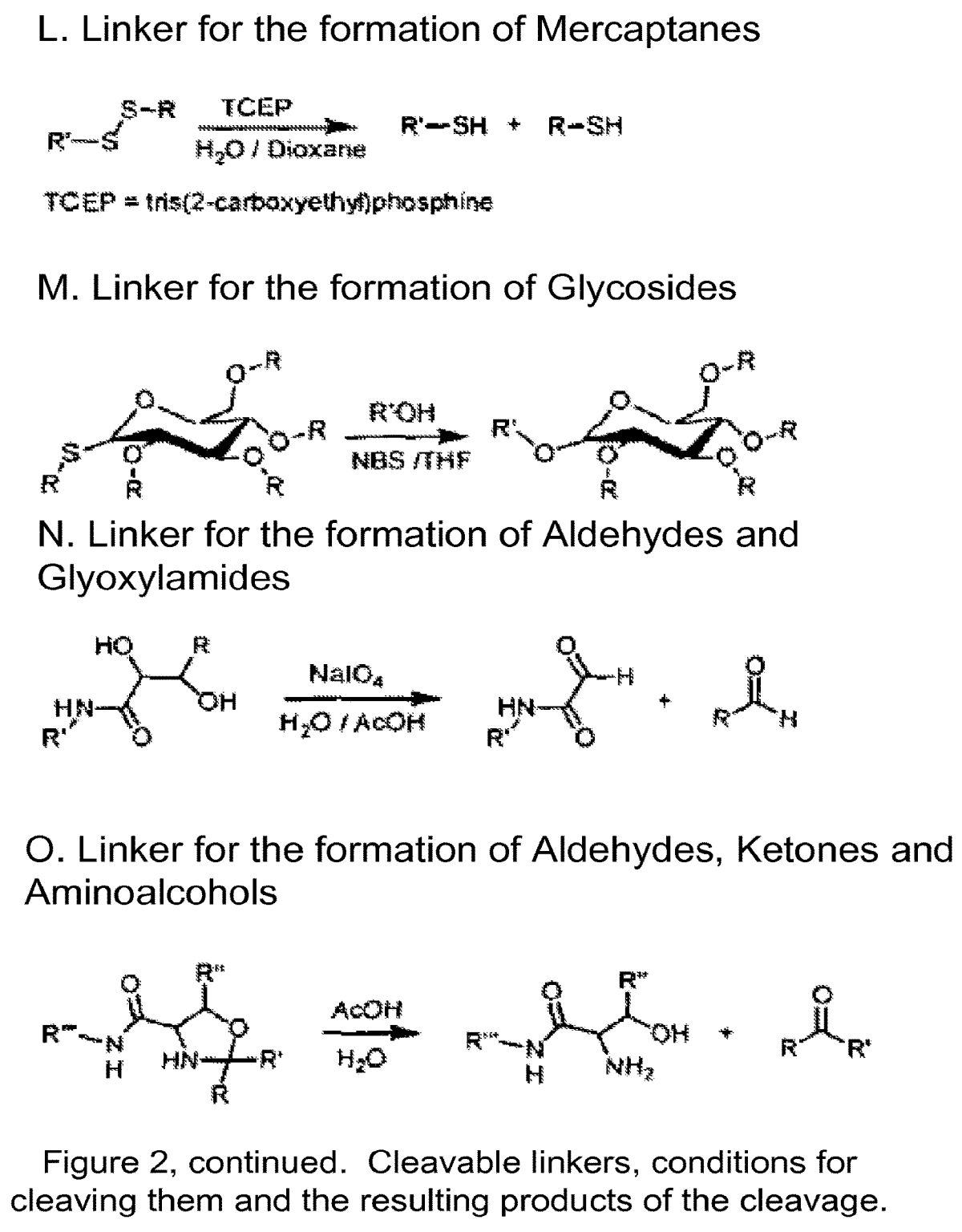

L. Linker for the formation of Mercaptanes

R'—S–S—R $\xrightarrow[\text{H}_2\text{O / Dioxane}]{\text{TCEP}}$ R'—SH + R–SH

TCEP = tris(2-carboxyethyl)phosphine

M. Linker for the formation of Glycosides

N. Linker for the formation of Aldehydes and Glyoxylamides

O. Linker for the formation of Aldehydes, Ketones and Aminoalcohols

Figure 2, continued. Cleavable linkers, conditions for cleaving them and the resulting products of the cleavage.

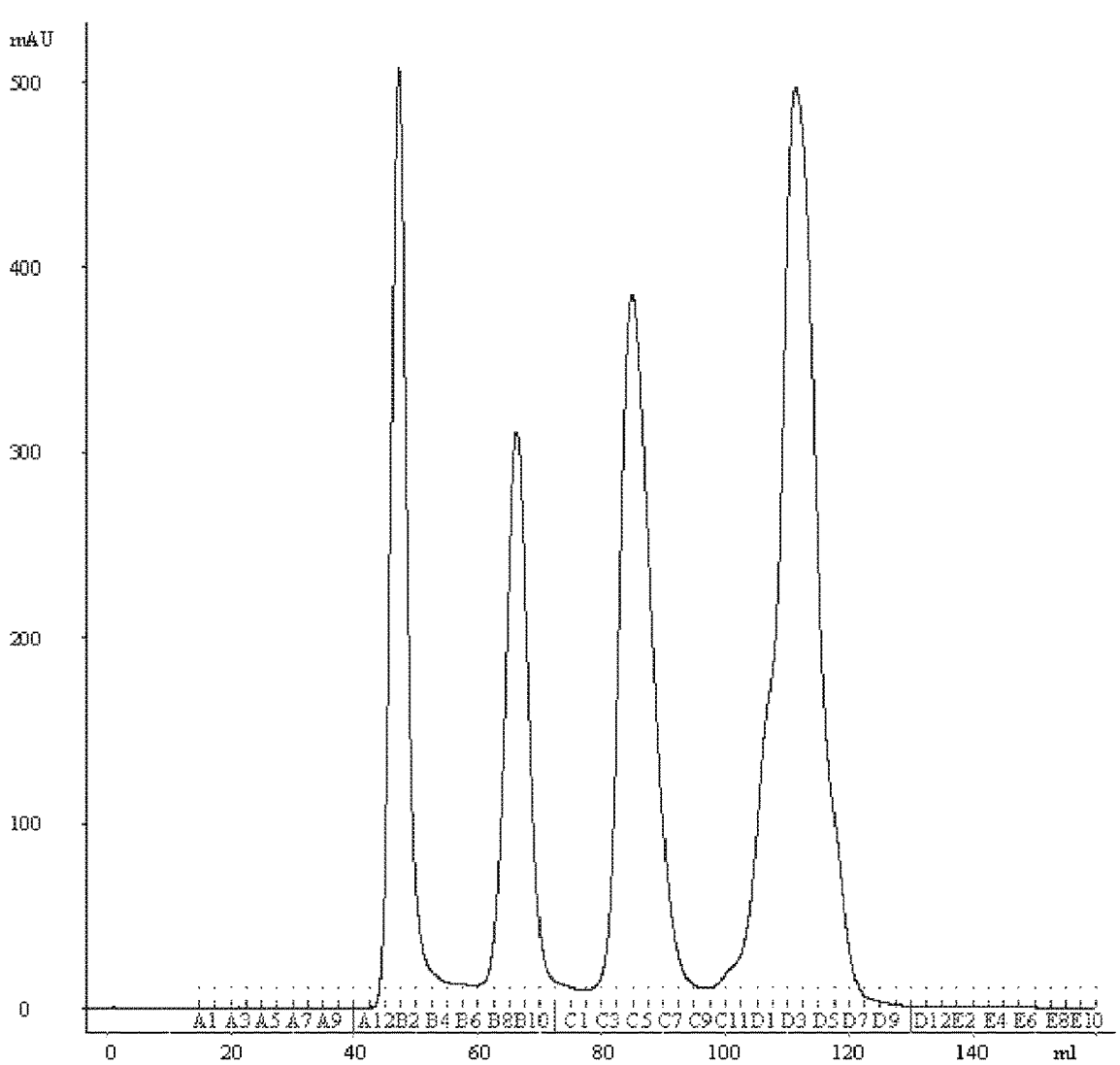
Figure 3. Size exclusion chromatography of folded
HLA-A*0201-β2m-QLFEELQEL-complex.

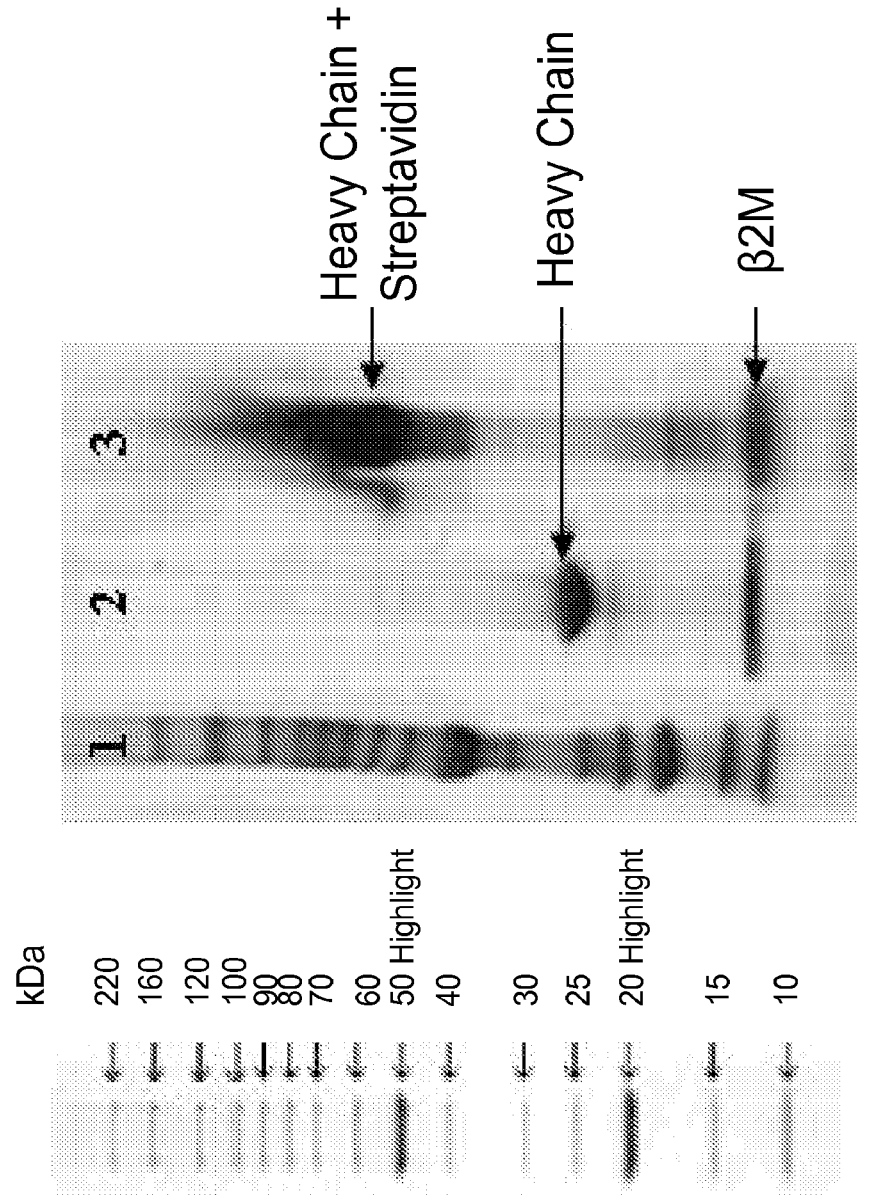
Figure 4. MHC-SHIFT Assay

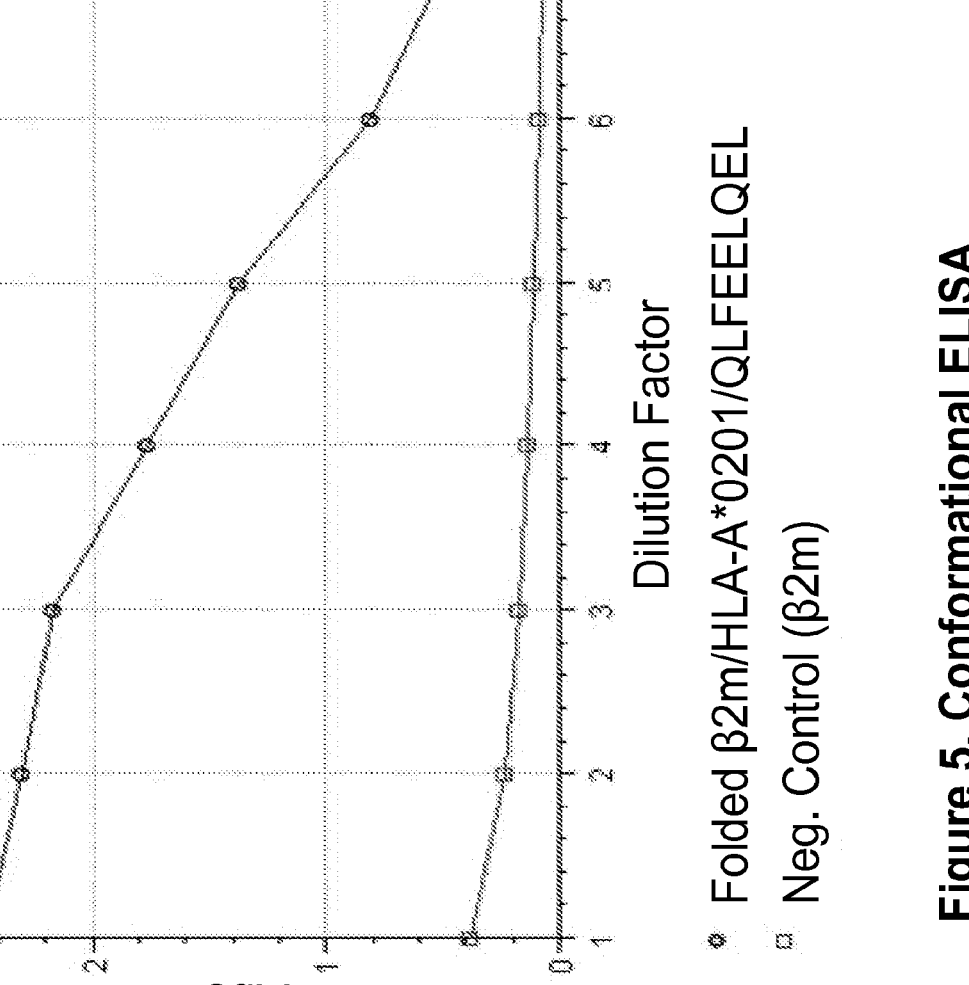
Figure 5. Conformational ELISA

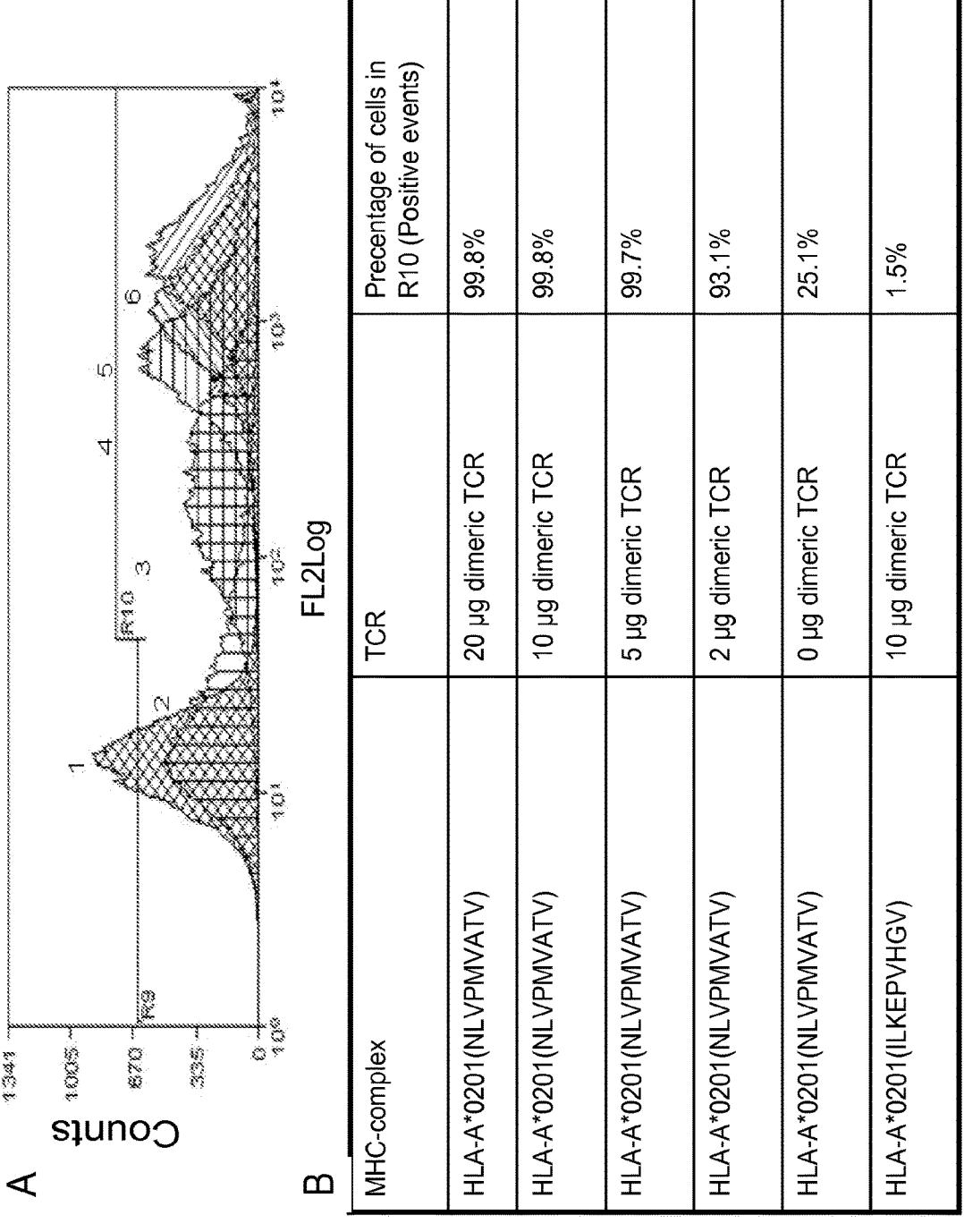
| MHC-complex | TCR | Precentage of cells in R10 (Positive events) |
|---|---|---|
| HLA-A*0201(NLVPMVATV) | 20 µg dimeric TCR | 99.8% |
| HLA-A*0201(NLVPMVATV) | 10 µg dimeric TCR | 99.8% |
| HLA-A*0201(NLVPMVATV) | 5 µg dimeric TCR | 99.7% |
| HLA-A*0201(NLVPMVATV) | 2 µg dimeric TCR | 93.1% |
| HLA-A*0201(NLVPMVATV) | 0 µg dimeric TCR | 25.1% |
| HLA-A*0201(ILKEPVHGV) | 10 µg dimeric TCR | 1.5% |
Figure 6. Carboxylate-modified beads coupled to TCR and stained with HLA-A*0201(NLVPMVATV)/RPE or HLA-A*0201(ILKEPVHGV)/RPE.

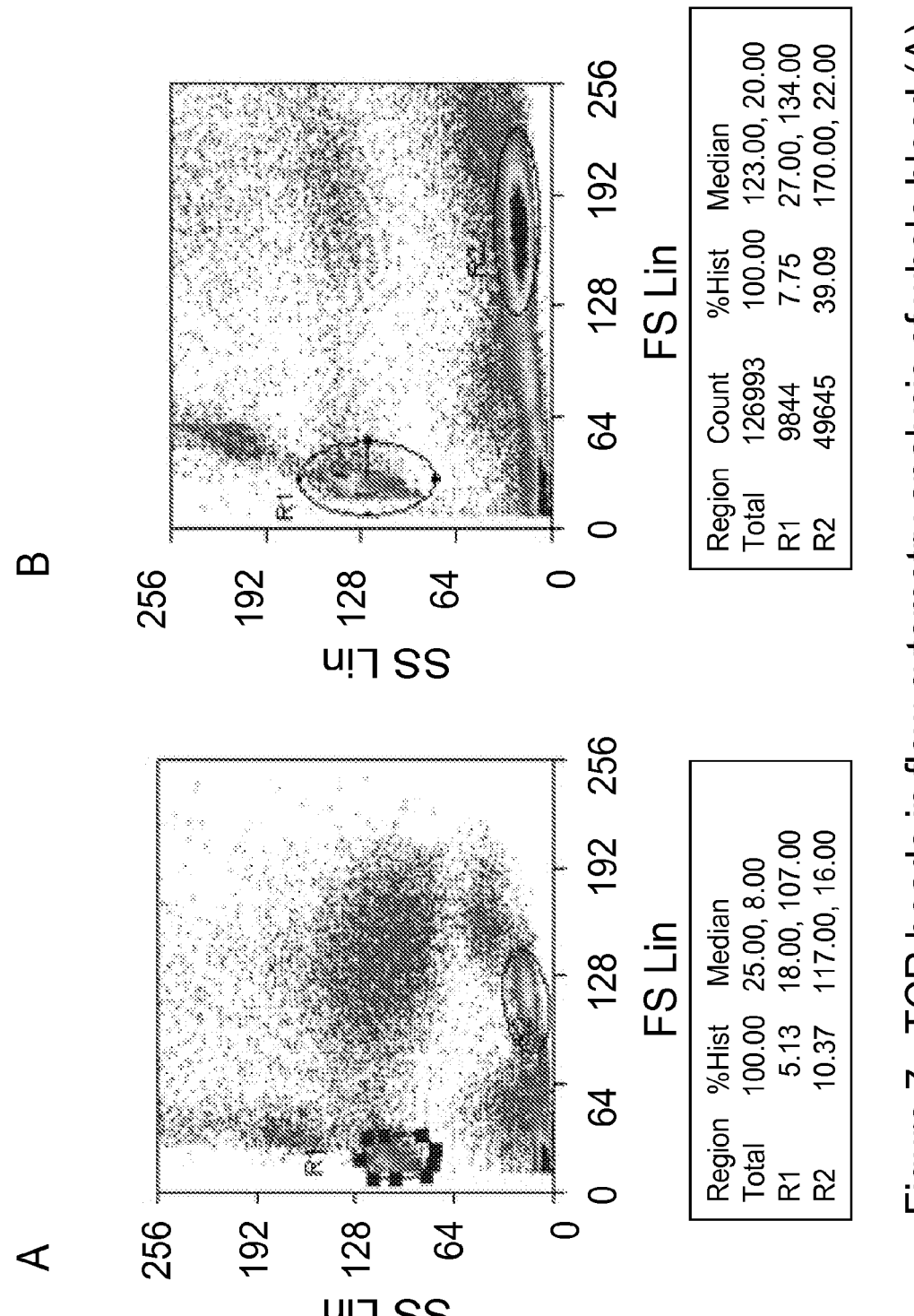
Figure 7. TCR beads in flow cytometry analysis of whole blood (A), or HPBMC's (B).

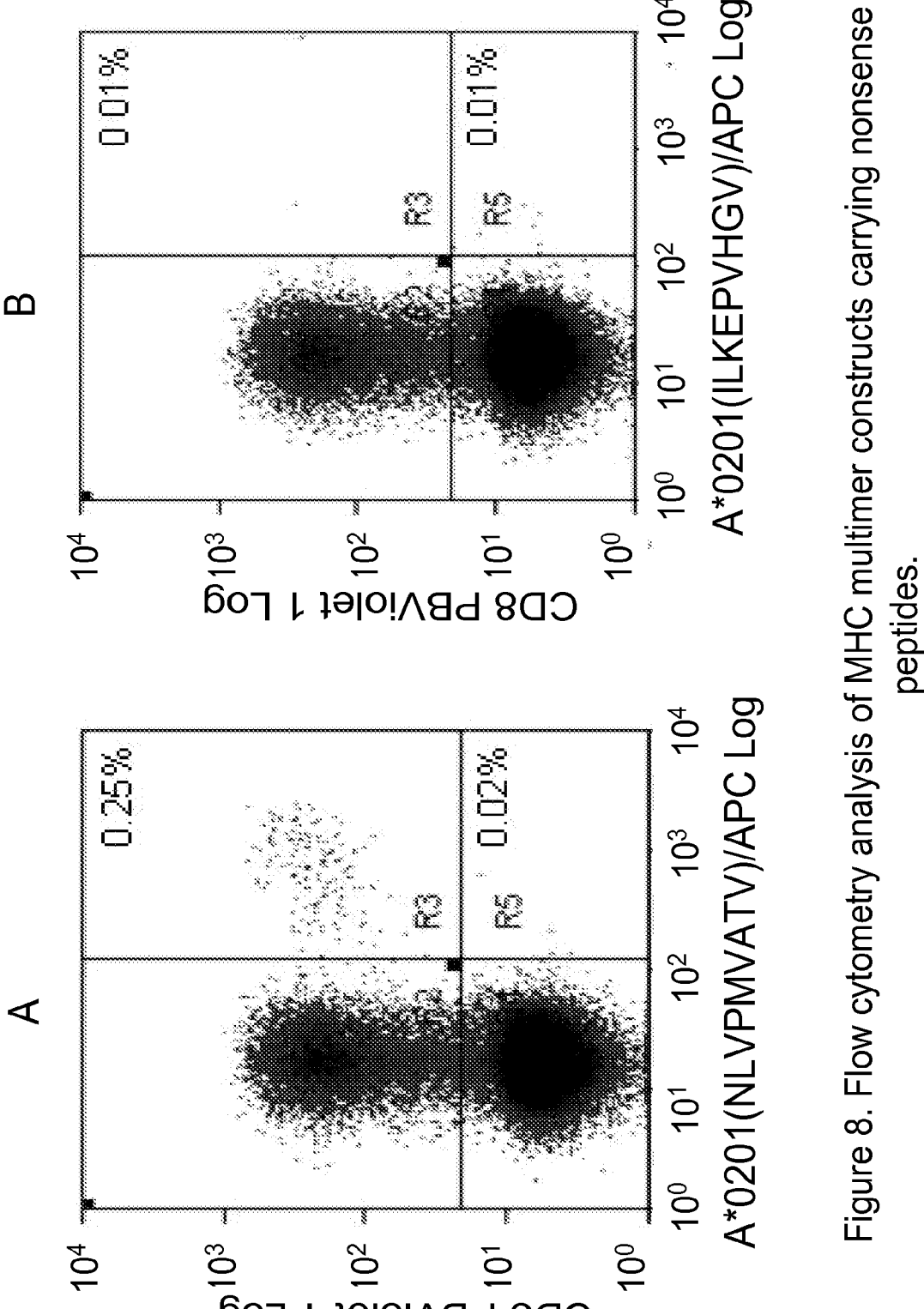
Figure 8. Flow cytometry analysis of MHC multimer constructs carrying nonsense peptides.

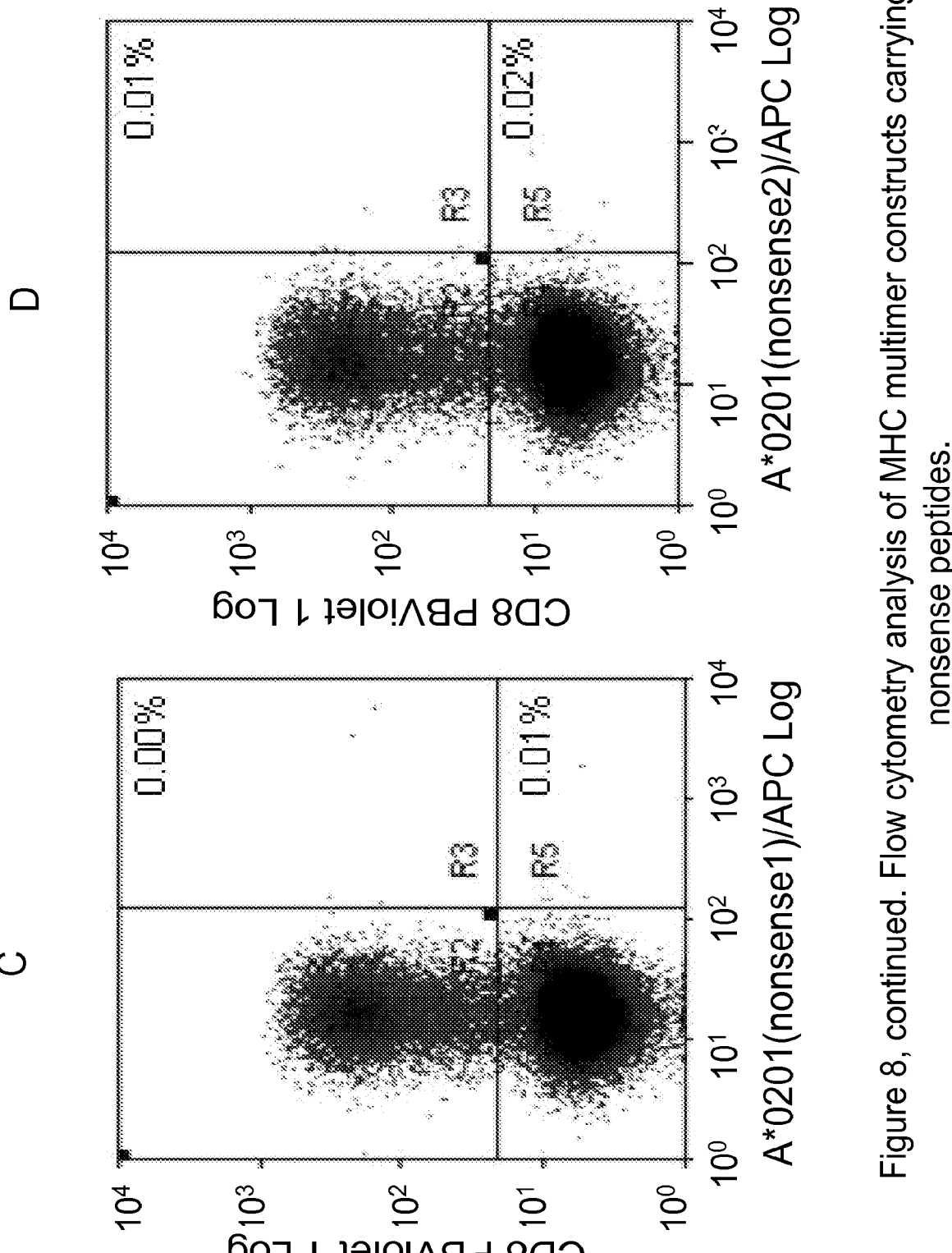
Figure 8, continued. Flow cytometry analysis of MHC multimer constructs carrying nonsense peptides.

| Donor | Positive | Negative | Construct 1 | Construct 2 | Construct 3 | Construct 4 | Construct 5 |
|---|---|---|---|---|---|---|---|
| 1 | – | A2(NLVPMVATV)/A2(ILKEPVHGV) | - | - | - | nt | - |
| 2 | A2(NLVPMVATV) | A2(ILKEPVHGV) | - | - | + | nt | - |
| 3 | A2(NLVPMVATV) | A2(ILKEPVHGV) | - | - | + | nt | - |
| 4 | A2(NLVPMVATV) | A2(ILKEPVHGV) | - | - | + | nt | - |
| 5 | A2(NLVPMVATV) | A2(ILKEPVHGV) | - | - | + | nt | - |
| 6 | A2(NLVPMVATV) | A2(ILKEPVHGV) | - | - | + | nt | - |
| 7 | - | A2(ILKEPVHGV)/A2(GLCTLVAML) | - | - | nt | - | - |
| 8 | A2(GLCTLVAML) | A2(ILKEPVHGV) | - | - | nt | + | - |
| 9 | A2(GLCTLVAML) | A2(ILKEPVHGV) | - | - | nt | + | - |

Figure 9. Summary of flow cytometry analysis of the binding of different MHC multimer constructs to specific T cells in purified Human Peripheral Blood.

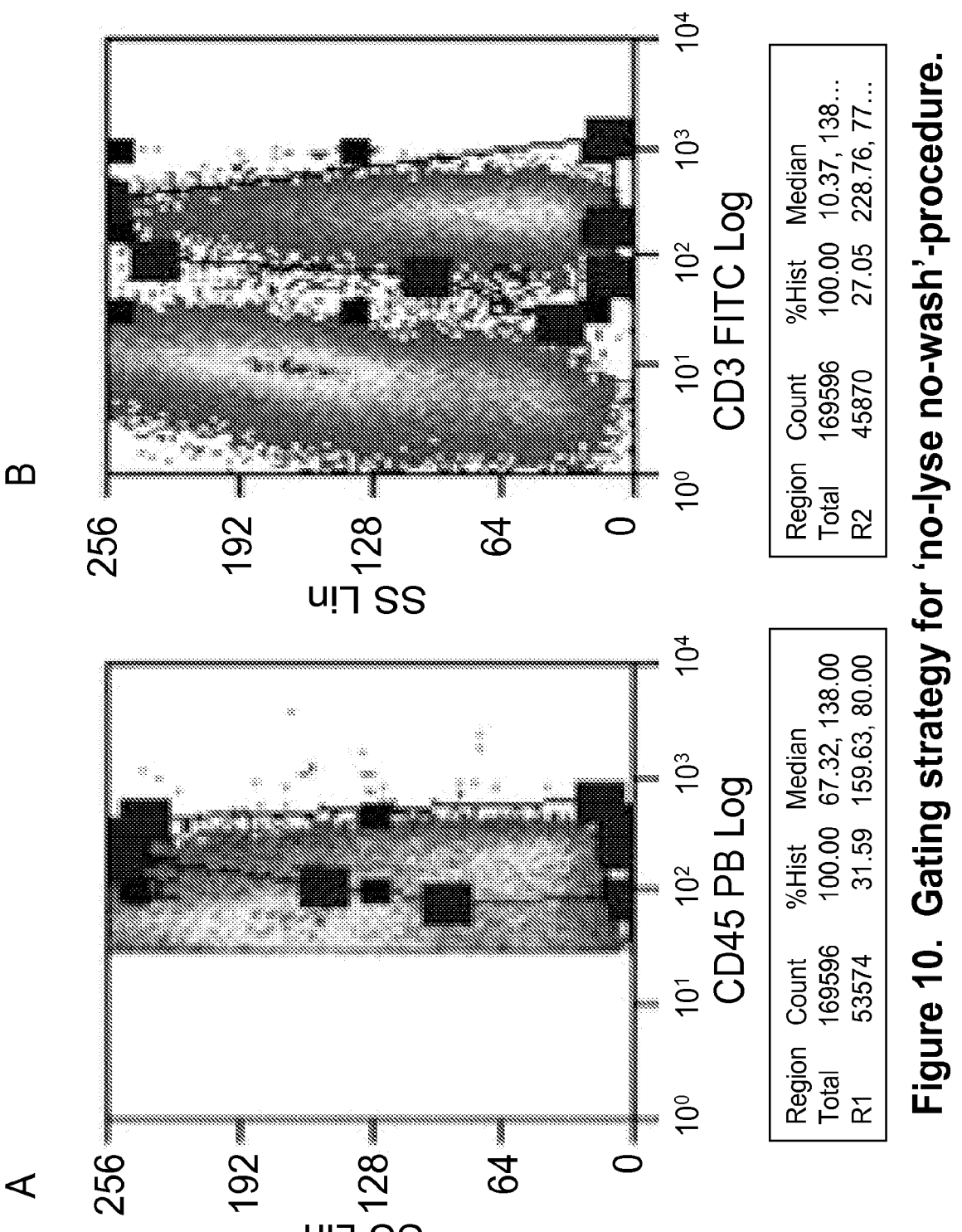
Figure 10. Gating strategy for 'no-lyse no-wash'-procedure.

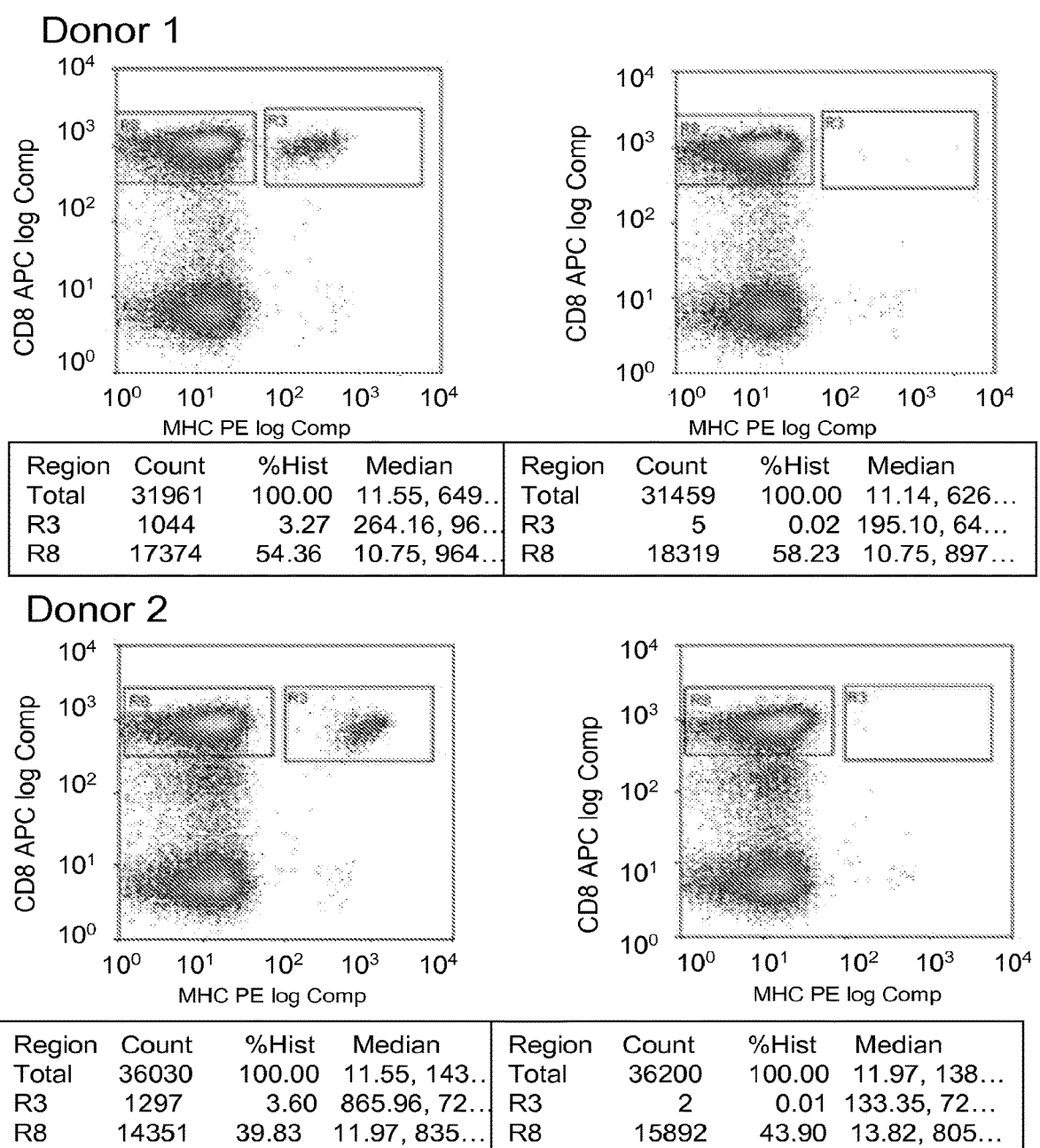
Figure 11. Identification of CMV-specific T cells in a blood sample using 'no-lyse no-wash'-procedure.

Donor 3
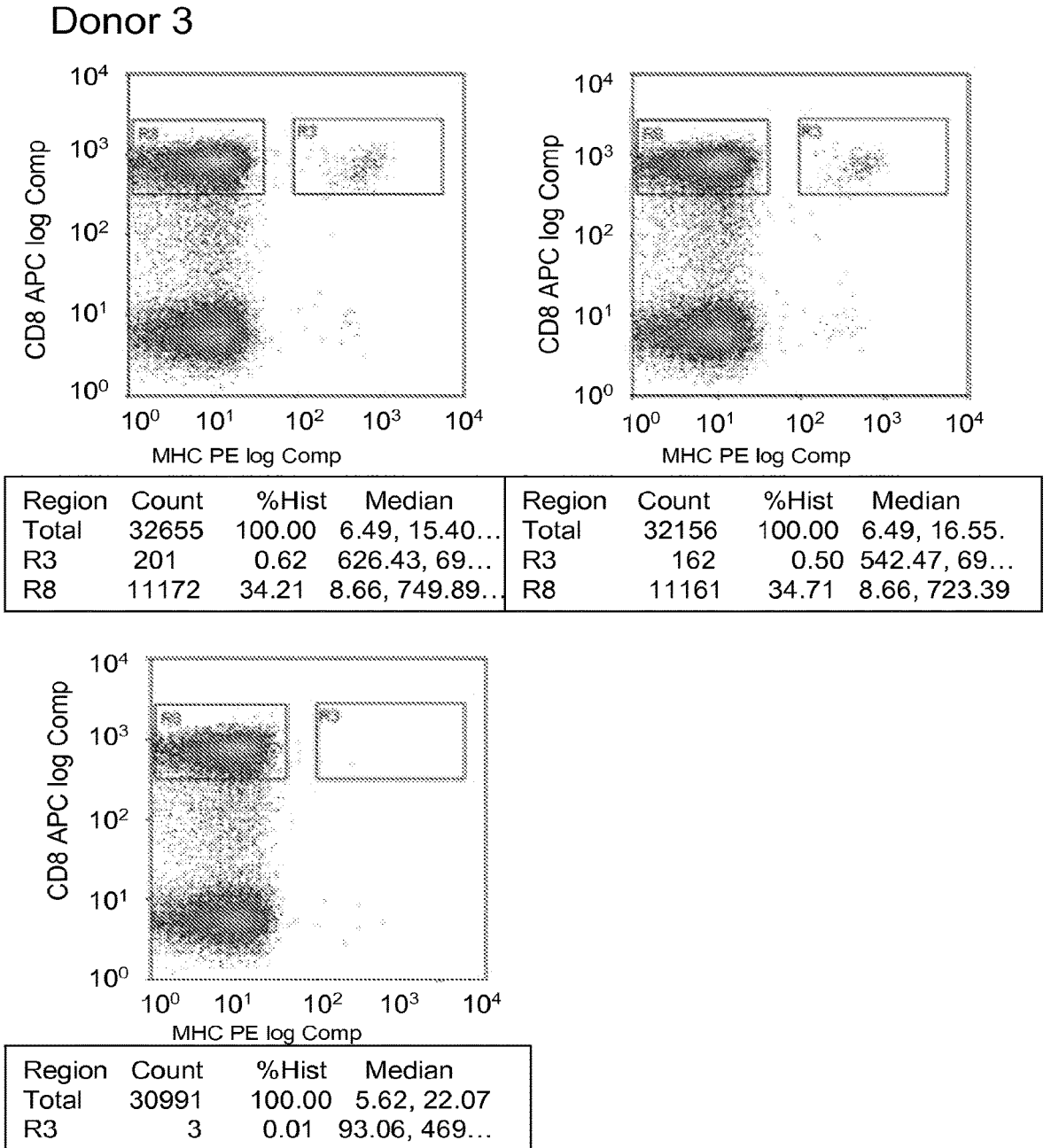
| Region | Count | %Hist | Median |
|--------|-------|--------|--------|
| Total | 32655 | 100.00 | 6.49, 15.40... |
| R3 | 201 | 0.62 | 626.43, 69... |
| R8 | 11172 | 34.21 | 8.66, 749.89... |
| Region | Count | %Hist | Median |
|--------|-------|--------|--------|
| Total | 32156 | 100.00 | 6.49, 16.55. |
| R3 | 162 | 0.50 | 542.47, 69... |
| R8 | 11161 | 34.71 | 8.66, 723.39 |
| Region | Count | %Hist | Median |
|--------|-------|--------|--------|
| Total | 30991 | 100.00 | 5.62, 22.07 |
| R3 | 3 | 0.01 | 93.06, 469... |
| R8 | 10259 | 33.10 | 8.66, 697.83 |
Figure 11, continued. Identification of CMV-specific T cells in a blood sample using 'no-lyse no-wash'-procedure.

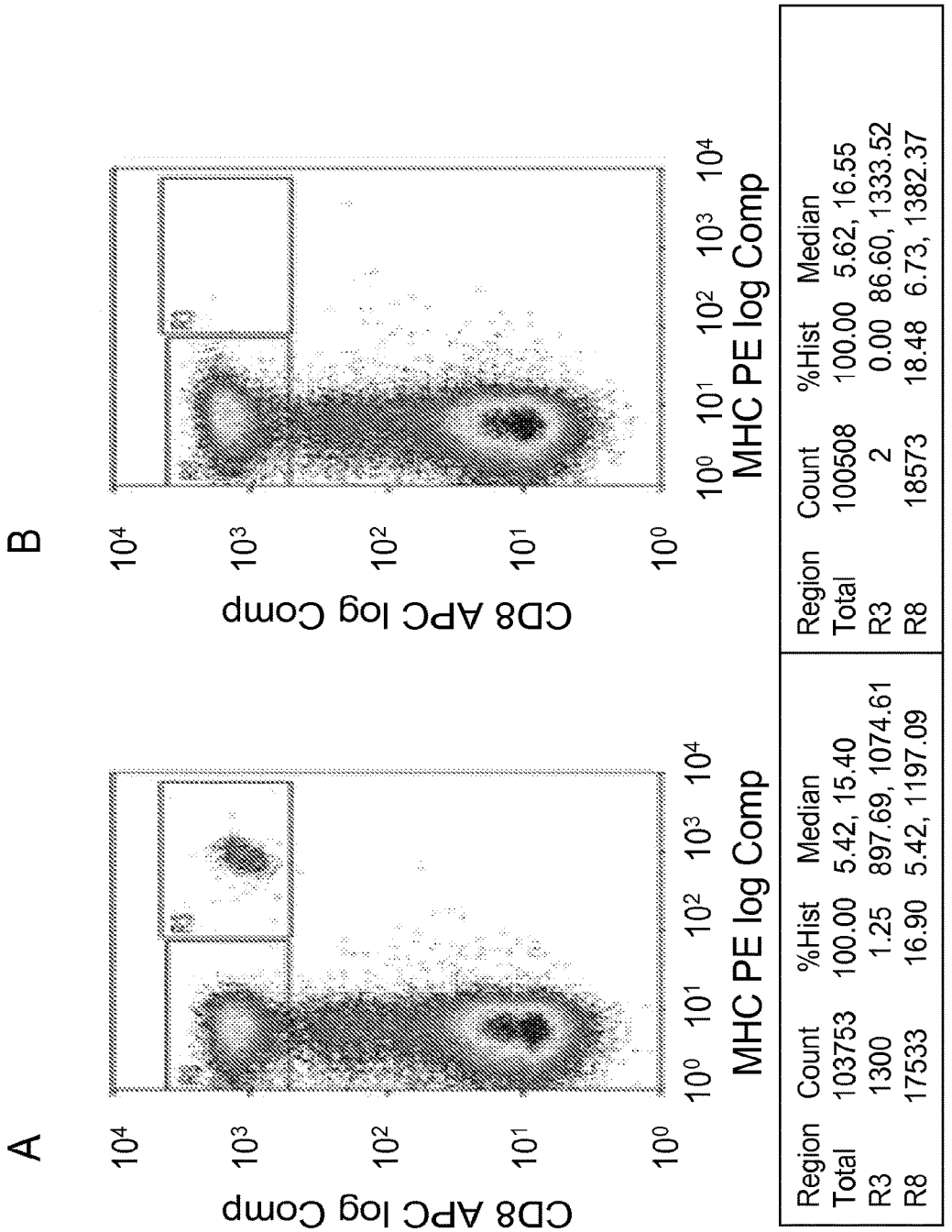
Figure 12   Enumeration of specific T cells using CytoCountTM beads.

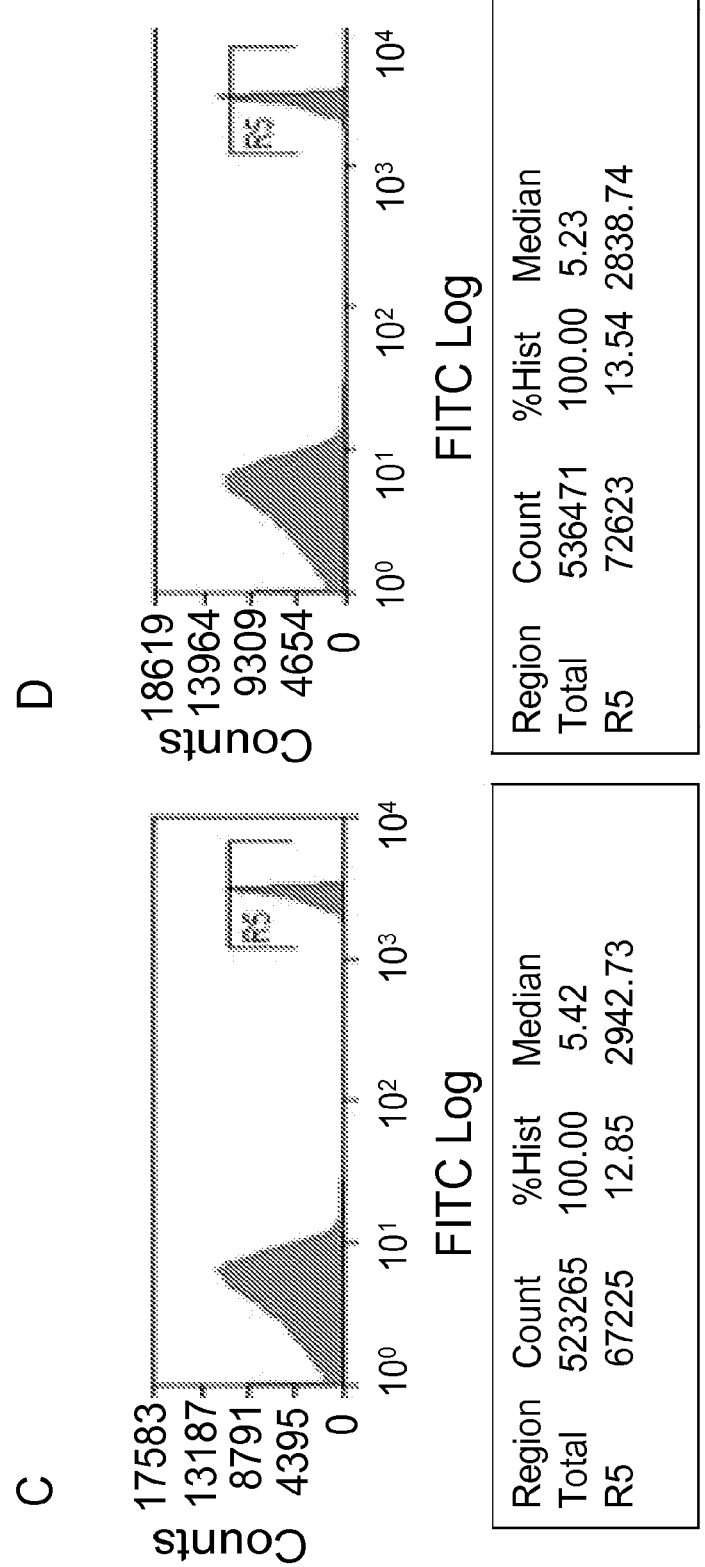
Figure 12, continued. Enumeration of specific T cells using CytoCountTM beads.

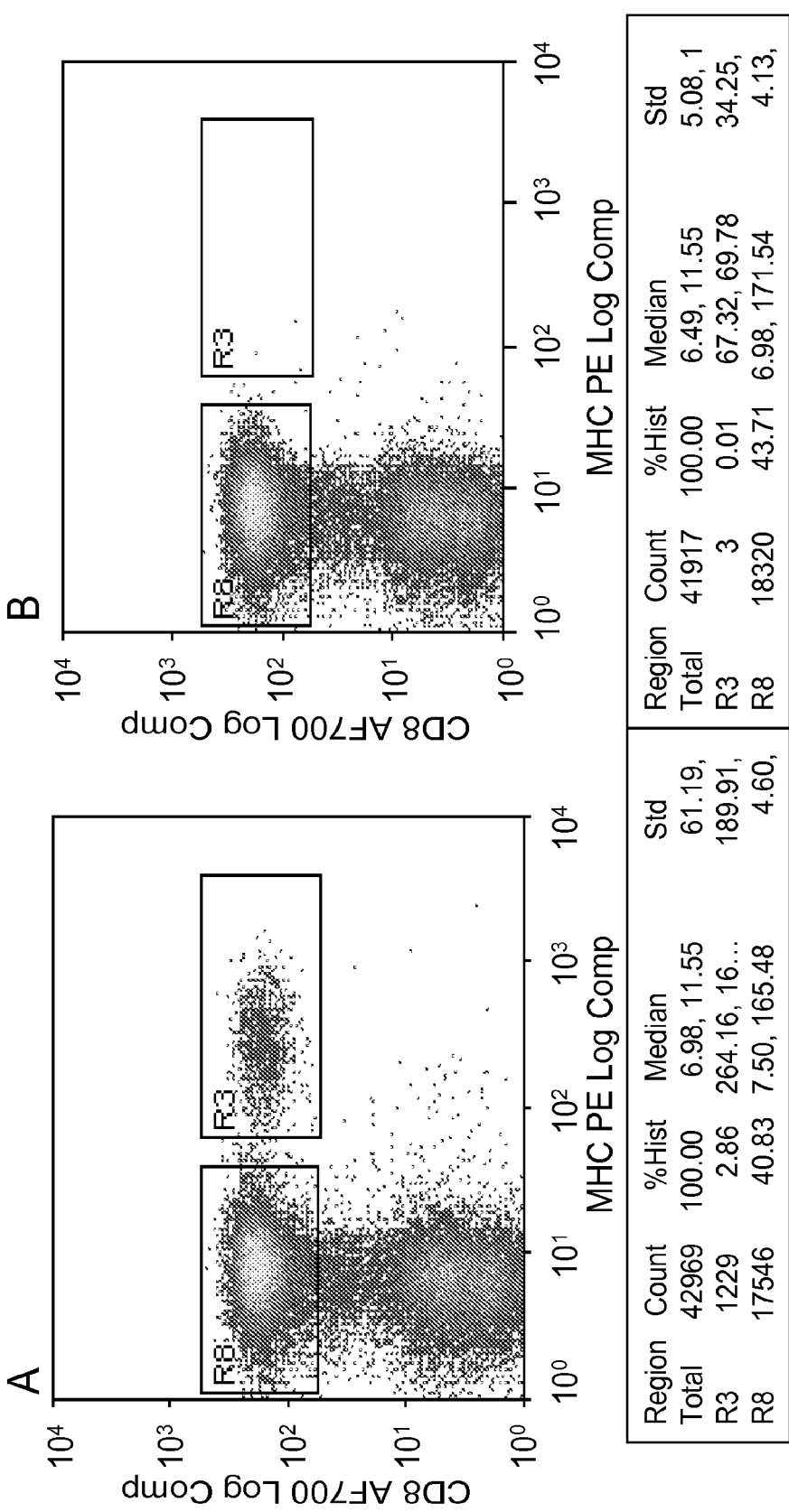
Figure 13. MHC-peptide complexes can be embedded in a sugar matrix together with antibodies and used for detection of specific T cells in a blood sample

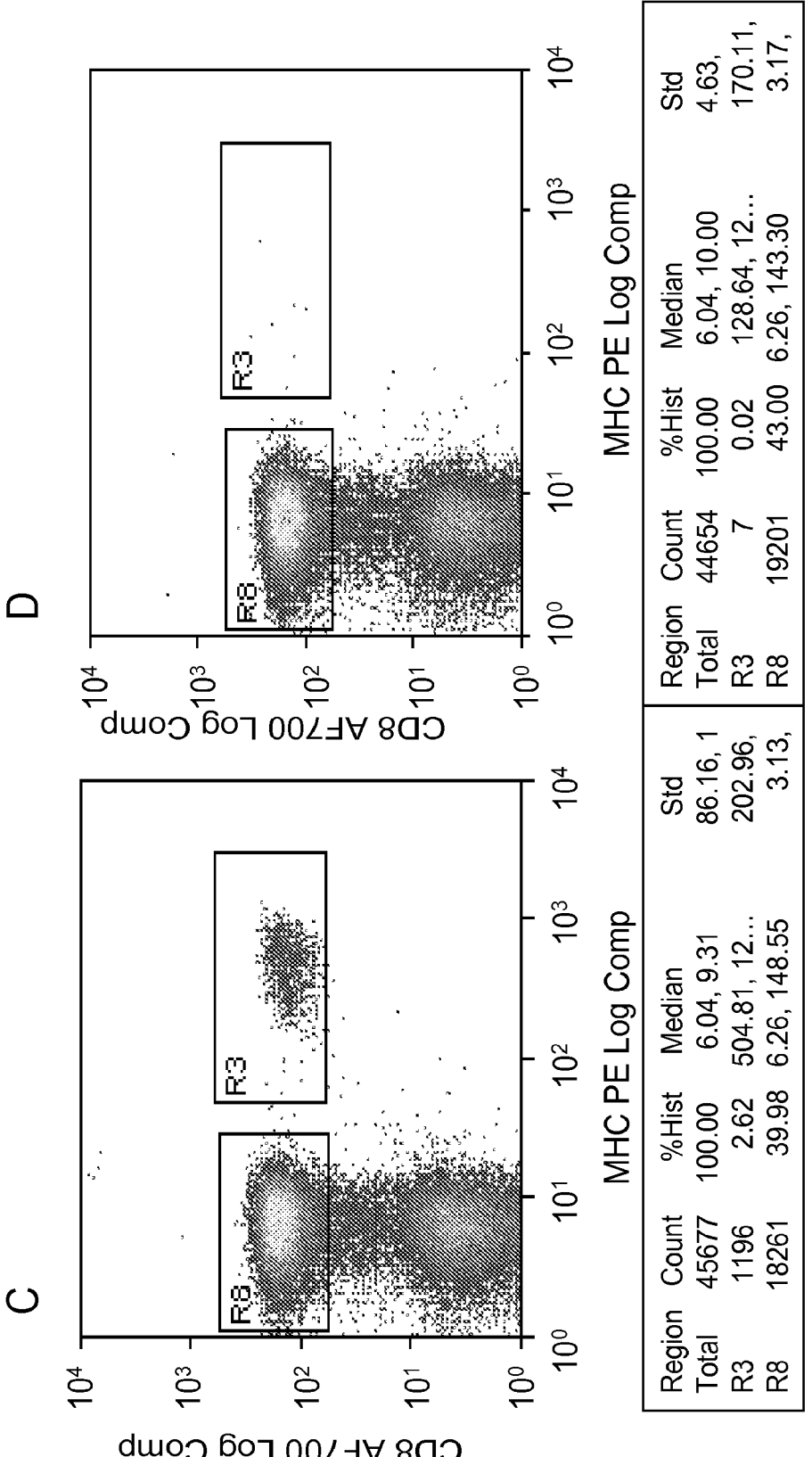
Figure 13 continued. MHC-peptide complexes can be embedded in a sugar matrix together with antibodies and used for detection of specific T cells in a blood sample A)
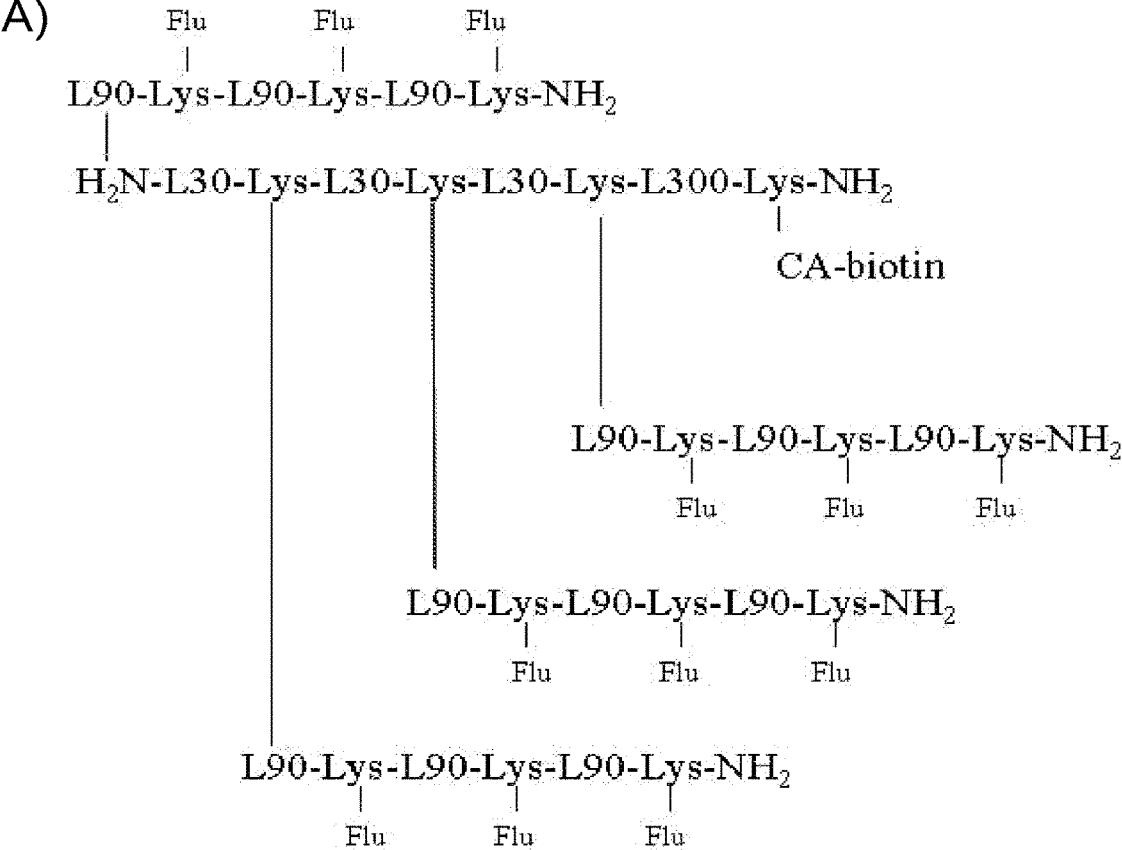
B)     L15 linker composition
Figure 14. Composition of a Fluorescein-linker molecule.

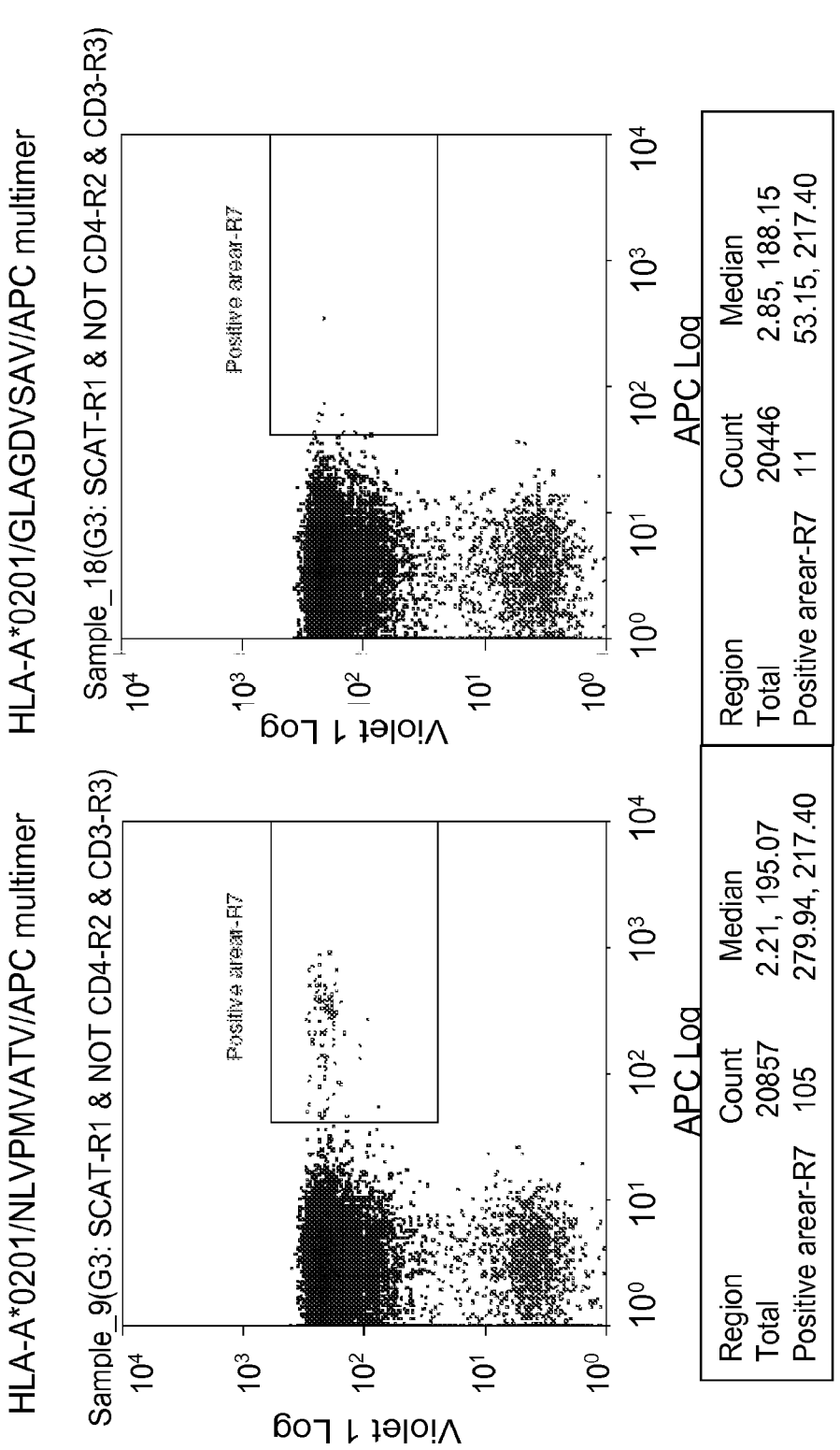
Figure 15. Flow cytometry analysis of human blood sample using MHC dextramers where the MHC molecules are chemically biotinylated.

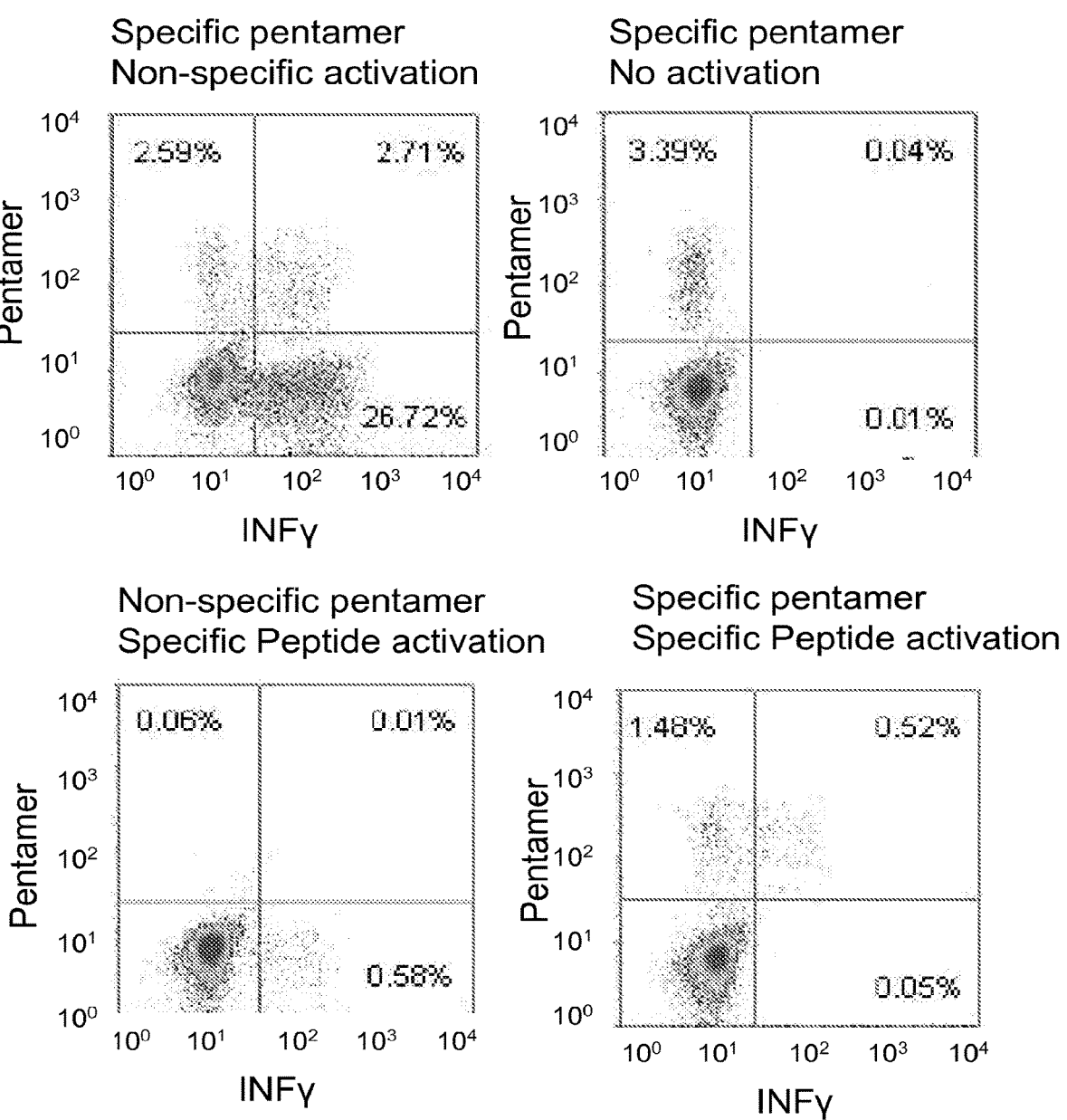
Figure 16. Detection of antigen specific T cells using MHC multimer constructs simultaneously with activation and intracellular staining of cytokines.

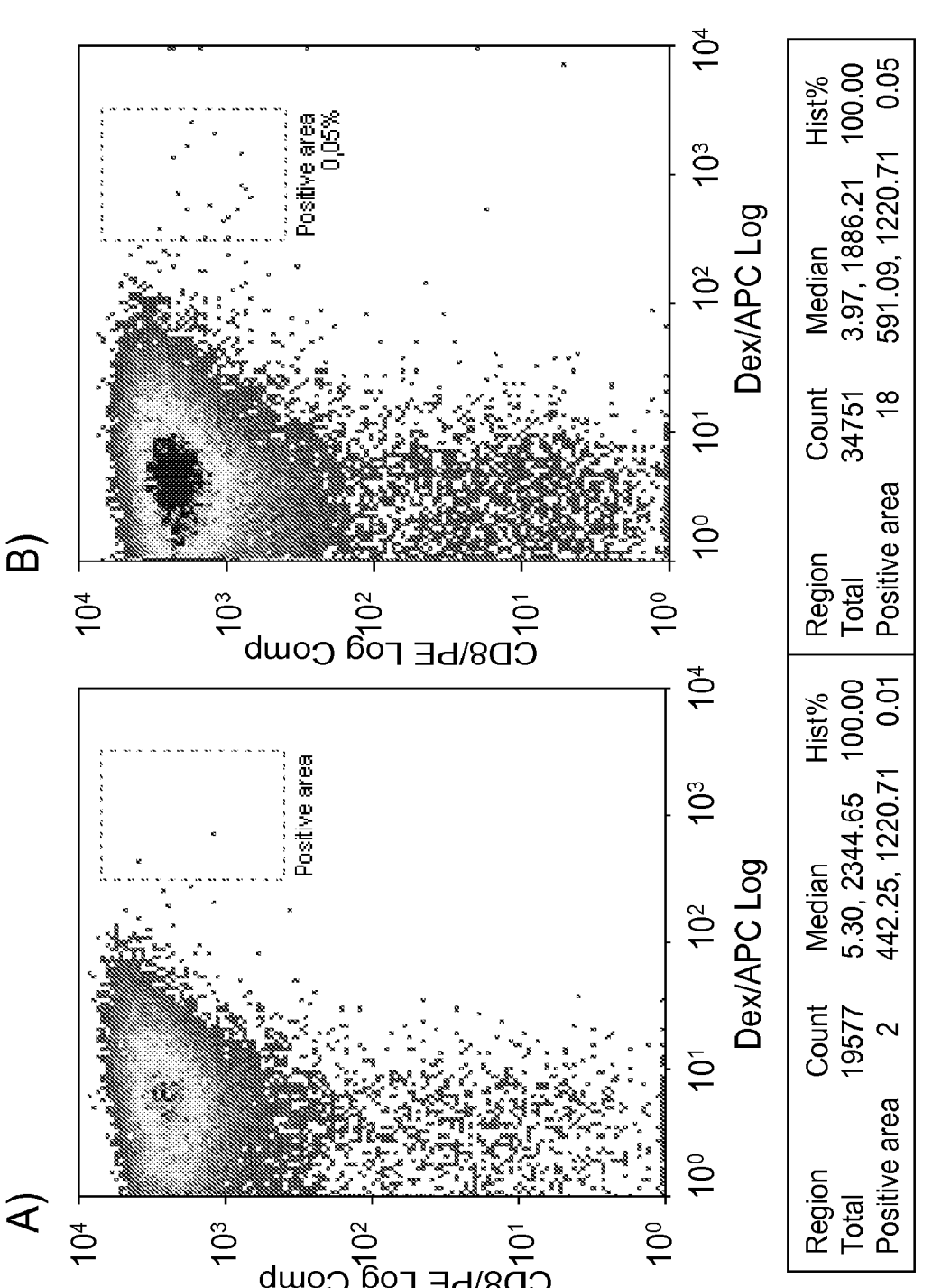
| Region | Count | Median | Hist% |
|---|---|---|---|
| Total | 19577 | 5.30, 2344.65 | 100.00 |
| Positive area | 2 | 442.25, 1220.71 | 0.01 |
| Region | Count | Median | Hist% |
|---|---|---|---|
| Total | 34751 | 3.97, 1886.21 | 100.00 |
| Positive area | 18 | 591.09, 1220.71 | 0.05 |
Figure 17. Detection of Borrelia specific T cells in sample from human donor.

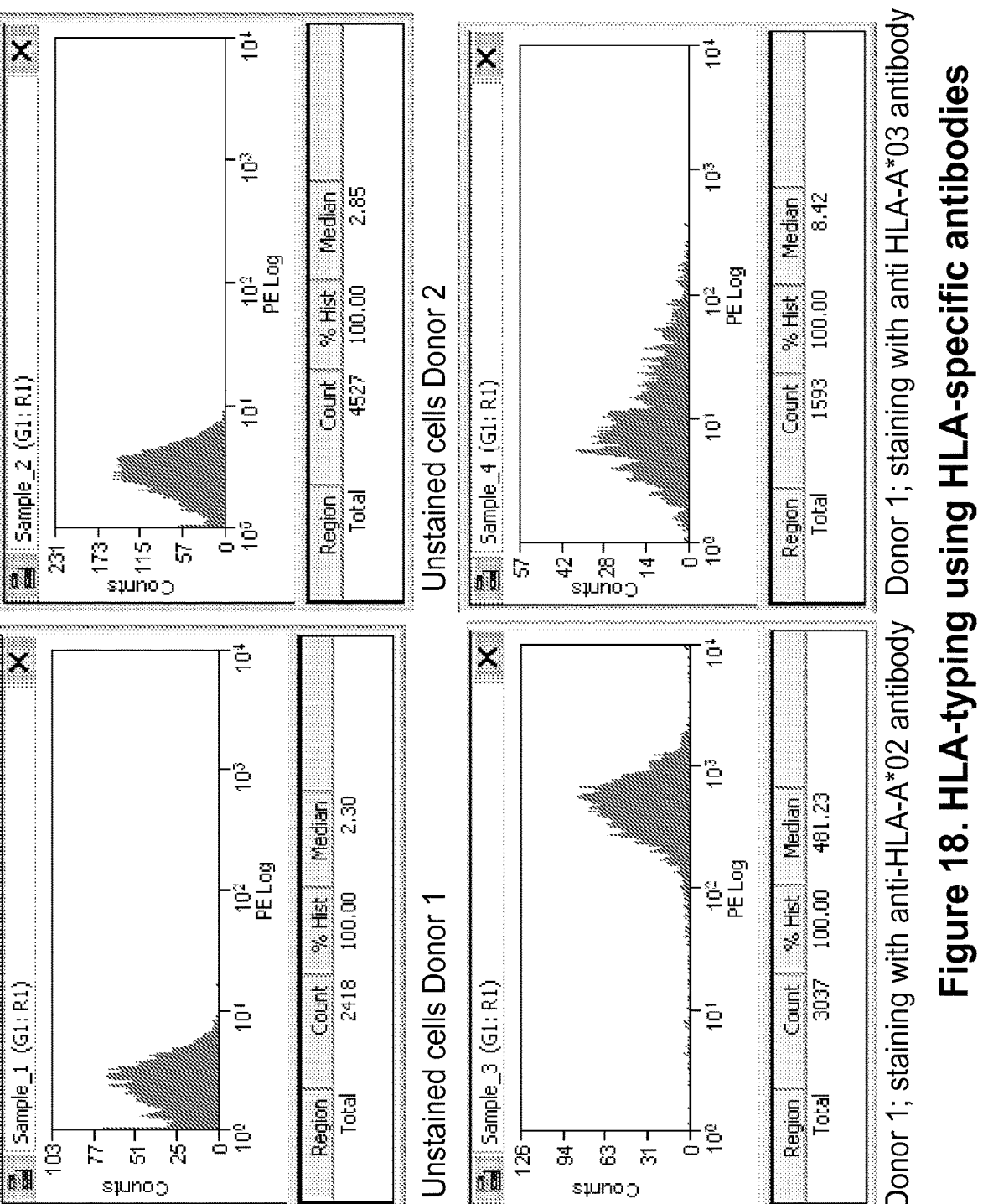
Figure 18. HLA-typing using HLA-specific antibodies

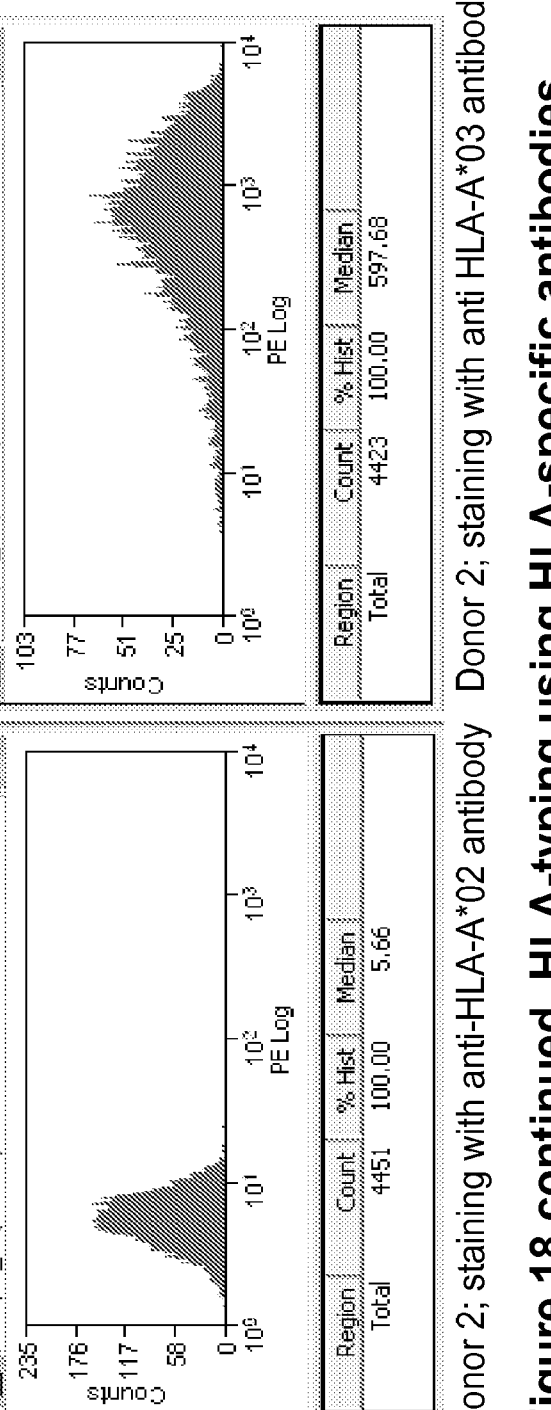
Donor 2; staining with anti-HLA-A*02 antibody  Donor 2; staining with anti HLA-A*03 antibody
Figure 18 continued. HLA-typing using HLA-specific antibodies

SEQUENCE LISTING

```
Sequence total quantity: 36
SEQ ID NO: 1            moltype = AA  length = 341
FEATURE                 Location/Qualifiers
source                  1..341
                        mol_type = protein
                        organism = Homo sapiens
SEQUENCE: 1
GSHSMRYFFT SVSRPGRGEP RFIAVGYVDD TQFVRFDSDA ASQRMEPRAP WIEQEGPEYW   60
DGETRKVKAH SQTHRVDLGT LRGYYNQSEA GSHTVQRMYG CDVGSDWRFL RGYHQYAYDG  120
KDYIALKEDL RSWTAADMAA QTTKHKWEAA HVAEQLRAYL EGTCVEWLRR YLENGKETLQ  180
RTDAPKTHMT HHAVSDHEAT LRCWALSFYP AEITLTWQRD GEDQTQDTEL VETRPAGDGT  240
FQKWAAVVVP SGQEQRYTCH VQHEGLPKPL TLRWEPSSQP TIPIVGIIAG LVLFGAVITG  300
AVVAAVMWRR KSSDRKGGSY SQAASSDSAQ GSDVSLTACK V                     341

SEQ ID NO: 2            moltype = AA  length = 275
FEATURE                 Location/Qualifiers
source                  1..275
                        mol_type = protein
                        organism = Homo sapiens
SEQUENCE: 2
GSHSMRYFFT SVSRPGRGEP RFIAVGYVDD TQFVRFDSDA ASQRMEPRAP WIEQEGPEYW   60
DGETRKVKAH SQTHRVDLGT LRGYYNQSEA GSHTVQRMYG CDVGSDWRFL RGYHQYAYDG  120
KDYIALKEDL RSWTAADMAA QTTKHKWEAA HVAEQLRAYL EGTCVEWLRR YLENGKETLQ  180
RTDAPKTHMT HHAVSDHEAT LRCWALSFYP AEITLTWQRD GEDQTQDTEL VETRPAGDGT  240
FQKWAAVVVP SGQEQRYTCH VQHEGLPKPL TLRWE                            275
```

-continued

```
SEQ ID NO: 3              moltype = AA  length = 119
FEATURE                   Location/Qualifiers
source                    1..119
                          mol_type = protein
                          organism = Homo sapiens
SEQUENCE: 3
MSRSVALAVL ALLSLSGLEG IQRTPKIQVY SRHPAENGKS NFLNCYVSGF HQSDIEVDLL   60
KNGERIEKVE HSDLSFSKDW SFYLLYYTEF TPTEKDEYAC RVNHVTLSQP KIVKWDRDM   119

SEQ ID NO: 4              moltype = AA  length = 229
FEATURE                   Location/Qualifiers
source                    1..229
                          mol_type = protein
                          organism = Homo sapiens
SEQUENCE: 4
IKEEHVIIQA EFYLNPDQSG EFMFDFDGDE IFHVDMAKKE TVWRLEEFGR FASFEAQGAL   60
ANIAVDKANL EIMTKRSNYT PITNVPPEVT VLTNSPVELR EPNVLICFID KFTPPVVNVT   120
WLRNGKPVTT GVSETVFLPR EDHLFRKFHY LPFLPSTEDV YDCRVEHWGL DEPLLKHWEF   180
DAPSPLPETT ENVVCALGLT VGLVGIIIGT IFIIKGVRKS NAAERRGPL              229

SEQ ID NO: 5              moltype = AA  length = 191
FEATURE                   Location/Qualifiers
source                    1..191
                          mol_type = protein
                          organism = Homo sapiens
SEQUENCE: 5
IKEEHVIIQA EFYLNPDQSG EFMFDFDGDE IFHVDMAKKE TVWRLEEFGR FASFEAQGAL   60
ANIAVDKANL EIMTKRSNYT PITNVPPEVT VLTNSPVELR EPNVLICFID KFTPPVVNVT   120
WLRNGKPVTT GVSETVFLPR EDHLFRKFHY LPFLPSTEDV YDCRVEHWGL DEPLLKHWEF   180
DAPSPLPETT E                                                       191

SEQ ID NO: 6              moltype = AA  length = 237
FEATURE                   Location/Qualifiers
source                    1..237
                          mol_type = protein
                          organism = Homo sapiens
SEQUENCE: 6
GDTRPRFLEQ VKHECHFFNG TERVRFLDRY FYHQEEYVRF DSDVGEYRAV TELGRPDAEY   60
WNSQKDLLEQ KRAAVDTYCR HNYGVGESFT VQRRVYPEVT VYPAKTQPLQ HHNLLVCSVN   120
GFYPGSIEVR WFRNGQEEKT GVVSTGLIQN GDWTFQTLVM LETVPRSGEV YTCQVEHPSL   180
TSPLTVEWRA RSESAQSKML SGVGGFVLGL LFLGAGLFIY FRNQKGHSGL QPTGFLS     237

SEQ ID NO: 7              moltype = AA  length = 199
FEATURE                   Location/Qualifiers
source                    1..199
                          mol_type = protein
                          organism = Homo sapiens
SEQUENCE: 7
GDTRPRFLEQ VKHECHFFNG TERVRFLDRY FYHQEEYVRF DSDVGEYRAV TELGRPDAEY   60
WNSQKDLLEQ KRAAVDTYCR HNYGVGESFT VQRRVYPEVT VYPAKTQPLQ HHNLLVCSVN   120
GFYPGSIEVR WFRNGQEEKT GVVSTGLIQN GDWTFQTLVM LETVPRSGEV YTCQVEHPSL   180
TSPLTVEWRA RSESAQSKM                                               199

SEQ ID NO: 8              moltype = AA  length = 9
FEATURE                   Location/Qualifiers
source                    1..9
                          mol_type = protein
                          organism = Homo sapiens
SEQUENCE: 8
QLFEELQEL                                                            9

SEQ ID NO: 9              moltype = AA  length = 9
FEATURE                   Location/Qualifiers
source                    1..9
                          mol_type = protein
                          organism = Human cytomegalo virus (HCMV)
SEQUENCE: 9
NLVPMVATV                                                            9

SEQ ID NO: 10             moltype = AA  length = 9
FEATURE                   Location/Qualifiers
source                    1..9
                          mol_type = protein
                          organism = Human Immunodeficiency virus (HIV)
SEQUENCE: 10
ILKEPVHGV                                                            9

SEQ ID NO: 11             moltype = AA  length = 9
FEATURE                   Location/Qualifiers
```

-continued

```
REGION                         1..9
                               note = Synthetic construct
source                         1..9
                               mol_type = protein
                               organism = synthetic construct
SEQUENCE: 11
GLAGDVSAV                                                                     9

SEQ ID NO: 12                  moltype = AA  length = 9
FEATURE                        Location/Qualifiers
REGION                         1..9
                               note = Synthetic construct
source                         1..9
                               mol_type = protein
                               organism = synthetic construct
SEQUENCE: 12
ALIAPVHAV                                                                     9

SEQ ID NO: 13                  moltype = AA  length = 9
FEATURE                        Location/Qualifiers
source                         1..9
                               mol_type = protein
                               organism = Epstein-Barr Virus (EBV)
SEQUENCE: 13
GLCTLVAML                                                                     9

SEQ ID NO: 14                  moltype = AA  length = 9
FEATURE                        Location/Qualifiers
source                         1..9
                               mol_type = protein
                               organism = Human cytomegalo virus (HCMV)
SEQUENCE: 14
VTEHDTLLY                                                                     9

SEQ ID NO: 15                  moltype = AA  length = 9
FEATURE                        Location/Qualifiers
source                         1..9
                               mol_type = protein
                               organism = Homo sapiens
SEQUENCE: 15
IVDCLTEMY                                                                     9

SEQ ID NO: 16                  moltype = AA  length = 10
FEATURE                        Location/Qualifiers
source                         1..10
                               mol_type = protein
                               organism = Human cytomegalo virus (HCMV)
SEQUENCE: 16
TPRVTGGAM                                                                    10

SEQ ID NO: 17                  moltype = AA  length = 11
FEATURE                        Location/Qualifiers
source                         1..11
                               mol_type = protein
                               organism = Human cytomegalo virus (HCMV)
SEQUENCE: 17
RPHERNGFTV L                                                                 11

SEQ ID NO: 18                  moltype = AA  length = 10
FEATURE                        Location/Qualifiers
source                         1..10
                               mol_type = protein
                               organism = Human Immunodeficiency virus (HIV)
SEQUENCE: 18
TPGPGVRYPL                                                                   10

SEQ ID NO: 19                  moltype = AA  length = 8
FEATURE                        Location/Qualifiers
source                         1..8
                               mol_type = protein
                               organism = Epstein-Barr Virus (EBV)
SEQUENCE: 19
RAKFKQLL                                                                      8

SEQ ID NO: 20                  moltype = AA  length = 14
FEATURE                        Location/Qualifiers
source                         1..14
                               mol_type = protein
                               organism = Homo sapiens
```

-continued

```
SEQUENCE: 20
GLNDIFEAQK IEWH                                                              14

SEQ ID NO: 21          moltype = AA  length = 13
FEATURE                Location/Qualifiers
source                 1..13
                       mol_type = protein
                       organism = Homo sapiens
SEQUENCE: 21
AGFKGEQGPK GEP                                                               13

SEQ ID NO: 22          moltype = AA  length = 9
FEATURE                Location/Qualifiers
source                 1..9
                       mol_type = protein
                       organism = Haemophilus influenzae
SEQUENCE: 22
GILGFVFTL                                                                    9

SEQ ID NO: 23          moltype = AA  length = 9
FEATURE                Location/Qualifiers
source                 1..9
                       mol_type = protein
                       organism = Human cytomegalo virus (HCMV)
SEQUENCE: 23
IPSINVHHY                                                                    9

SEQ ID NO: 24          moltype = AA  length = 8
FEATURE                Location/Qualifiers
source                 1..8
                       mol_type = protein
                       organism = Human cytomegalo virus (HCMV)
SEQUENCE: 24
GLCLVALM                                                                     8

SEQ ID NO: 25          moltype = AA  length = 9
FEATURE                Location/Qualifiers
source                 1..9
                       mol_type = protein
                       organism = Homo sapiens
SEQUENCE: 25
ILAKFLHWL                                                                    9

SEQ ID NO: 26          moltype = AA  length = 38
FEATURE                Location/Qualifiers
REGION                 1..38
                       note = Synthetic construct
source                 1..38
                       mol_type = protein
                       organism = synthetic construct
SEQUENCE: 26
AQLEKELQAL EKENAQLEWE LQALEKELAQ GGCGGSCG                                    38

SEQ ID NO: 27          moltype = AA  length = 9
FEATURE                Location/Qualifiers
source                 1..9
                       mol_type = protein
                       organism = Borrelia sp.
SEQUENCE: 27
ALIACKQNV                                                                    9

SEQ ID NO: 28          moltype = AA  length = 8
FEATURE                Location/Qualifiers
source                 1..8
                       mol_type = protein
                       organism = Borrelia sp.
SEQUENCE: 28
FTKEDTIT                                                                     8

SEQ ID NO: 29          moltype = AA  length = 9
FEATURE                Location/Qualifiers
source                 1..9
                       mol_type = protein
                       organism = Borrelia sp.
SEQUENCE: 29
SIQIEIEQL                                                                    9

SEQ ID NO: 30          moltype = AA  length = 9
FEATURE                Location/Qualifiers
```

-continued

```
source                  1..9
                        mol_type = protein
                        organism = Borrelia sp.
SEQUENCE: 30
NLNEVEKVL                                                    9

SEQ ID NO: 31           moltype = AA  length = 9
FEATURE                 Location/Qualifiers
source                  1..9
                        mol_type = protein
                        organism = Borrelia sp.
SEQUENCE: 31
SLAKIENAI                                                    9

SEQ ID NO: 32           moltype = AA  length = 15
FEATURE                 Location/Qualifiers
source                  1..15
                        mol_type = protein
                        organism = Homo sapiens
SEQUENCE: 32
SLNDIFEAQK IEWHE                                             15

SEQ ID NO: 33           moltype = AA  length = 15
FEATURE                 Location/Qualifiers
source                  1..15
                        mol_type = protein
                        organism = Camelus dromedarius
SEQUENCE: 33
PQPQPKPQPK PEPET                                             15

SEQ ID NO: 34           moltype = AA  length = 9
FEATURE                 Location/Qualifiers
source                  1..9
                        mol_type = protein
                        organism = Human cytomegalo virus (HCMV)
SEQUENCE: 34
QYDPVAALF                                                    9

SEQ ID NO: 35           moltype = AA  length = 9
FEATURE                 Location/Qualifiers
MOD_RES                 4
                        note = pivaloyl coupled to lysine
source                  1..9
                        mol_type = protein
                        organism = Homo sapiens
SEQUENCE: 35
ILAKFLHWL                                                    9

SEQ ID NO: 36           moltype = AA  length = 37
FEATURE                 Location/Qualifiers
MOD_RES                 33
                        note = cystein is deprotected with tert-Butylthio
REGION                  1..37
                        note = Synthetic construct
source                  1..37
                        mol_type = protein
                        organism = synthetic construct
SEQUENCE: 36
AQLEKELQAL EKENAQLEWE LQALEKELAQ GGCGGSC                     37
```

MHC MULTIMERS, METHODS FOR THEIR GENERATION, LABELING AND USE

CROSS-REFERENCE TO RELATED APPLICATIONS

This application is a continuation of U.S. application Ser. No. 16/015,955, filed 22 Jun. 2018, which is a continuation of U.S. application Ser. No. 12/644,554, filed 22 Dec. 2009, which issued on 24 Jul. 2018 as U.S. Pat. No. 10,030,065 and is a continuation of PCT Appl. No. PCT/DK2008/050167, filed 3 Jul. 2008, which claims the priority of U.S. Prov. Appl. No. 60/929,583, filed 3 Jul. 2007, and U.S. Prov. Appl. No. 60/929,581, filed 3 Jul. 2007, and U.S. Prov. Appl. No. 60/929,586, filed 3 Jul. 2007, and U.S. Prov. Appl. No. 60/929,582, filed 3 Jul. 2007, which PCT application also claims the priority of Danish Appl. No. PA 2007 00974, filed 3 Jul. 2007, and Danish Appl. No. PA 2007 00972, filed 3 Jul. 2007, and Danish Appl. No. PA 2007 00975, filed 3 Jul. 2007, and Danish Appl. No. PA 2007 00973, filed 3 Jul. 2007. Each of the aforementioned applications is hereby incorporated by reference in its entirety.

Further, all patent and non-patent references cited in this application are hereby incorporated by reference in their entirety. All patent and non-patent references cited in U.S. 60/929,583, U.S. 60/929,586, U.S. 60/929,582, U.S. 60/929,581, PA 2007 00972, PA 2007 00975 and PA 2007 00973 are hereby incorporated by reference in their entirety.

BACKGROUND

Biochemical interactions between peptide epitope specific membrane molecules encoded by the Major Histocompatibility Complex (MHC, in humans HLA) and T-cell receptors (TCR) are required to elicit specific immune responses. This requires activation of T-cells by presentation to the T-cells of peptides against which a T-cell response should be raised. The peptides are presented to the T-cells by the MHC complexes.

The Immune Response

The immune response is divided into two parts termed the innate immune response and the adaptive immune response. Both responses work together to eliminate pathogens (antigens). Innate immunity is present at all times and is the first line of defence against invading pathogens. The immediate response by means of pre-existing elements, i.e. various proteins and phagocytic cells that recognize conserved features on the pathogens, is important in clearing and control of spreading of pathogens. If a pathogen is persistent in the body and thus only partially cleared by the actions of the innate immune system, the adaptive immune system initiate a response against the pathogen. The adaptive immune system is capable of eliciting a response against virtually any type of pathogen and is unlike the innate immune system capable of establishing immunological memory.

The adaptive response is highly specific to the particular pathogen that activated it but it is not so quickly launched as the innate when first encountering a pathogen. However, due to the generation of memory cells, a fast and more efficient response is generated upon repeated exposure to the same pathogen. The adaptive response is carried out by two distinct sets of lymphocytes, the B-cells producing antibodies leading to the humoral or antibody mediated immune response, and the T-cells leading to the cell mediated immune response.

T-cells express a clonotypic T-cell receptor (TCR) on the surface. This receptor enable the T-cell to recognize peptide antigens bound to major histocompatibility complex (MHC) molecules, called human leukocyte antigens (HLA) in man. Depending on the type of pathogen, being intracellular or extracellular, the antigenic peptides are bound to MHC class I or MHC class II, respectively. The two classes of MHC complexes are recognized by different subsets of T-cells; Cytotoxic CD8+ T-cells recognizing MHC class I and CD4+ helper cells recognizing MHC class II. In general, TCR recognition of MHC-peptide complexes result in T-cell activation, clonal expansion and differentiation of the T-cells into effector, memory and regulatory T-cells.

B-cells express a membrane bound form of immunoglobulin (Ig) called the B-cell receptor (BCR). The BCR recognizes an epitope that is part of an intact three dimensional antigenic molecule. Upon BCR recognition of an antigen the BCR:antigen complex is internalized and fragments from the internalized antigen is presented in the context of MHC class II on the surface of the B-cell to CD4+ helper T-cells (Th). The specific Th cell will then activate the B-cell leading to differentiation into an antibody producing plasma cell.

A very important feature of the adaptive immune system is its ability to distinguish between self and non-self antigens, and preferably respond against non-self. If the immune system fails to discriminate between the two, specific immune responses against self-antigens are generated. These autoimmune reactions can lead to damage of self-tissue.

The adaptive immune response is initiated when antigens are taken up by professional antigen presenting cells such as dendritic cells, Macrophages, Langerhans cells and B-cells. These cells present peptide fragments, resulting from the degradation of proteins, in the context of MHC class II proteins (Major Histocompatibility Complex) to helper T-cells. The T helper cells then mediate help to B-cells and antigen specific cytotoxic T-cells, both of which have received primary activation signals via their BCR respective TCR. The help from the Th-cell is mediated by means of soluble mediators e.g. cytokines.

In general the interactions between the various cells of the cellular immune response is governed by receptor-ligand interactions directly between the cells and by production of various soluble reporter substances e.g. cytokines by activated cells.

The function of the immune system is to protect the body against foreign invaders or aberrant self-molecules (e. g. parasites, bacteria, viruses and cancer). Such threats can normally be eliminated or neutralised efficiently by the immune system. To administrate this potential, the immune system must discriminate normal molecules in the healthy body from the presence of foreign or aberrant self-molecules, which can be expressed during genesis of diseases e. g. cancer. Ideally, foreign or aberrant molecules should be eliminated, while the body itself should be left unharmed. One major hallmark of the immune system is therefore one of specificity i. e. the ability to discriminate between various targets and in particular to distinguish between self and non-self. The specific- or adaptive-immune system involves a large number of different cell types. Immune responses develop from an orchestral interplay of antigen-processing/presenting cells and effector cells. The central effector cells are lymphocytes, with a major subdivision into B- and T-cells representing humoral and cellular responses, respectively. Both cell populations use receptors, which in their genome are encoded in many bits and pieces allowing enormous recombinatorial receptor diversity. Each B- or T-cell carries one, and only one, of these receptors which recognise their tiny but unique fragments of the universe. All human lymphocytes combined divide the entire universe into two major groups of targets: a group of self-antigens that are tolerated by the immune system and a group of non-self or aberrant antigens that can elicit a response. The overall specificity of the immune system is generated, regulated and co-ordinated through processes controlling individual lymphocytes. Deleting, or inactivating a lymphocyte clone removes the corresponding specificity from the repertoire. Activation and propagation of a lymphocyte clone enhances the corresponding specificity- and allows the immune system to respond quickly and strongly toward the antigen.

The cells of the immune system include the following: Lymphocytes are a type of white blood cells found in the blood and many other parts of the body. Types of lymphocytes include B-cells, T-cells, and Natural Killer (NK) cells.

The B- and T-cells recognise and respond specifically to aberrant substances, thus being a part of the specific immune system. B-cells (or B-lymphocytes) mature into plasma cells that secrete antibodies (immunoglobulins), the proteins that recognise and attach to foreign substances known as antigens. Each type of B-cell produces one specific antibody, which recognises one specific epitope on the antigen. The T-cells recognise and respond towards aberrant substances by interaction with antigen presenting cells (APC) that display antigens in form of "non-self" (or aberrant) peptides in context of MHC molecules. Each T-cell clone expresses one unique specificity of T-cell receptors (TCR), which recognise one specific peptide/MHC epitope.

T-cells comprise two major subpopulations. Cytolytic T-cells directly attack infected, foreign, or cancerous cells displaying foreign or aberrant forms of endogenous peptides in context of MHC Class I molecules (described below). "Helper" T-cells that are activated by foreign exogenous peptides in MHC Class II molecules, contribute to regulation of the immune response by signalling other immune system defenders. T-cells also work by producing proteins called lymphokines.

NK cells produce powerful chemical substances that bind to and kill any foreign invader. They attack without first having to recognise a specific antigen, thus being an immune cell type that also relate to the innate immune system.

Monocytes are white blood cells that are able to swallow and digest microscopic organisms and particles in a process known as phagocytosis and antigen processing.

Dendritic cells (DC) are of particular interest as they present peptide epitopes in a "professional way" which leads to effective activation of T-cells. The professional APC express a variety of co-stimulatory molecules that ligate with a variety of counter receptors expressed on the T-cells.

Cells in the immune system secrete two types of proteins, namely antibodies and cytokines. Specific antibodies match epitopes on specific antigens, fitting together much the way a key fits a lock. Conventional vaccine approaches, in particular, work through activation of helper T-cells and B-cells leading to secretion of antigen specific antibodies. Cytokines are substances produced by some immune cells to communicate with other cells. Types of cytokines include lymphokines, interferons, interleukins, and colony-stimulating factors.

Antigen-recognition by B- and T-cells. B- and T-cells use entirely different mechanisms to recognise their targets. B-cells recognise soluble antigens, and since they can secrete their receptors as antibodies, they can potentially interact with antigen throughout the fluid phase of the extra-cellular space. In sharp contrast, the T-cell receptor is always membrane-bound and it only recognises antigen, which is presented on the membrane of an antigen-presenting cell (APC). In other words, T-cell recognition involves a direct physical interaction between two cells; a T-cell and an APC. B- and T-cells also differ with respect to what they recognise. B-cells can recognise organic substances of almost any kind, whereas T-cells predominantly recognise proteins (as a biological target, proteins are particularly important since they constitute the structural and functional basis of all life). B-cells recognise the three-dimensional structure of proteins as illustrated by their ability to distinguish between native and denatured proteins. In contrast, T-cells cannot distinguish between native and denatured proteins.

Today, we know that T-cells only recognise antigenic peptides presented in association with MHC molecules on the surface of APC's. In general, cytotoxic T-cells recognise short peptides (corresponding in general to 8-11 residues), the amino and carboxy-termini of which are deeply embedded within the MHC Class I molecule (i. e. the peptide length is restricted). In comparison, helper T-cells tend to recognise longer peptides (corresponding in general to 13-30 residues) with amino and carboxy terminal ends extending out of the MHC Class II molecule.

MHC restriction and T-cell immunity. T-cells determine the reactivity and specificity of the adaptive immune system, including the activity of B-cells. It is therefore appropriate to focus the attention on these cells. T-cells can only recognise a given antigen, when it is presented in the context of a particular MHC molecule. They are "educated" during ontogeny and further activated during the first priming in processes designed to develop T-cells carrying receptors specific for a particular antigen-MHC molecule combination. These T-cells are subsequently only able to recognise the same antigen-MHC molecule combination. This phenomenon is known as "MHC restriction". Another immune phenomenon; that of "responder status", is also determined by the MHC molecules. Individuals of one MHC haplotype will respond to some antigens, and not to others. Other individuals with other MHC haplotypes will respond differently. These two phenomena are of obvious importance for any rational immune manipulation. As mentioned, we now know that MHC molecules control them both. These molecules have specifically evolved for the purpose of antigen presentation. Our current under-standing of antigen presentation can be summarised as follows. Firstly, the foreign substance, the antigen, is taken up by APC's. An intracellular pool of antigenic peptides is generated through proteolytic fragmentation of all the protein available to the cell (which can include both normal cell proteins ("self-proteins") and antigens ("non-self proteins") from infective organisms. This pool of peptides is offered to the MHC molecules of the individual and sampled according to length and sequence; some are bound, while others are ignored (the MHC molecule is said to perform "determinant selection"). Subsequently, MHC molecules protect the selected peptides against further degradation, transport them to the surface of the APC and display them for T-cell scrutiny. Antigenic peptides from "non-self proteins" are, in contrast to peptides from "self-proteins", recognised by T-cells that consequently can become activated.

A plurality of receptors is involved in antigen specific activation of immune cells. Several ligand-receptor interactions related to control this network of cells are complex, in comparison to more "conventional" ligand-receptor models comprising simple hormone-receptor interaction e. g. insulin and IR. For example, full activation of T-cells acquires simultaneous signalling through a variety of receptors in addition to TCR signalling. The binding energy yielded from ligation of multiple membrane molecules expressed on APC and T-cells, ensure a close physical contact between the involved cells. One of the most important additional receptors related to activation of T-cells is CD28 molecules, which bind proteins of the B7 family expressed on professional APCs. Other known examples of regulatory receptors expressed on T-cells are a variety of NK receptors (NKR), which comprise both inhibitory and activating isoforms. The balance between expressed forms of activating and inhibiting NKRs is believed to determine a threshold for activation of specific T-cells.

It has recently been reported that molecular interactions between many of the receptors and ligands involved in this cellular interplay, including TCR and MHC molecules, are unstable i. e. of low affinity. By example, it has been measured that monovalent MHC molecule-TCR interaction has an affinity constant of Ko=10 uM with a dissociation constant less than a minute. Molecular interaction of CD28 and B7 protein has an affinity constant of same level. In comparison, the stability and affinity of complexes formed by high-affinity interactions e. g. hormone ligand-receptor binding (insulin/IR) and antibody-antigen binding, are significantly higher (affinity constant KD in the range of 0.1-10 nM).

The plurality of proteins related to activation of T-cells do, however, not only stabilise cellular contact between APC and T-cells, they also contribute to a variety of signalling events required for activation of T-cells. It is-orchestrated actions of these signalling events that determines the activation of T-cells. For example, it has been shown that naive cytolytic T-cells require at least two signals for activation. The first signal is delivered through ligation of MHC molecules (expressed on APCs) to TCRs on T-cells. The second signal is delivered through co-stimulatory molecules from e. g. B7 protein family, which ligate with the CD28 receptor on T-cells.

The genes located in the human MHC locus (HLA locus) encode a set of highly polymorph membrane proteins that sample peptides in intracellular compartments and present such peptide epitopes on surfaces of APCs to scrutinising T-cells. The extensive genetic polymorphism of the MHC locus is the background for the unique genetic finger print of the immune system in individuals and defines the repertoire of antigenic peptide epitopes which the human population is capable of recognising and responds to.

Two subtypes of MHC molecules exist, MHC Class I and II molecules. These subtypes correspond to two subsets of T-lymphocytes: 1) CD8+ cytotoxic T-cells, which usually recognize peptides presented by MHC Class I molecules, and kill infected or mutated T-cells, and 2) CD4+ helper T-cells, which usually recognise peptides presented by MHC Class II molecules, and regulate the responses of other cells of the immune system. MHC Class I molecules consist of a 43,000 MW transmembrane glycoprotein (the a chain) non-covalently associated with a 12,000 MW non-glycosylated protein (the light (ß) chain, also known as B2-microglobulin). MHC Class II molecules have an overall structure similar to MHC Class I molecules although the domain distribution is different. The MHC Class II molecule consists of two non-covalently associated trans-membrane glycoproteins of approximately 34,000 and 29,000 MW. The detailed structures of MHC Class I and II molecules have been solved at the X-ray crystallography level. The most interesting part of the MHC molecule structure is the "upper" part that shows a unique peptide-binding groove consisting of two alpha helixes forming the walls of the groove and eight beta-pleated sheaths forming the floor of the groove.

The peptides are the essential target structures in recognition of "non-self" by the adaptive immune system and, one could say, the group of MHC molecules comprises a port to the immune system, thus being a major player in determining penetrance and spreading of human diseases.

MHC molecules of other higher vertebrate species exert identical biological functions as those of HLA in man.

The MHC locus is extremely polymorphic i. e. many different versions (alleles, allotypes) exist in the population, but each individual has only inherited two of these (one from the father and one from the mother). It is also polygenic i. e. several MHC encoding loci exist in the genome allowing for simultaneous expression of several isotypes. Importantly, the majority of the polymorphic residues points towards the peptide binding groove affecting its size, shape and functionality. Peptide-MHC interactions are specific, albeit broad, allowing the binding of many unrelated peptides to each MHC allotype. The polymorphism dictates the specificity of peptide binding and the biological consequence of this is that each individual in the population educates and shapes a unique T-cell repertoire.

A variety of relatively invariant MHC Class I molecule like molecules have been identified. This group comprises CDId, HLA E, HLA G, HLA H, HLA F, MIC A, MIC B, ULBP-1, ULBP-2, and ULBP-3. These non-classical molecules have a tissue distribution and functions distinct from HLA A, B and C. Some of them comprise only a heavy chain protein i. e. do not associate with B12m molecules and peptides. As described previously, the immune responses develop from an orchestral interplay of antigen-processing/presenting cells and effector cells.

Monomer and soluble forms of cognate as well as modified MHC molecules e. g. single chain protein with peptide, heavy and light chains fused into one construct, have been produced in bacteria as well as eucaryotic cells. Recent advances in recombinant technology and in vitro protein folding methods have provided efficient protocols for large-scale production of multimeric MHC molecules, which bind with high avidity to appropriate T-cell receptors.

NK cells and MHC molecules. NK cells remained mysterious until recently. These cells were defined by their ability to lyse certain tumours in the absence of prior stimulation. NK cell activity is regulated by a number of ligands including MHC molecule. NK cells recognise MHC Class I molecules through surface receptors that deliver an inhibitory signal. Thus, NK cells can lyse targeT-cells that have lost expression of MHC molecules. It is well known that tumour cells often reduce or loose their expression of MHC molecules presumably due to a selective pressure from cytotoxic T-cells that recognise tumour associated antigens (peptides) in context of MHC molecules. The ability of NK cells to discriminate between normal and tumour cells is then explained by the "missing-self hypothesis". However, NK cells are not simply equipped with receptors that recognise a broad spectrum of MHC molecules. The complexity of NK receptors is also reflected by expression of different isoforms, some of which are activating whereas others are inhibitory. Interestingly, 5-10% of the (alpha beta) T-cells also express different NK receptors such as KIR, ILT or CD94/NKG2, which belong to the inhibitory-receptor superfamily. Such receptors can serve to raise the activation threshold for cellular immune responses. The balances between stimulating and inhibitory receptors presumably control the activation of T-cells and NK cells. Some of the different NK receptors expressed on NK cells and T-cells recognise broader specificity of MHC Class I molecules, whereas others recognise more rarely expressed allelic determinants. Thus, the MHC molecules can be involved in both stimulation and inhibition of specific immune responses.

The T-cell receptor (TCR), a member of the immunoglobulin super-family, consists of two non-covalently associated trans-membrane glycoproteins of approximately 30,000 MW; each comprising two extra-cellular domains. The two chains form a dimmer, which associate with a larger protein complex, CD3. The detailed structures of TCR in association with MHC Class I molecules have been solved at the X-ray crystallography level. Recombinant forms of soluble TCRs (consisting of extracellular domains) have been produced in bacteria and eucaryotic cells. The specific interplay of specific TCR ligands i. e. immunogenic peptide/HLA complexes and specific T-cell receptors results in ligand induced formation of a signalosome composed by the TCR/CD3 complex and its interplay with intracellular pools of tyrosine kinases (Ick, Fyn, Syk, Zap-70) and adaptors (LAT, TRIM and Grp2). As described above, the TCRs are expressed clonally and only appropriate peptide-specific MHC complexes can elicit an immune response.

The adaptive immune responses require two signals for initial activation: one signal provided through the binding of peptide-MHC on the antigen presenting cell (APC) to the T-cell receptor (TCR), and a second antigen-independent signal called co-stimulation. CD28 is a membrane receptor on T-cells that provides co-stimulatory function when T-cells encounter APCs that express CD28 ligands, B7-1 (CD80) of B7-2 (CD86). The functions of CD28 are predominantly to influence signals initiated through the TCR, which results in qualitative and quantitative changes in the cascade of events leading to proliferation, cytokine production, and cell survival. Triggering of naive T-cells without the co-stimulatory signal can render the T-cells functionally unresponsive (anergy, apoptosis). CD28 induces greater proliferation of CD4+ T-cells compared with CD8+ T-cells. Other members of the CD28 immunoglobulin (Ig) superfamily such as includes inducible co-stimulator (ICOS) provides co-stimulatory signals on activated CD4+ and CD8+ T-cells to enhance their proliferation.

Lymphocyte responses are regulated by inhibitory as well as activating signals. CTLA-4 and PD-1 mediated such inhibitory signals. CTLA-4 has higher affinity for shared ligands B7-1 and B7-2 compared with CD28, and it is up-regulated upon TCR-CD28 engagement. PD-1 appears to mediate an inhibitory signal, and it is widely expressed on hematopoietic-derived tissues and on activated T-cells. Interleukin-2 and co-stimulatory signals are the two most important factors required for maintenance of continuous cell division. Although CD28 provides a critical co-stimulatory signal on naive T-cells, other co-stimulatory molecules in the tumour necrosis receptor (TNFR) superfamily, such as 4-1BB (CD137), CD27 and OX40 (CD134), provides co-stimulatory signals on activated T-cells to orient the quality of T-cell response towards cell survival or apoptosis. Some CD8+ effector T-cells lack CD28 expression. However, these cells express the lectin-like NKG2D homodimer, a receptor for the MHC Class I-like molecules called MIC. NKG2D serves as a co-stimulatory molecule for CD28-CD8+ T-cells and with combined triggering of TCR/CD3 complexes induced IL-2 and T-cell proliferation. Expression and function of NKG2D are selectively up-regulated by the cytokine IL-15. Human NKG2D is expressed on gamma, delta T-cells, CD8+ T-cells, NK cells, and a small subset of CD4+ T-cells. The stress-induced MIC A and MIC B molecules are expressed in the intestinal epithelium as well as in diverse tumours of epithelial origin. NK cells are able to reject tumours expressing MHC Class I molecules if the tumour expresses a ligand for NKG2D, i. e. MIC A or MIC B. A family of receptors (NKp46, NKp30, NKp44) termed natural cytotoxicity receptors (NCR) expressed on NK cells are involved in NK-mediated lysis of various tumours.

MHC-Peptide Complexes

MHC complexes function as antigenic peptide receptors, collecting peptides inside the cell and transporting them to the cell surface, where the MHC-peptide complex can be recognized by T-lymphocytes. Two classes of classical MHC complexes exist; MHC class I and II. The most important difference between these two molecules lies in the protein source from which they obtain their associated peptides. MHC class I molecules present peptides derived from endogenous antigens degraded in the cytosol and are thus able to display fragments of viral proteins and unique proteins derived from cancerous cells. Almost all nucleated cells express MHC class I on their surface even though the expression level varies among different cell types. MHC class II molecules bind peptides derived from exogenous antigens. Exogenous proteins enter the cells by endocytosis or phagocytosis, and these proteins are degraded by proteases in acidified intracellular vesicles before presentation by MHC class II molecules. MHC class II molecules are only expressed on professional antigen-presenting cells like B-cells and macrophages.

The three-dimensional structure of MHC class I and II molecules are very similar but important differences exist. MHC class I molecules consist of two polypeptide chains, a heavy chain, a, spanning the membrane and a light chain, β2-microglobulin (β2m). The heavy chain is encoded in the gene complex termed the major histocompatibility complex (MHC), and its extracellular portion comprises three domains, α1, α2 and α3. The β2m chain is not encoded in the MHC gene and consists of a single domain, which together with the α3 domain of the heavy chain make up a folded structure that closely resembles that of the immunoglobulin. The α1 and α2 domains pair to form the peptide binding cleft, consisting of two segmented α helices lying on a sheet of eight β-strands. In humans as well as in mice three different types of MHC class I molecule exist. HLA-A, B, C are found in humans while MHC class I molecules in mice are designated H-2K, H-2D and H-2L. The MHC class II molecule is composed of two membrane spanning polypeptide chains, α and β, of similar size (about 30,000 Da). Genes located in the major histocompatibility complex encode both chains. Each chain consists of two domains, where α1 and β1 forms a 9-pocket peptide-binding cleft, where pocket 1, 4, 6 and 9 are considered as major peptide binding pockets. The α2 and β2, like the α2 and β2m in the MHC class I molecules, have amino acid sequence and structural similarities to immunoglobulin constant domains. In contrast to MHC class I complexes, where the ends of the antigenic peptide is buried, peptide-ends in MHC class II complexes are not. HLA-DR, DQ and DP are the human class II molecules, H-2A, M and E are those of the mice. A remarkable feature of MHC genes is their polymorphism accomplished by multiple alleles at each gene. The polygenic and polymorphic nature of MHC genes is reflected in the peptide-binding cleft so that different MHC complexes bind different sets of peptides. The variable amino acids in the peptide binding cleft form pockets where the amino acid side chains of the bound peptide can be buried. This permits a specific variant of MHC to bind some peptides better than others.

SUMMARY OF THE INVENTION

Measurement of antigen specific T-cells during an immune response are important parameters in vaccine development, autologous cancer therapy, transplantation, infectious diseases, inflammation, autoimmunity, toxicity studies etc. MHC multimers are crucial reagents in monitoring of antigen specific T-cells. The present invention describes novel methods to generate MHC multimers and methods to improve existing and new MHC multimers. The invention also describes improved methods for the use of MHC multimers in analysis of T-cells in samples including diagnostic and prognostic methods. Furthermore the use of MHC multimers in therapy are described, e.g. anti-tumour and anti-virus therapy, including isolation of antigen specific T-cells capable of inactivation or elimination of undesirable targeT-cells or isolation of specific T-cells capable of regulation of other immune cells.

MHC Multimers

Due to the short half-life of the peptide-MHC-T-cell receptor ternary complex (typically between 10 and 25 seconds), it is difficult to label specific T-cells with labelled MHC-peptide complexes, and like-wise, it is difficult to employ such monomers of MHC-peptide for therapeutic and vaccine purposes because of their weak binding. In order to circumvent this problem, MHC multimers have been developed. These are complexes that include multiple copies of MHC-peptide complexes, providing these complexes with an increased affinity and half-life of interaction, compared to that of the monomer MHC-peptide complex. The multiple copies of MHC-peptide complexes are attached, covalently or non-covalently, to one or more multimerization domain(s). Known examples of such MHC multimers include the following:

MHC-dimers: Each MHC dimer contains two copies of MHC-peptide. IgG is used as one or more multimerization domain(s), and one of the domains of the MHC protein is covalently linked to IgG.

MHC-tetramers: Each MHC-tetramer contains four copies of MHC-peptide, each of which is biotinylated. The MHC complexes are held together in a complex by the streptavidin tetramer protein, providing a non-covalent linkage between a streptavidin monomer and the MHC protein. Tetramers are described in U.S. Pat. No. 5,635,363.

MHC pentamers: Five copies of MHC-peptide complexes are multimerised by a self-assembling coiled-coil domain, to form a MHC pentamer. MHC pentamers are described in the US patent 2004209295

MHC dextramers: A large number of MHC-peptide complexes, typically more than ten, are attached to a dextran polymer. MHC-dextramers are described in the patent application WO 02/072631 A2.

Use of MHC Multimers in Flow Cytometry and Related Techniques

The concentration of antigen specific T-cells in samples from e.g. peripheral blood can be very low. Flow cytometry and related methods offer the ability to analyze a large number of cells and simultaneously identify the few of interest. MHC multimers have turned out to be very valuable reagents for detection and characterization of antigen specific T-cells in flow cytometer experiments. The relative amount of antigen specific T-cells in a sample can be determined and also the affinity of the binding of MHC multimer to the T-cell receptor can be determined.

The basic function of a flow cytometer is its ability to analyse and identify fluorochrome labelled entities in a liquid sample, by means of its excitation, using a light source such as a laser beam and the light emission from the bound fluorochrome.

MHC multimers is used as detections molecule for identification of antigen specific T-cells in flow cytometry, by labelling the MHC multimer with a specific fluorochrome, which is detectable, by the flow cytometer used.

In order to facilitate the identification of a small amount of cells, the cells can be sub-categorized using antibodies or other fluorochrome labelled detections molecules directed against surface markers other than the TCR on the specific T-cells population. Antibodies or other fluorochrome labelled detections molecules can also be used to identify cells known not to be antigen specific T-cells. Both kinds of detections molecules are in the following referred to as gating reagents. Gating reagents, helps identify the "true" antigen specific T-cells bound by MHC multimers by identifying specific subpopulations in a sample, e.g. T-cells and by excluding cells that for some reason bind MHC multimers without being antigen specific T-cells. Other cytometry methods, e.g. fluorescence microscopy and IHC can like flow cytometry be employed in identification of antigen specific T-cells in a cell sample using MHC multimers.

Application of MHC Multimers in Immune Monitoring, Diagnostics, Prognostics, Therapy and Vaccines T-cells are pivotal for mounting an adaptive immune response. It is therefore of importance to be able to measure the number of specific T-cells when performing a monitoring of a given immune response. For example in connection with vaccine development, autologous cancer therapy, transplantation, infectious diseases, toxicity studies etc.

BRIEF DESCRIPTION OF THE DRAWINGS

Figure 1:
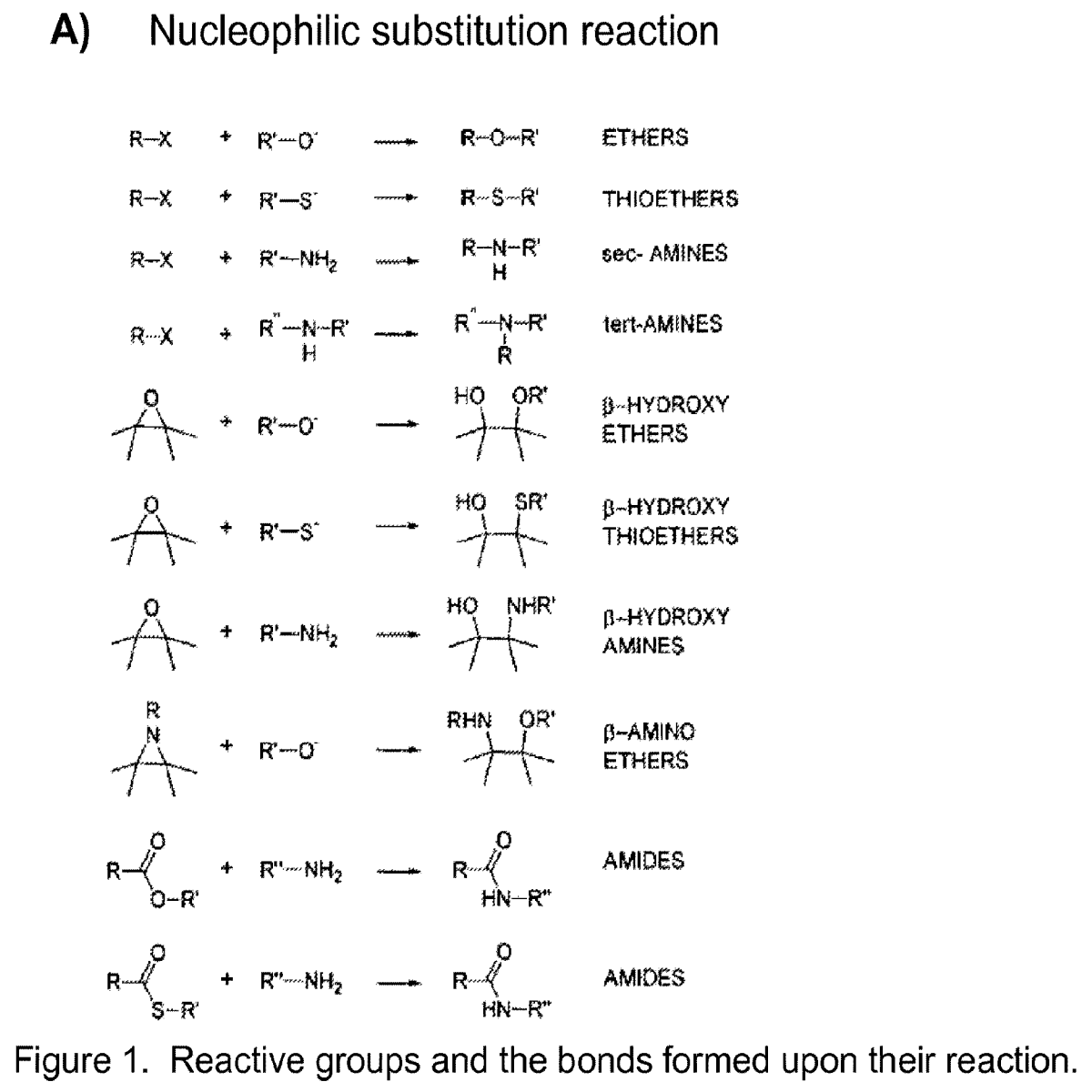
Figure 1:
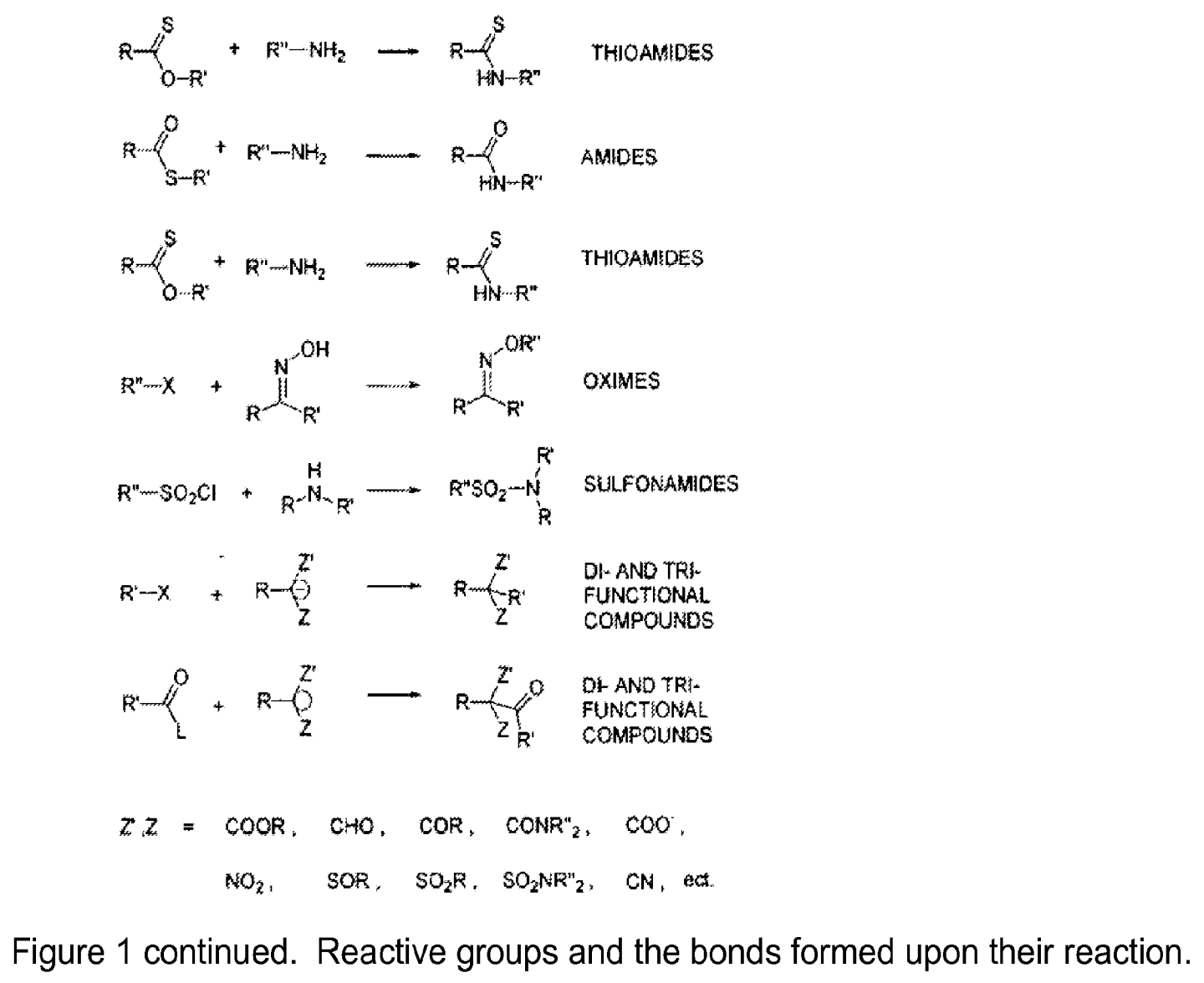
Figure 1:
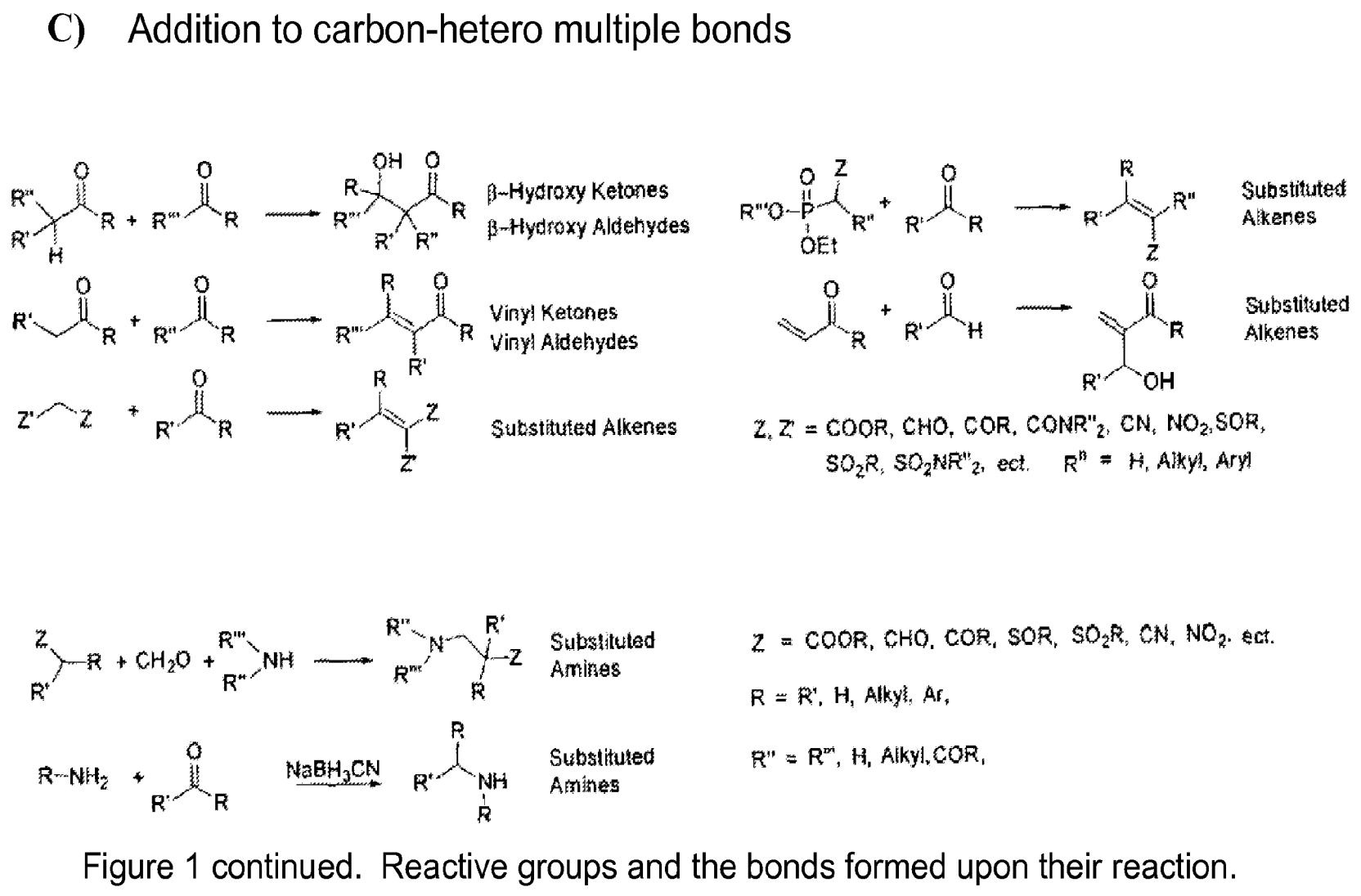

FIG. 1. Reactive groups and the bonds formed upon their reaction. Shown in A, B and C are reactive groups, relevant for the present invention, and the bonds that are formed upon their reaction.

FIG. 2. Cleavable linkers, conditions for cleaving them and the resulting products of the cleavage. Shown are cleavable linkers relevant for the present invention, as well as the conditions that lead to their cleavage, and the products of the cleavage reaction.

FIG. 3. Size exclusion chromatography of folded HLA-A*0201-β2m—QLFEELQEL peptide-complex. Purification of HLA-A*0201-β2m—QLFEELQEL (SEQ ID NO:8) peptide-complex by size exclusion chromatography on a HiLoad 16/60 SUPERDEX 75 column. Eluted protein was followed by measurement of the absorbance at 280 nm. The elution profile consisted of 4 peaks, corresponding to aggregated Heavy Chain, correctly folded MHC-complex, β2m and excess biotin and peptide.

FIG. 4. MHC-SHIFT Assay. The SHIFT Assay shows that heavy chain is efficiently biotinylated, since the band corresponding to biotinylated heavy chain (lane 2) is shifted up-wards upon incubation with streptavidin.

Lane 1: Benchmark protein-ladder

Lane 2: Folded HLA-A*0201-β2m—QLFEELQEL (SEQ ID NO:8) peptide-complex

Lane 3: Folded HLA-A*0201-β2m—QLFEELQEL (SEQ ID NO:8) peptide-complex incubated with molar excess Streptavidin.

FIG. 5. Conformational ELISA. The ELISA is carried out as a sandwich-ELISA. The ELISA-plate was coated with W6/32 mouse-anti-hHLA-ABC (DAKO M0736) antibody, which recognizes a conformational epitope on correctly folded MHC-complex. Then MHC complex in various concentration was added. β2m in various concentrations was used as negative control. HRP-conjugated rabbit anti-β2m (DAKO P0174) was used for detection of bound MHC complex. TMB One-step substrate system (Dako) was used as a substrate for HRP, and color formation was followed by measurement of absorbance at 450 nm.

FIG. 6. Carboxylate-modified beads coupled to TCR and stained with HLA-A*0201(NLVPMVATV (SEQ ID NO:9))/RPE or HLA-A*0201(ILKEPVHGV (SEQ ID NO:10))/RPE dextramers. TCR in various concentrations were coupled to carboxylate-modified beads and then stained with HLA-A*0201(NLVPMVATV (SEQ ID NO:9))/RPE or HLA-A*0201(ILKEPVHGV SEQ ID NO:10)/RPE dextramers in a flow cytometry experiment. A) Histogram showing x-axis: Fluorescence intensity measured in the RPE channel (FL2), y-axis: events counted. Events measured in the Region R9 are regarded as negative, and events measured in Region R10 are regarded as positive. B) Percentage of positively stained beads is shown for each preparation of beads. Negative control samples:

1) Beads coupled with 10 μg TCR stained with HLA-A*0201(ILKEPVHGV (SEQ ID NO:10))/RPE
2) Beads coupled with 0 μg TCR stained with HLA-A*0201(NLVPMVATV (SEQ ID NO:9))/RPE Positive Control Samples:

3) Beads coupled with 2 μg TCR stained with HLA-A*0201(NLVPMVATV (SEQ ID NO:9))/RPE
4) Beads coupled with 5 μg TCR stained with HLA-A*0201(NLVPMVATV (SEQ ID NO:9))/RPE
5) Beads coupled with 10 μg TCR stained with HLA-A*0201(NLVPMVATV (SEQ ID NO:9))/RPE
6) Beads coupled with 20 μg TCR stained with HLA-A*0201(NLVPMVATV (SEQ ID NO:9))/RPE FIG. 7. Flow cytometry analysis of human cell samples added TCR-coated beads. TCR-beads were added into human peripheral whole blood (A) or HPBMC (B) and then the samples were analysed by flow cytometry. Region R1 represents TCR-beads; region R2 represents lymphocyte cell population of interest.

FIG. 8. Flow cytometry analysis of MHC multimer constructs carrying nonsense peptides. Human Peripheral Blood Lymphocytes were FICOLL® purified from blood from a human donor and stained with mouse anti-human CD3/PE antibody and mouse anti-human CD8/PB antibody together with either of the MHC Dextramer molecule constructs A) HLA-A*0201(NLVPMVATV (SEQ ID NO:9))/APC, B) HLA-A*0201 (ILKEPVHGV (SEQ ID NO:10))/APC, C) HLA-A*0201(nonsense peptide 1)/APC or D) HLA-A*0201 (nonsense peptide 2)/APC. The staining was analysed on a CYAN ADP flow cytometer. Live-gated and CD3 positive lymphocytes are shown.

FIG. 9. Summary of flow cytometry analysis of the binding of different MHC multimer constructs to specific T-cells in purified Human Peripheral Blood. Mononuclear Cell samples. Purified HPBMC were stained with different MHC (peptide) molecules attached to APC labeled dextran270 multimerization domain and analyzed by flow cytometry. See example 30 for details on experimental procedures. 5 different MHC (peptide) molecules were investigated. Construct 1: HLA-A*0201(GLAGDVSAV (SEQ ID NO:11)), construct 2: HLA-A*0201(ALIAPVHAV (SEQ ID NO:12)), construct 3: HLA-A*0201(NLVPM- VATV SEQ ID NO:9), construct 4: HLA-A*0201(GLCTL-VAML (SEQ ID NO:13)) and construct 5: HLA-A*0201 (ILKEPVHGV (SEQ ID NO:10)). A positive staining is symbolized with a (+) and is here defined as the identification of a distinct CD8 positive and MHC (peptide) positive population when visualized in a dot plot (se FIG. 8). Negative staining is symbolized wit a (−) and is defined as absence of a distinct CD8 positive and MHC (peptide) positive population when visualized in a dot plot. Nt means not determined. All samples have previously been analyzed for the presence of T-cells restricted by HLA-A*0201 (NLVPMVATV (SEQ ID NO:9)), HLA-A*0201 (GLCTL-VAML (SEQ ID NO:13)) and HLA-A*0201(ILKEPVHGV) and these results are shown in italics in the figure (column 2 and 3).

FIG. 10. Gating strategy for 'no-lyse no-wash'-procedure. Whole blood was stained with MHC multimer, anti-CD8/APC, anti-CD3/PB and CD45/CY antibody in a no-lyse no-wash procedure. For further details see text in example 37. During analysis of data the following gating strategy was used: CD45/PB antibody was used to set a trigger discriminator to allow the flow cytometer to distinguish between red blood cells and stained white blood cells. This was done during data collection by gating on CD45/PB positive cells in a CD45/PB vs. side scatter dot plot as shown in A. After data collection and during data analysis CD3 positive cells were selected by gating CD3/FITC positive cells in a CD3/FITC vs side scatter plot as shown in B. The final data was illustrated in a MHC multimer/PE vs CD8/APC plot (see FIG. 11).

FIG. 11. Identification of CMV-specific T-cells in a blood sample using 'no-lyse no-wash'-procedure. Whole blood from three different donors were analysed for the presence of CMV-specific T-cells by flow cytometry using a no-lyse no-wash procedure. Donor 1 was stained with a MHC multimer consisting of PE-conjugated 270 kDa dextran coupled with HLA-A*0201 in complex with beta2microglobulin and the peptide NLVPMVATV (SEQ ID NO:9) derived from Human Cytomegalo Virus (HCMV) (left panel) and with a negative control MHC multimer consisting of PE conjugated 270 kDa dextran coupled with HLA-A*0201 in complex with beta2microglobulin and the peptide ILKEPVHGV (SEQ ID NO:10) derived from Human Immunodeficiency Virus (HIV) (right panel). Donor 2 was stained with a MHC multimer consisting of PE-conjugated 270 kDa dextran coupled with HLA-A*0101 in complex with beta2microglobulin and the peptide VTEHDTLLY (SEQ ID NO:14) derived from Human Cytomegalo Virus (HCMV) (left panel) and a negative control MHC multimer consisting of PE-conjugated 270 kDa dextran coupled with HLA-A*0101 in complex with beta2microglobulin and the peptide IVDCLTEMY (SEQ ID NO:15) derived from ubiquitin specific peptidase 9 (USP9) (right panel). Donor 3 was stained with twoMHC multimers consisting of PE conjugated 270 kDa dextran coupled with HLA-B*0207 in complex with beta2microglobulin and either of the peptides TPRVTGGGAM (SEQ ID NO:16) (left panel) or RPHERNGFTVL (SEQ ID NO:17) (center panel) both derived from Human Cytomegalo Virus (HCMV) and with a negative control MHC multimer consisting of PE-conjugated 270 kDa dextran coupled with HLA-B*0207 in complex with beta2microglobulin and the peptide TPGPGVRYPL (SEQ ID NO:18) derived from Human Immunodeficiency Virus (HIV) (right panel). All samples were also added Anti-CD45/PB, anti-CD3/FITC and anti-CD8/APC antibodies. The samples were gated as shown in FIG. 10.

FIG. 12. Enumeration of specific T-cells using Cyto-Count™ beads. Whole blood from a human donor were analysed for the presence of CMV-specific T-cells with MHC multimers by flow cytometry using a no-lyse no-wash procedure. 2×100 μl donor blood was analysed with two different MHC multimers: A) PE-conjugated 270 kDa dextran coupled with HLA-A*0101 in complex with beta2microglobulin and the peptide VTEHDTLLY (SEQ ID NO:14) derived from Human Cytomegalo Virus (HCMV) and a negative control construct B) consisting of PE-conjugated 270 kDa dextran coupled with HLA-A*0101 in complex with beta2microglobulin and the peptide IVDCLTEMY (SEQ ID NO:15) derived from ubiquitin specific peptidase 9 (USP9). To each sample Anti-CD45/CY, anti-CD3/APC and anti-CD8/PB antibody was added together with 50 μl CytoCount beads (1028 beads/I). Following staining for 15 minutes PBS was added to 1 ml and the samples analysed on a CYAN flow cytometer. During analysis CD45/CY antibody was used to set a trigger discriminator to allow the flow cytometer to distinguish between red blood cells and stained white blood cells and CD3/APC antibody was used to gate for CD3 positive T lymphocytes. Amount of counted beads in sample A are shown in the histogram C and amount of beads counted in the negative control sample B are show in histogram D. Concentration of HLA-A*0101(VTEHDTLLY SEQ ID NO:14) specific T-cells in the blood sample was determined as follows: ((count of MHC multimer+CD8+ cells in A×concentration of beads×dilution factor of beads)/counted beads C))− ((counted MHC multimer+CD8+ cells in B×concentration of beads×dilution factor of beads)/counted beads D)=((1300 cells×1028 beads/μl×0.05)/67225 beads)~((2 cells×1028 beads/μl×0.05)/72623 beads)=0,9926 cells/μl=992.6 cells/ml.

FIG. 13. MHC dextramers can be embedded in a sugar matrix together with antibodies and used for detection of specific T-cells in a blood sample. MHC dextramer constructs was embedded in a sugar matrix together with relevant gating reagents (anti-CD3/Pacific Blue, anti-CD8/Alexa700 and anti-CD45/Cascade Yellow antibodies) and the matrix dried. Then EDTA stabilized blood from a human donor were added and the samples analyzed by flow cytometry. Two different MHC construct were used HLA-A*0101 (VTEHDTLLY SEQ ID NO:14)/PE dextramer (A) and the negative control construct HLA-A*0101(IVDCLTEMY SEQ ID NO:15)/PE (B). As a control antibodies and MHC dextramer constructs were used to stain blood from the same donor following a general staining procedure without embedding the antibodies and MHC dextramers in a sugar matrix as described elsewhere herein. (C) Staining with HLA-A*0101(VTEHDTLLY (SEQ ID NO:14))/PE dextramer following a normal staining procedure and (D) Staining with HLA-A*0101(IVDCLTEMY SEQ ID NO:15)/PE dextramer following a normal staining procedure.

FIG. 14. Composition of FLUORESCEIN™-linker molecule. (A) Schematic representation of an example of a FLUORESCEIN™-linker molecule. (B) Composition of a L15 linker.

FIG. 15. Flow cytometry analysis of human blood sample using MHC dextramers where the MHC molecules are chemically biotinylated. Human peripheral blood lymphocytes were FICOLL® purified from a human donor and stained with either of the MHC dextramer constructs HLA-A*0201/NLVPMVATV (SEQ ID NO:9)/APC or the negative control construct HLA-A*0201/ GLAGDVSAV (SEQ ID NO:11)/APC together with mouse-anti-human CD3/PE, mouse-anti-human CD8/PB and mouse-anti-human CD4/FITC antibodies. Following staining the sample was analysed on a CYAN flow cytometer. Live-gated and CD3 positive lymphocytes are shown. Positive staining of T-cells directed against HLA-A*0201/ NLVPMVATV (SEQ ID NO:9) dextramer are shown left and negative staining with HLA-A*0201/GLAGDVSAV (SEQ ID NO:11) MHC dextramer is shown right. MHC dextramers were generated as follows: MHC-peptide complexes were made by in vitro refolding of heavy chain and β2m together with peptide and then the complexes were chemically biotinylated. Biotinylated complexes were coupled to a 270 kDa dextran multimerization domains containing Streptavidin (SA) and APC.

FIG. 16. Detection of antigen specific T cells using MHC multimer constructs simultaneously with activation and intracellular staining of cytokines. The figures illustrate IFN-γ versus Pentamer staining of live lymphocytes I a blood sample from a human donor. PBMCs were incubated with either a negative control (non-specific) Pentamer (A*0201/EBV (GLCTLVAML (SEQ ID NO:13))) or a Pentamer specific for the cells of interest (B*0801/EBV (RAKFKQLL SEQ ID NO:19)), then stimulated with LAC (non-specific activation) or B*0801/EBV peptide (specific peptide activation) for 15 hours in the presence of Brefeldin A. Fixation, permeabilization and staining for IFN-γ were carried out exactly as detailed in the protocol in example 55.

FIG. 17. Detection of *Borrelia* specific T cells in sample from human donor. Human peripheral blood lymphocytes were FICOLL® purified and stained with either of a pool of MHC/APC dextramer molecule constructs containing peptides derived from *Borrelia* antigen Osp A and FlaB or the cells were stained with the negative control construct HLA-A*0201/GLAGDVSAV (SEQ ID NO:11)/APC. Both samples were also stained with the antibodies mouse-anti-human CD3/PB (clone UCHT1 from Dako), mouse-anti-human CD4/FITC (clone MT310 from Dako) and mouse-anti-human CD8/PE (clone DK25 from Dako). Following staining the sample was analysed on a CYAN flow cytometer. Live-gated, CD4 negative and CD3 positive lymphocytes are shown. Dot plots showing live gated CD3$^+$/CD4$^-$ lymphocytes from *Borrelia* patient stained with (A) Negative Control MHC Dextramer (HLA-A*0201 (GLAGDVSAV (SEQ ID NO:11)) or (B) pool of MHC Dextramers containing peptides from *Borrelia* antigen Osp A and Fla B pool of MHC Dextramers containing peptides from *Borrelia* antigen are shown. 0.05% of the live gated CD3$^+$/CD4$^-$ lymphocytes are positive for one or more of the MHC Dextramers in the pool.

FIG. 18. HLA-typing using HLA-specific antibodies.

Human peripheral blood lymphocytes were FICOLL® purified from two donors, donor 1 and donor 2. Samples of cells from each donor were stained with PE-labeled anti-HLA-A*02 and anti-HLA-A*03 antibodies respectively and then analysed on a flow cytometer. As a control unstained cell samples from each donor was also analysed. Cells were gated using a lymphocyte gate in a FCS/SSC plot and the presence of PE positive staining was determined in each sample. As shown by the histogram plots in the figure, donor 1 was positive for HLA-A*02 and negative for HLA-A*03 and donor 2 was negative for HLA-A*02 and positive for HLA-A*03.

DETAILED DESCRIPTION OF THE INVENTION

Design, Generation and Use of MHC Multimers

As used in the description of this invention, the term "MHC multimers" will be used interchangeably with the terms MHC'mers and MHCmers, and will include any number, (larger than one) of MHC-peptide complexes, held together in a large complex by covalent or non-covalent interactions between one or more multimerization domain(s) and one or more MHC-peptide complexes. MHC multimers thus include MHC-dimers, MHC-tetramers, MHC-tetramers, MHC-pentamers, MHC-hexamers, as well as organic molecules, cells, membranes, polymers and particles that comprise two or more MHC-peptide complexes. Example organic molecule-based multimers include functionalized cyclic structures such as benzene rings where e.g. a benzene ring is functionalized and covalently linked to e.g. three MHC complexes; example cell-based MHC multimers include dendritic cells and antigen presenting cells (APCs); example membrane-based MHC multimers include liposomes and micelles carrying MHC-peptide complexes in their membranes; example polymer-based MHC multimers include MHC-dextramers (dextran to which a number of MHC-peptide complexes are covalently or non-covalently attached) and example particles include beads or other solid supports with MHC complexes immobilized on the surface. Obviously, any kind of multimerization domain can be used, including any kind of cell, polymer, protein or other molecular structure, or particles and solid supports.

Different approaches to the generation of various types of MHC multimers are described in U.S. Pat. No. 5,635,363 (Altmann et al.), patent application WO 02/072631 A2 (Winther et al.), patent application WO 99/42597, US patent application 2004209295, U.S. Pat. No. 5,635,363, and is described elsewhere in the present patent application as well. In brief, MHC multimers can be generated by first expressing and purifying the individual protein components of the MHC protein, and then combining the MHC protein components and the peptide, to form the MHC-peptide complex. Then an appropriate number of MHC-peptide complexes are linked together by covalent or non-covalent bonds to one or more multimerization domain(s). This can be done by chemical reactions between reactive groups of the multimerization domain (e.g. vinyl sulfone functionalities on a dextran polymer) and reactive groups on the MHC protein (e.g. amino groups on the protein surface), or by non-covalent interaction between a part of the MHC protein (e.g. a biotinylated peptide component) and the multimerization domain (e.g. four binding sites for biotin on the strepavidin tetrameric protein). As an alternative, the MHC multimer can be formed by the non-covalent association of amino acid helices fused to one component of the MHC protein, to form a pentameric MHC multimer, held together by five helices in a coiled-coil structure making up the multimerization domain(s).

Appropriate chemical reactions for the covalent coupling of MHC and the multimerization domain(s) include nucleophilic substitution by activation of electrophiles (e.g. acylation such as amide formation, pyrazolone formation, isoxazolone formation; alkylation; vinylation; disulfide formation), addition to carbon-hetero multiple bonds (e.g. alkene formation by reaction of phosphonates with aldehydes or ketones; arylation; alkylation of arenes/hetarenes by reaction with alkyl boronates or enolethers), nucleophilic substitution using activation of nucleophiles (e.g. condensations; alkylation of aliphatic halides or tosylates with enolethers or enamines), and cycloadditions.

Appropriate molecules, capable of providing non covalent interactions between the one or more multimerization domain and the MHC-peptide complex, involve the following molecule pairs and molecules: streptavidin/biotin, avidin/biotin, antibody/antigen, DNA/DNA, DNA/PNA, DNA/RNA, PNA/PNA, LNA/DNA, leucine zipper e.g. Fos/Jun, IgG dimeric protein, IgM multivalent protein, acid/base coiled-coil helices, chelate/metal ion-bound chelate, streptavidin (SA) and avidin and derivatives thereof, biotin, immunoglobulins, antibodies (monoclonal, polyclonal, and recombinant), antibody fragments and derivatives thereof, leucine zipper domain of AP-1 (jun and fos), hexa-his (metal chelate moiety), hexa-hat GST (glutathione S-transferase) glutathione affinity, Calmodulin-binding peptide (CBP), STREP-TAG®, Cellulose Binding Domain, Maltose Binding Protein, S-Peptide Tag, Chitin Binding Tag, Immunoreactive Epitopes, Epitope Tags, E2Tag, HA Epitope Tag, Myc Epitope, FLAG Epitope, AU1 and AU5 Epitopes, Glu-Glu Epitope, KT3 Epitope, IRS Epitope, Btag Epitope, Protein Kinase-C Epitope, VSV Epitope, lectins that mediate binding to a diversity of compounds, including carbohydrates, lipids and proteins, e.g. Con A (Canavalia ensiformis) or WGA (wheat germ agglutinin) and tetranectin or Protein A or G (antibody affinity). Combinations of such binding entities are also comprised. In particular, when the MHC complex is tagged, the multimerization domain(s) can be an "anti-tag". By "anti-tag" is meant an antibody binding to the tag and any other molecule capable of binding to such tag.

The MHC multimers can be used in a number of applications, including analyses such as flow cytometry, immunohistochemistry (IHC), and ELISA-like analyses, and can be used for diagnostic, prognostic or therapeutic purposes including autologous cancer therapy or vaccines such as HIV vaccine or cancer vaccine. The MHC multimers can be labelled with one or more fluorophores and used in flow cytometry. MHC multimers can be used to label T-cells carrying specific T-cell receptors (TCR). For IHC, the MHC multimers can be labelled with chromophores, in order to specifically stain specific T-cells carrying TCRs that specifically bind the MHC multimer in question.

ELISA and ELISA-like analyses can be performed with MHC multimers that are labelled with e.g. chromophores, fluorophores or enzymes. For the purpose of making cancer vaccines or other types of vaccines it can be desirable to employ MHC multimers that comprise a polymer such as dextran, or that are cell-based (e.g. specialized dendritic cells such as described by Banchereau and Palucka, Nature Reviews, Immunology, 2005, vol. 5, p. 296-306).

In one embodiment the multimerization domain(s) in the present invention is preferable less than 1,000 Da (small molecule scaffold). In another embodiment the multimerization domain(s) is preferable between 1,000 Da and 10,000 Da (small molecule scaffold, small peptides, small polymers). In another embodiment the multimerization domain(s) is between 10,000 Da and 100,000 Da (Small molecule scaffold, polymers e.g. dextran, streptavidin, IgG, pentamer structure). In another embodiment the multimerization domain(s) is preferable between 100,000 Da and 1,000,000 Da (Small molecule scaffold, polymers e.g. dextran, streptavidin, IgG, pentamer structure). In another embodiment the multimerization domain(s) is preferable larger than 1,000, 000 Da (Small molecule scaffold, polymers e.g. dextran, streptavidin, IgG, pentamer structure, cells, liposomes, artificial lipid bi layers, polystyrene beads and other beads.

In one preferred embodiment the MHC multimer is between 50,000 Da and 1,000,000 Da, such as from 50,000 Da to 980,000; for example from 50,000 Da to 960,000; such as from 50,000 Da to 940,000; for example from 50,000 Da to 920,000; such as from 50,000 Da to 900,000; for example from 50,000 Da to 880,000; such as from 50,000 Da to 860,000; for example from 50,000 Da to 840,000; such as from 50,000 Da to 820,000; for example from 50,000 Da to 800,000; such as from 50,000 Da to 780,000; for example from 50,000 Da to 760,000; such as from 50,000 Da to 740,000; for example from 50,000 Da to 720,000; such as from 50,000 Da to 700,000; for example from 50,000 Da to 680,000; such as from 50,000 Da to 660,000; for example from 50,000 Da to 640,000; such as from 50,000 Da to 620,000; for example from 50,000 Da to 600,000; such as from 50,000 Da to 580,000; for example from 50,000 Da to 560,000; such as from 50,000 Da to 540,000; for example from 50,000 Da to 520,000; such as from 50,000 Da to 500,000; for example from 50,000 Da to 480,000; such as from 50,000 Da to 460,000; for example from 50,000 Da to 440,000; such as from 50,000 Da to 420,000; for example from 50,000 Da to 400,000; such as from 50,000 Da to 380,000; for example from 50,000 Da to 360,000; such as from 50,000 Da to 340,000; for example from 50,000 Da to 320,000; such as from 50,000 Da to 300,000; for example from 50,000 Da to 280,000; such as from 50,000 Da to 260,000; for example from 50,000 Da to 240,000; such as from 50,000 Da to 220,000; for example from 50,000 Da to 200,000; such as from 50,000 Da to 180,000; for example from 50,000 Da to 160,000; such as from 50,000 Da to 140,000; for example from 50,000 Da to 120,000; such as from 50,000 Da to 100,000; for example from 50,000 Da to 80,000; such as from 50,000 Da to 60,000; such as from 100,000 Da to 980,000; for example from 100,000 Da to 960,000; such as from 100,000 Da to 940,000; for example from 100,000 Da to 920,000; such as from 100,000 Da to 900,000; for example from 100,000 Da to 880,000; such as from 100,000 Da to 860,000; for example from 100,000 Da to 840,000; such as from 100,000 Da to 820,000; for example from 100,000 Da to 800,000; such as from 100,000 Da to 780,000; for example from 100,000 Da to 760,000; such as from 100,000 Da to 740,000; for example from 100,000 Da to 720,000; such as from 100,000 Da to 700,000; for example from 100,000 Da to 680,000; such as from 100,000 Da to 660,000; for example from 100,000 Da to 640,000; such as from 100,000 Da to 620,000; for example from 100,000 Da to 600,000; such as from 100,000 Da to 580,000; for example from 100,000 Da to 560,000; such as from 100,000 Da to 540,000; for example from 100,000 Da to 520,000; such as from 100,000 Da to 500,000; for example from 100,000 Da to 480,000; such as from 100,000 Da to 460,000; for example from 100,000 Da to 440,000; such as from 100,000 Da to 420,000; for example from 100,000 Da to 400,000; such as from 100,000 Da to 380,000; for example from 100,000 Da to 360,000; such as from 100,000 Da to 340,000; for example from 100,000 Da to 320,000; such as from 100,000 Da to 300,000; for example from 100,000 Da to 280,000; such as from 100,000 Da to 260,000; for example from 100,000 Da to 240,000; such as from 100,000 Da to 220,000; for example from 100,000 Da to 200,000; such as from 100,000 Da to 180,000; for example from 100,000 Da to 160,000; such as from 100,000 Da to 140,000; for example from 100,000 Da to 120,000; such as from 150,000 Da to 980,000; for example from 150,000 Da to 960,000; such as from 150,000 Da to 940,000; for example from 150,000 Da to 920,000; such as from 150,000 Da to 900,000; for example from 150,000 Da to 880,000; such as from 150,000 Da to 860,000; for example from 150,000 Da to 840,000; such as from 150,000 Da to 820,000; for example from 150,000 Da to 800,000; such as from 150,000 Da to 780,000; for example from 150,000 Da to 760,000; such as from 150,000 Da to 740,000; for example from 150,000 Da to 720,000; such as from 150,000 Da to 700,000; for example from 150,000 Da to 680,000; such as from 150,000 Da to 660,000; for example from 150,000 Da to 640,000; such as from 150,000 Da to 620,000; for example from 150,000 Da to 600,000; such as from 150,000 Da to 580,000; for example from 150,000 Da to 560,000; such as from 150,000 Da to 540,000; for example from 150,000 Da to 520,000; such as from 150,000 Da to 500,000; for example from 150,000 Da to 480,000; such as from 150,000 Da to 460,000; for example from 150,000 Da to 440,000; such as from 150,000 Da to 420,000; for example from 150,000 Da to 400,000; such as from 150,000 Da to 380,000; for example from 150,000 Da to 360,000; such as from 150,000 Da to 340,000; for example from 150,000 Da to 320,000; such as from 150,000 Da to 300,000; for example from 150,000 Da to 280,000; such as from 150,000 Da to 260,000; for example from 150,000 Da to 240,000; such as from 150,000 Da to 220,000; for example from 150,000 Da to 200,000; such as from 150,000 Da to 180,000; for example from 150,000 Da to 160,000.

For all applications, it is important to choose the right MHC allele as well as a peptide that binds well to the MHC protein. It is also important that the chosen MHC allele and peptide forms a MHC-peptide complex that is efficiently and specifically recognized by the TCR. For applications that involve binding as well as activation of cells, further restrictions on the choice of MHC and peptide can apply.

The peptide P in the MHC-peptide complexe(s) can be any natural or non-natural peptide capable of being presented by the MHC complex in question. In one embodiment, the peptide P is a peptide disclosed in U.S. 60/907, 217, the text of which is hereby incorporated by reference herein in its entirety.

Synthesis of MHC Multimers with Different Multimerization Domains

The MHC Multimer

One of the benefits of the MHC multimers of the present invention is clearly that the MHC multimers overcome low intrinsic affinities of monomer ligands and counter receptors. It should be noted, however, that such MHC multimers can have a large variety of applications that include targeting of high affinity receptors (e. g. hormone peptide receptors for insulin) on targeT-cells. Taken together, poly-ligand binding to target T-cells does have practical, clinical and scientifically uses of immediate commercial interest.

Thus, the present invention provides constructs of MHC molecules, which present multi-valent binding sites for MHC recognising cells. The constructs of the present invention have highly advantageous properties and are an important tool with a broad range of valuable uses.

Thus, in a first aspect, the present invention relates to MHC molecule construct comprising one or more multimerization domain(s) having attached thereto one or more MHC molecules, said MHC molecules being attached to the one or more multimerization domain(s) either directly or via one or more binding entities. This applies i.e. to the MHC molecule and the one or more multimerization domain(s). The multimerization domain(s) can thus have attached thereto a MHC molecule or a plurality of MHC molecules, and/or a multimerization domain or a plurality of binding entities. When a plurality of MHC molecules is attached to the multimerization domain(s), the number can only be limited by the capacity of the multimerization domain(s) or the binding entity, as the case can be. The number of binding entities can only be limited by the capacity and nature of the multimerization domain(s).

Depending on the use of the MHC multimers of the present invention, the construct as such can be provided in soluble or non-soluble form by carefully selecting the multimerization domain(s). Both the soluble and the non-soluble format display the advantageous properties.

A "MHC Class I molecule" as used everywhere herein is defined as a molecule which comprises 1-3 subunits, including a heavy chain, a heavy chain combined with a light chain (ß12m), a heavy chain combined with a light chain (D2m) through a flexible linker, a heavy chain combined with a peptide, a heavy chain combined with a peptide through a flexible linker, a heavy chains dimer combined with a peptide, and a heavy chain/P2m dimer with a peptide through a flexible linker to the heavy or light chain. The MHC molecule chain can be changed by substitution of single or by cohorts of native amino acids or by inserts, or deletions to enhance or impair the functions attributed to said molecule. By example, it has been shown that substitution of XX with YY in position nn of human P2m enhance the biochemical stability of MHC Class I molecule complexes and thus can lead to more efficient antigen presentation of subdominant peptide epitopes.

A "MHC Class II molecule" as used everywhere herein is defined as a molecule which comprises 2-3 subunits including an a-chain and a P-chain (oc/ß-dimer), an axa dimer with a peptide, and an axa dimer combined with a peptide through a flexible linker to the a or p chain, an a/p dimer combined through an interaction by affinity tags e. g. jun-fos, an oc/ß dimer combined through an interaction by affinity tags e.g. jun-fos and further combined with a peptide through a flexible linker to the a or ß chain. The MHC molecule chains can be changed by substitution of single or by cohorts of native amino acids or by inserts, or deletions to enhance or impair the functions attributed to said molecule.

MHC Class I like molecules (including non-classical MHC Class I molecules) include CDId, HLA E, HLA G, HLA F, HLA H, MIC A, MIC B, ULBP-1, ULBP-2, and ULBP-3.

MHC Class II like molecules (including non-classical MHC Class II molecules) include HLA DM, HLA DO, I-A beta2, and I-E beta2.

The MHC molecule can suitably be a vertebrate MHC molecule such as a human, a mouse, a rat, a porcine, a bovine or an avian MHC molecule. Such MHC molecules from different species have different names. E. g. in humans, MHC molecules are denoted HLA. The person skilled in the art will readily know the name of the MHC molecules from various species.

In general, the term "MHC molecule" is intended to include alleles. By way of example, in humans e. g. HLA A, HLA B, HLA C, HLA D, HLA E, HLA F, HLA G, HLA H, HLA DR, HLA DQ and HLA DP alleles are of interest, and in the mouse system, H-2 alleles are of interest. Likewise, in the rat system RT1-alleles, in the porcine system SLA-alleles, in the bovine system BoLA, in the avian system e. g. chicken-B alleles, are of interest.

The definition of the MHC molecule construct of the present invention enables various valuable possibilities as regards the MHC molecules. Thus, examples of valuable MHC multimers are such wherein at least two of the MHC molecules are different, wherein the MHC molecules are the same, wherein at least two of the peptides harboured by the MHC molecules are different, wherein the peptides harboured by the MHC molecules are the same, wherein the peptides harboured by the MHC molecules are chemically modified or synthesised to contain not natural amino acids, or to contain hydrophilic or hydrophobic groups, wherein the peptides harboured by the MHC Class I molecules are linked to the MHC Class I heavy chain by a flexible linker, wherein the peptides harboured by the MHC Class I molecules are linked to the MHC Class I light chain (ß2m) by a flexible linker, wherein the peptides are harboured by MHC Class I molecules comprising MHC Class I heavy chain in association with a light chain (ß2m) by a flexible linker, wherein the peptide harboured by the MHC Class II molecules are linked to the alpha-chain by a flexible linker, wherein the peptide harboured by the MHC Class II molecules are linked to the p-chain by a flexible linker, wherein the MHC Class I molecules are mutated, wherein the MHC Class II molecules are mutated.

The above list is not exhaustive in any way, but out-lines a number of valuable possibilities.

In particular, if the peptides harboured by a plurality of MHC molecules are different from each other, such can be used to detect several types of MHC recognising cells simultaneously. This can be achieved either by employing one MHC molecule construct with MHC molecules filled with different peptides, or by employing several MHC molecule constructs, where each MHC molecule construct have MHC molecules with the same type of peptide, e. g. one MHC molecule construct displaying one peptide, and another MHC molecule construct displaying another peptide.

In one embodiment of the MHC multimers of the present invention, the one or more MHC molecules are attached to the multimerization domain(s) directly. In another embodiment, the one or more MHC molecules are attached to the multimerization domain(s) via one or more binding entities.

When the MHC molecules are attached via one or more binding entities, each binding entity suitably has attached thereto from 1 to 10, such as from 1 to 8, from 1 to 6, from 1 to 4, from 1 to 3, or 1 or 2 MHC molecules. However, it is to be understood that the possible number of MHC molecules depends on the binding entity in question (i. e. how many MHC molecules that can be attached). Thus, by choosing the binding entity carefully, it can be possible to attach more than 10 MHC molecules to each binding entity. However, it is to be understood that this number can be the average number of MHC molecules attached to each binding entity. Thus, the number of MHC molecules can be evenly or unevenly distributed on the binding entity as the MHC multimers are most often made and purified with a certain desired weight distribution. Thus, the average number needs not be an integer, but can be anything between two integers (i.e. a decimal number), e. g. 2.8, 4.7 or 5.3, to mention a few, non-limiting examples.

The total number of MHC molecules of the MHC molecule construct is in principle unlimited. Thus, the total number of MHC molecules of the construct can suitably be at least 4, at least 5, at least 6, at least 7, at least 8, at least 9, at least 10, at least 12, at least 16, at least 20, at least 24, at least 28, at least 32, or at least 64. In particular, the total number of MHC molecules of the construct can be within from 1 to 100000, within from 1 to 95, within from 1 to 90, within from 1 to 85, within from 1 to 80, within from 1 to 75, within from 1 to 70, within from 1 to 65, within from 1 to 60, within from 1 to 55, within from 1 to 50, within from 1 to 45, within from 1 to 40, within from 1 to 35, within from 1 to 30, within from 1 to 25, within from 1 to 20, within from 1 to 15, within from 1 to 10, within from 1 to 5, within from 1 to 4, within from 1 to 3, or 1 or 2.

A non-exhaustive list of possible MHC mono- and multimers illustrates the possibilities. n indicates the number of MHC complexes comprised in the multimer:

| a) n = 1, | Monomers |
| b) n = 2, | Dimers, multimerization can be based on IgG scaffold, SA with two MHC's, coiled-coil dimerization e.g. Fos.Jun dimerization |
| c) n = 3, | Trimers, multimerization can be based on SA as scaffold with three MHC's, TNFalpha-MHC hybrids, triplex DNA-MHC konjugates or other trimer structures |
| d) n = 4, | Tetramers, multimerization can be based on SA with all four binding sites occupied by MHC molecules or on dimeric IgA |
| e) n = 5, | Pentamers, multimerization can take place around a pentameric coil-coil structure |
| f) n = 6, | Hexamers |
| g) n = 7, | Heptamers |
| h) n = 8-12, | Octa- dodecamers, multimerization can take place using Streptactin |
| i) n = 10, | Decamers, multimerization could take place using IgM |
| j) 1 < n < 100, | Dextramers, as multimerization domain polymers such as polypeptide, polysaccharide and Dextrans can be used |
| k) 1 < n < 1000, | Multimerization make use of DC, APC, micelles, liposomes, beads, surfaces surfaces e.g. microtiterplate, tubes, microarray devices, micro-fluidic systems |
| l) 1 < n, | n in billions or trillions or higher, multimerization take olace on beads, and surfaces e.g. microtiterplate, tubes, microarray devices, micro-fluidic systems |

The total number of MHC molecules of the MHC molecule construct is in principle unlimited. Thus, the total number of MHC molecules of the construct can suitably be in the range from 100 MHC molecules to 1,000,000 MHC molecules such as from 100 to 1,000 MHC molecules, for example from 1,000 to 5,000 MHC molecules, such as from 5,000 to 10,000 MHC molecules, for example from 10,000 to 20,000 MHC molecules, such as from 20,000 to 30,000 MHC molecules, for example from 30,000 to 40,000 MHC molecules, such as from 40,000 to 50,000 MHC molecules, for example from 50,000 to 60,000 MHC molecules, such as from 60,000 to 70,000 MHC molecules, for example from 70,000 to 80,000 MHC molecules, such as from 80,000 to 90,000 MHC molecules, for example from 90,000 to 100, 000 MHC molecules, such as from 100,000 to 200,000 MHC molecules, for example from 200,000 to 300,000 MHC molecules, such as from 300,000 to 400,000 MHC molecules, for example from 400,000 to 500,000 MHC molecules, such as from 500,000 to 600,000 MHC molecules, for example from 600,000 to 700,000 MHC molecules, such as from 700,000 to 800,000 MHC molecules, for example from 800,000 to 900,000 MHC molecules, such as from 900,000 to 1,000,000 MHC molecules.

The number of MHC molecules can be evenly or unevenly distributed among a plurality of MHC molecule constructs. Thus, the average number needs not be an integer, but can be any number between two integers (i.e. a decimal number), e. g. 28.4, 44.5 or 57.2, to mention a few, non-limiting examples.

The binding entity is any such suited for attachment of the MHC molecules, while rendering the MHC molecules capable of binding to MHC recognising cells. Examples of suitable binding entities are streptavidin (SA) and avidin and derivatives thereof, biotin, immunoglobulins, antibodies (monoclonal, polyclonal, and recombinant), antibody fragments and derivatives thereof, leucine zipper domain of AP-1 (Jun and fos), hexa-his (metal chelate moiety), hexa-hat GST (glutathione S-tranferase) glutathione affinity, Calmodulin-binding peptide (CBP), STREP-TAG®, Cellulose Binding Domain, Maltose Binding Protein, S-Peptide Tag, Chitin Binding Tag, Immuno-reactive Epitopes, Epitope Tags, E2Tag, HA Epitope Tag, Myc Epitope, FLAG Epitope, AU1 and AU5 Epitopes, Glu-Glu Epitope, KT3 Epitope, IRS Epitope, Btag Epitope, Protein Kinase-C Epitope, VSV Epitope, lectins that mediate binding to a diversity of compounds, including carbohydrates, lipids and proteins, e. g. Con A (Canavalia *ensiformis*) or WGA (wheat germ agglutinin) and tetranectin or Protein A or G (antibody affinity) or coiled-coil polypeptides e.g. leucine zipper.

Combinations of such binding entities are also comprised. Non-limiting examples are streptavidin-biotin and jun-fos and other leucine zipper like structures. In particular, when the MHC molecule is tagged, the binding entity can be an "anti-tag". By "anti-tag" is meant an antibody binding to the tag and any other molecule capable of binding to such tag.

The number, density, and nature of the binding entities can vary for each multimerization domain(s). It is to be understood that the binding entity can be attached to the multimerization domain(s) by a linker. Suitable linkers include Calmodulin-binding peptide (CBP), 6×HIS, Protein A, Protein G, biotin, Avidin, Streptavidin, STREP-TAG®, Cellulose Binding Domain, Maltose Binding Protein, S-Peptide Tag, Chitin Binding Tag, Immuno-reactive Epitopes, Epitope Tags, GST tagged proteins, E2Tag, HA Epitope Tag, Myc Epitope, FLAG Epitope, AU1 and AU5 Epitopes, Glu-Glu Epitope, KT3 Epitope, IRS Epitope, Btag Epitope, Protein Kinase-C Epitope, VSV Epitope or any other linker as described elsewhere herein.

The one or more MHC molecules can suitably be attached to the binding entity by tags. Examples of tags are given above under the definition of suitable binding entities. Thus, MHC molecules being recombinantly tagged or chemically tagged bind specifically to the binding entity due to high affinity. The recombinant tags of MHC molecules furthermore allow regio-specific attachment sites in the constructs. The tags can be located at any part of the MHC molecule, but it is presently believed that the tags should preferably be located away from the cell binding part of the MHC molecule. By way of example, a tagged MHC molecule could be a recombinant MHC fusion molecule consisting of MHC Class I heavy chain molecule and a C-terminal target peptide sequence for enzymatic mono-biotinylation. The C-terminal location of the affinity tag allows optimal exposure of the N-terminal cell binding part of the MHC molecule. It is presently believed that target sequences for biotinylation also can be located at P2M molecules.

Chemically biotinylated MHC protein binds to a streptavidin binding entity. Biotinylated MHC molecule binds to streptavidin with high affinity. The ratio of MHC molecules per streptavidin is theoretically 4:1 due to four biotin-binding sites in streptavidin complexes.

Generation of Components of MHC-Peptide Complexes

MHC-peptide complexes in multimers of the present invention can be of any of the below mentioned origins. The list is non-exhaustive. A complete list would encompass all Chordate species. By origin is meant that the sequence is identical or highly homologous to a naturally occurring sequence of the specific species.

List of origins:

Human

Mouse

Primate

Chimpansee

Gorilla

Orang Utan

Monkey

Macaques

Porcine (Swine/Pig)

Bovine (Cattle/Antilopes)

Equine (Horse)

Camelides (Camels)

Ruminants (Deears)

Canine (Dog)

Feline (Cat)

Bird

Chicken

Turkey

Fish

Reptiles

Amphibians

The MHC complexes in MHC multimers of the present invention may be MHC I complexes, MHC II complexes, MHC like molecule or other TCR binding molecules as described elsewhere herein. The polypeptide chains of the MHC complexes can be from the same or different species. The MHC-peptide complexes may be a natural part of the MHC multimer, or may be generated separately and then combined with the multimerization domain.

Example MHC multimers where the MHC-peptide complexes are a natural part of the MHC multimer include:

MHC expressing cells of natural origin like dendritic cells, B-cells, Macrophages, other professional antigen presenting cells, NK cells, T-cells, granolycetes, other nucleated cells or any cell naturally expressing MHC-peptide molecules Cell or cell lines transfected with MHC encoding genes, including but not limited to mammalian cells, bacterial cell, insecT-cells, yeasT-cells Hybridoma cell lines Phages or virions expressing MHC molecules on their surface. Genes encoding MHC complexes may be fused to genes encoding surface proteins of the phages thereby creating a fusion protein enabling the phage to express MHC molecules on their surface fused to one or more coat proteins Liposomes or micelles made from MHC expressing cells Individual MHC-peptide complexes may be generated as whole molecules by elution from cells expressing MHC molecules or the individual polypeptide chains may be produced separately and then combined with peptide. Principles for generation of individual MHC I and MHC II molecules are described below.

Generation of MHC I and MHC II Polypeptide Chains

MHC class I and/or MHC II can be obtained from a variety of sources involving different methods:

a) Natural sources by means of purification from eukaryotic cells naturally expressing the MHC class I and/or MHC II molecules.

b) MHC molecules can be generated by recombinant methods e.g. using a. in vitro translation of mRNA obtained from cells naturally expressing MHC I and/or II b. Expression and isolation of MHC I or MHC II or any of the polypeptide chains of either complex (HC, $\beta$2m, $\alpha$-chain and/or $\beta$-chain) from cells transfected or transformed with genes encoding the MHC molecules or polypeptide chains. The transfected cells may be of mammalian, yeast, bacterial or other origin. The genetic material used for transfection/ transformation can be:

i. of natural origin directly isolated from cells, tissue or organisms expressing MHC I and/or MHC IImolecules.

ii. Genes amplified from cells and/or tissue expressing MHC I and/or MHC II molecules. This can be done by isolation of DNA from cells/tissue expressing MHC molecules and then amplifying relevant genes encoding HC and/or $\beta$2m or $\alpha$-chain and/or $\beta$-chain e.g. using PCR. Alternative mRNA may be isolated and changed into DNA using e.g. reverse transcriptase or other method known by persons skilled in the art, and then the relevant genes amplified by PCR.

iii. DNA synthesized in vitro manufactured by e.g. solid phase protein synthesis. Synthetic DNA may correspond to the natural DNA sequence encoding MHC I and/or MHC II or any of the polypeptide chains of either complex (HC, $\beta$2m $\alpha$-chain and/or $\beta$-chain). The genes may be modified from the original natural DNA sequence in order to improve expression of the final protein, increase/ decrease solubility of expressed protein or increase/decrease protein stability as described elsewhere herein.

For MHC I molecules, the HC and $\beta$2m may be expressed in separate cells as individual polypeptides or in the same cell as a fusion protein consisting of HC and $\beta$2m connected through a linker. The peptide of the MHC I-peptide complex may be produced separately and added during in vitro refolding or expressed together with HC and/or $\beta$2m connected to either chain through a linker. The genetic material can encode all or only a fragment of $\beta$2m, all or only a fragment of MHC class I heavy chain. Of special interest are MHC class I heavy chain fragments consisting of, the complete chain minus the intramembrane domain, a chain consisting of only the extracellular $\alpha$1 and $\alpha$2 class I heavy chain domains, or any $\beta$2m and/or heavy chain fragments containing modified or added designer domain(s) or sequence(s) as described elsewhere herein.

For MHC II molecules the $\alpha$-chain and $\beta$-chain may be expressed in separate cells as individual polypeptides or in the same cell as a fusion protein. The peptide of the MHC II-peptide complex may be produced separately and added following purification of whole MHC complexes or added during in vitro refolding or expressed together with $\alpha$-chain and/or $\beta$-chain connected to either chain through a linker. The genetic material can encode all or only a fragment of MHC class II $\alpha$- and $\beta$-chains. Of special interest are MHC class II $\alpha$- and $\beta$-chain fragments consisting of, the complete $\alpha$- and $\beta$-chains minus the intramembrane domains of either or both chains; and $\alpha$- and $\beta$-chains consisting of only the extracellular domains of either or both, i.e $\alpha$1 plus $\alpha$2 and $\beta$1 plus $\beta$2 domains, respectively. The genetic material can be modified to encode the interesting MHC class II molecule fragments consisting of domains starting from the amino terminal in consecutive order, MHC class II $\beta$1 plus MHC class II $\alpha$1 plus MHC class I $\alpha$3 domains or in alternative order, MHC class II $\alpha$1 plus MHC class II $\beta$1 plus MHC class I $\alpha$3 domains. Lastly, the genetic material can encode any of the above mentioned MHC class II $\alpha$- and $\beta$-chain molecules or fragments containing modified or added designer domain(s) or sequence(s). The genetic material may be fused with genes encoding other proteins, including proteins useful in purification of the expressed polypeptide chains, proteins useful in increasing/decreasing solubility of the polypeptide(s), proteins useful in detection of polypeptide(s), proteins involved in coupling of MHC complex to multimerization domains and/or coupling of labels to MHC complex and/or MHC multimer.

Example proteins useful in purification of expressed polypeptide chain include polyhistidine tag, Polyargenine tag, STREP-TAG®, STREP-TAG® II, FLAG tag, S-tag, c-myc, Calmodulin-binding peptide, Streptavidin binding peptide (SBP-tag), Cellulose-binding domain, Chitin-binding domain, Glutathione S-transferase-tag (GST-tag), Maltose-binding protein (MBP), protein-A, protein-G, AviTag, Pin-Point $X_a$, biotin, antigens, Bio-tag or any other tag that can bind a specific affinity matrix useful in purification of proteins. Example proteins useful for detection include enterokinase cleavage site (ECS), hemaglutinin (HA), Glu-Glu, bacteriophage T/ and V5 epitopes, all the above mentioned tags or any other tag able to be measured in a detection system.

Example proteins useful in increasing solubility of expressed polypeptide chains include hydrophilic tags such as transcription anti-termination factor (NusA), E. coli thioredoxin (TrxA), protein disulfide isomerise I (DsbA), large affinity tags such as GST, MBP or other proteins or peptides increasing solubility of protein.

Once expressed the MHC complexes can be purified directly as whole MHC or MHC-peptide complexes from MHC expressing cells. The MHC complexes may be expressed on the surface of cells, and are then isolated by disruption of the cell membrane using e.g. detergent followed by purification of the MHC complex as described elsewhere herein. Alternatively MHC complexes are expressed into the periplasm and expressing cells are lysed and released MHC complexes purified.

Finally, MHC complexes may be purified from the supernatant of cells secreting expressed proteins into culture supernatant.

Whole MHC complexes may be purified using standard protein purification methods known by persons skilled in the art. Briefly, purification using affinity tags, as described elsewhere herein, together with affinity chromatography, beads coated with ant-tag and/or other techniques involving immobilisation of MHC protein to affinity matrix; size exclusion chromatography using e.g. gelfiltration, ion exchange or other methods able to separate MHC molecules from cell and/or cell lysate.

As an alternative to expression and purification of whole MHC complexes, the polypeptides chains of MHC can be expressed in cells, cells lysed, the polypeptides chains isolated by purification and then refolded in vitro. In one aspect of the present invention a preferred cell for this type of expression is E. coli, where MHC polypeptide chains accumulate as insoluble inclusion bodies in the bacterial cell. In vitro refolding occurs in a refolding buffer where the polypeptides are added by e.g. dialysis or dilution. Refolding buffers can be any buffer wherein the MHC polypeptide chains and peptide are allowed to reconstitute their native trimer fold. The buffer may contain oxidative and/or reducing agents thereby creating a redox buffer system helping the MHC proteins to establish the correct fold. Examples of suitable refoldings buffer of the present invention include but is not limited to Ttris-buffer, CAPS buffer, TAPs buffer, PBS buffer, other phosphate buffer, carbonate buffer and Ches buffer. Chaperone molecules or other molecules improving correct protein folding may also be added and likewise agents increasing solubility and preventing aggregate formation may be added to the buffer. Examples of such molecules include but is not limited to Arginine, GroE, HSP70, HSP90, small organic compunds, DnaK, ClpB, proline, glycin betaine, glycerol, tween, salt, PLURONIC®.

Both MHC I and MHC II molecules may be generated using any of the above described procedures. In the present invention a preferred method is using recombinant expression systems.

In one embodiment of the present invention E. coli expression followed by refolding in vitro is preferred for generation of MHC I molecules. Another preferred embodiment of the present invention is generation of MHC II complexes made by coexpression of MHC II α-chain and β-chain subunits in baculovirus-infected or stably transfected insecT-cells.

Using the above described methods MHC I and MHC II molecules may be generated with or without peptide bound in the peptide binding groove. Loading of peptide into MHC molecules are described elsewhere herein.

Generation of Peptide Able to Bind the Peptide Binding Cleft of MHC I or MHC II

MHC class I molecules normally binds octa-, nona-, deca- or ondecamer (8-, 9-, 10, -11-mer) peptides in their peptide binding groove. The individual MHC class I1 alleles have individual preferences for the peptide length within the given range. MHC class II molecules bind peptides most often with a total length of 13-18 amino acids around a 9-mer core motif containing the important amino acid anchor residues. However the total length is not strictly defined as for most MHC class I molecules.

Peptides binding MHC I or MHC II can be derived from a variety of sources including:

a) Natural sources.

Peptides can be obtained from natural sources by enzymatic digestion or proteolysis of natural proteins or proteins derived by in vitro translation of mRNA. Peptides may also be eluted from the MHC binding groove.

b) Recombinant sources:

As monomeric or multimeric peptide

Peptides can be produced recombinantly by transfected cells either as monomeric antigenic peptides or as multimeric (contatemeric) antigenic peptides.

as part of a bigger recombinant protein

Binding peptides may also constitute a part of a bigger recombinant protein e.g. consisting of:

For MHC class I binding peptides, Peptide-linker-β2m, β2m being full length or truncated; Peptide-linker-MHC class 1 heavy chain, the heavy chain being full length or truncated. Most importantly the truncated class I heavy chain will consist of the extracellular part i.e the α1, □α2, and a domains. The heavy chain fragment may also only contain the α1 and α2 domains, or α1 domain alone, or any fragment or full length β2m or heavy chain attached to a designer domain(s) or protein fragment(s).

For MHC class II binding peptides the recombinant construction can consist of, Peptide-linker-MHC class 2 α-chain, full length or truncated; Peptide-linker-MHC class 2 β-chain, full length or truncated; Peptide-linker-MHC class 2 α-chain-linker-MHC class 2 β-chain, both chains can be full length or truncated, truncation may involve, omission of α- and/or β-chain intermembrane domain, or omission of α- and/or β-chain intermembrane plus cytoplasmic domains. MHC class 2 part of the construction may consist of fused domains from NH2-terminal, MHC class 2 β1domain-MHC class 2 α1domain-constant α3 of MHC class 1, or alternatively of fused domains from NH2-terminal, MHC class 2 α1domain-MHC class 2 β1domain-constant α3 of MHC class 1. In both cases β2m will be associated non-covalently in the folded MHC complex. β2m can also be covalently associated in the folded MHC class 2 complex if the following constructs are used from NH2 terminal, MHC class 2 β1domain-MHC class 2 α1domain-constant α3 of MHC class 1-linker-β2m, or alternatively of fused domains from NH2-terminal, MHC class 2 α1domain-MHC class 2 β1domain-constant α3 of MHC class 1-linker-β2m; the construct may also consist of any of the above MHC class 2 constructs with added designer domain(s) or sequence(s).

c) From Chemical Synthesis

MHC binding peptide can also be chemically synthesized by solid phase or fluid phase synthesis.

Loading of Peptide into the MHC Complex

Loading of peptides into the peptide binding cleft of MHC complexes being either MHC class I or class II can be performed in a number of ways depending on the source of the peptide and the MHC. MHC class II molecules can in principle be loaded with peptides in similar ways as MHC class I.

a) During MHC Complex Folding as a free peptide

MHC class I molecules are most often loaded with peptide during assembly in vitro by the individual components in a folding reaction i.e. consisting of purified recombinant heavy chain α with the purified recombinant β2 microglobulin and a peptide or a peptide mix.

as part of a recombinant protein construct

Alternatively the peptide to be folded into the binding groove can be encoded together with e.g. the a heavy chain or fragment hereof by a gene construct having the structure, heavy chain-flexible linker-peptide. This recombinant molecule is then folded in vitro with P2-microglobulin.

b) by exchange reaction in solution

Loading of desired peptide can also be made by an in vitro exchange reaction where a peptide already in place in the binding groove are being exchanged by another peptide species.

"in situ"

Peptide exchange reactions can also take place when the parent molecule is attached to other molecules, structures, surfaces, artificial or natural membranes and nano-particles.

by aided exchange

This method can be refined by making the parent construct with a peptide containing a meta-stable amino acid analog that is split by either light or chemically induction thereby leaving the parent structure free for access of the desired peptide in the binding groove.

by in vivo loading

Loading of MHC class I and II molecules expressed on the cell surface with the desired peptides can be performed by an exchange reaction. Alternatively cells can be transfected by the peptides themselves or by the mother proteins that are then being processed leading to an in vivo analogous situation where the peptides are bound in the groove during the natural cause of MHC expression by the transfected cells. In the case of professional antigen presenting cells e.g. dendritic cells, macrophages, Langerhans cells, the proteins and peptides can be taken up by the cells themselves by phagocytosis and then bound to the MHC complexes the natural way and expressed on the cell surface in the correct MHC context.

Coupling of MHC Complexes and Multimerization Domains

The coupling of one or more multimerization domains and MHC complexes can involve the association of an entity X (attached to or part of the one or more multimerization domain) and an entity Y (attached to or part of the MHC complex). Thus, the linker that connects the one or more multimerization domain(s) and the MHC complex can comprise an XY portion.

The XY linkage can be covalent, in which case X and Y are reactive groups. In this case, X can be a nucleophilic group (such as —NH$_2$, —OH, —SH, —NH—NH$_2$), and Y an electrophilic group (such as CHO, COOH, CO) that react to form a covalent bond XY; or Y can be a nucleophilic group and X an electrophilic group that react to form a covalent bond XY. Other possibilities exist, e.g. either of the reactive groups can be a radical, capable of reacting with the other reactive group. A number of reactive groups X and Y, and the bonds that are formed upon reaction of X and Y, are shown in FIG. 1.

X and Y can be reactive groups naturally comprised within the multimerization domain(s) and/or the MHC complex, or they can be artificially added reactive groups. Thus, linkers comprising reactive groups can be linked to either of the multimerization domain(s) and MHC complex; subsequently the introduced reactive group(s) can be used to covalently link the one or more multimerization domain(s) and MHC complex.

Example natural reactive groups of MHC complexes include amino acid side chains comprising —NH$_2$, —OH, —SH, and —NH—. Example natural reactive groups of multimerization domains include hydroxyls of polysaccharides such as dextrans, but also include amino acid side chains comprising —NH$_2$, —OH, —SH, and —NH— of polypeptides, when the polypeptide is used as one or more multimerization domain(s). In some MHC multimers, one of the polypeptides of the MHC complex (i.e. the β2M, MHC I heavy chain, MHC II α-chain, MHC II β-chain or the antigenic peptide) is linked by a protein fusion to the one or more multimerization domain(s). Thus, during the translation of the fusion protein, an acyl group (reactive group X or Y) and an amino group (reactive group Y or X) react to form an amide bond. Example MHC multimers where the bond between the one or more multimerization domain(s) and the MHC complex is covalent and results from reaction between natural reactive groups, include MHC-pentamers (described in US patent 2004209295) and MHC-dimers, where the linkage between the one or more multimerization domain(s) and MHC complex is in both cases generated during the translation of the fusion protein. Another example is MHC multimers where either of the MHC polypeptide chains are fused to one alpha-helix of a coiled-coil structure and where the other alpha helix of a coiled-coil structure is attached to the multimerisation domain. MHC complexes are then attached to the multimerisation domain through interaction of the two alpha-helices. Example coiled-coil structure include leucine zipper, fos-jun or other coiled coil structures as described elsewhere herein. Example non-native reactive groups include reactive groups that are attached to the one or more multimerization domain(s) or MHC complex, through association of a linker molecule comprising the reactive group. The activation of dextran by reaction of the dextran hydroxyls with divinyl sulfone, introduces a reactive vinyl group that can react with e.g. amines of the MHC complex, to form an amine that now links the one or more multimerization domain(s) (the dextran polymer) and the MHC complex. Reactive vinyl groups may also react with thiols of the MHC complex. An alternative activation of the dextran multimerization domain(s) involves a multistep reaction that results in the decoration of the dextran with maleimide groups, as described in the patent Siiman et al. U.S. Pat. No. 6,387,622. In this approach, the amino groups of MHC complexes are converted to —SH groups, capable of reacting with the maleimide groups of the activated dextran. Alternatively —SH groups of natural occuring Cysteine or artificial incorporated Cysteine can react with the maleimide. Thus, in the latter examples, both the reactive group of the multimerization domain(s) (the maleimide) and the reactive group of the MHC complex (the thiol) are artificially introduced.

Sometimes activating reagents are used in order to make the reactive groups more reactive. For example, acids such as glutamate or aspartate can be converted to activated esters by addition of e.g. carbodiimid and NHS or nitrophenol, or by converting the acid moiety to a tosyl-activated ester. The activated ester reacts efficiently with a nucleophile such as —NH$_2$, —SH, —OH, etc.

For the purpose of this invention, the multimerization domain(s) (including small organic scaffold molecules, proteins, protein complexes, polymers, beads, liposomes, micelles, cells) that form a covalent bond with the MHC complexes can be divided into separate groups, depending on the nature of the reactive group that the one or more multimerization domain(s) contains. One group comprise multimerization domain(s) that carry nucleophilic groups (e.g. —NH$_2$, —OH, —SH, —CN, —NH—NH$_2$), exemplified by polysaccharides, polypeptides comprising e.g. lysine, serine, and cysteine; another group of multimerization domain(s) carry electrophilic groups (e.g. —COOH, —CHO, —CO, NHS-ester, tosyl-activated ester, and other activated esters, acid-anhydrides), exemplified by polypeptides comprising e.g. glutamate and aspartate, or vinyl sulfone activated dextran; yet another group of multimerization domains carry radicals or conjugated double bonds.

The one or more multimerization domain(s) appropriate for this invention can be those that comprise any of the reactive groups shown in FIG. 1 or that can react with other reactive groups to form the bonds shown in FIG. 1.

The MHC complexes can be divided in a similar way, according to the nature of their reactive groups.

In another preferred embodiment the linker can be selected from, but is not limited to, the group consisting of a disulfide-bridge connecting amino acids, heparin or heparan sulfate-derived oligosaccharides (glycosoaminoglycans), bifunctional or chemical cross-linkers, peptide linker, polypeptide linker, flexible linker, synthetic linker, hydrazones, thioethers, esters, disulfides and peptide-containing linkers.

Examples of linkers include but are not limited to a disulfide-bridge connecting amino acids from both polypeptides; heparin or heparan sulfate-derived oligosaccharides (glycosoaminoglycans) connecting both polypeptides; bifunctional or chemical cross-linkers; and a peptide or polypeptide linker. The unimolecular protein can also be a chimera or fusion polypeptide.

The peptide linker sequence is typically flexibly disposed in the fusion protein so as to position the V-alpha and V-beta chains in a configuration which optimally binds an antigen. The peptide linker preferably predominantly comprises amino acids with small side chains, such as glycine, alanine and serine, to provide flexibility. Preferably, about 80 or 90 percent or greater of the linker sequence comprises glycine, alanine or serine residues, particularly glycine and serine residues. Preferably, the linker sequence does not contain any proline residues, which could inhibit flexibility. The linker sequence is suitably attached to the C-terminus of the V-alpha chain and the N-terminus of the V-beta chain of a fusion protein.

Crosslinkers can be either homobifunctional or heterobifunctional. Homobifunctional crosslinkers have two identical reactive groups and often are used in one-step reaction procedures to crosslink proteins to each other or to stabilize quaternary structure. Heterobifunctional crosslinkers possess two different reactive groups that allow for sequential (two-stage) conjugations, helping to minimize undesirable polymerization or self-conjugation. Crosslinkers that are amine-reactive at one end and sulfhydryl-reactive at the other end are especially useful in this regard.

The most widely-used heterobifunctional crosslinkers are those having an amine-reactive succinimidyl ester (i.e., NHS-ester) at one end and a sulfhydrylreactive group on the other end. The sulfhydryl-reactive groups are usually maleimides, pyridyl disulfides and haloacetyls. The NHS-ester reactivity is less stable in aqueous solution and is usually reacted first in sequential crosslinking procedures. NHS-esters react with amines to form amide bonds. Carbodiimides are zero-length crosslinkers and effect direct coupling between carboxylates (—COOH) and primary amines (—NH$_2$).

Other heterobifunctional reagents have one reactive group that is photoreactive rather than thermoreactive. This reactivity allows for specific attachment of the labile thermoreactive group first; subsequently, conjugation to any adjacent N—H or C—H sites can be initiated through the photoreactive group by activation with UV light. Crosslinkers preferably comprise at least two reactive groups. Functional groups that can be targeted for crosslinking include primary amines, sulfhydryls, carbonyls, carbohydrates and carboxylic acids (Table 1). Coupling also can be nonselective using a photoreactive phenyl azide crosslinker.

TABLE 1

| Reactive Crosslinker Groups and Their Functional Group Targets | |
|---|---|
| Reactive Group | Functional Group |
| Aryl Azide | Non-selective (or primary amine) |
| Carbodiimide | Amine/Carboxyl |
| Hydrazide | Carbohydrate (oxidized) |
| Hydroxymethyl Phosphine | Amine |
| Imidoester | Amine |
| Isocyanate | Hydroxyl (non-aqueous) |
| Maleimide | Sulfhydryl |
| NHS-ester | Amine |
| PFP-ester | Amine |
| Psoralen | Thymine (photoreactive intercalator) |
| Pyridyl Disulfide | Sulfhydryl |
| Vinyl Sulfone | Sulfhydryl, amine, hydroxyl |

The linker that connects the one or more multimerization domain(s) and the MHC complex can comprise an XY portion. Above different kinds of covalent linkages XY were described. However, the XY linkage can also be non-covalent.

Non-covalent XY linkages can comprise natural dimerization pairs such as antigen-antibody pairs, DNA-DNA interactions, or can include natural interactions, for example between biotin and streptavidin. Likewise, the interaction of MHC complexes (comprising full-length polypeptide chains, including the transmembrane portion) with the cell membrane of for example dendritic cells, is an example of a non-covalent XY interaction.

Artificial XY examples include XY pairs such as $His_6$ tag (X) interacting with Ni-NTA (Y) and PNA-PNA, A list of dimerization- and multimerization domains, appropriate for use as XY non-covalent linkers between the multimerization domain(s) and the MHC complex, can be found elsewhere in this application.

The abovementioned dimerization- and multimerization domains represent specific binding interactions. Another type of non-covalent interactions involves the non-specific adsorption of e.g. proteins onto surfaces. As an example, the non-covalent adsorption of proteins onto glass beads represents this class of XY interactions.

A preferred embodiment involving non-covalent interactions between X and Y are represented by the pentamer structure described in US patent 2004209295.

Another preferred embodiment involves the use of antibodies, with affinity of the surface of MHC opposite to the peptide-binding groove. Thus, an anti-MHC antibody, with its two binding site, will bind two MHC complexes and in this way generate a bivalent MHC multimer. In addition, the antibody can stabilize the MHC complex through the binding interactions, in which case the MHC multimer is particularly relevant for MHC class II complexes, as these are less stable than class I MHC complexes.

The antibodies mentioned above can be selected from, but is not limited to, the group consisting of polyclonal antibody, monoclonal antibody, IgA, IgG, IgM, IgD, IgE, IgG1, IgG2, IgG3, IgG4, IgA1, IgA2, IgM1, IgM2, humanized antibody, humanized monoclonal antibody, Chimeric antibody, mouse antibody, rat antibody, rabbit antibody, human antibody, camel antibody, sheep antibody, engineered human antibody, epitope-focused antibody, agonist antibody, antagonist antibody, neutralizing antibody, naturally-occurring antibody, isolated antibody, monovalent antibody, bispecific antibody, trispecific antibody, multispecific antibody, Heteroconjugate antibody, immunoconjugates, immunoliposomes, labeled antibody, antibody fragment, domain antibody, nanobody, minibody, maxibody, diabody, fusion antibody.

Another preferred embodiment involves use of Streptavidin or Avidin binding biotin on biotinylated MHC complexes. MHC complexes can be biotinylated enzymatically e.g. using a biotinylation tag recognised by BirA enzyme or they can be chemically biotinylated e.g. using Sulfo-NHS esters of biotin reacting with amino groups or maleimide activated biotin reacting with —SH groups.

The Streptavdin or avidin may further be conjugated to a polymer e.g. dextran as described by Winther et al. in patent WO 02/072631.

Also included in the present invention is genetically or chemically modified Streptavidin/Avidin binding natural biotin and/or chemically or genetically modified biotin; and chemically or genetically modified biotin binding natural Streptavidin/Avidin or chemically or genetically Streptavidin/Avidin.

In the present invention another preferred embodiment involving non-covalent interactions between X and Y are use of dimer coiled-coil structures, where one half the coiled structure are attached to the MHC molecule, e.g. as a fusion protein and the other half is attached to the multimerization domain. Example coiled-coil structures include but are not limited to leucine zippers like Fos-Jun, GCN4 leucine zipper, Fos-Jun like leucine zippers, heterodimeric coiled coil structures consisting of a basic peptide and an acidic peptide, heterodimeric coiled coil structures consisting of a basic peptide and an acidic peptide where Cystein are added to the C-termini of the acid and base peptides either directly or through a linker e.g. Gly-Gly, other heterodimeric coiled-coil structures or homodimeric structures.

Multimerisation Domains

The MHC multimers of the invention in one embodiment comprise one or more multimerization domain(s). The multimerization domain(s) can be a soluble multimerization domain(s) or a not soluble multimerization domain(s). The multimerization domain(s) can be any such which enables attachment of the MHC molecules, the binding entities, and/or the biologically active compounds, while providing the advantageous properties of the construct.

Examples of suitable multimerization domain(s)s are polysaccharides including dextrans, carboxy methyl dextran, dextran polyaldehyde, carboxymethyl dextran lactone, and cyclodextrins, pullulans, schizophyllan, scleroglucan, xanthan, gellan, O-ethylamino guaran, chitins and chitosans inducing 6-O-carboxymethyl chitin and N-carboxymethyl chitosan, derivatised cellolosics including carboxymethyl cellulose, carboxymethyl hydroxyethyl cellulose, hydroxyethyl cellulose, 6-amino-6-deoxy cellulose and O-ethylamine cellulose, hydroxylated starch, hydroxypropyl starch, hydroxyethyl starch, carrageenans, alginates, and agarose, synthetic polysaccharides including FICOLL® and carboxy-methylated FICOLL®, vinyl polymers including poly (acrylic acid), poly (acryl amides), poly (acrylic esters), poly (2-hydroxy ethyl methacrylate), poly (methyl methacrylate), poly (maleic acid), poly (maleic anhydride), poly (acrylamide), poly (ethyl-co-vinyl acetate), poly (methacrylic acid), poly (vinyl-alcohol), poly (vinyl alcohol-co-vinyl chloroacetate), aminated poly (vinyl alcohol), and co block polymers thereof, poly ethylene glycol (PEG) or polypropylene glycol or poly (ethylene oxide-co-propylene oxides) comprising polymer backbones including linear, comb-shaped or StarBurst dendrimers, poly amino acids including polylysines, polyglutamic acid, polyurethanes, poly (ethylene imines), pluriol, proteins including peptides, polypeptides, antigenbinding peptides, albumins, immunoglobulins, coiled-coil helixes e.g. Fos-Jun or Fos-Jun like or coiled-coiled dimers/trimers/tetramers/pentamers, Streptavidin, Avidin, Streptactin, T-cell receptors orther protein receptors and virus-like proteins (VLP), and polynucleotides, DNA, RNA, PNA, LNA, oligonucleotides and oligonucleotide dendrimer constructs and small organic molecules including but not limited to steroids, peptides, linear or cyclic structures, aromatic structures, aliphatic structures.

Also included are cells e.g. dendritic cells, antigen presenting cell, B-cell, T-cell Macrophages, Kupfer cells, Langerhans cells, transfected cells expressing MHC comlexes, hybriddoma cells expressing MHC complexes, YeasT-cells, insecT-cells, CHO cells, any cell expressing MHC complexes or MHC-like complexes and cell-like structures e.g. micelles, liposomes, other structures of MHC and phages e.g. filamentious phages and viral or viral-like particles.

Other suitable multimerization domains are solid supports including but not limited to beads, particulate matters and other surfaces.

Also included are self-assembling multimeric structures as described elsewhere herein.

Also included in this definition of the multimerization domain(s) is mixed forms, i.e. one or more multimerization domain(s) composed of one or more of the above examples. An example of this is dextran coupled with Streptavidin whereto biotinylated MHC-peptidecomlexes can bind.

The choice of multimerization domain(s) depend i.e. on the application of the MHC molecule construct. Of course, several parameters can be varied in the above-given examples of multimerization domain(s), including the length and branching. Furthermore, the multimerization domain(s) can carry various substitutions, including such, which can be protected and/or activated, enabling further derivatisation.

It is to be understood that the MHC molecule construct of the invention can further comprise one or more additional substituents. Such biologically active molecules can be attached to the construct in order to affect the characteristics of the constructs, e. g. with respect to binding properties, effects, MHC molecule specificities, solubility, stability, or detectability. For instance, spacing could be provided between the MHC molecules, one or both chromophores of a Fluorescence Resonance Energy Transfer (FRET) donor/acceptor pair could be inserted, functional groups could be attached, or groups having a biological activity could be attached.

One preferred embodiment of the present invention includes multimerisation domains made of Streptavidin or Avidin whereto biotin, biotin-like peptides or other biotin-like molecules can bind.

Another preferred embodiment includes dextran whereto MHC-peptide complexes arebe attached directly through a linker as described elsewhere herein. The MHC-peptide complexes can also be attached through a second multimerization domain or an entity as described elsewhere herein. Examples include but is not limited to divinylsulfone activated dextran whereto MHC-peptide complexes are coupled directly e.g. through —SH group(s) or amine(s) in the MHC-peptide complex, dextran coupled with SA whereto MHC-peptide complexes are attached through a biotin on the MHC-peptide complex, dextran with MHC-peptide complexes are attached through a coiled-coil structure where on α-helix of a coiled-coil dimer is coupled to dextran and the other α-helix is coupled to MHC-peptide complex e.g. as a fusion protein.

A preferred embodiment include beads or bead-like structures having an excluded volume (e.g. polysaccharide beads, polystyrene beads, magnetic polystyrene beads, polycarbamate beads, or any other kind of beads that can be dissolved or suspended in aqueous buffer) that carry electrophilic groups (e.g. divinyl sulfone activated polysaccharide, polystyrene beads that have been functionalized with tosyl-activated esters, magnetic polystyrene beads functionalized with tosyl-activated esters), and where MHC complexes have been covalently immobilized to these by reaction of nucleophiles comprised within the MHC complex with the electrophiles of the beads.

In another preferred embodiment, the MHC multimers described immediately above (where the one or more multimerization domain(s) is a bead) further comprises a flexible or rigid, and water soluble, linker that allows for the immobilized MHC complexes to interact efficiently with cells, such as T-cells with affinity for the MHC complexes. In yet another embodiment, the linker is cleavable, allowing for release of the MHC complexes from the bead. If T-cells have been immobilized, by binding to the MHC complexes, the T-cells can very gently be released by cleavage of this cleavable linker. Appropriate cleavable linkers are shown in FIG. 2. Most preferably, the linker is cleaved at physiological conditions, allowing for the integrity of the isolated cells.

In another preferred embodiment the bead is covalently or non-covalently coated with MHC multimers or single MHC complexes, through non-cleavable or cleavable linkers. As an example, the bead can be coated with streptavidin monomers, which in turn are associated with biotinylated MHC complexes; or the bead can be coated with streptavidin tetramers, each of which are associated with 0, 1, 2, 3, or 4 biotinylated MHC complexes; or the bead can be coated with MHC-dextramers where e.g. the reactive groups of the MHC-dextramer (e.g. the divinyl sulfone-activated dextran backbone) has reacted with nucleophilic groups on the bead, to form a covalent linkage between the dextran of the dextramer and the beads.

A preferred embodiment including self-assembling multimeric structures are trimer, tetramer or pentamer coiled-coil structures holding together 3, 4 or 5 MHC complexes. The coiled-coil structures may be attached to MHC-peptide complex through covalent or non-covalent.

In some of the abovementioned embodiments, several multimerization domains (e.g. streptavidin tetramers bound to biotinylated MHC complexes) are linked to another multimerization domain (e.g. the bead). For the purpose of the invention we shall call both the smaller and the bigger multimerization domain, as well as the combined multimerization domain, for multimerization domain.

In another preferred embodiment the one or more multimerization domain(s) can be any support capable of binding the MHC complex. Well-known supports or multimerization domains include glass, polystyrene, polypropylene, polyethylene, dextran, nylon, amylases, natural and modified celluloses, polyacrylamides, gabbros, and magnetite. The nature of the one or more multimerization domain(s) can be either soluble to some extent or insoluble for the purposes of the present invention. The support material can have virtually any possible structural configuration so long as the coupled molecule is capable of binding to the MHC complex. The support configuration can be spherical, as in a bead, or cylindrical, as in the inside surface of a test tube, or the external surface of a rod. Alternatively, the surface can be flat such as a sheet, test strip, a membrane, or a plastic surface such as that on a microtiter plate etc.

In another preferred embodiment the multimerization domain(s) can be a polymer or an oligomer or a non-repeating moiety. The polymer or oligomer moiety can comprise repeat units consisting of a repeat moiety selected from alkyl (e.g., —CH$_2$—), substituted alkyl (e.g., —CHR—), alkenyl, substituted alkenyl, alkynyl, substituted alkynyl, phenyl, aryl, heterocyclic, amine, ether, sulfide, disulfide, hydrazine, and any of the foregoing substituted with oxygen, sulfur, sulfonyl, phosphonyl, hydroxyl, alkoxyl, amine, thiol, ether, carbonyl, carboxyl, ester, amide, alkyl, alkenyl, alkynyl, aryl, heterocyclic, as well as moieties comprising combinations thereof. Generally, a non-repeating multifunctional bridge moiety can be a moiety selected from alkyl, phenyl, aryl, alkenyl, alkynyl, heterocyclic, amine, ether, sulfide, disulfide, hydrazine, and any of the foregoing substituted with oxygen, sulfur, sulfonyl, phosphonyl, hydroxyl, alkoxyl, amine, thiol, ether, carbonyl, carboxyl, ester, amide, alkyl, alkenyl, alkynyl, aryl, heterocyclic, and moieties comprising combinations thereof (in each permutation). A non-repeating moiety can include repeating units (e.g., methylene) within portions or segments thereof without repeating as a whole.

The oligomer (or oligomer moiety) or the polymer (or polymer moiety), can generally be soluble or insoluble; can generally be a cross-linked oligomer (or oligomer moiety) or a cross-linked polymer (or polymer moiety); can generally be a homopolymer or a copolymer (including polymers having two monomer-repeat-units, terpolymers and higher-order polymers), including for example random copolymer moieties and block copolymer moieties; can generally include one or more ionic monomer moieties such as one or more anionic monomer moieties; can generally include one or more hydrophobic monomer moieties; can generally include one or more hydrophilic monomer moieties; and can generally include any of the foregoing features in combination.

The polymer moiety can be soluble or insoluble, existing for example as dispersed micelles or particles, such as colloidal particles or (insoluble) macroscopic beads. Polymer moieties can be hydrophobic, hydrophilic, amphiphilic, uncharged or non-ionic, negatively or positively charged, or a combination thereof, and can be organic or inorganic. Inorganic polymers, also referred to as inorganic multimerization domains in some cases, include silica (e.g., multi-layered silica), diatomaceous earth, zeolite, calcium carbonate, talc, and the like.

Suitable water-soluble polymers include polyethylene glycol (PEG), monomethoxy-PEG, mono-($C_1$-$C_{10}$)alkoxy-PEG, aryloxy-PEG, poly-(N-vinyl pyrrolidone)PEG, tresyl monomethoxy PEG, PEG propionaldehyde, bis-succinimidyl carbonate PEG, propylene glycol homopolymers, a polypropylene oxide/ethylene oxide co-polymer, polyoxy-ethylated polyols (e.g., glycerol), polyvinyl alcohol, dextran, cellulose, or other carbohydrate-based polymers. A conjugate can also comprise a mixture of such water-soluble polymers.

Examples of polysaccharides useful in the present invention include materials from vegetal or animal origin, including cellulose materials, hemicellulose, alkyl cellulose, hydroxyalkyl cellulose, carboxymethylcellulose, sulfoethyl-cellulose, starch, xylan, amylopectine, chondroitin, hyarulonate, heparin, guar, xanthan, mannan, galactomannan, chitin, and/or chitosan.

The type of multimerization domain can also be selected from, but is not limited to, the group consisting of agarose, SEPHAROSE®, resin beads, glass beads, pore-glass beads, glass particles coated with a hydrophobic polymer, chitosan-coated beads, SH beads, latex beads spherical latex beads, allele-type beads, SPA bead, PEG-based resins, PEG-coated bead, PEG-encapsulated bead, polystyrene beads, magnetic polystyrene beads, glutathione agarose beads, magnetic bead, paramagnetic beads, protein A and/or protein G SEPHAROSE® beads, activated carboxylic acid bead, macroscopic beads, microscopic beads, insoluble resin beads, silica-based resins, cellulosic resins, cross-linked agarose beads, polystyrene beads, cross-linked polyacrylamide resins, beads with iron cores, metal beads, DYNABEADS®, Polymethylmethacrylate beads activated with NHS, streptavidin-agarose beads, polypropylene, polyethylene, dextran, nylon, amylases, natural and modified celluloses, nitrocellulose, polyacrylamides, gabbros, magnetite, polymers, oligomers, non-repeating moieties, polyethylene glycol (PEG), monomethoxy-PEG, mono-($C_1$-$C_{10}$)alkoxy-PEG, aryloxy-PEG, poly-(N-vinyl pyrrolidone)PEG, tresyl monomethoxy PEG, PEG propionaldehyde, bis-succinimidyl carbonate PEG, polystyrene bead crosslinked with divinylbenzene, propylene glycol homopolymers, a polypropylene oxide/ethylene oxide co-polymer, polyoxyethylated polyols (e.g., glycerol), polyvinyl alcohol, dextran, aminodextran, carbohydrate-based polymers, cross-linked dextran beads, polysaccharide beads, polycarbamate beads, polyvinylcarbamate, divinyl sulfone activated polysaccharide, polystyrene beads that have been functionalized with tosyl-activated esters, magnetic polystyrene beads functionalized with tosyl-activated esters, streptavidin beads, streptavidin-monomer coated beads, streptavidin-tetramer coated beads, Streptavidin Coated Compel Magnetic beads, avidin coated beads, dextramer coated beads, divinyl sulfone-activated dextran, Carboxylate-modified bead, amine-modified beads, antibody coated beads, cellulose beads, grafted co-poly beads, poly-acrylamide beads, dimethylacrylamide beads optionally crosslinked with N—N'-bis-acryloylethylenedi-amine, hollow fiber membranes, fluorescent beads, collagen-agarose beads, gelatin beads, collagen-gelatin beads, collagen-fibronectin-gelatin beads, collagen beads, chitosan beads, collagen-chitosan beads, protein-based beads, hydrogel beads, hemicellulose, alkyl cellulose, hydroxyalkyl cellulose, carboxymethylcellulose, sulfoethylcellulose, starch, xylan, amylopectine, chondroitin, hyarulonate, heparin, guar, xanthan, mannan, galactomannan, chitin and chitosan.

Immuno Active Molecules

In many applications, it will be advantageous that the MHC multimer construct further comprises one or more Immuno active molecules. By the term "Immuno active" is meant that the compound can affect the binding characteristics or the effects of the MHC multimer construct. The MHC multimer construct can comprise several immuno active molecules which can be the same or different.

Such immuno active molecules can in particular be selected from the group of biological active molecules including proteins, co-stimulatory molecules, cell modulating molecules, receptors, accessory molecules, adhesion molecules, natural ligands, and toxic molecules, as well as antibodies and recombinant binding molecules to any of the foregoing, and combinations thereof.

"Recombinant binding molecules" is intended to mean molecules such as peptide fragment prepared by recombinant technology, and which have the ability to mimic the activity (e. g. up-regulation or down-regulation) of natural molecules, or to inhibit or block the activity of natural molecules.

In particular, the Immuno active molecule can be selected from proteins such as MHC Class I-like proteins like MIC A, MIC B, CDId, HLA E, HLA F, HLA G, HLA H, ULBP-1, ULBP-2, and ULBP-3, co-stimulatory molecules such as CD2, CD3, CD4, CD5, CD8, CD9, CD27, CD28, CD30, CD69, CD134 (OX40), CD137 (4-1BB), CD147, CDw150 (SLAM), CD152 (CTLA-4), CD153 (CD30L), CD40L (CD154), NKG2D, ICOS, HVEM, HLA Class II, PD-1, Fas (CD95), FasL expressed on T and/or NK cells, CD40, CD48, CD58, CD70, CD72, B7.1 (CD80), B7.2 (CD86), B7RP-1, B7-H3, PD-L1, PD-L2, CD134L, CD137L, ICOSL, LIGHT expressed on APC and/or tumour cells, cell modulating molecules such as CD16, NKp30, NKp44, NKp46, NKp80, 2B4, KIR, LIR, CD94/NKG2A, CD94/NKG2C expressed on NK cells, IFN-alpha, IFN-beta, IFN-gamma, IL-1, IL-2, IL-3, IL-4, IL-6, IL-7, IL-8, IL-10, IL-11, IL-12, IL-15, CSFs (colony-stimulating factors), vitamin D3, IL-2 toxins, cyclosporin, FK-506, rapamycin, TGF-beta, clotrimazole, nitrendipine, and charybdotoxin, accessory molecules such as LFA-1, CDIIa/18, CD54 (ICAM-1), CD106 (VCAM), and CD49a, b, c, d, e, f/CD29 (VLA-4), adhesion molecules such as ICAM-1, ICAM-2, GlyCAM-1, CD34, anti-LFA-1, anti-CD44, anti-beta7, chemokines, CXCR4, CCR5, anti-selectin L, anti-selectin E, and anti-selectin P, toxic molecules selected from toxins, enzymes, antibodies, radioisotopes, chemiluminescent substances, bioluminescent substances, polymers, metal particles, and haptens, such as cyclophosphamide, methrotrexate, Azathioprine, mizorib-ine, 15-deoxuspergualin, neomycin, staurosporine, genest-ein, herbimycin A, *Pseudomonas* exotoxin A, saporin, Rit-uxan, Ricin, gemtuzumab ozogamicin, Shiga toxin, heavy metals like inorganic and organic mercurials, and FN18-CRM9, radioisotopes such as incorporated isotopes of iodide, cobalt, selenium, tritium, and phosphor, and haptens such as DNP, and digoxiginin, and combinations of any of the foregoing, as well as antibodies (monoclonal, poly-clonal, and recombinant) to the foregoing, where relevant. Antibody derivatives or fragments thereof can also be used. The biologically active molecules may also derive from viral or bacterial proteins or fragments thereof.

The immuno active molecule can suitably be attached to the multimerization domain(s) either directly, thorugh one or more linkers or via one or more of the binding entities or one or more multimerization domains as described elsewhere herein. The immunoactive molecules can aslo be linked to another immunoactive molecule and then attached to one or more multimerization domains.

MHC multimers can be covalently or non-covalently associated with various molecules: having adjuvant effects; being immune targets e.g. antigens; having biological activ-ity e.g. enzymes, regulators of receptor activity, receptor ligands, immune potentiators, drugs, toxins, co-receptors, proteins and peptides in general; sugar moieties; lipid groups; nucleic acids including siRNA; nano particles; small molecules. In the following these molecules are collectively called biologically active molecules. Such molecules can be attached to the MHC multimer using the same principles as those described for attachment of MHC complexes to mul-timerisation domains as described elsewhere herein. In brief, attachment can be done by chemical reactions between reactive groups on the biologically active molecule and reactive groups of the multimerisation domain and/or between reactive groups on the biologically active molecule and reactive groups of the MHC-peptide complex. Alterna-tively, attachment is done by non-covalent interaction between part of the multimerisation domain and part of the biological active molecule or between part of the MHC-peptide complex and part of the biological active molecule. In both covalent and non-covalent attachment of the bio-logically molecule to the multimerisation domain a linker molecule can connect the two. The linker molecule can be covalent or non-covalent attached to both molecules. Examples of linker molecules are described elsewhere herein.

Biological active molecules can be attached repetitively aiding to recognition by and stimulation of the innate immune system via Toll or other receptors.

MHC multimers carrying one or more additional groups can be used as therapeutic or vaccine reagents.

An example of a vaccine reagent could be one against HIV. In this case antigens of the viral particle or the cell membrane surrounding the particle could be relevant to attach to the MHC multimer. The resulting MHC multimer e.g. a MHC class I Dextramer could have additional mol-ecules like HIV gp120, HIV-GAG gp 27, HSP70, and MHC class II proteins or peptides attached or combinations thereof.

Immobilization to Multimerization Domain

In a number of applications, it can be advantageous to immobilise the MHC molecule construct onto a solid or semi-solid support. Such support can be any which is suited for immobilisation, separation etc. Non-limiting examples include particles, beads, biodegradable particles, sheets, gels, filters, membranes (e. g. nylon membranes), fibres, capillaries, needles, microtitre strips, tubes, plates or wells, combs, pipette tips, micro arrays, chips, slides, or indeed any solid surface material. The solid or semi-solid support can be labelled, if this is desired. The support can also have scattering properties or sizes, which enable discrimination among supports of the same nature, e. g. particles of different sizes or scattering properties, colour or intensities.

Conveniently the support can be made of glass, silica, latex, plastic or any polymeric material. The support can also be made from a biodegradable material. Generally speaking, the nature of the support is not critical and a variety of materials can be used. The surface of support can be hydrophobic or hydrophilic.

Preferred are materials presenting a high surface area for binding of the MHC molecule constructs. Such supports can be for example be porous or particulate e. g. particles, beads, fibres, webs, sinters or sieves. Particulate materials like particles and beads are generally preferred due to their greater binding capacity. Particularly polymeric beads and particles can be of interest. Conveniently, a particulate support (e.g. beads or particles) can be substantially spheri-cal. The size of the particulate support is not critical, but it can for example have a diameter of at least 1 um and preferably at least 2 um, and have a maximum diameter of preferably not more than 10 um and more preferably not more than 6 urn. For example, particulate supports having diameters of 2.8 um and 4.5 um will work well. An example of a particulate support is monodisperse particles, i.e. such which are substantially uniform in size (e. g. size having a diameter standard deviation of less than 5%). Such have the advantage that they provide very uniform reproducibility of reaction.

Non-magnetic polymer beads can also be applicable. Such are available from a wide range of manufactures, e. g. Dynal Particles AS, Qiagen, Amersham Biosciences, Sero-tec, Seradyne, Merck, Nippon Paint, Chemagen, Promega, Prolabo, Polysciences, Agowa, and Bangs Laboratories.

Another example of a suitable support is magnetic beads or particles. The term "magnetic" as used everywhere herein is intended to mean that the support is capable of having a magnetic moment imparted to it when placed in a magnetic field, and thus is displaceable under the action of that magnetic field. In other words, a support comprising mag-netic beads or particles can readily be removed by magnetic aggregation, which provides a quick, simple and efficient way of separating out the beads or particles from a solution. Magnetic beads and particles can suitably be paramagnetic or superparamagnetic. Superparamagnetic beads, magnetic beads and particles are available from several manufactur-ers, e. g. Dynal Biotech ASA (Oslo, Norway, previously Dynal AS, e. g. DYNABEADS®@).

The support can suitably have a functionalised surface. Different types of functionalisation include making the surface of the support positively or negatively charged, or hydrophilic or hydrophobic. This applies in particular to beads and particles.

The MHC multimers of the present invention can be attached (immobilised) to the solid or semi-solid support by any method known in the art for attachment (or immobili-sation) to supports. In particular, the MHC multimers can be immobilised to the support by way of linkers, spacers or antibodies, or any combination thereof. Examples of suitable linkers include Calmodulin-binding peptide (CBP), 6×HIS, Protein A, Protein G, biotin, Avidin, Streptavidin, STREP-TAG®, Cellulose Binding Domain, Maltose Binding Pro-tein, S-Peptide Tag, Chitin Binding Tag, Immuno-reactive Epitopes, Epitope Tags, GST tagged proteins, E2Tag, HA Epitope Tag, Myc Epitope, FLAG Epitope, AU1 and AU5 Epitopes, Glu-Glu Epitope, KT3 Epitope, IRS Epitope, Btag Epitope, Protein Kinase-C Epitope, VSV Epitope, "zero length cross-linkers" such as 1-ethyl-3 (3-dimethylamino-propyl)-carbodiimide hydrochloride (EDAC), homobifunc-tional cross-linkers such as glutaric dialdehyde, disuccinim-idyl suberate (DSS) dimethyl adipimidate dihydrochloride (DMA), divinylfulfone (DVS), or bismaleimidohexane, and heterobifunctional cross-linkers such as 4-(N-maleimidom-ethyl) cyclohexane-I-carboxyl hydrazide hydro-chloride (M2C2H), succinimidyl-4-(N-maleimidomethyl) (SMCC), N-succinimidyl-3-(2-pyridyldithio) propionate (SPDP), and N-(gamma-maleimidobutyryloxy) succinimide (GMBS). Examples of suitable spacers include multi-functional mol-ecules such as diamino alkanes, dicarboxyls and dihydrox-yls. The spacers can additionally include functionalities such as e. g. ethers, amides, and amines.

Examples of suitable antibodies (polyclonal, monoclonal, recombinant) include antibodies directed against the multi-merization domain(s) and antibodies against the binding entity. It is to be understood that the MHC multimers can be attached covalently or reversibly. By "reversibly" is meant that the attachment can be reversed such that the MHC multimers can be liberated from the support.

By way of example, if the multimerization domain(s) is a dextran molecule, the MHC molecule construct can be immobilised using anti-dextran antibodies. By way of example, a PNA could be attached to the MHC molecule construct, and an anti-PNA antibody could be used for immobilisation.

It is to be understood that several or only one type of support can be applied at the same time. Likewise, a support can have immobilised thereto one or more MHC molecule constructs. The MHC multimers immobilised onto the sup-port can be the same or different. E. g. on type of MHC molecule construct can be immobilised to one type of support, and another type of MHC molecule construct to another type of support. In principle, the number of different MHC molecule construct is unlimited.

Alternative MHC Multimers

In the following alternatives ways to make MHC multi-mers compared to traditional methods are described.

MHC trimers can be generated by attaching three MHC complexes to the same multimerization domain together with a labelling molecule, e.g. 3 MHC complexes attached to SA through biotin and with a biotinylated labelling molecule attached to the fourth biotin-binding pocket of SA. Alternatively the MHC complexes can be covalent linked to SA, e.g. by genetic fusion. The labelling molecules can be any labelling molecule suitable for direct or indirect detec-tion, including fluorophores, chromophores or enzymes as described elsewhere herein.

MHC dextramers are as described elsewhere made by coupling MHC complexes to dextran via a streptavidin-biotin interaction. In principle biotin-streptavidin can be replaced by any dimerization domain where one half of the dimerization domain is coupled to the MHC-peptide com-plex and the other half is coupled to dextran. E.g. an acidic helix (one half of a coiled-coil dimer) is coupled/fused to MHC and a basic helix (other half of a coiled-coil dimmer) is coupled/fused to dextran. Mixing the two results in MHC binding to dextran by forming a coiled-coil structure between the two.

MHC dextramers can also be made by covalent coupling of MHC complexes to the dextran backbone, e.g. by chemi-cal coupling of MHC complexes to dextran backbones. The MHC complexes can be coupled through either heavy chain or β2-microglobulin if the MHC complexes are MHC I or through α-chain or β-chain if the MHC complexes are MHC II. MHC complexes can be coupled as folded complexes comprising heavy chain/beta2microglobulin or α-chain/β-chain or either combination together with peptide in the peptide binding cleft. Alternatively either of the protein chains can be coupled to dextran and then folded in vitro together with the other chain of the MHC complex not coupled to dextran and together with peptide. Direct cou-pling of MHC complexes to dextran multimerization domain can be via an amino group or via a sulphide group. Either group can be a naturally component of the MHC complex or attached to the MHC complex chemically. Alternatively a gene encoding an amino or sulphide comprising amino acid can be fused to the genes of either chain in the MHC complex.

Another way to couple MHC complexes to dextran mul-timerization domains is to use peptide as a linker between MHC and dextran. Linker containing antigenic peptide in one end is coupled to dextran. Antigenic peptide here means a peptide able to bind MHC complexes in the peptide binding cleft. E.g. 10 or more antigenic peptides are coupled to one dextran molecule. When MHC complexes are added to such peptide-dextran construct the MHC complexes will bind the antigenic peptides and thereby MHC-peptide com-plexes are displayed around the dextran multimerization domain. The antigenic peptides can be identical or different from each other. Similarly MHC complexes can be either identical or different from each other as long as they are capable of binding one or more of the peptides on the dextran multimerization domain.

MHC complexes can be multimerized by other means than coupling to one or more multimerization domain(s). One method is to extend the bound peptide with dimeriza-tion domains. One end of the peptide is extended with dimerization domain A (e.g. acidic helix, half of a coiled-coil dimer) and the other end is extended with dimerization domain B (e.g. basic helix, other half of a coiled-coil dimer). When MHC complexes are loaded/mixed with these extended peptides the following multimer structure will be formed: A-MHC-BA-MHC-BA-MHC-B etc. The peptides in the mixture can either be identical or a mixture of peptides with comparable extended dimerization domains. Alterna-tively both ends of a peptide are extended with the same dimerization domain A and another peptide (same amino acid sequence or a different amino acid sequence) is extended with dimerization domain B. When MHC and peptides are mixed the following structures are formed: A-MHC-AB-MHC-BA-MHC-AB-MHC-B etc. Multim-erization of MHC complexes by extension of peptides are restricted to MHC II molecules since the peptide binding groove of MHC I molecules are closed in both ends thereby limit the size of peptide embedded in the groove and preventing the peptide from extending out of the groove.

Another multimerization approach applicable to both MHC I and MHC II complexes is based on extension of N- and C-terminal of the MHC complex. For example the N-terminal of the MHC complex is extended with dimeriza-tion domain A and the C-terminal is extended with dimeriza-tion domain B. When MHC complexes are incubated together they pair with each other and form multimers like: A-MHC-BA-MHC-BA-MHC-BA-MHC-B etc. Alterna-tively the N-terminal and the C-terminal of a MHC complex are both extended with dimerization domain A and the N-terminal and C-terminal of another preparation of MHC complex (either the same or a different MHC) are extended with dimerization domain B. When these to types of MHC complexes are incubated together multimers will be formed: A-MHC-AB-MHC-BA-MHC-AB-MHC-B etc.

In all the above-described examples the extension can be either chemically coupled to the peptide/MHC complex or introduced as extension by gene fusion.

Dimerization domain AB can be any molecule pair able to bind to each other like: acid/base coiled-coil helices, antibody-antigen, DNA-DNA, PNA-PNA, DNA-PNA, DNA-RNA, LNA-DNA, leucine zipper e.g. Fos/Jun, streptavidin-biotin and other molecule pairs as described elsewhere herein.

Stabilization of Empty MHC Complexes and MHC-Peptide Complexes

Classical MHC complexes are in nature embedded in the membrane. A preferred embodiment includes multimers comprising a soluble form of MHC II or I where the transmembrane and cytosolic domains of the membrane-anchored MHC complexes are removed. The removal of the membrane-anchoring parts of the molecules can influence the stability of the MHC complexes. The stability of MHC complexes is an important parameter when generating and using MHC multimers.

MHC I complexes consist of a single membrane-anchored heavy chain that contains the complete peptide binding groove and is stable in the soluble form when complexed with β2m. The long-term stability is dependent on the binding of peptide in the peptide-binding groove. Without a peptide in the peptide binding groove the heavy chain and β2m tend to dissociate. Similarly, peptides with high affinity for binding in the peptide-binding groove will typically stabilize the soluble form of the MHC complex while peptides with low affinity for the peptide-binding groove will typically have a smaller stabilizing effect.

In contrast, MHC II complexes consist of two membrane-anchored chains of almost equal size. When not attached to the cell membrane the two chains tend to dissociate and are therefore not stable in the soluble form unless a high affinity peptide is bound in the peptide-binding groove or the two chains are held together in another way.

In nature MHC I molecules consist of a heavy chain combined with β2m, and a peptide of typically 8-11 amino acids. Herein, MHC I molecules also include molecules consisting of a heavy chain and β2m (empty MHC), or a heavy chain combined with a peptide or a truncated heavy chain comprising α1 and α2 subunits combined with a peptide, or a full-length or truncated heavy chain combined with a full-length or truncated β2m chain. These MHC I molecules can be produced in *E. coli* as recombinant proteins, purified and refolded in vitro (Garboczi et al., 1992), Proc. Natl. Acad. Sci. 89, 3429-33). Alternatively, insecT-cell systems or mammalian cell systems can be used. To produce stable MHC I complexes and thereby generate reliable MHC I multimers several strategies can be followed. Stabilization strategies for MHC I complexes are described in the following.

Generation of Covalent Protein-Fusions

MHC I molecules can be stabilized by introduction of one or more linkers between the individual components of the MHC I complex. This could be a complex consisting of a heavy chain fused with β2m through a linker and a soluble peptide, a heavy chain fused to β2m through a linker, a heavy chain/β2m dimer covalently linked to a peptide through a linker to either heavy chain or β2m, and where there can or can not be a linker between the heavy chain and β2m, a heavy chain fused to a peptide through a linker, or the α1 and α2 subunits of the heavy chain fused to a peptide through a linker. In all of these example protein-fusions, each of the heavy chain, β2m and the peptide can be truncated.

The linker could be a flexible linker, e.g. made of glycine and serine and e.g. between 5-20 residues long. The linker could also be rigid with a defined structure, e.g. made of amino acids like glutamate, alanine, lysine, and leucine creating e.g. a more rigid structure.

In heavy chain-β2m fusion proteins the COOH terminus of β2m can be covalently linked to the NH₂ terminus of the heavy chain, or the NH₂ terminus of β2m can be linked to the COOH terminus of the heavy chain. The fusion-protein can also comprise a β2m domain, or a truncated β2m domain, inserted into the heavy chain, to form a fusion-protein of the form "heavy chain (first part)-β2m-heavy chain (last part)". Likewise, the fusion-protein can comprise a heavy chain domain, or a truncated heavy chain, inserted into the β2m chain, to form a fusion-protein of the form "β2m(first part)-heavy chain-β2m(last part)".

In peptide-β2m fusion proteins the COOH terminus of the peptide is preferable linked to the NH₂ terminus of β2m but the peptide can also be linked to the COOH terminal of β2m via its NH₂ terminus. In heavy chain-peptide fusion proteins it is preferred to fuse the NH₂ terminus of the heavy chain to the COOH terminus of the peptide, but the fusion can also be between the COOH terminus of the heavy chain and the NH₂ terminus of the peptide. In heavy chain-βR2m-peptide fusion proteins the NH₂ terminus of the heavy chain can be fused to the COOH terminus of β2m and the NH₂ terminus of β2m can be fused to the COOH terminus of the peptide.

Non-Covalent Stabilization by Binding to an Unnatural Component

Non-covalent binding of unnatural components to the MHC I complexes can lead to increased stability. The unnatural component can bind to both the heavy chain and the β2m, and in this way promote the assembly of the complex, and/or stabilize the formed complex. Alternatively, the unnatural component can bind to either β2m or heavy chain, and in this way stabilize the polypeptide in its correct conformation, and in this way increase the affinity of the heavy chain for β2m and/or peptide, or increase the affinity of β2m for peptide. Here, unnatural components mean antibodies, peptides, aptamers or any other molecule with the ability to bind peptides stretches of the MHC complex. Antibody is here to be understood as truncated or full-length antibodies (of isotype IgG, IgM, IgA, IgE), Fab, scFv or bi-Fab fragments or diabodies.

An example of special interest is an antibody binding the MHC I molecule by interaction with the heavy chain as well as β2m. The antibody can be a bispecific antibody that binds with one arm to the heavy chain and the other arm to the β2m of the MHC complex. Alternatively the antibody can be monospecific, and bind at the interface between heavy chain and β2m.

Another example of special interest is an antibody binding the heavy chain but only when the heavy chain is correct folded. Correct folded is here a conformation where the MHC complex is able to bind and present peptide in such a way that a restricted T-cell can recognize the MHC-peptide complex and be activated. This type of antibody can be an antibody like the one produced by the clone W6/32 (M0736 from Dako, Denmark) that recognizes a conformational epitope on intact human and some monkey MHC complexes comprising β2m, heavy chain and peptide.

Generation of Modified Proteins or Protein Components

One way to improve stability of a MHC I complex am to increase the affinity of the binding peptide for the MHC complex. This can be done by mutation/substitution of amino acids at relevant positions in the peptide, by chemical modifications of amino acids at relevant positions in the peptide or introduction by synthesis of non-natural amino acids at relevant positions in the peptide. Alternatively, mutations, chemical modifications, insertion of natural or non-natural amino acids or deletions could be introduced in the peptide binding cleft, i.e. in the binding pockets that accommodate peptide side chains responsible for anchoring the peptide to the peptide binding cleft. Moreover, reactive groups can be introduced into the antigenic peptide; before, during or upon binding of the peptide, the reactive groups can react with amino acid residues of the peptide binding cleft, thus covalently linking the peptide to the binding pocket.

Mutations, chemical modifications, insertion of natural or non-natural amino acids or deletions could also be introduced in the heavy chain and/or $\beta 2m$ at positions outside the peptide-binding cleft. A preferred embodiment is removal of "unwanted cysteine residues" in the heavy chain by mutation, chemical modification, amino acid exchange or deletion. "Unwanted cysteine residues" is here to be understood as cysteines not involved in the correct folding of the final MHC I molecule. The presence of cysteine not directly involved in the formation of correctly folded MHC I molecules can lead to formation of intra molecular disulfide bridges resulting in a non correct folded MHC complex during in vitro refolding. Another method for covalent stabilization of MHC I complex am to covalently attach a linker between two of the subunits of the MHC complex. This can be a linker between peptide and heavy chain or between heavy chain and beta2microglobulin.

MHC II complexes consist of a $\alpha$-chain and a $\beta$-chain combined with a peptide. It could also be a molecule only consisting of $\alpha$-chain and $\beta$-chain (so-called empty MHC II), a truncated $\alpha$-chain (e.g. the $\alpha 1$ domain) combined with full-length $\beta$-chain either empty or loaded with a peptide, a truncated $\beta$-chain (e.g. the $\beta 1$ domain) combined with a full-length $\alpha$-chain, either empty or loaded with a peptide or a truncated $\alpha$-chain combined with a truncated $\beta$-chain (e.g. $\alpha 1$ and $\beta 1$ domain), either empty or loaded with a peptide.

In contrast to MHC I complexes, MHC II complexes are not easily refolded after denaturation in vitro. Only some MHC II alleles can be expressed in *E. coli* and refolded in vitro. Therefore, preferred expression systems for production of MHC II molecules are eukaryotic systems where refolding after expression of protein is not necessary. Preferred expression systems include stable *Drosophila* cell transfectants, baculovirus infected insecT-cells, CHO cells or other mammalian cell lines suitable for expression of proteins.

Stabilization of soluble MHC II complexes is even more important than for MHC I molecules, since both $\alpha$- and $\beta$-chain are participants in formation of the peptide binding groove and tend to dissociate when not embedded in the cell membrane. Stabilization strategies for MHC II complexes are described in the following.

Generation of Covalent Protein-Fusions

MHC II complexes can be stabilized by introduction of one or more linkers between the individual components of the MHC II complex. This can be a $\alpha/\beta$ dimer with a linker between $\alpha$-chain and $\beta$-chain; a $\alpha/\beta$ dimer covalently linked to the peptide via a linker to either the $\alpha$-chain or $\beta$-chain; a $\alpha/\beta$ dimer, covalently linked by a linker between the $\alpha$-chain and $\beta$-chain, and where the dimer is covalently linked to the peptide; a $\alpha/\beta$ dimer with a linker between $\alpha$-chain and $\beta$-chain, where the dimer is combined with a peptide covalently linked to either $\alpha$-chain or $\beta$-chain.

The linker can be a flexible linker, e.g. made of glycine and serine, and is typically between 5-20 residues long, but can be shorter or longer. The linker can also be more rigid with a more defined structure, e.g. made of amino acids like glutamate, alanine, lysine, and leucine.

The peptides can be linked to the $NH_2$- or COOH-terminus of either $\alpha$-chain or $\beta$-chain. Of special interest are peptides linked to the $NH_2$-terminus of the $\beta$-chain via their COOH-terminus, since the linker required is shorter than if the peptide is linked to the COOH-terminus of the $\beta$-chain.

Linkage of $\alpha$-chain to $\beta$-chain can be via the COOH-terminus of the $\beta$-chain to the $NH_2$-terminus of the $\alpha$-chain or from the COOH-terminus of the $\alpha$-chain to the NH2-terminus of the $\beta$-chain.

In a three-molecule fusion protein consisting of $\alpha$-chain, $\beta$-chain and peptide a preferred construct is where one linker connect the COOH-terminus of the $\beta$-chain with the $NH_2$-terminus of the $\alpha$-chain and another linker connects the COOH-terminal of the peptide with the $NH_2$-terminal of the $\beta$-chain. Alternatively one linker joins the COOH-terminus of the $\alpha$-chain with the $NH_2$-terminus of the $\beta$-chain and the second linker joins the $NH_2$-terminus of the peptide with the COOH-terminus of the $\beta$-chain. The three peptides of the MHC complex can further be linked as described above for the three peptides of the MHC complex, including internal fusion points for the proteins.

Non-Covalent Stabilization by Binding Ligand

Non-covalent binding of ligands to the MHC II complex can promote assembly of $\alpha$- and $\beta$-chain by bridging the two chains, or by binding to either of the $\alpha$- or $\beta$-chains, and in this way stabilize the conformation of $\alpha$ or $\beta$, that binds $\beta$ or $\alpha$, respectively, and/or that binds the peptide. Ligands here mean antibodies, peptides, aptamers or any other molecules with the ability to bind proteins.

A particular interesting example is an antibody binding the MHC complex distal to the interaction site with TCR, i.e. distal to the peptide-binding cleft. An antibody in this example can be any truncated or full length antibody of any isotype (e.g. IgG, IgM, IgA or IgE), a bi-Fab fragment or a diabody. The antibody could be bispecific with one arm binding to the $\alpha$-chain and the other arm binding to the $\beta$-chain. Alternatively the antibody could be monospecific and directed to a sequence fused to the $\alpha$-chain as well as to the $\beta$-chain. Alternatively the antibody is monospecific and binds to a surface of the complex that involves both the $\alpha$- and $\beta$-chain, e.g. both the $\alpha 2$- and $\beta 2$-domain or both the $\alpha 1$- and $\beta 1$-domain.

The antibodies described above can be substituted with any other ligand that binds at the $\alpha$-/$\beta$-chain interface, e.g. peptides and aptamers. The ligand can also bind the peptide, although, in this case it is important that the ligand does not interfere with the interaction of the peptide or binding cleft with the TCR.

Non-Covalent Stabilization by Induced Multimerization

In nature the anchoring of the $\alpha$- and $\beta$-chains in the cell membrane stabilizes the MHC II complexes considerably. As mentioned above, a similar concept for stabilization of the $\alpha/\beta$-dimer was employed by attachment of the MHC II chains to the Fc regions of an antibody, leading to a stable $\alpha/\beta$-dimer, where $\alpha$ and $\beta$ are held together by the tight interactions between two Fc domains of an antibody. Other dimerization domains can be used as well.

In one other example of special interest MHC II molecules are incorporated into artificial membrane spheres like liposomes or lipospheres. MHC II molecules can be incorporated as monomers in the membrane or as dimers like the MHC II-antibody constructs describes above. In addition to stabilization of the MHC II complex an increased avidity is obtained. The stabilization of the dimer will in most cases also stabilize the trimeric MHC-peptide complex.

Induced multimerization can also be achieved by biotinylation of α- as well as β-chain and the two chains brought together by binding to streptavidin. Long flexible linkers such as extended glycine-serine tracts can be used to extend both chains, and the chains can be biotinylated at the end of such extended linkers. Then streptavidin can be used as a scaffold to bring the chains together in the presence of the peptide, while the flexible linkers still allow the chains to orientate properly.

Generation of Modified Proteins or Protein Components

Stability of MHC II complexes can be increased by covalent modifications of the protein. One method is to increase the affinity of the peptide for the MHC complex. This can be done by exchange of the natural amino acids with other natural or non-natural amino acids at relevant positions in the peptide or by chemical modifications of amino acids at relevant positions in the peptide. Alternatively, mutations, chemical modifications, insertion of natural or non-natural amino acids or deletions can be introduced in the peptide-binding cleft. Mutations, chemical modifications, insertion of natural or non-natural amino acids or deletions can alternatively be introduced in α- and/or β-chain at positions outside the peptide-binding cleft.

In this respect a preferred embodiment is to replace the hydrophobic transmembrane regions of α-chain and β-chain by leucine zipper dimerisation domains (e.g. Fos-Jun leucine zipper; acid-base coiled-coil structure) to promote assembly of α-chain and β-chain.

Another preferred embodiment is to introduce one or more cysteine residues by amino acid exchange at the COOH-terminal of both α-chain and β-chain, to create disulfide bridges between the two chains upon assembly of the MHC complex.

Another embodiment is removal of "unwanted cysteine residues" in either of the chains by mutation, chemical modification, amino acid exchange or deletion. "Unwanted cysteine residues" is here to be understood as cysteines not involved in correct folding of the MHC II-peptide complex. The presence of cysteines not directly involved in the formation of correctly folded MHC II complexes can lead to formation of intra molecular disulfide bridges and incorrectly folded MHC complexes.

MHC II complexes can also be stabilized by chemically linking together the subunits and the peptide. That can be a linker between peptide and α-chain, between peptide and β-chain, between α-chain and β-chain, and combination thereof.

Such linkages can be introduced prior to folding by linking two of the complex constituents together, then folding this covalent hetero-dimer in the presence of the third constituent. An advantage of this method is that it only requires complex formation between two, rather than three species.

Another possibility is to allow all three constituents to fold, and then to introduce covalent cross-links on the folded MHC-complex, stabilizing the structure. An advantage of this method is that the two chains and the peptide will be correctly positioned relatively to each other when the cross linkages are introduced.

Chemically Modified MHC Complexes

There are a number of amino acids that are particularly reactive towards chemical cross linkers. In the following, chemical reactions are described that are particularly preferable for the cross-linking or modification of MHC I or MHC II complexes.

The amino group at the N-terminal of both chains and of the peptide, as well as amino groups of lysine side chains, are nucleophilic and can be used in a number of chemical reactions, including nucleophilic substitution by activation of electrophiles (e.g. acylation such as amide formation, pyrazolone formation, isoxazolone formation; alkylation; vinylation; disulfide formation), addition to carbon-hetero multiple bonds (e.g. alkene formation by reaction of phosphonates with aldehydes or ketones; arylation; alkylation of arenes/hetarenes by reaction with alkyl boronates or enolethers), nucleophilic substitution using activation of nucleophiles (e.g. condensations; alkylation of aliphatic halides or tosylates with enolethers or enamines), and cycloadditions. Example reagents that can be used in a reaction with the amino groups are activated carboxylic acids such as NHS-ester, tetra and pentafluoro phenolic esters, anhydrides, acid chlorides and fluorides, to form stable amide bonds. Likewise, sulphonyl chlorides can react with these amino groups to form stable sulphone-amides. Iso-Cyanates can also react with amino groups to form stable ureas, and isothiocyanates can be used to introduce thio-urea linkages. Aldehydes, such as formaldehyde and glutardialdehyde will react with amino groups to form shiff's bases, than can be further reduced to secondary amines. The guanidino group on the side chain of arginine will undergo similar reactions with the same type of reagents. Another very useful amino acid is cysteine. The thiol on the side chain is readily alkylated by maleimides, vinyl sulphones and halides to form stable thioethers, and reaction with other thiols will give rise to disulphides. Carboxylic acids at the C-terminal of both chains and peptide, as well as on the side chains of glutamic and aspartic acid, can also be used to introduce cross-links. They will require activation with reagents such as carbodiimides, and can then react with amino groups to give stable amides.

Thus, a large number of chemistries can be employed to form covalent cross-links. The crucial point is that the chemical reagents are bi-functional, being capable of reacting with two amino acid residues. They can be either homo bi-functional, possessing two identical reactive moieties, such as glutardialdehyde or can be hetero bi-functional with two different reactive moieties, such as GMBS (MaleimidoButyryloxy-Succinimide ester).

Alternatively, two or more reagents can be used; i.e. GMBS can be used to introduce maleimides on the α-chain, and iminothiolane can be used to introduce thiols on the β-chain; the malemide and thiol can then form a thioether link between the two chains.

For the present invention some types of cross-links are particularly useful. The folded MHC-complex can be reacted with dextrans possessing a large number (up to many hundreds) of vinyl sulphones. These can react with lysine residues on both the α and β chains as well as with lysine residues on the peptide protruding from the binding site, effectively cross linking the entire MHC-complex. Such cross linking is indeed a favoured reaction because as the first lysine residue reacts with the dextran, the MHC-complex becomes anchored to the dextran favouring further reactions between the MHC complex and the dextran multimerization domain. Another great advantage of this dextran chemistry is that it can be combined with fluorochrome labelling; i.e. the dextran is reacted both with one or several MHC-complexes and one or more fluorescent protein such as APC.

Another valuable approach is to combine the molecular biological tools described above with chemical cross linkers. As an example, one or more lysine residues can be inserted into the α-chain, juxtaposed with glutamic acids in the β-chain, where after the introduced amino groups and carboxylic acids are reacted by addition of carbodiimide. Such reactions are usually not very effective in water, unless as in this case, the groups are well positioned towards reaction. This implies that one avoids excessive reactions that could otherwise end up denaturing or changing the conformation of the MHC-complex.

Likewise one or more dextran multimerization domain(s) can be cross-linked with appropriately modified MHC-complexes; i.e. one or both chains of the MHC complex can be enriched with lysine residues, increasing reactivity towards the vinylsulphone dextran. The lysine's can be inserted at positions opposite the peptide binding cleft, orienting the MHC-complexes favourably for T-cell recognition.

Another valuable chemical tool is to use extended and flexible cross-linkers. An extended linker will allow the two chains to interact with little or no strain resulting from the linker that connects them, while keeping the chains in the vicinity of each other should the complex dissociate. An excess of peptide should further favour reformation of dissociated MHC-complex.

Stabilization with One or More Soluble Additives

Salts, detergents, organic solvent, polymers and any other soluble additives can be added to increase the stability of MHC complexes. Of special interest are additives that increase surface tension of the MHC complex. Examples are sucrose, mannose, glycine, betaine, alanine, glutamine, glutamic acid and ammonium sulfate. Glycerol, mannitol and sorbitol are also included in this group even though they are able to bind polar regions.

Another group of additives of special interest increases surface tension of the MHC complex and simultaneously can interact with charged groups in the protein. Examples are $MgSO_4$, NaCl, polyethylenglycol, 2-methyl-2,4-pentanediol and guanidiniumsulphate.

Correct formation of MHC complexes is dependent on binding of peptide in the peptide-binding cleft; the bound peptide appears to stabilize the complex in its correct conformation. Addition of molar excess of peptide will force the equilibrium towards correctly folded MHC-peptide complexes. Likewise, excess β2m is also expected to drive the folding process in direction of correctly folded MHC complexes. Therefore peptide identical to the peptide bound in the peptide-binding cleft and β2m can be included as stabilizing soluble additives.

Other additives of special interest for stabilization of MHC complexes are BSA, fetal and bovine calf serum, and other protein components in serum with a protein stabilizing effect.

All of the above mentioned soluble additives could be added to any solution comprising MHC complexes in order to increase the stability of the molecule. This can be during the refolding process, to the formed MHC complex or to a solution of MHC multimers comprising several MHC complexes.

TCR-Binding Molecules

MHC I and MHC II complexes bind to TCRs. However, other molecules also bind TCR. Some TCR-biding molecules are described in the following.

Modified MHC I or MHC II complexes: MHC I and MHC II complexes modified in any way as described above, may bind TCR. Modifications include mutations (substitutions, deletions or insertions of natural or non-natural amino acids, or any other organic molecule. The mutations are not limited to those that increase the stability of the MHC complex, and could be introduced anywhere in the MHC complex. One example of special interest is mutations introduced in the α3 subunit of MHC I heavy chain. The α3-subunit interacts with CD8 molecules on the surface of T-cells. To minimize binding of MHC multimer to CD8 molecules on the surface of non-specific T-cells, amino acids in α3 domain involved in the interaction with CD8 may be mutated. Such a mutation may result in altered or abrogated binding of MHC to CD8 molecules. Another example of special interest is mutations in areas of the β2-domain of MHC II molecules responsible for binding CD4 molecules.

Another embodiment is chemically modified MHC complexes where the chemical modification could be introduced anywhere in the complex, e.g. a MHC complex where the peptide in the peptide-binding cleft has a dinitrophenyl group attached. A chemical modification of special interest is chemical biotinylation of any of the three components (α-chain, β-chain or peptide) in the MHC-peptide complex. Biotin may be covalent coupled to primary amines in the MHC-peptide complex, e.g. to Lysine, using chemical reactions as described elsewhere herein. Particularly suited for biottinylation reactions are N-hydroxy succinimide esters.

Modified MHC complexes could also be MHC I or MHC II fusion proteins where the fusion protein is not necessarily more stable than the native protein. Of special interest is MHC complexes fused with genes encoding an amino acid sequence capable of being biotinylated with a Bir A enzyme (Schatz, P. J., (1993), Biotechnology 11(10):1138-1143). This biotinylation sequence could be fused with the COOH-terminal of β2m or the heavy chain of MHC I molecules or the COOH-terminal of either the α-chain or β-chain of MHC II. Other sequences capable of being enzymatically or chemically modified, may be fused to the $NH_2$ or COOH-terminal ends of the MHC complex. Both enzymatic and chemical biotinylation may be carried out in vitro as well as in vivo.

Non-classical MHC complexes and other MHC-like molecules: Non-classical MHC complexes include protein products of MHC Ib and MHC IIb genes. MHC Ib genes encode β2m-associated cell-surface molecules but show little polymorphism in contrast to classical MHC class I genes. Protein products of MHC class Ib genes include HLA-E, HLA-G, HLA-F, HLA-H, MIC A, MIC B, ULBP-1, ULBP-2, ULBP-3 in humans and H2-M, H2-Q, H2-T and Rae1 in mice.

Non-classical MHC II molecules (protein products of MHC IIb genes) include HLA-DM, HLA-DO in humans and H2-DM and H2-DO in mice that are involved in regulation of peptide loading into MHC II molecules.

Another MHC-like molecule of special interest is the MHC I-like molecule CD1. CD1 is similar to MHC I molecules in its organization of subunits and association with β2m but presents glycolipids and lipids instead of peptides.

Artificial molecules capable of binding specific TCRs: Of special interest are antibodies that bind TCRs. Antibodies herein include full length antibodies of isotype IgG, IgM, IgE, IgA and truncated versions of these, antibody fragments like Fab fragments and scFv. Antibodies also include antibodies of antibody fragments displayed on various supramolecular structures or solid supports, including filamentous phages, yeast, mammalian cells, fungi, artificial cells or micelles, and beads with various surface chemistries.

Another embodiment of special interest is peptides that bind TCRs. Peptides herein include peptides composed of natural, non-natural and/or chemically modified amino acids with a length of 8-20 amino acids. The peptides could also be longer than 20 amino acids or shorter than 8 amino acids. The peptides can or can not have a defined tertiary structure.

Aptamers are another preferred group of TCR ligands. Aptamers are herein understood as natural nucleic acids (e.g. RNA and DNA) or unnatural nucleic acids (e.g. PNA, LNA, morpholinos) capable of binding TCR. The aptamer molecules consist of natural or modified nucleotides in various lengths.

Other TCR-binding molecules can be ankyrin repeat proteins or other repeat proteins, Avimers, or small chemical molecules, as long as they are capable of binding TCR with a dissociation constant smaller than $10^{-3}$ M.

Technical Applications for MHC Multimers

MHC multimers as described herein can be used to identify and isolate specific T-cells in a wide array of applications. In principle all kind of samples possessing T-cells and/or T-cell receptors (TCR's) can be analyzed with MHC multimers.

Technical applications for MHC multimers include but is not limited to the methods and principles described in the following.

MHC multimers can be used to detect T-cells and/or TCR's in a sample by binding specific TCR's in a given sample. In general T-cells can be detected as individual cells or as populations of cells and the sample may be fluid, solid, semifluid or semisolid.

Example fluid sample include, but is not limited to, blood, lymph, cerebrospinal fluid, synovial fluid, sputum, lymph, semen, fluid cultures of cells, suspensions of solid tissue fluid samples with TCR coated beads, fluid samples with soluble TCR's and any fluid sample containing T-cells and/or TCR's.

Example solid sample include, but is not limited to, solid tissue, tissue sections, organ, part of organ or tissue, human bodies or any part thereof, animal bodies of any part thereof and cells embedded in a solid matrix, e.g. parafin.

In the following applications of MHC multimers for detection of T-cells in fluid are explained.

Flow Cytometry Analysis:

In one embodiment of the present invention MHC multimers can be used for detection of individual T-cells in fluid samples using flow cytometry or flow cytometry-like analysis.

Liquid cell samples can be analyzed using a flow cytometer, able to detect and count individual cells passing in a stream through a laser beam. For identification of specific T-cells using MHC multimers, cells are stained with fluorescently labeled MHC multimer by incubating cells with MHC multimer and then forcing the cells with a large volume of liquid through a nozzle creating a stream of spaced cells. Each cell passes through a laser beam and any fluorochrome bound to the cell is excited and thereby fluoresces. Sensitive photomultipliers detect emitted fluorescence, providing information about the amount of MHC multimer bound to the cell. By this method MHC multimers can be used to identify individual T-cells and/or specific T-cell populations in liquid samples.

Cell samples capable of being analyzed by MHC multimers in flow cytometry analysis include, but is not limited to, blood samples or fractions thereof, T-cell lines (hybridomas, transfected cells) and homogenized tissues like spleen, lymph nodes, tumors, brain or any other tissue comprising T-cells.

When analyzing blood samples whole blood can be used with or without lysis of red blood cells prior to analysis on flow cytometer. Lysing reagent can be added before or after staining with MHC multimers. When analysing blood samples without lysis of red blood cells one or more gating reagents may be included to distinguish lymphocytes from red blood cells. Preferred gating reagent are marker molecules specific for surface proteins on red blood cells, enabling subtraction of this cell population from the remaining cells of the sample. As an example, a fluorochrome labelled CD45 specific marker molecule e.g. an antibody can be used to set the trigger discriminator to allow the flow cytometer to distinguish between red blood corpuscles and stained white blood cells.

Alternative to analysis of whole blood, lymphocytes can be purified before flow cytometry analysis e.g. using standard procedures like a FICOLL®-Hypaque gradient. Another possibility is to isolate T-cells from the blood sample for example by adding the sample to antibodies or other T-cell specific markers immobilized on solid support. Marker specific T-cells will then attached to the solid support and following washing specific T-cells can be eluted. This purified T-cell population can then be used for flow cytometry analysis together with MHC multimers.

T-cells may also be purified from other lymphocytes or blood cells by rosetting. Human T-cells form spontaneous rosettes with sheep erythrocytes also called E-rossette formation. E-rossette formation can be carried out by incubating lymphocytes with sheep red erythrocytes followed by purification over a density gradient e.g. a FICOLL®-Hypaque gradient.

Instead of actively isolating T-cells unwanted cells like B-cells, NK cells or other cell populations can be removed prior to the analysis. A preferred method for removal of unwanted cells is to incubate the sample with marker molecules specific or one or more surface proteins on the unwanted cells immobilised unto solid support. An example include use of beads coated with antibodies or other marker molecule specific for surface receptors on the unwanted cells e.g. markers directed against CD19, CD56, CD14, CD15 or others. Briefly beads coated with the specific surface marker (s) are added to the cell sample. Cells different from the wanted T-cells with appropriate surface receptors will bind the beads. Beads are removed by e.g. centrifugation or magnetic withdrawal (when using magnetic beads) and remaining cell are enriched for T-cells.

Another example is affinity chromatography using columns with material coated with antibodies or other markers specific for the unwanted cells.

Alternatively, specific antibodies or markers can be added to the blood sample together with complement, thereby killing cells recognized by the antibodies or markers.

Various gating reagents can be included in the analysis. Gating reagents here means labeled antibodies or other labelled marker molecules identifying subsets of cells by binding to unique surface proteins or intraccellular components or intracellular secreted components. Preferred gating reagents when using MHC multimers are antibodies and marker molecules directed against CD2, CD3, CD4, and CD8 identifying major subsets of T-cells. Other preferred gating reagents are antibodies and markers against CD11a, CD14, CD15, CD19, CD25, CD30, CD37, CD49a, CD49e, CD56, CD27, CD28, CD45, CD45RA, CD45RO, CD45RB, CCR7, CCR5, CD62L, CD75, CD94, CD99, CD107b, CD109, CD152, CD153, CD154, CD160, CD161, CD178, CDw197, CDw217, Cd229, CD245, CD247, Foxp3, or other antibodies or marker molecules recognizing specific proteins unique for different lymphocytes, lymphocytes populations or other cell populations. Also included is antibodies and markers directed against interleukins e.g. IL-2, IL-4, 11-6, IL-10, IL-12, IL-21; Interferons e.g. INF-γ, TNF-α, TNF-β or other cytokine or chemokines.

Gating reagents can be added before, after or simultaneous with addition of MHC multimer to the sample.

Following labelling with MHC multimers and before analysis on a flow cytometer stained cells can be treated with a fixation reagent e.g. formaldehyde, ethanol or methanol to cross-link bound MHC multimer to the cell surface. Stained cells can also be analyzed directly without fixation.

The number of cells in a sample can vary. When the targeT-cells are rare, it is preferable to analyze large amounts of cells. In contrast, fewer cells are required when looking at T-cell lines or samples comprising many cells of the targeT-cell type.

The flow cytometer can in one embodiment be equipped to separate and collect particular types of cells. This is called cell sorting. MHC multimers in combination with sorting on a flow cytometer can be used to isolate antigen specific T-cell populations. Gating reagents as described above can be including further specifying the T-cell population to be isolated. Isolated and collected specific T-cell populations can then be further manipulated as described elsewhere herein e.g. expanded in vitro. This can e.g. be useful in autologous cancer therapy.

Direct determination of the concentration of MHC-peptide specific T-cells in a sample can be obtained by staining blood cells or other cell samples with MHC multimers and relevant gating reagents followed by addition of an exact amount of counting beads of known concentration. In general, the counting beads are microparticles with scatter properties that put them in the context of the cells of interest when registered by a flow cytometer. They can be either labelled with antibodies, fluorochromes or other marker molecules or they may be unlabelled. In some embodiments of the invention, the beads are polystyrene beads with molecules embedded in the polymer that are fluorescent in most channels of the flow-cytometer. Inhere the terms "counting bead" and "microparticle" are used interchangeably.

The counting beads employed in the methods and compositions described here should preferably be small, and are preferably between 0.1 μm and 100 μm, preferably about 5 μm in diameter. The microparticles should preferably be made of such material and be of such size as to stay suspended, with minimal agitation if necessary, in solution or suspension (i.e., once the sample is added). It should preferably not settle any faster than the cells of interest in the sample. The material from which the microparticles are made should be such as to avoid clumping or aggregation, i.e., the formation of doublets, triplets, quadruplets and other multiplets. Generally, a final count of counting beads of at least 1000/μl is preferred but any number can be counted.

The counting beads should preferably be labelled with one or more reporter molecule(s), such as one or more fluorescent molecule(s) (which is described in further detail elsewhere). Alternatively, or in addition, a microparticle which is autofluorescent may be employed.

Counting beads may in one embodiment be selected from the group consisting of fixed chicken red blood cells, coumarin beads, liposomes containing a fluorescent dye, FLUORESCEIN™ beads, rhodamine beads, fixed fluorescenT-cells, fluorescenT-cell nuclei, microorganisms and other beads tagged with a fluorescent dye. However, particularly advantageous examples of compact particles that may be used in the invention include microbeads, such as agarose beads, polyacrylamide beads, polystyrene beads, silica gel beads, etc.

Beads or microparticles suitable for use include those which are used for gel chromatography, for example, gel filtration media such as SEPHADEX®®. Suitable microbeads of this sort include, but is not limited to, SEPHADEX® G-10 having a bead size of 40-120 m (Sigma Aldrich catalogue number 27,103-9), SEPHADEX®® G-15 having a bead size of 40-120 m (Sigma Aldrich catalogue number 27,104-7), SEPHADEX®® G-25 having a bead size of 20-50 m (Sigma Aldrich catalogue number 27,106-3), SEPHADEX®® G-25 having a bead size of 20-80 m (Sigma Aldrich catalogue number 27,107-1), SEPHADEX®® G-25 having a bead size of 50-150 m (Sigma Aldrich catalogue number 27,109-8), SEPHADEX®® G-25 having a bead size of 100-300 m (Sigma Aldrich catalogue number 27,110-1), SEPHADEX®® G-50 having a bead size of 20-50 m (Sigma Aldrich catalogue number 27,112-8), SEPHADEX®® SEPHADEX® G-50 having a bead size of 20-80 m (Sigma Aldrich catalogue number 27,113-6), Sephadex G-50 having a bead size of 50-150 m (Sigma Aldrich catalogue number 27,114-4), SEPHADEX®® G-50 having a bead size of 100-300 μm (Sigma Aldrich catalogue number 27,115-2), SEPHADEX® G-75 having a bead size of 20-50 m (Sigma Aldrich catalogue number 27,116-0), SEPHADEX® G-75 having a bead size of 40-120 m (Sigma Aldrich catalogue number 27,117-9), SEPHADEX® G-100 having a bead size of 20-50 m (Sigma Aldrich catalogue number 27,118-7), SEPHADEX® G-100 having a bead size of 40-120 m (Sigma Aldrich catalogue number 27,119-5), SEPHADEX® G-150 having a bead size of 40-120 m (Sigma Aldrich catalogue number 27,121-7), and SEPHADEX® G-200 having a bead size of 40-120 m (Sigma Aldrich catalogue number 27,123-3).

SEPHAROSE® beads, for example, as used in liquid chromatography, may also be used. Examples include Q-SEPHAROSE®, S-SEPHAROSE® and SP-SEPHAROSE® beads, available for example from Amersham Biosciences Europe GmbH (Freiburg, Germany) as Q SEPHAROSE® XL (catalogue number 17-5072-01), Q SEPHAROSE® XL (catalogue number 17-5072-04), Q SEPHAROSE® XL (catalogue number 17-5072-60), SP SEPHAROSE® XL (catalogue number 17-5073-01), SP SEPHAROSE® XL (catalogue number 17-5073-04) and SP SEPHAROSE® XL (catalogue number I 17-5073-60) etc.

Other preferred particles for use in the methods and compositions described here comprise plastic microbeads. While plastic microbeads are usually solid, they may also be hollow inside and could be vesicles and other microcarriers. They do not have to be perfect spheres in order to function in the methods described here. Plastic materials such as polystyrene, polyacrylamide and other latex materials may be employed for fabricating the beads, but other plastic materials such as polyvinyl chloride, polypropylene and the like may also be used. Polystyrene is a preferred material. The microparticles include unlabelled beads, beads with antibodies, fluorochromes or other small molecules conjugated to the surface or beads with fluorochromes embedded in the polymer.

The counting beads are used as reference population to measure the exact volume of analyzed sample. The sample(s) are analyzed on a flow cytometer and the amount of MHC-specific T-cell is determined using e.g. a predefined gating strategy and then correlating this number to the number of counted counting beads in the same sample using the following equation:

$$\begin{aligned}\text{Concentration of MHC-specific } T\text{-cell in sample}= \\ \text{(number of MHC-peptide specific } T\text{-cells} \\ \text{counted/number of counting beads counted)}\times \\ \text{concentration of counting beads in sample}\end{aligned}$$

MHC multimers, gating reagents and/or counting beads can be added to the sample simultaneously or one by one in any order and with incubation and/or washes in between, before and/or after addition of the various components. Alternatively the MHC multimers, gating reagents and/or counting beads can be kept in a container to which the sample may be added directly either during collection of sample (e.g. during blood collection) or immediate prior to sample analysis. The container features a predetermined quantity of MHC multimers, gating reagents and/or counting beads and the reagents can be in suspension or alternatively embedded in a solid or semisolid medium or matrix.

When embedded in a matrix the matrix is such that it retains the reagents in the container when dry but releases the reagents into the sample medium when a sample containing cells of interest is added to the container. Preferably, the matrix dissolves in the sample medium to effect release.

For this purpose, the matrix preferably comprises a gelatinous, viscous, material, which may be liquid, semi-solid or gel-like in consistency. Preferably, the matrix is a viscous liquid.

The matrix may be substantially free of water, or it may comprise water. Preferably (although appearing dry) the matrix contains some water. Preferably less than 30% of the matrix is water, such as less than 25%, for example less than 20%, such as less than 15%, for example less than 10% and such as less than 5%. The matrix may comprise liquid other than water, such as glycerol, ethylene glycol, propylene glycol or others.

The matrix may preferably exist as a single contiguous mass, or it may be attached to the container as a number of separate pieces. Preferably it is contiguous. Preferably, however, the matrix is such that during handling or storage no portion of the matrix effectively detaches from the container to cause loss of reagents.

In preferred various embodiments, therefore, the matrix is water soluble, preferably readily soluble in aqueous media. In one preferred embodiment, the matrix dissolves when a sample containing the cells of interest is added into a container comprising the matrix, or otherwise breaks up in such a manner as to release the reagents into the sample medium. Preferably, all or substantially all of the reagents are released into the sample medium such as at least 75%, for example at least 85%, such as at least 90%, for example at least 95%, such as at least 99%.

Preferably, the matrix should comprise a non-oxidising (reducing) environment in order to avoid any unwanted redox-reactions. Thus, where a carbohydrate matrix (see below) is employed, the carbohydrates should be non-reducing. Furthermore the matrix should preferably be composed such that is does not crystallise, crack or change phase at any temperature that it may be subjected to under normal transportation and/or storage.

It is preferable to use a matrix with low melting point to avoid crystallization of the matrix. A high molecular weight is preferable to reduce the osmotic effect on the sample preparation.

In preferred embodiments, the matrix is based on a water soluble sugar mixture. The matrix or embedding medium may comprise one or more compounds including carbohydrates, polymers, small proteins or others or any combination thereof.

Examples of suitable carbohydrates for use in a matrix include, but are not limited to, saccharose, arabinose, ribulose, fructose, sorbose, glucose, mannose, gulose, galactose, sucrose, lactose, maltose, trehalose, raffinose and melizitose. Cellulose as well as carboxylated or otherwise derivatised cellulose products may also be employed.

Examples of suitable polymers for use in a matrix include polyvinylalcohols, polyethylene glycols, polyethylene imines, polyacryl amides, polyaziridines, glycols, polyacrylic acids, esters or derivatives thereof. It should be clear, that block co-polymers of the aforementioned could also be used.

Examples of small proteins include BSA other albumins or protein fragments such as Byco A.

Mixtures of two or more of the above may also be used. The components of the matrix may be present in any suitable proportion consistent with the desirable properties outlined above. Specifically, we disclose matrices comprising mixtures of carbohydrates, for example, fructose, trehalose and raffinose. Thus, the matrix may comprise any two of fructose, trehalose and raffinose, preferably at a 2:1 ratio, a 1:1 ratio or a 1:2 ratio.

The matrix may comprise 2:1, 1:1 or 1:2 of fructose and trehalose. One highly preferred advantageous embodiment is 3 mg of a 1:1 mixture of fructose and trehalose. The amount of carbohydrate has been determined as the maximum amount that still allows good lysing of the sample.

The matrix may perform other functions, such as providing a stable and inert medium for preserving the reagents during storage. For this purpose, other components may also be included.

These may include any one or more of preservatives, detergents, fixatives, antioxidants and pH-stabilizers. Examples of preservatives include bronidix, sodium azide and thiomersal. Examples of detergents include Tween, Triton, BRIJ®, PLURONIC® and TETRONIC® as well as derivatives and mixtures of the aforementioned. Examples of fixatives include vinylsulfone and glutaraldehyde.

The matrix may comprise one or more antioxidants, which are molecules that are radical scavengers. The radicals can e.g. be O-, N- C- or S-radicals. In some embodiments, the matrix may comprise scavengers for oxygen-derived radicals such as the superoxide anion or the hydroxyl radical formed by atmospheric oxygen under influence of light, heat or other environmental factors. Examples of such radical scavengers are ascorbic acid, beta-carotene, bilirubin, butylated hydroxytoluene (BHT), butylated hydroxyanisol (BHA) tert-butylhydroquinone (TBHQ) d-alpha-tocopherol, trolox and hydroxyanisol. Examples of pH-stabilizers include Good buffers, HEPES, MES, phosphate, citrate.

Staining fluid cell samples with MHC multimers may be combined with detecting of intracellular substances. The intracellular substances include, but are not limited to, detection of soluble factors like interleukins, hormones, proteins, peptides, DNA, RNA or other intracellular structures. In principle the T-cell is first labeled with MHC multimer, then fixated and the cell membrane made permeable using methanol, detergent e.g. saponin, digitonin, Leucoperm, Tween 20, triton, NP-40 or other agent able to make the membrane permeable. Then the intracellular substance can be detected using labeled antibody or other molecules capable of binding the intracellular substance.

Example MHC multimer staining combined with detection of intracellular substances is measurement of activation status of antigen specific T-cells. Activation status of antigen specific T-cells can e.g. be measured by detection of the TCR using MHC multimer combined with measurement of up- or down-regulation of intracellular molecules e.g. measurement of level of intracellular interleukines or other soluble factors. The method comprises one or more of the following steps: 1) MHC multimers and other marker molecules recognising surface exposed proteins are added to T-cells sample. Optionally the sample is washed. 2) An reagent able to block extracellular secretion of cytokine is added, e.g. monensin that interrupt intracellular transport processes leading to accumulation of produced soluble factor, e.g. interleukine-2 in the Golgi complex, 3) Fixation of cell membrane using mild fixator followed by permeabilization of cell membrane by. e.g. saponine. 4) Addition of labelled marker specific for the produced soluble factor to be determined; the labbelled cell samples are analysed using a flow cytometer.

An alternative to this procedure is to trap secreted soluble factors on the surface of the secreting T-cell as described by Manz, R. et al., Proc. Natl. Acad. Sci. USA 92:1921 (1995).

Detection of specific T-cells in a sample combined with simultaneous detection of activation status of T-cells can also be measured using marker molecules specific for up- or down-regulated surface exposed receptors together with MHC multimers. The marker molecule and MHC multimer can be labelled with the same label or different labelling molecules and added to the sample simultaneously or sequentially or separately.

Detection of Individual T-Cells in Fluid Samples Using Microscopy

Another preferred method for detection of individual T-cells in fluid samples is using microscopy. Microscopy comprises any type of microscopy including optical, electron and scanning probe microscopy, Bright field microscopy, Dark field microscopy, Phase contrast microscopy, Differential interference contrast microscopy, Fluorescence microscopy, Confocal laser scanning microscopy, X-ray microscopy, Transmission electron microscopy, Scanning electron microscopy, atomic force microscope, Scanning tunneling microscope and photonic force microscope. This can be done as follows: A suspension of T-cells are added MHC multimers, the sample washed and then the amount of MHC multimer bound to each cell are measured. Bound MHC multimers may be labelled directly or measured through addition of labelled marker molecules. The sample is then spread out on a slide or similar in a thin layer able to distinguish individual cells and labelled cells identified using a microscope. Depending on the type of label different types of microscopes may be used, e.g. if fluorescent labels are used a fluorescent microscope is used for the analysis. For example MHC multimers can be labeled with a flourochrome or bound MHC multimer detected with a fluorescent antibody. Cells with bound fluorescent MHC multimers can then be visualized using e.g. an immunofluorescence microscope or a confocal fluorescence microscope.

Immunohistochemistry (IHC)

MHC multimers can also be used to directly detect T-cells in solid samples for example solid tissue. In the present invention solid tissue includes tissue, tissue biopsies, frozen tissue or frozen tissue biopsies, paraffin embedded tissue or tissue biopsies and sections of either of the above mentioned.

IHC is a method where MHC multimers can be used to directly detect specific T-cells e.g. in sections of solid tissue.

In a preferred embodiment of the present invention sections of fixed or frozen tissue sample are incubated with MHC multimer allowing MHC multimer to bind specific T-cells in the tissue. The MHC multimer may be labelled with a fluorochrome, chromophore, or any other labelling molecule that can be detected. The labbeling of the MHC multimer may be directly or through a second marker molecule. As an example, the MHC multimer can be labelled with a tag that can be recognized by e.g. a secondary antibody, optionally labelled with HRP or another label. The bound MHC multimer is then detected by its fluorescence or absorbance (for fluorophore or chromophore), or by addition of an enzyme-labelled antibody directed against this tag, or another component of the MHC multimer (e.g. one of the protein chains, a label on the one or more multimerization domain). The enzyme can e.g. be Horseradish Peroxidase (HRP) or Alkaline Phosphatase (AP), both of which convert a colourless substrate into a coloured reaction product in situ. This coloured deposit identifies the binding site of the MHC multimer, and can be visualized under e.g. a light microscope. The MHC multimer can also be directly labelled with e.g. HRP or AP, and used in IHC without an additional antibody.

A preferred embodiment for detection of T-cells in solid tissue includes use of tissue embedded in paraffin, from which tissue sections are made and fixed in formalin before staining. Antibodies are standard reagents used for staining of formalin-fixed tissue sections; these antibodies often recognize linear epitopes. In contrast, most MHC multimers are expected to recognize a conformational epitope on the TCR. In this case, the native structure of TCR needs to be at least partly preserved in the fixed tissue. Fixation of tissue therefore should be gentle.

Another preferred embodiment and an alternative to stain fixed tissue section is staining performed tissue sections from frozen tissue blocks. In this type of staining fixation is done after MHC multimer staining.

Immunofluorescence Microscopy

This is an alternative technical application to IHC where MHC multimers can be used to identify specific T-cells in sections of solid tissue. Instead of visualization of bound MHC multimer by an enzymatic reaction, MHC multimers are labelled with a flourochrome or bound MHC multimer are detected by a fluorescent antibody. Cells with bound fluorescent MHC multimers can be visualized in an immunofluorescence microscope or in a confocal fluorescence microscope. This method can also be used for detection of T-cells in fluid samples using the principles described for detection of T-cells in fluid sample described elsewhere herein.

Detection of T-Cells in Solid Tissue In Vivo

MHC multimers may also be used for detection of T-cells in solid tissue in vivo. For in vivo detection of T-cells labeled MHC multimers are injected in to the body of the individual to be investigated. The MHC multimers may be labeled with e.g. a paramagnetic isotope. Using a magnetic resonance imaging (MRI) scanner or electron spin resonance (ESR) scanner MHC multimer binding T-cells can then be measured and localized. In general, any conventional method for diagnostic imaging visualization can be utilized. Usually gamma and positron emitting radioisotopes are used for camera and paramagnetic isotopes for MRI.

Detection of T-Cells Immobilized on Solid Support.

In a number of applications, it may be advantageous to immobilise the T-cell onto a solid or semi-solid support. Such support may be any which is suited for immobilisation, separation etc. Non-limiting examples include particles, beads, biodegradable particles, sheets, gels, filters, membranes (e. g. nylon membranes), fibres, capillaries, needles, microtitre strips, tubes, plates or wells, combs, pipette tips, micro arrays, chips, slides, or indeed any solid surface material. The solid or semi-solid support may be labelled, if this is desired. The support may also have scattering properties or sizes, which enable discrimination among supports of the same nature, e.g. particles of different sizes or scattering properties, colour or intensities.

An example of a method where MHC multimers can be used for detection of immobilized T-cells is ELISA (Enzyme-Linked Immunosorbent Assay). ELISA is a binding assay originally used for detection of antibody-antigen interaction. Detection is based on an enzymatic reaction, and commonly used enzymes are e.g. HRP and AP. MHC multimers can be used in ELISA-based assays for analysis of purified TCR's and T-cells immobilized in wells of a microtiter plate. The bound MHC multimers can be labelled either by direct chemical coupling of e.g. HRP or AP to the MHC multimer (e.g. the one or more multimerization domain or the MHC proteins), or e.g. by an HRP- or AP-coupled antibody or other marker molecule that binds to the MHC multimer. Detection of the enzyme-label is then by addition of a substrate (e.g. colourless) that is turned into a detectable product (e.g. coloured) by the HRP or AP enzyme.

Conveniently the support may be made of e.g. glass, silica, latex, plastic or any polymeric material. The support may also be made from a biodegradable material. Generally speaking, the nature of the support is not critical and a variety of materials may be used. The surface of support may be hydrophobic or hydrophilic.

Preferred are materials presenting a high surface area for binding of the T-cells. Such supports may be for example be porous or particulate e.g. particles, beads, fibres, webs, sinters or sieves. Particulate materials like particles and beads are generally preferred due to their greater binding capacity. Particularly polymeric beads and particles may be of interest.

Conveniently, a particulate support (e.g. beads or particles) may be substantially spherical. The size of the particulate support is not critical, but it may for example have a diameter of at least 1 μm and preferably at least 2 μm, and have a maximum diameter of preferably not more than 10 μm and more preferably not more than 6 μm. For example, particulate supports having diameters of 2.8 μm and 4.5 μm will work well. An example of a particulate support is monodisperse particles, i.e. such which are substantially uniform in size (e. g. size having a diameter standard deviation of less than 5%). Such have the advantage that they provide very uniform reproducibility of reaction. Monodisperse particles, e.g. made of a polymeric material, produced by the technique described in U.S. Pat. No. 4,336,173 (ref. 25) are especially suitable.

Non-magnetic polymer beads may also be applicable. Such are available from a wide range of manufactures, e.g. Dynal Particles AS, Qiagen, Amersham Biosciences, Serotec, Seradyne, Merck, Nippon Paint, Chemagen, Promega, Prolabo, Polysciences, Agowa, and Bangs Laboratories.

Another example of a suitable support is magnetic beads or particles. The term "magnetic" as used everywhere herein is intended to mean that the support is capable of having a magnetic moment imparted to it when placed in a magnetic field, and thus is displaceable under the action of that magnetic field. In other words, a support comprising magnetic beads or particles may readily be removed by magnetic aggregation, which provides a quick, simple and efficient way of separating out the beads or particles from a solution. Magnetic beads and particles may suitably be paramagnetic or superparamagnetic. Superparamagnetic beads and particles are e.g. described in EP 0 106 873 (Sintef, ref. 26). Magnetic beads and particles are available from several manufacturers, e.g. Dynal Biotech ASA (Oslo, Norway, previously Dynal AS, e.g. DYNABEADS®).

The support may suitably have a functionalised surface. Different types of functionalisation include making the surface of the support positively or negatively charged, or hydrophilic or hydrophobic. This applies in particular to beads and particles. Various methods therefore are e.g. described in U.S. Pat. No. 4,336,173 (ref. 25), U.S. Pat. No. 4,459,378 (ref. 27) and U.S. Pat. No. 4,654,267 (ref. 28).

Immobilized T-cells may be detected in several ways including:

Direct detection of T-cells directly immobilized on solid support. T-cells may be directly immobilized on solid support e.g. by non-specifically adhesion. Then MHC multimers are added to the immobilized T-cells thereby allowing specific T-cells to bind the MHC multimers. Bound MHC multimer may be measured through label directly attached to the multimer or through labeled marker molecules. Individual T-cells may be detected if the method for analysis is able to distinguish individual labeled cells, e.g. cells are immobilized in a monolayer on a cell culture well or a glass slide. Following staining with labeled multimer a digital picture is taken and labeled cells identified and counted. Alternatively a population of T-cells is detected by measurement of total signal from all labeled T-cells, e.g. cells are plated to wells of a microtiter plate, stained with labeled MHC multimer and total signal from each well are measured.

Direct detection of T-cells immobilized on solid support through linker molecule T-cell can also be immobilized to solid support through a linker molecule. The linker molecule can be an antibody specific for the T-cell, the linker can be MHC multimer or the linker can be any molecule able to bind the T-cells. In any case the linker may be attached directly to the solid support, the linker may be attached to the solid support through another linker or the linker is embedded in a matrix, e.g. a sugar matrix.

Then MHC multimers are added to the immobilized T-cells thereby allowing specific T-cells to bind the MHC multimers. Bound MHC multimer may be measured through label directly attached to the multimer or through labeled marker molecules. Individual T-cells may be detected if the method for analysis is able to distinguish individual labeled cells, e.g. a digital picture is taken and labeled cells identified and counted.

Alternatively a population of T-cells is detected by measurement of total signal from all labeled T-cells.

Phenotyping T-cell sample using MHC multimer beads.

Different MHC multimers are immobilized to different beads with different characteristics (e.g. different size, different fluorescence's or different fluorescence intensities) where each kind of bead has a specific type of MHC multimer molecule immobilized. The immobilization may be direct or through a linker molecule as described above. The amount of bound T-cells to a specific populations of beads can be analyzed, thereby, phenotyping the sample. The TCR on the T-cell is defined by the bead to which it binds.

Direct detection of T-cells immobilized to solid support in a defined pattern. Different MHC multimers are immobilized to a support to form a spatial array in a defined pattern, where the position specifies the identity of the MHC multimer immobilized at this position. The immobilization may be direct or through a linker molecule as described above. Then a suspension of labeled T-cells are added or passed over the array of MHC multimers and specific T-cells will bind the immobilized MHC multimer molecules. The label will thus be located at specific regions of the array, which will allow identification of the MHC multimers that bind the cells, and thus, allows the identification of T-cells with recognition specificity for the immobilized MHC multimers. Alternatively, the cells can be labelled after they have been bound to the MHC multimers. The label can be specific for the type of cell that is expected to bind the MHC multimer (e.g. anti-CD4 for the labelling of T-helper cells in general, where some of the T-helper cells can be specific for a Class II MHC complex), or the label can stain cells in general (e.g. a label that binds DNA).

In this way T-cells bound to the defined areas of the support are analyzed, thereby, phenotyping the sample. Each individual T-cell is defined by the TCR it expose and depending on these TCRs each entity will bind to different types of MHC multimer molecules immobilized at defined positions on the solid support.

MHC Multimers and Cell Sorting

In another preferred application of the present invention MHC multimers can be used to isolate particular, TCR-specific T-cells, either through the use of MHC multimers in flow cytometry or through the use of MHC complexes or MHC multimers immobilized on a solid surface, e.g. beads, immunotubes, microtiter plates. Isolation of specific T-cells using MHC multimers and flow cytometry are described elsewhere herein.

T-cells immobilized to solid support in either of the ways described elsewhere herein can following washing be eluted from the solid support and treated further. This is a method to sort out specific T-cells from a population of different T-cells. Specific T-cells can e.g.be isolated through the use of bead-based MHC multimers. Bead-based MHC multimers are beads whereto monomer MHC-peptide complexes or MHC multimers are immobilized either directly or through a linker. After the cells have been isolated they can be manipulated in many different ways. The isolated cells can be activated (to differentiate or proliferate), they can undergo induced apoptosis, or undesired cells of the isolated cell population can be removed. Then, the manipulated cell population can be re-introduced into the patient, or can be introduced into another patient.

For some applications it can be a problem if the cell intracellularizes the MHC multimer during e.g. flow cytometry. When beads coated with MHC complexes are employed, the size of the bead eliminates the intracellularization. This can be an advantage for certain applications.

A typical cell sorting experiment, based on bead-based MHC multimers, would comprise some of the steps of the general procedure outlined in general terms in the following:

Acquire the sample, e.g. a cell sample from the bone marrow of a cancer patient.

Block the sample with a protein solution, e.g. BSA or skim milk.

Block the beads coated with MHC complexes, with BSA or skim milk.

Mix MHC-coated beads and the cell sample, and incubate.

Wash the beads with washing buffer, to remove unbound cells and non-specifically bound cells.

Isolate the immobilized cells, by either cleavage of the linker that connects MHC complex and bead; or alternatively, release the cells by a change in pH, salt-concentration addition of competitive binder or the like. Preferably, the cells are released under conditions that do not disrupt the integrity of the cells.

Manipulate the isolated cells (induce apoptosis, proliferation or differentiation)

Other solid supports than beads may be used for sorting out specific T-cells and examples of such solid supports are given elsewhere herein. However, the principles for binding, washing, elution and further manipulation is the same as described for bead-based sorting.

Microchip MHC Multimer Technology

A microarray of MHC multimers can be formed, by immobilization of different MHC multimers or MHC complexes on solid support, to form a spatial array where the position specifies the identity of the MHC-peptide complex or specific empty MHC immobilized at this position. When labelled cells are passed over the microarray (e.g. blood cells stained with anti-CD8 antibody, conjugated to APC), the cells carrying TCRs specific for MHC multimers in the microarray will become immobilized. The label will thus be located at specific regions of the microarray, which will allow identification of the MHC multimers that bind the cells, and thus, allows the identification of e.g. T-cells with recognition specificity for the immobilized MHC multimers. Alternatively, the cells can be labelled after they have been bound to the MHC multimers. The label can be specific for the type of cell that is expected to bind the MHC multimer (e.g. anti-CD4 for the labelling of T-helper cells in general, where some of the T-helper cells can be specific for a class 2 MHC complex), or the label can stain cells in general (e.g. a label that binds DNA). Alternatively, cytokine capture antibodies can be co-spotted together with MHC multimers or MHC complexes on the solid support and the cytokine secretion from bound antigen specific T-cells analyzed. This is possible because T-cells are stimulated to secrete cytokines when recognizing and binding specific MHC-peptide complexes.

The above-mentioned techniques are not restricted to the analysis of T-cells and TCRs, but can in principle be applied to any molecule or cell that binds a MHC-complex.

Indirect Detection of T-Cell Using MHC Multimer

T-cells in a sample may also be detected indirectly using MHC multimers. In indirect detection, the number or activity of T-cells are measured, by detection of events that are the result of TCR-MHC-peptide complex interaction. Interaction between MHC multimer and T-cell may stimulate the T-cell resulting in activation of T-cells, in cell division and proliferation of T-cell populations or alternatively result in inactivation of T-cells. All these mechanism can be measured using detection methods able to detect these events.

Example measurement of activation include measurement of secretion of specific soluble factor e.g. cytokine that can be measured using flow cytometry as described in the section with flow cytometry, measurement of expression of activation markers e.g. measurement of expression of CD27 and CD28 and/or other receptors by e.g. flow cytometry and/or ELISA-like methods and measurement of T-cell effector function e.g. CD8 T-cell cytotoxicity that can be measured in cytotoxicity assays like chromium release assay's know by persons skilled in the art.

Example measurement of proliferation include but is not limited to measurement of mRNA, measurement of incorporation of thymidine or incorporation of other molecules like bromo-2'-deoxyuridine (BrdU).

Example measurements of inactivation of T-cells include but is not limited to measurement of effect of blockade of specifc TCR and measurement of apoptosis.

Labelling Molecules

Labelling molecules are molecules that can be detected in a certain analysis, i.e. the labelling molecules provide a signal detectable by the used method. The amount of labelling molecules can be quantified.

Different principles of labelling and detection exist, based on the specific property of the labelling molecule. Examples of different types of labelling are emission of radioactive radiation (radionuclide, isotopes), absorption of light (e.g. dyes, chromophores), emission of light after excitation (fluorescence from fluorochromes), NMR (nuclear magnetic resonance form paramagnetic molecules) and reflection of light (scatter from e.g. such as gold-, plastic- or glass-beads/particles of various sizes and shapes). Alternatively, the labelling molecules can have an enzymatic activity, by which they catalyze a reaction between chemicals in the near environment of the labelling molecules, producing a signal, which include production of light (chemiluminescence), precipitation of chromophor dyes, or precipitates that can be detected by an additional layer of detection molecules. The enzymatic product can deposit at the location of the enzyme or, in a cell based analysis system, react with the membrane of the cell or diffuse into the cell to which it is attached. Examples of labelling molecules and associated detection principle are shown in table 2 below.

TABLE 2

Examples of labelling molecules and associated detection principles.

| Labelling substance | Effect | Assay-principle |
|---|---|---|
| Fluorochromes | emission of light having a specific spectra | [□]Photometry, Microscopy, spectroscopy PMT, photographic film, CCD's (Colour-Capture Device or Charge-coupled device). |
| Radionuclide | irradiation, $\alpha$, $\beta$ or $\gamma\square$rays | Scintillation counting, GM-tube, photographic film, excitation of phosphor-imager screen |
| Enzyme; HRP, (horseradish peroxidase), peroxidases in general | catalysis of $H_2O_2$ reduction using luminol as Oxygen acceptor, resulting in oxidized luminal + light catalysis of $H_2O_2$ reduction using a soluble dye, or molecule comprising a hapten, such as a biotin residue as Oxygen acceptor, resulting in precipitation. The habten can be recognized by a detection molecule. | [□]Photometry, Microscopy, spectroscopy PMT, photographic film, CCD's (Colour-Capture Device or Charge-coupled device), Secondary label linked antibody |
| Particles; gold, polystyrene beads, pollen and other particles | Change of scatter, reflection and transparency of the associated entity | Microscopy, cytometry, electron microscopy PMT's, light detecting devices, flowcytometry scatter |
| AP (Alkaline Phosphatase) | Catalyze a chemical conversion of a non-detectable to a precipitated detectable molecule, such as a dye or a hapten | [□]Photometry, Microscopy, spectroscopy Secondary label linked antibody |

TABLE 2-continued

Examples of labelling molecules and associated detection principles.

| Labelling substance | Effect | Assay-principle |
|---|---|---|
| Ionophores or chelating chemical compounds binding to specific ions, e.g. $Ca^{2+}$ | Change in absorption and emission spectrums when binding. Change in intensity | [□]Photometry, Cytometry, spectroscopy |
| Lanthanides | Fluorescence Phosphorescence Paramagnetic | [□]photometry, cytometry, spectroscopy NMR (Nuclear magnetic resonance) |
| DNA fluorescing stains | Propidium iodide Hoechst stain DAPI AMC DraQ5 ™ Acridine orange 7-AAD | [□]Photometry, cytometry, spectroscopy |

[□]Photometry; is to be understood as any method that can be applied to detect the intensity, analyze the wavelength spectra, and or measure the accumulation of light derived form a source emitting light of one or multiple wavelength or spectra.

"Photometry; is to be understood as any method that can be applied to detect the intensity, analyze the wavelength spectra, and or measure the accumulation of light derived form a source emitting light of one or multiple wavelength or spectra.

Labelling molecules can be used to label MHC multimers as well as other reagents used together with MHC multimers, e.g. antibodies, aptamers or other proteins or molecules able to bind specific structures in another protein, or in sugar, DNA or other molecules. In the following molecules able to bind a specific structure in another molecule (protein, sugar, DNA etc.) are named a marker or marker molecule.

MHC multimers and/or marker molecules can be used to positively select the entities they bind or they can be used to deselect or negatively select the entities they bind.

Labelling molecules can be attached to a given MHC multimer or any other protein marker by covalent or non-covalent linkage as described for attachment of MHC complexes to multimerisation domains elsewhere herein. The attachment can be directly between reactive groups in the labelling molecule and reactive groups in the marker molecule or the attachment can be through a linker connecting labelling molecule and marker, both as described elsewhere herein. The linker can be covalently attached to the labelling molecule and in that case the whole complex consisting of linker and labelling molecule is regarded as one labelling molecule. An example of such a molecule is the FLUORESCEIN™ linker molecule shown in FIG. 14. Other types of linkers can be covalently coupled to one or more labelling molecules such linkers are described elsewhere herein and in patent application WO 2007/015168 A2 (Lohse (2007).

When labelling MHC multimers the label can be attached directly to the multimer either to the MHC complex (heavy chain, β2m or peptide) or to the one or more multimerization domain(s). MHC multimers can also be labelled indirectly by binding one or more marker molecule carrying one or more labels.

A single labelling molecule on a marker does not always generate sufficient signal intensity. The signal intensity can be improved by assembling single label molecules into large multi-labelling compounds, comprising two or more label molecule residues. Generation of multi-label compounds can be achieved by covalent or non-covalent, association of labelling molecules with a major structural molecule. Examples of such structures are synthetic or natural polymers (e.g. dextramers), proteins (e.g. streptavidin), or polymers as DNA or PNA. The labelling molecules in a multi-labelling compound can all be of the same type or can be a mixture of different labelling molecules.

Detection principles, such as those listed in Table 2, can be applied to flow cytometry, stationary cytometry, and batch-based analysis. Most batch-based approaches can use any of the labelling substances depending on the purpose of the assay. Flow cytometry primarily employs fluorescence, whereas stationary cytometry primarily employs light absorption, e.g. dyes or chromophore deposit from enzymatic activity. In the following section, principles involving fluorescence detection will be exemplified for flow cytometry, and principles involving chromophore detection will be exemplified in the context of stationary cytometry. However, the labelling molecules can be applied to any of the analyses described in this invention.

In another aspect, the present invention relates to a MHC molecule construct as defined above further comprising one or more labelling compounds. A plurality of labelling compounds should everywhere be interpreted as two or more labelling compounds which can be the same or different.

In particular, one or more labelling compounds can be attached to the one or more multimerization domain(s), or one or more labelling compounds can be attached to one or more of the binding entities, or one or more labelling compounds can be attached to one or more of the MHC molecules, or one or more labelling compounds can be attached to the one or more multimerization domain(s) and/or one or more of the binding entities and/or one or more of the MHC molecules, or one or more labelling compounds can be attached to the peptide harboured by the MHC molecule.

In some applications, it can be advantageous to apply different MHC multimer constructs, either as a combination or in individual steps. Such different MHC multimers can be differently labelled (i. e. by labelling with different labelling compounds) enabling visualisation of different target MHC recognising cells individually. For example in one preferred embodiment each MHC multimer binding MHC multimer is labeled with an individual label.

Thus, if several different MHC multimers with different labelling compounds are present, it is possible simultaneously to identify more than one specific receptor, if each of the MHC multimers present a different peptide.

In another preferred embodiment of the present invention the different MHC multimers used in same application all have same label enabling visualization of different target MHC recognizing cells as a group. Alternatively groups of MHC multimers are labeled with same label and other groups of MHC multimers in same preparation are labeled with other labels. MHC multimers identified by same label can be positively selected as a group or negatively selected as a group.

In another preferred embodiment of the present invention different MHC multimers specific for different TCRs are labeled with same label thereby identifying subpopulations of MHC expressing cells for which one or more is also positive for one or more additional MHC multimers labeled with another label. For example 6 different MHC multimers (A, B, C, D, E, F) are labeled using 3 different labels (1, 2, 3) as follows: MHC multimer A, B and E are labeled with label 1, MHC multimer C, D and E are labeled with label 2 and MHC multimer B, C and F are labeled with label 3. Thereby all 6 MHC multimers can be distinguished from each other by one or more labels: MHC multimer A is labeled with label 1, MHC multimer B is labeled with label 1 and 3, MHC multimer C is labeled with label 2 and 3, MHC multimer D is labeled with label 2, MHC multimer E is labeled with label 1 and 2 and MHC multimer F is labeled with label 3.

Using this form for labeling few types of labeling molecules may be used for labeling many different MHC multimers.

The above mentioned principles for labeling not only apply to MHC multimers but are also useful for other marker molecules.

The labelling compound is preferably such which is directly or indirectly detectable.

The labelling compound can be any labelling compound suitable for directly or indirectly detection. By the term "directly" is meant that the labelling compound can be detected per se without the need for a secondary compound, i. e. is a "primary" labelling compound. By the term "indirectly" is meant that the labelling compound can be detected by using one or more "secondary" compounds, i. e. the detection is performed by the detection of the binding of the secondary compound (s) to the primary compound.

The labelling compound can further be attached via a suitable linker. Linkers suitable for attachment to labelling compounds are described elsewhere herein or would be readily known by the person skilled in the art.

Examples of such suitable labelling compounds are fluorescent labels, enzyme labels, radioisotopes, chemiluminescent labels, bioluminescent labels, polymers, metal particles, haptens, antibodies, and dyes.

The labelling compound can suitably be selected from fluorescent labels such as 5-(and 6)-carboxy-FLUORESCEIN™, 5- or 6-carboxyFLUORESCEIN™ 6-(FLUORESCEIN™)-5-(and 6)-carboxamido hexanoic acid, FLUORESCEIN™ isothio-cyanate (FITC), rhodamine, tetramethylrhodamine, and dyes such as Cy2, Cy3, and CY5™, optionally substituted coumarin including AMCA, PerCP, phycobiliproteins including R-phycoerythrin (RPE) and allophycoerythrin (APC), Texas Red, Princeston Red, Green fluorescent protein (GFP) and analogues thereof, and conjugates of R-phycoerythrin or allophycoerythrin and e. g. CY5™ or Texas Red, and inorganic fluorescent labels based on semiconductor nanocrystals (like quantum dot and QDOT® Im nanocrystals), and time-resolved fluorescent labels based on lanthanides like $Eu3+$ and $Sm3+$, from haptens such as DNP, biotin, and digoxiginin, from enzymatic labels such as horseradish peroxidase (HRP), alkaline phosphatase (AP), beta-galactosidase (GAL), glucose-6-phosphate dehydrogenase, beta-N-acetyl-glucosaminidase, R-glucuronidase, invertase, Xanthine Oxidase, firefly luciferase and glucose oxidase (GO), from luminiscence labels such as luminol, isoluminol, acridinium esters, 1,2-dioxetanes and pyridopyridazines, and from radioactivity labels such as incorporated isotopes of iodide, cobalt, selenium, tritium, and phosphor.

Radioactive labels can in particular be interesting in connection with labelling of the peptides harboured by the MHC molecules.

Labelling Molecules of Particular Utility in Flow Cytometry

In flow cytometry the typical label is detected by its fluorescence. Most often a positive detection is based on the presents of light from a single fluorochrome, but in other techniques the signal is detected by a shift in wavelength of emitted light; as in FRET based techniques, where the exited fluorochrome transfer its energy to an adjacent bound fluorochrome that emits light, or when using $Ca^{2+}$ chelating fluorescent props, which change the emission (and absorption) spectra upon binding to calcium. Preferably labelling molecules employed in flow cytometry are illustrated in Table 3a and 3b and described in the following.

Simple fluorescent labels:

Fluor dyes, Pacific Blue™, Pacific Orange™, Cascade Yellow™,

ALEXA FLUOR® (AF);

AF405, AF488, AF500, AF514, AF532, AF546, AF555, AF568, AF594, AF610, AF633, AF635, AF647, AF680, AF700, AF710, AF750, AF800

Quantum Dot based dyes, QDOT@Nanocrystals (Invitrogen, MolecularProbs)

QDOT®525, QDOT®565, QDOT®585, QDOT®605, QDOT®655, QDOT®705, QDOT®800

DyLight™ Dyes (Pierce) (DL);

DL549, DL649, DL680, DL800

FLUORESCEIN™ (Flu) or any derivate of that, ex. FITC

Cy-Dyes;

Cy2, Cy3, Cy3.5, CY5™, CY5™ 0.5, Cy7

Fluorescent Proteins;

RPE, PerCp, APC

Green fluorescent proteins;

GFP and GFP derived mutant proteins; BFP, CFP, YFP, DsRed, T1, Dimer2, mRFP1, MBanana, mOrange, dTomato, tdTomato, mTangerine, mStrawberry, mCherry Tandem dyes:

RPE-CY5™, RPE-CY5™ 0.5, RPE-Cy7, RPE-ALEXA FLUOR® tandem conjugates; RPE-Alexa610, RPE-TxRed APC-Aleca600, APC-Alexa610, APC-Alexa750, APC-CY5™, APC-CY5™ 0.5

Multi fluorochrome assemblies;

Multiple fluorochromes attached to a polymer molecule, such as a peptide/protein, Dextran, polysaccharide.

Any combination of the fluorescent dyes involving in generation of FRET (Fluorescence resonance energy transfer) based techniques.

Ionophors; ion chelating fluorescent props

Props that change wavelength when binding a specific ion, such as Calcium

Props that change intensity when binding to a specific ion, such as Calcium

Combinations of fluorochromes on the same marker. Thus, the marker is not identified by a single fluorochrome but by a code of identification being a specific combination of fluorochromes, as well as inter related ratio of intensities. Example: Antibody Ab3 and Ab2, are conjugated to both FITC and BP but Ab1 have 1 FITC to 1 BP whereas Ab2 have 2 FITC to 1 BP. Each antibody can then be identified individually by the relative intensity of each fluorochrome. Any such combinations of n fluorochromes with m different ratios can be generated.

TABLE 3a

Examples of preferable fluorochromes

| Fluorophor/Fluorochrome | Excitation nm | Emission nm |
|---|---|---|
| 2-(4'-maleimidylanilino)naphthalene-6-sulfonic acid, sodium salt | 322 | 417 |
| 5-((((2-iodoacetyl)amino)ethyl)amino)naphthalene-1-sulfonic acid | 336 | 490 |
| Pyrene-1-butanoic acid | 340 | 376 |
| ALEXA FLUOR ® 350 (7-amino-6-sulfonic acid-4-methyl coumarin-3-acetic acid | 346 | 442 |

TABLE 3a-continued

Examples of preferable fluorochromes

| Fluorophor/Fluorochrome | Excitation nm | Emission nm |
|---|---|---|
| AMCA (7-amino-4-methyl coumarin-3-acetic acid | 353 | 442 |
| 7-hydroxy-4-methyl coumarin-3-acetic acid | 360 | 455 |
| Marina Blue (6,8-difluoro-7-hydroxy-4-methyl coumarin-3-acetic acid | 362 | 459 |
| 7-dimethylamino-coumarin-4-acetic acid | 370 | 459 |
| Fluorescamin-N-butyl amine adduct | 380 | 464 |
| 7-hydroxy-coumarine-3-carboxylic acid | 386 | 448 |
| CascadeBlue (pyrene-trisulphonic acid acetyl azide | 396 | 410 |
| Cascade Yellow | 409 | 558 |
| Pacific Blue (6,8 difluoro-7-hydroxy coumarin-3-carboxylic acid | 416 | 451 |
| 7-diethylamino-coumarin-3-carboxylic acid | 420 | 468 |
| N-(((4-azidobenzoyhamino)ethyl)- 4-amino-3,6-disulfo-1,8-naphthalimide, dipotassium salt | 426 | 534 |
| Alexa Fluor 430 | 434 | 539 |
| 3-perylenedodecanoic acid | 440 | 448 |
| 8-hydroxypyrene-1,3,6-trisulfonic acid, trisodium salt | 454 | 511 |
| 12-(N-(7-nitrobenz-2-oxa-1,3-diazol-4-yl)amino)dodecanoic acid | 467 | 536 |
| N,N'-dimethyl-N-(iodoacetyl)-N'-(7-nitrobenz-2-oxa-1,3-diazol-4-yl)ethylenediamine | 478 | 541 |
| Oregon Green 488 (difluoro carboxy FLUORESCEIN ™) | 488 | 518 |
| 5-iodoacetamidoFLUORESCEIN ™ | 492 | 515 |
| propidium iodide-DNA adduct | 493 | 636 |
| Carboxy FLUORESCEIN ™ | 495 | 519 |

TABLE 3b

Examples of preferable fluorochrome families

| Fluorochrome family | Example fluorochrome |
|---|---|
| ALEXA FLUOR ®(AF) | AF ®350, AF405, AF430, AF488, AF500, AF514, AF532, AF546, AF555, AF568, AF594, AF610, AF633, AF635, AF647, AF680, AF700, AF710, AF750, AF800 |
| Quantum Dot (QDOT ®) based dyes | QDOT ®525, QDOT ®565, QDOT ®585, QDOT ®605, QDOT ®655, QDOT ®705, QDOT ®800 |
| DyLight ™ Dyes (DL) | DL549, DL649, DL680, DL800 |
| Small fluorescing dyes | FITC, Pacific Blue ™, Pacific Orange ™, Cascade Yellow ™, Marina blue ™, DSred, DSred-2, 7-AAD, TO-Pro-3, |
| Cy-Dyes | Cy2, Cy3, Cy3.5, CY5 ™, CY5 ™.5, Cy7 |
| Phycobili Proteins: | R-Phycoerythrin (RPE), PerCP, Allophycocyanin (APC), B-Phycoerythrin, C-Phycocyanin |
| Fluorescent Proteins | (E)GFP and GFP ((enhanced) green fluorescent protein) derived mutant proteins; BFP,CFP, YFP, DsRed, T1, Dimer2, mRFP1,MBanana, mOrange, dTomato, tdTomato, mTangerine, mStrawberry, mCherry |
| Tandem dyes with RPE | RPE-CY5 ™, RPE-CY5 ™.5, RPE-Cy7, RPE-ALEXA FLUOR ® tandem conjugates; RPE-Alexa610, RPE-TxRed |
| Tandem dyes with APC | APC-Aleca600, APC-Alexa 610, APC-Alexa 750, APC-CY5 ™, APC-CY5 ™.5 |
| Calcium dyes | Indo-1-Ca$^{2+}$ Indo-2-Ca$^{2+}$ |

Preferable Labelling Molecules Employed in Stationary Cytometry and IHC

Enzymatic labelling, as exemplified in Table 4:

Horseradish peroxidase; reduces peroxides ($H_2O_2$), and the signal is generated by the Oxygen acceptor when being oxidized.

Precipitating dyes; Dyes that when they are reduced they are soluble, and precipitate when oxidized, generating a coloured deposit at the site of the reaction.

Precipitating agent, carrying a chemical residue, a hapten, for second layer binding of marker molecules, for amplification of the primary signal.

Luminol reaction, generating a light signal at the site of reaction.

Other enzymes, such as Alkaline Phosphatase, capable of converting a chemical compound from a non-detectable molecule to a precipitated detectable molecule, which can be coloured, or carries a hapten as described above.

Fluorescent labels, as exemplified in Table 3a and b; as those described for Flow cytometry are likewise important for used in stationary cytometry, such as in fluorescent microscopy.

TABLE 4

| | Example preferable labels for stationary cytometry | | |
| Label | Enzyme substrate, Oxygen acceptor Chromogen/ precipitating agent | Precipitate or Residue, hapten* for secondary detection layer | Binding partner to hapten |
| --- | --- | --- | --- |
| HRP | diaminobenzidine (DAB) | Coloured precipitate | — |
| HRP | 3-amino-9-ethyl-carbazole (AEC+) | Coloured precipitate | — |
| AP | Fast red dye | Red precipitate | — |
| HRP | biotinyl tyramide | Exposed Biotin residue | Streptavidin, avidin |
| HRP | FLUORESCEIN ™ tyramide | Exposed FLUORESCEIN ™ residue | Anti-Fluorecein Antibody |
| "Enzyme" | Substrate that when reacted precipitate | Primary label; being a dye, chemiluminescence's, or exposure of a hapten | Secondary label in case the primary label is a hapten |

In another preferred embodiment the labelling of an antibody is through linkage to a readily detectable enzyme, such as an enzyme immunoassay (EIA). The enzyme which is bound to the antibody will react with an appropriate substrate, preferably a chromogenic substrate, in such a manner as to produce a chemical moiety that can be detected, for example, by spectrophotometric, fluorimetric or by visual means. Enzymes that can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods that employ a chromogenic substrate for the enzyme. Detection can also be accomplished by visual comparison of the extent of enzymatic reaction of a substrate in comparison with similarly prepared standards.

Detection can also be accomplished using any of a variety of other immunoassays. For example, by radioactively labelling the antibodies or antibody fragments known as radioimmunoassay (RIA). The radioactive isotope can be detected by such means as the use of a gamma counter or a scintillation counter or by autoradiography.

It is also possible to label the antibody with a fluorescent compound. When the fluorescently labelled antibody is exposed to light of the proper wave length, its presence can then be detected due to fluorescence. Among the most commonly used fluorescent labelling compounds are FLUORESCEIN™ isothiocyanate, rhodamine, phycoerythrin, phycocyanin, allophycocyanin, o-phthaldehyde and fluorescamine.

The antibody can also be detectably labelled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labelled by coupling it to a chemiluminescent compound. The presence of the chemiluminescent-tagged antibody is then determined by detecting the presence of luminescence that arises during the course of a chemical reaction. Examples of particularly useful chemiluminescent labelling compounds are luminol, isoluminol, theromatic acridinium ester, imidazole, acridinium salt and oxalate ester.

Likewise, a bioluminescent compound can be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labelling are luciferin, luciferase and aequorin.

In one embodiment, the peptide P is a peptide disclosed in U.S. 60/907,217, the text of which is hereby incorporated by reference herein in its entirety.

In another preferred embodiment the MHC multimer(s) can be labelled as described in WO/2007/015168, the text of which is hereby incorporated by reference herein in its entirety. This method for labelling of the MHC multimer is described in detail below.

Linkers

The instant "linker" is a molecule that may help to join other atoms, molecules, or functional groups together through chemical bonds. For example, one of the instant linkers may be conjugated to a protein as well as to another group such as a fluorophore, joining those substances together through the intervening chemical bonds in the linker.

In some embodiments of the invention, the "linker" comprises a molecular entity derived from the reaction of at least one amine, such as a diamine, and a di-carboxylic acid anhydride. In some embodiments, the amine comprises no more than two ethyleneoxy ($CH_2$—$CH_2$—O) units. For example, the instant "linker" may comprise an alternating copolymer of such amine and di-carboxylic acid anhyride-derived units. In some embodiments, the amine comprises a structural formula with no more than two methylene units in a row. For example, the amine may comprise a structural formula such as: $NH_2$—$CH_2$—$CH_2$—O—$CH_2$—$CH_2$—O—$CH_2$—$CH_2$—$NH_2$ or $NH_2$—$CH_2$—$CH_2$—O—$CH_2$—$CH_2$—O—$CH_2$—$CH_2$—O—$CH_2$—$CH_2$—$NH_2$, or other structural formulas in which a heteroatom is placed after every two methylene units.

In some embodiments of this invention, the "linker" comprises at least one monomeric unit referred to herein as "L15." In other embodiments, the instant "linker" comprises two or more L15 units arranged in a linear or branched fashion.

For example, in some embodiments, the linker is a linear polymer chain comprising two L15 units, called "L30" herein. In yet other embodiments, the linker comprises a longer linear polymer comprising several L15 units, and may be called, for example, "L45," or "L60," "L90," or "L120," or "L300," and so forth herein, depending on the number of L15 units the polymer chain comprises. In some embodiments comprising more than one L15 unit, the L15 units may be connected covalently via one or more intervening chemical bonds.

In some embodiments of this invention, L15 comprises the unit shown below in Formula I.

Formula I

In Formula I, Ri and $R_2$ may comprise either NH or O, while $R_3$ may comprise methyl, ethyl, propyl, $CH_2$—O—$CH_2$, and $(CH_2$—O—$CH_2)_2$. Further, when Formula I is conjugated to other groups, atoms, or molecules, and, for instance, Ri and/or $R_2$ is an oxygen, no more than three consecutively repeating ethyleneoxy $(CH_2$—$CH_2$—O) groups are present.

Thus, some of the L15 units according to this invention may have the following molecular structures:

Formula II

Formula III

Formula IV

Formula V

Other possible L15 structures not shown above may be envisioned based upon the choice of R-i, $R_2$, and $R_3$ groups.

In some embodiments, the instant linkers are comprised of a linear polymer of L15 units in which each L15 unit has the same molecular formula, for example, that of structural formula II. In other embodiments, one or more L15 units may differ from the others in the linker chain. For example, a linker may comprise several units of formula II, and one or more units comprising one or more different structures. Such a differing L15 unit may be useful in attaching a particular atom, group, or molecule at a defined location in the chain, for example. Because each unit may be added iteratively to the growing linker chain, such as by solid phase synthesis, a variety of mixed L15 polymers may be constructed simply and in a controlled fashion.

In some embodiments, one or more of the heteroatom groups in the linker comprises a further substituent. That substituent may comprise a variety of atoms or functional groups such as a simple hydrogen atom, a protecting group, or a conjugating group which serves to attach the linker to a atom, group, or molecule. In some embodiments, the substituent is a detectable label or another linker. Attachment via the heteroatom groups to a further linker forms a branched linker polymer.

Design and Synthesis of Linkers

The present invention also comprises novel methods of synthesizing an L15 linker and linear polymers of the L15 linker in high yield. According to this synthesis method, long linkers of, for example, L120, L200, L300, or even longer, such as L600 or L990, may be constructed by consecutive additions of L15 units or portions of L15 units, for example, on solid phase. Alternatively, long linkers may be formed by joining two intermediate length linkers together. Linkers of L30 or larger synthesized according to this method may comprise individual L15 units of the same or different molecular structure.

L15 units according to this invention may be prepared by contacting a protected amine with a di-carboxylic acid anhydride and acetic anhydride, resulting in a cyclic imide terminal group, which may then be opened once the linker reaches its desired length, for instance by basic aqueous hydrolysis in dioxane using a tertiary amine such as diisopropylethyl amine. A 3,9,12-trioxa-6,15-diaza-5-oxo-pentadecanoic acid molecule has been synthesized from 2,2'-(ethylenedioxy)bis(ethylamine) at about 87-91% yield (see Pieters et al., Bioorg. Med. Chem. Lett. 9: 161-6 (1999)). In contrast, the controlled methods of synthesizing L15 units according to the present invention may provide yields of 96%, for example.

The synthesis may be carried out in solution. The amine may be protected with $(Boc)_2\theta$, monomethoxytrityl (MMT), benzyloxycarbonyl (Z), or fluorenylmethyloxycarbonyl (Fmoc), or another suitable protecting group. In some embodiments, the amine is 2,2'-(ethylenedioxy)bis(ethylamine). In some embodiments, the amine is present in excess over the di-carboxylic acid anhydride and acetic anhydride. The addition of the di-carboxylic acid anhydride may be carried out at a wide range of temperature. Suitable di-carboxylic acid anhydrides include those from diglycolic acid, 1,5-dipentanoic acid, 1,4-dibutyric acid, 1,3 dipropanoic acid, and 3,6 dioxaoctane dioic acid, depending on the desired $R_3$ group. Subsequent addition of acetic anhydride may force the product into the cyclic imide form in high yield. The cyclic imide may be quantitatively opened if desired, for example, in excess dioxane and di-isopropylethylamine (DIPEA). To initiate the preparation of an L30 linker, the cyclic imide may be reacted with another amine. Then, di-carboxylic acid anhydride and acetic anhydride may be added and the resulting cyclic imide opened. In some embodiments, the terminal cyclic imide on the linker may be left unopened in order to serve as a reactive group for the formation of other bonds such as to reactive groups or other attachments.

For example, a 3,9,12-trioxa-6,15-diaza-b-oxo-pentade-canoic acid-derived L15 monomer may be prepared by protecting one of the two amine groups of 2,2'-(ethylenedi-oxy)bis(ethylamine) with (Boc)$_2$O. After dissolving the mono-protected 2,2'-(ethylenedioxy)bis(ethylamine) in pyridine, diglycolic acid and then acetic anhydride may be added at high temperature, such as at about 100° C., to form a cyclic L15 structure. Excess 2,2'-(ethylenedioxy)bis(eth-ylamine) reacts with the cyclic imide terminal to form structure 3. To form an L30 linker, an additional diglycolic acid may be added, and the cyclic terminal opened by addition of 1,4 dioxane and diisopropylethylamine (DIPEA) in aqueous solution.

In some embodiments of the invention in which one or both of Ri and R$_2$ are oxygens rather than amine groups, amino-alcohols or di-alcohols may be substituted for the amine in the reactions described above. Conditions may also be adjusted to account for the different reactivities of alco-hols and amines. For instance, reactions may be run at higher temperatures when coupling with alcohols rather than ami-nes.

Using the instant methods, large batches, such as 100 g, of protected L30 linkers may be prepared in pure form by an extractive work-up using one-liter scale laboratory equip-ment. The examples below provide a more detailed descrip-tion of the synthesis of exemplary molecules comprising L15 and L30 linkers according to this invention.

The same synthetic principles apply to the preparation of larger linker polymer chains used in some embodiments of this invention. For example, linkers such as L45, L60, L90, L120, L150, L200, L300, or even larger, for instance, comprising as many as 40 L15 units, may be prepared by repeating the steps described above successively: first react-ing the cyclic imide of the preceding L15 unit in the growing chain with excess amine, and adding acid anhydride and then acetic anhydride to build on a further L15 unit. Once the desired length is achieved, the terminal ring may be opened. If desired, those successive steps may also be performed on solid support, which may be convenient in preparing linkers longer than L30 or L60, for example In fact, compounds of molecular weights of 8 to 15 KDa may be prepared with the methods of the present invention because successive syn-thetic steps are not inhibited by the growing poly-L15 chains. This is quite unusual for peptide chemistry.

Alternatively, to shorten the number of steps needed to prepare longer linkers, intermediate length linkers such as L30, for example, can be directly combined together or conjugated indirectly through an intervening chemical group such as a reactive group or a detectable label. For instance, a single chromatographic purification step allows the prepa-ration of high purity Boc-L30, which may be readily oli-gomerized to prepare longer linkers such as L300 at high purity. Even linkers such as L600 and longer such as L1000 may be prepared by such methods, the only limitations being the yield of each step and the amount of materials available. Further, two long linkers may be joined along their chains to form very long branched linkers comprising, for instance, as many as 10, 20, 40, or even 60 L15 units in total.

Because it is possible to control the synthesis conditions, the present invention further comprises linkers and linker derivatives comprising a homogeneous molecular and struc-tural formula. A homogeneous molecular formula means herein that the molecular weight of the linker may be obtained via mass spectrometry with less than 1% deviation from the expected molecular weight based upon the synthe-sis protocol used, in some embodiments less than 0.1% or even less than 0.01%. This is possible even with very long linkers such as L300, L600, or L990. A homogeneous structural formula means herein that the structural compo-sition of each L15 unit and its location within the linker chain is controlled by the synthesis protocol used to prepare the linker. In contrast, many PEG-based linkers comprise a mixture of lengths and structural formulae. Thus, substances that comprise those mixed linkers inherently are heteroge-neous, regardless of the purity or homogeneity of the mol-ecules, groups, or atoms to which the linkers were conju-gated.

Many currently used linkers, such as certain nucleic acid or nucleic acid analog-based linkers, carry a charge on each monomer of the chain, for example, from a backbone phosphate or phosphorothioate group. Such charges may cause those linkers to aggregate with substances of opposite charge, including the walls of a plate or vessel, or to attract unwanted metal ions, or to precipitate in the presence of salts. In contrast, the instant linkers may be designed such that they carry no charge, or only one or a few charges at defined locations along the chain. Because one may control the synthesis of the instant linkers, they may be designed to place charges at only specific locations or to carry no charges at all. This allows for a precise modulation of the location and amount of charge in a given linker and linker derivative and is a further method of avoiding unwanted aggregation or tertiary interactions.

Nevertheless, for some embodiments, the instant linkers may also be prepared using an uncontrolled polymerization reaction. For example, a one-pot synthesis may be con-ducted based upon the reaction steps above, such as by mixing a diamine in solution with an excess of di-carboxylic anhydride. The synthesis may also be terminated, for example, by adding a reagent that would form an end group, such as an amino acid or fluorophore. Controlling the amount of such a terminating reagent may help dictate the actual length distribution of the mixture. Such methods may be useful, for instance, when absolute length is unimportant, or to generate linkers of a variety of different lengths at once. The products may be fractionated by length, for instance by chromatography.

Linker Derivatives

Linkers of the present invention may be covalently bound to another atom, group, or molecule to form a "linker derivative." Linker derivatives may comprise only one linker conjugated to another atom, group, or molecule, or may comprise multiple linkers conjugated to more than one of the same atom, group, or molecule, or conjugated to different atoms, groups, or molecules. The binding of the atom, group, or molecule may occur at one or more free ends of the linker, or along its length such as at one of its heteroatoms. Examples of atoms, groups, or molecules that may be conjugated to linkers to form linker derivatives include hydrogen atoms, terminal groups such as protecting groups, methyl groups, or acetyl groups. Other examples include heavy or radioactive isotopes, leaving groups; fluo-rophores; chromophores; enzyme substrates; antigens; anti-bodies; other proteins and peptides; amino acids and amino acid analogs; nucleic acids and nucleic acid analogs; com-ponents of a membrane or a solid support; and other small or large molecules. Linkers according to this invention may thus be conjugated to several atoms, groups, or molecules of the same type, such as multiple fluorophores, or may be conjugated to different types of groups or molecules, such as a PNA and a fluorophore or a protein and a solid surface or an acetyl group and an antibody. The covalent binding may be direct, with no intervening bonds or atoms, or indirect, with one or more intervening bonds or atoms. As used herein, any atom, group, or molecule that is covalently attached to a linker, either directly or indirectly, is "conjugated to" the linker. Hence, "linker derivatives" include molecular entities referred to as "conjugates." Atoms, groups, or molecules may also be non-covalently attached to the instant linkers or linker derivatives, for example, by adsorption on a surface, intercalation, hybridization of complementary nucleic acids or nucleic acid analogs, or other interactions.

Atoms, groups, or molecules may be conjugated at one end of the linker, or the same or different atoms, groups, or molecules may be placed at both ends. Alternatively, conjugated atoms, groups, or molecules may be placed between two linkers, for example, at a defined spacing that prevents unwanted interactions between them. Hence, linker derivatives such as X-L, L-X, or X-L-X or L-X-L may be prepared where X represents a directly or indirectly conjugated atom, group, or molecule and L represents a linker. Such linker derivatives can also include different atoms, groups, or molecules, for example, X1-L-X2, or X1-L1-X2-L2 or L1-X1-L2-X2. An atom, group, or molecule can also be conjugated, for example, via one of the heteroatoms in the linker. In addition, several linkers may be conjugated to one linker derivative to form branched structures. Linkers conjugated to multiple atoms, groups, or molecules such as color labels or radioactive isotopes are advantageous, for example, in amplifying signals in detection assays as an alternative to antibody-based amplification methods and radioactivity.

Indirect Conjugation

A linker may be conjugated to another group, atom, or molecule indirectly through a group that is more reactive with the anticipated atom, group, or molecule than the linker itself. As used herein, such groups are called "conjugating groups." In some embodiments, the linkers are conjugated to carbodiimide-based conjugating groups. Amino acids may also serve as conjugating groups. For example, amino acids with amino side chains may be used to conjugate, for example, fluorophores. The sulfhydryl of cysteine is also useful as a conjugating group for forming disulfide cross-links to other substances. In some embodiments, the linkers are conjugated to Lys(Cys), which is a C-terminal lysine-carboxamide with a cysteine amino acid bound to the N of the lysine side-chain, and which may serve as a conjugating group. The juxtaposed amine and sulfhydryl groups of this cysteine moiety unexpectedly provided significantly higher reactivity toward dextran, for example, than carbodiimide conjugating groups. In some embodiments, the linker is conjugated to amino groups such as to a lysine amino acid in which the N is derivatized with beta-alanine-N,N-diacetic acid. The lysine derivative can be quantitatively converted into its cyclic N-2,6-Dioxo-morpholino anhydride form. That form was highly amino reactive under weakly basic aqueous conditions when compared to previously used amino reactive groups such as NHS-esters. Hence, it may also serve as a conjugating group. One of ordinary skill in the art may readily envision other conjugating groups that may be conjugated to the instant linkers in order to assist in conjugating a variety of substances to the instant linkers.

Detectable Labels

In some embodiments, one or more detectable labels are conjugated to a linker. According to this invention, a "detectable label" is any molecule or functional group that allows for the detection of a biological or chemical characteristic or change in a system, such as the presence of a target substance in the sample.

Examples of detectable labels which may be used in the invention include fluorophores, chromophores, electrochemiluminescent labels, bioluminescent labels, polymers, polymer particles, bead or other solid surfaces, gold or other metal particles or heavy atoms, spin labels, radioisotopes, enzyme substrates, haptens, antigens, Quantum Dots, aminohexyl, pyrene, nucleic acids or nucleic acid analogs, or proteins, such as receptors, peptide ligands or substrates, enzymes, and antibodies (including antibody fragments).

Examples of polymer particles labels which may be used in the invention include micro particles, beads, or latex particles of polystyrene, PMMA or silica, which can be embedded with fluorescent dyes, or polymer micelles or capsules which contain dyes, enzymes or substrates. Examples of metal particles which may be used in the invention include gold particles and coated gold particles, which can be converted by silver stains. Examples of haptens that may be conjugated in some embodiments are fluorophores, myc, nitrotyrosine, biotin, avidin, streptavidin, 2,4-dinitrophenyl, digoxigenin, bromodeoxy uridine, sulfonate, acetylaminoflurene, mercury trintrophonol, and estradiol.

Examples of enzymes which may be used in the invention comprise horse radish peroxidase (HRP), alkaline phosphatase (AP), beta-galactosidase (GAL), glucose-6-phosphate dehydrogenase, beta-N-acetylglucosaminidase, β-glucuronidase, invertase, Xanthine Oxidase, firefly luciferase and glucose oxidase (GO). Examples of commonly used substrates for horse radish peroxidase (HRP) include 3,3'-diaminobenzidine (DAB), diaminobenzidine with nickel enhancement, 3-amino-9-ethylcarbazole (AEC), Benzidine dihydrochloride (BDHC), Hanker-Yates reagent (HYR), Indophane blue (IB), tetramethylbenzidine (TMB), 4-chloro-1-naphtol (CN), alpha-naphtol pyronin (α-NP), o-dianisidine (OD), 5-bromo-4-chloro-3-indolylphosphate (BCIP), Nitro blue tetrazolium (NBT), 2-(p-iodophenyl)-3-p-nitrophenyl-5-phenyl tetrazolium chloride (INT), tetranitro blue tetrazolium (TNBT), δ-bromoˆ-chloro-S-indoxyl-beta-D-galactoside/ferro-ferricyanide (BCIG/FF). Examples of commonly used substrates for Alkaline Phosphatase include Naphthol-AS-B1-phosphate/fast red TR (NABP/FR), Naphthol-AS-MX-phosphate/fast red TR (NAMP/FR), Naphthol-AS-B1-phosphate/fast red TR (NABP/FR), Naphthol-AS-MX-phosphate/fast red TR (NAMP/FR), Naphthol-AS-B1-phosphate/new fuschin (NABP/NF), bromochloroindolyl phosphate/nitroblue tetrazolium (BCIP/NBT), δ-Bromoˆ-chloro-S-indolyl-beta-delta-galactopyranoside (BCIG).

Examples of luminescent labels which may be used in the invention include luminol, isoluminol, acridinium esters, 1,2-dioxetanes and pyridopyridazines. Examples of electrochemiluminescent labels include ruthenium derivatives. Examples of radioactive labels which may be used in the invention include radioactive isotopes of iodide, cobalt, selenium, hydrogen, carbon, sulfur, and phosphorous.

Some "detectable labels" according to this invention comprise "colour labels," in which the biological change or event in the system may be assayed by the presence of a colour, or a change in colour. Examples of "colour labels" are chromophores, fluorophores, chemiluminescent compounds, electrochemiluminescent labels, bioluminescent labels, and enzymes that catalyze a colour change in a substrate.

"Fluorophores" as described herein are molecules that emit detectable electro-magnetic radiation upon excitation with electro-magnetic radiation at one or more wavelengths. A large variety of fluorophores are known in the art and are developed by chemists for use as detectable molecular labels and can be conjugated to the linkers of the present invention. Examples include FLUORESCEIN™ or its derivatives, such as FLUORESCEIN™-5-isothiocyanate (FITC), 5-(and 6)-carboxyFLUORESCEIN™, 5- or 6-carboxyFLUORES-CEIN™, 6-(FLUORESCEIN™)-5-(and 6)-carboxamido hexanoic acid, FLUORESCEIN™ isothiocyanate, rhodamine or its derivatives such as tetramethylrhodamine and tetramethylrhodamine-5-(and-6)~isothiocyanate (TRITC). Other example fluorophores that could be conjugated to the instant linkers include: coumarin dyes such as (diethyl-amino)coumarin or 7-amino-4-methylcoumarin-3-acetic acid, succinimidyl ester (AMCA); sulforhodamine 101 sulfonyl chloride (TexasRed™ or TexasRed™ sulfonyl chloride; 5-(and-6)-carboxyrhodamine 101, succinimidyl ester, also known as 5-(and-6)-carboxy-X-rhodamine, succinimidyl ester (CXR); lissamine or lissamine derivatives such as lissamine rhodamine B sulfonyl Chloride (LisR); 5-(and-6)-carboxyFLUORESCEIN™, succinimidyl ester (CFI); FLUORESCEIN™-5-isothiocyanate (FITC); 7-diethylaminocoumarin-3-carboxylic acid, succinimidyl ester (DECCA); 5-(and-6)-carboxytetramethyl-rhodamine, succinimidyl ester (CTMR); 7-hydroxycoumarin-3-carboxylic acid, succinimidyl ester (HCCA); 6→FLUORESCEIN™-5-(and-6)-carboxamidolhexanoic acid (FCHA); N-(4,4-dif-luoro-5,7-dimethyl-4-bora-3a,4a-diaza-3-indacenepropionic acid, succinimidyl ester; also known as 5,7-dimethyl-BODIPY™ propionic acid, succinimidyl ester (DMBP); "activated FLUORESCEIN™ derivative" (FAP), available from Probes, Inc.; eosin-5-isothiocyanate (EITC); erythrosin-5-isothiocyanate (ErITC); and Cascade™ Blue acetylazide (CBAA) (the O-acetylazide derivative of 1-hydroxy-3,6,8-pyrene-trisulfonic acid). Yet other potential fluorophores useful in this invention include fluorescent proteins such as green fluorescent protein and its analogs or derivatives, fluorescent amino acids such as tyrosine and tryptophan and their analogs, fluorescent nucleosides, and other fluorescent molecules such as Cy2, Cy3, Cy 3.5, CY5™, CY5™.5, Cy 7, IR dyes, Dyomics dyes, phycoerythrine, Oregon green 488, pacific blue, rhodamine green, and Alexa dyes. Yet other examples of fluorescent labels which may be used in the invention include and conjugates of R-phycoerythrin or allophyco-erythrin, inorganic fluorescent labels such as particles based on semiconductor material like coated CdSe nanocrystallites.

A number of the fluorophores above, as well as others, are available commercially, from companies such as Probes, Inc. (Eugene, OR), Pierce Chemical Co. (Rockford, IL), or Sigma-Aldrich Co. (St. Louis, MO).

In some embodiments the detection unit may comprise from 1 up to 500 detectable label molecules. In some embodiments, the detectable label is an enzyme, which may be conjugated to a polymer, such that the number of enzyme molecules conjugated to each polymer molecule is, for instance, 1 to 200, 2 to 50, or 2 to 25. In some embodiments, the detectable label is a gold particle, a radioactive isotope, or a colour label, e.g. a low molecular weight fluorophore, and the number of detectable labels conjugated to each polymer molecule is, for instance, 1 to 500, or for instance, 2 to 200. In some embodiments, the detectable label is a protein fluorophore and the number of detectable labels conjugated to each polymer molecule is 1-50, 2-20. In some embodiments, the number of detectable label molecules conjugated to each polymer is 1-200, 2-50, 2-25, or is 10-20, 5-10, or 1-5.

The detectable label can be detected by numerous methods, including, for example, reflectance, transmittance, light scatter, optical rotation, and fluorescence or combinations hereof in the case of optical labels or by film, scintillation counting, or phosphorimaging in the case of radioactive labels. See, e.g., Larsson, 1988, Immunocytochemistry: Theory and Practice, (CRC Press, Boca Raton, FL); Methods in Molecular Biology, vol. 80 1998, John D. Pound (ed.) (Humana Press, Totowa, NJ). In some embodiments, more than one detectable label is employed.

Probes

Some linker derivatives according to this invention may be comprise a conjugated "probe" which, as used herein, is a functional group or molecule which monitors events or changes in a system, for example, by binding, reacting with, or hybridizing to a target substance in the system directly or indirectly. An example of a probe is a nucleic acid or nucleic acid analog capable of binding to or hybridizing with a particular target sequence. Other examples include antibodies, such as primary or secondary antibodies, antigens, enzyme substrates and protein ligands, haptens, proteins, and peptides.

Antibodies

In some embodiments, the instant linker derivatives comprise, for example, at least one polyclonal, monoclonal, monospecific, polyspecific, humanized, single-chain, chimeric, synthetic, recombinant, hybrid, mutated, and CDR-grafted antibodies. Various techniques for producing antibodies and preparing recombinant antibody molecules are known in the art and have been described, see, e.g., Kohler and Milstein, (1975) Nature 256:495; Harlow and Lane, Antibodies: a Laboratory Manual, (1988) (Cold Spring Harbor Press, Cold Spring Harbor, NY). Antibodies used in the invention may be derived from any mammal species, e.g., rat, mouse, goat, guinea pig, donkey, rabbit, horse, lama, camel, or any avian species e.g., chicken, duck. The origin of the antibody is defined by the genomic sequence irrespective of the method of production.

The antibody may be of any isotype, e.g., IgG, IgM, IgA, IgD, IgE or any subclass, e.g., IgGl, IgG2, IgG3, IgG4. The skilled artisan will appreciate that antibodies produced recombinantly, or by other means, for use in the invention include any antibody fragment which can still bind antigen, e.g. an Fab, an F(ab)$_2$, Fv, scFv. In certain embodiments, the antibody, including an antibody fragment, may be recombinantly engineered to include a hapten, e.g, a peptide. In certain embodiments the hapten may be a myc tag. Inclusion of a hapten in an antibody or antibody fragment facilitates subsequent binding of a binding agent, probe, or label Certain embodiments employ linker derivatives comprising a primary antibody containing an antigen binding region. Some embodiments employ linker derivatives comprising a secondary antibody containing an antigen binding region which specifically binds to a primary antibody, e.g., the constant region of the primary antibody. In certain embodiments, the linker derivative is further conjugated to a polymer. Some embodiments employ linker derivatives comprising a tertiary antibody containing an antigen binding region which specifically binds to the secondary antibody, e.g., a constant region of the secondary antibody, or a hapten linked to the secondary antibody or a polymer conjugated to the secondary antibody. In certain embodiments, the tertiary antibody is further conjugated to a polymer.

Nucleic Acids and Nucleic Acid Analogs

In some embodiments, the linker is conjugated to at least one nucleic acid and/or nucleic acid analog. As used herein, a "nucleic acid" refers to a nucleobase sequence comprising any oligomer, polymer, or polymer segment, having a backbone formed solely from RNA or DNA nucleosides and comprising only the bases adenine (A), cytosine (C), guanine (G), thymine (T), and uracil (U), wherein an oligomer means a sequence of two or more nucleobases. Nucleic acids may also be referred to as nucleic acids.

Non-natural bases may include, for example, purine-like and pyrimidine-like molecules, such as those that may interact using Watson-Crick-type, wobble, or Hoogsteen-type pairing interactions. Examples include generally any nucleobase referred to elsewhere as "non-natural" or as an "analog."

Examples include: halogen-substituted bases, alkyl-substituted bases, hydroxy-substituted bases, and thiol-substituted bases, as well as 5-propynyl-uracil, 2-thio-5-propynyl-uracil, 5-methylcytosine, isoguanine, isocytosine, pseudoisocytosine, 4-thiouracil, 2-thiouracil and 2-thiothymine, inosine, 2-aminopurine, N9-(2-amino-6-chloropurine), N9-(2,6-diaminopurine), hypoxanthine, N9-(7-deazaguanine), N9-(7-deaza-8-aza-guanine) and N8-(7-deaza-8-aza-adenine).

Yet other examples include bases in which one amino group with a hydrogen is substituted with a halogen (small "h" below), such as 2-amino-6-"h"-purines, 6-amino-2-"h"-purines, 6-oxo-2-"h"-purines, 2-oxo-4-"h"-pyrimidines, 2-oxo-6-"h"-purines, 4-oxo-2-"h"-pyrimidines. Those will form two hydrogen bond base pairs with non-thiolated and thiolated bases; respectively, 2,4 dioxo and 4-oxo-2-thioxo pyrimidines, 2,4 dioxo and 2-oxo-4-thioxo pyrimidines, 4-amino-2-oxo and 4-amino-2-thioxo pyrimidines, 6-oxo-2-amino and 6-thioxo-2-amino purines, 2-amino-4-oxo and 2-amino-4-thioxo pyrimidines, and 6-oxo-2-amino and 6-thioxo-2-amino purines.

These and other non-natural bases are described further below and in the accompanying International Application entitled "New Non-Natural Base Pairs."

In other examples, one or more of the H or $CH_3$ are independently substituted with a halogen such as Cl or F. In some embodiments, the following types of base pairs are used: one or more of Us:A, T:D, C:G, and P:Gs. In some embodiments, T:A and P:G are used.

Nucleic acid analogs may also comprise monomer units in which natural bases A, C, G, T, and U or non-natural bases are connected to a non-natural backbone unit. Non-natural backbone units include, for example, those with a backbone other than ribose-phosphate or deoxyribose-phosphate. For example, in some embodiments, one or more phosphate oxygens may be replaced by another molecule, such as sulphur. In other embodiments, a different sugar or a sugar analog may be used, for example, one in which a sugar oxygen is replaced by hydrogen or an amine, or an O-methyl. In yet other embodiments, nucleic acid analogs comprise synthetic molecules that can bind to a nucleic acid or nucleic acid analog. For example, a nucleic acid analog may be comprised of peptide nucleic acids (PNAs), locked nucleic acids (LNAs), or any derivatized form of a nucleic acid.

As used herein, "peptide nucleic acid" or "PNA" means any oligomer or polymer comprising at least one or more PNA subunits (residues), including, but not limited to, any of the oligomer or polymer segments referred to or claimed as peptide nucleic acids in U.S. Pat. Nos. 5,539,082, 5,527,675, 5,623,049, 5,714,331, 5,718,262, 5,736,336, 5,773,571, 5,766,855, 5,786,461, 5,837,459, 5,891,625, 5,972,610, 5,986,053, 6,107,470 6,201,103, 6,228,982 and 6,357,163; all of which are herein incorporated by reference.

The term PNA also applies to any oligomer or polymer segment comprising one or more subunits of the nucleic acid mimics described in the following publications: Lagriffoul et al., Bioorganic & Medicinal Chemistry Letters, 4: 1081-1082 (1994); Petersen et al., Bioorganic & Medicinal Chemistry Letters, 6: 793-796 (1996); Diderichsen et al., Tett. Lett. 37: 475-478 (1996); Fujii et al., Bioorg. Med. Chem. Lett. 7: 637-627 (1997); Jordan et al., Bioorg. Med. Chem. Lett. 7: 687-690 (1997); Krotz et al., Tett. Lett. 36: 6941-6944 (1995); Lagriffoul et al., Bioorg. Med. Chem. Lett. 4: 1081-1082 (1994); Diederichsen, U., Bioorganic & Medicinal Chemistry Letters, 7: 1743-1746 (1997); Lowe et al., J. Chem. Soc. Perkin Trans. 1, (1997) 1: 539-546; Lowe et al., J. Chem. Soc. Perkin Trans. 11: 547-554 (1997); Lowe et al., J. Chem. Soc. Perkin Trans. 1 1:5 55-560 (1997); Howarth et al., J. Org. Chem. 62: 5441-5450 (1997); Altmann, K—H et al., Bioorganic & Medicinal Chemistry Letters, 7/1119-1122 (1997); Diederichsen, U., Bioorganic & Med. Chem. Lett., 8: 165-168 (1998); Diederichsen et al., Angew. Chem. Int. Ed., 37/302-305 (1998); Cantin et al., Tett. Lett., 38/4211-4214 (1997); Ciapetti et al., Tetrahedron, 53: 1167-1176 (1997); Lagriffoule et al., Chem. Eur. J., 3: 912-919 (1997); Kumar et al., Organic Letters 3(9): 1269-1272 (2001); and the Peptide-Based Nucleic Acid Mimics (PENAMs) of Shah et al. as disclosed in WO96/04000.

As used herein, the term "locked nucleic acid" or "LNA" means an oligomer or polymer comprising at least one or more LNA subunits. As used herein, the term "LNA subunit" means a ribonucleotide containing a methylene bridge that connects the 2'-oxygen of the ribose with the 4'-carbon. See generally, Kurreck, Eur. J. Biochem., 270:1628-44 (2003).

Linker Derivatives Comprising Fluorophores

In some embodiments, linkers may be conjugated to one or more fluorophores. For example, two fluorophores may be conjugated to form a fluorophore-linker-Lys(fluorophore)-linker-X derivative. Similarly, one may prepare longer derivatives in which several fluorophores are spaced in between linker units of the same or varying lengths, such as in a Fluorophore-[linker-Lys(fluorophore)]N-linker-X construct, in which X is a conjugating group, or another atom, group, or molecule. In some embodiments, two fluorophores are separated from each other by at least four L15 units (L90) in order to ensure that the fluorophores are separated beyond the Foerster Radius (typically not more than 5 nm) such that quenching due to fluorescence resonance energy transfer is minimized or eliminated. In some embodiments, two fluorophores may be separated by four to ten L15 units (L90 to L150), while in others, by four to six L15 units (L90 to L120). In fact, in some embodiments, FLUORESCEIN™S spaced by at least four L15 units (L90) showed negligible quenching in aqueous buffers, strongly indicating that the linker adopts an extended structure in water. In contrast, polyethylene glycol (PEG)-based spacers may adopt a collapsed, coiled structure in water.

Because the linkers of the present invention may allow for the separation of individual fluorophores such that quenching is minimized, two or more different types of fluorophores may be conjugated to one or more linkers to produce amplified or uniquely coloured signals. For example, 2, 3, 4, or 5 fluorophore groups may be conjugated to linkers, each spaced at least four L15 units apart, for example, spaced between four and ten L15 units or four and six L15 units apart. Some embodiments of this invention comprise Rhodamine-L-Lys(FLUORESCEIN™)-L-X in which L contains a sufficient length to avoid quenching of the rhodamine and FLUORESCEIN™ signals, for example, and in which X is another atom, group, or molecule or a conjugating group. The optimal spacing for a given fluorophore depends in part upon its size, but may readily be determined by testing the intensity of the fluorescent signal at various spacings, for example.

In some embodiments, a molecule such as a protein may be conjugated to several linker derivatives which are each conjugated to a detectable label such as a fluorophore. In conventional protein fluorescence labelling methods without linkers or with short linkers, the size of the conjugated protein determines how far apart the attached fluorophores can be placed, and consequently, primarily determines the fluorescence intensity. The same principle applies to other molecules as well. In contrast, embodiments of the present invention may relieve this size constraint because the instant linkers can: (1) conjugate to several fluorophores, (2) maintain an extended structure in solution that minimizes unwanted interactions between the individual fluorophores, and (3) conjugate to many types of proteins and other molecules. Thus, in some embodiments, this invention may greatly enhance the fluorescence intensity of a molecule, and may eliminate the need for the extra steps commonly employed to enhance a signal in a system. For example, attaching multiple linker derivatives each comprising multiple fluorophores to an antibody may allow for direct detection of minute quantities of an antigen without the need for secondary antibody signal-amplification procedures.

Linker Derivatives with Multiple Conjugated Substances

Some linker derivatives according to this invention include different types of conjugated detectable labels. In some embodiments, linkers are conjugated to two different detectable labels in which one label serves to monitor a change or event in a system by binding to or hybridizing with a target, while the other serves to detect that binding event via a colour change, radioactivity, or some other detectable signal. For example, a fluorophore may be combined with a different type of colour label. Derivatives such as DNP-linker-Lys(Fluorophore)-linker-X have been prepared. DNP (dinitrophenol) may be recognized by an anti-DNP antibody while the fluorescent emission provides a second type of signal, thus providing two alternative labelling methods.

Further, embodiments of the present invention may comprise other combinations of atoms, groups, or molecules such as a detectable label and a solid surface, membrane, protein, or other large molecule. Attachments may be covalent as well as non-covalent. Embodiments with more than one type of conjugated atom, group, or molecule are useful, for example, in immunoprecipitation or ELIZA assays, in situ detection assays, multi-layer assays, fluorescent microsphere assays, and capture assays.

In some embodiments, linkers are conjugated to fluorophores as well as to probes such as nucleic acids and nucleic acid analogs. For example, a nucleic acid or nucleic acid analog may be used to hybridize to a target sequence in a system, while the fluorophore conjugated to the probe through the linker provides a means to detect the hybridization. Such bifunctionally labelled linker derivatives may be useful, for example, in in situ hybridization assays such as FISH.

Other linker derivatives according to this invention comprise multiple nucleic acid or nucleic acid analog conjugates, optionally further conjugated with other types of detectable labels. For example, a single linker derivative molecule may comprise several different nucleic acid or nucleic acid analogs, each separated from the others by stretches of one or more L15 units. In some embodiments, the different nucleic acid or nucleic acid analogs are separated from each other by spacings of L120 to L300, L150 to L300, or L300.

In some embodiments, linkers are conjugated to fluorophores or other colour-based labels as well as to PNA or LNA probes. PNA-containing linker derivatives made according to the present invention include, for example, X-L-PNA-L-Lys(Cys) comprising linker derivatives, in which X may be an end-group such as acetyl, a conjugating group, or a colour label such as a fluorophore or enzyme substrate such as DNP. Attachment of a fluorophore such as FLUORESCEIN™ may allow simpler purification and analysis of the derivative. A spacing of L30 or larger between the X group and a PNA or oligonucleotide is generally a sufficient distance to avoid steric hindrance between the linker and the hybridization target, however longer spacing may be used, for example to increase entropy to further minimize unwanted tertiary interactions or aggregation. For instance, the distance between the PNA or oligonucleotide and a Lys(Cys) group may be, for example, up to L300, including from L120 to L300 or from L150 to L300. Spacing between the PNA and other conjugates may be, for example, from L120 to L300, from L150 to L300, or L300. Other exemplary PNA-comprising linker derivatives according to the invention also include multiple fluorophore or colour label attachments. For example, the derivative [Flu-L60)$_2$Lys-]$_2$Lys-L30-PNA was prepared and contains four FLUORESCEIN™ linker derivatives (Flu). In other embodiments, a linear linker derivative may be prepared, conjugated to PNA and multiple fluorophores. The embodiment Lys(Flu)-L30-PNA-L30-Lys(Flu)-L90-Lys(Flu)-L90-Lys(Flu) was also prepared and similarly contains four FLUORESCEIN™s. While fluorophores conjugated to the same linker derivative can be more likely to aggregate in solution than fluorophores conjugated to different linker derivatives, surprisingly, linker derivatives comprising a PNA probe and several fluorophores spaced by L90 linkers not only gave enhanced signals over others containing single fluorophores, but also showed a reduced background, indicating that the high entropy due to the flexible, extended structure of each L90 linker more than compensated for any increased tendency for the fluorophores to interact. In some embodiments, the linker derivatives may also form branched structures or may specifically hybridize with each other via the conjugated PNAs so as to amplify the signal.

Cross-Linking Agents

The linkers of the present invention may also be used as protein cross-linkers. For example, the instant linkers may be conjugated with a protein conjugating group such as malemide, and/or with an antigen, ligand, or substrate for a particular protein or antibody, and optionally also with a detectable label in order to visualize the cross-link. For instance, malemide-linker-X groups have been prepared, in which X represents a reactive group such as Lys(betaalanine-N$_1$N diacetic acid), or a specific ligand, antigen, or substrate of the protein of interest. Such a linker can be used, for example, to bind to a specific protein or antibody via the X group, and to cross link to other proteins in the vicinity of that specific protein via the malemide-linker. A detectable label may also be conjugated to the linker derivative to aid in detecting the cross-link. Even relatively short linker segments such as L30 between a label and a protein ligand may allow for detection of the label without significant interference from quenching of a fluorescent label, for example.

The extended, flexible structure of some of the instant linkers allows them to assist in the cross-linking of even two large molecules, such as a fluorescent protein (for example, RPE or green fluorescent protein) and an antibody. For example, long linkers according to the present invention may have lengths in solution of, for instance, 9 nm in the case of L90, or even 30 nm in the case of L300, or even longer. That length provides significant freedom for even very large proteins within a cross-linked complex to adopt their preferred orientations independently of others within the complex. Thus, the instant linkers allow for more accurate identification of interacting proteins because the complex is minimally perturbed by the presence of the linker.

Surface or Polymer Conjugation

In some embodiments, the instant linkers may serve to covalently or non-covalently attach a detectable label or other atom, group, or molecule to a polymer or a surface such as dextran or a membrane or an array or a plate. The instant linkers take up little space in the longitudinal direction. Hence, they may be useful in coating such surfaces at high density because they can access relatively narrow spaces or pores in such surfaces. Further, long linkers may be employed in order to maximize the distance between the surface and other components of the system, such that the system is minimally perturbed. For example, linker derivatives can be prepared for conjugation to dextran in conjunction with nucleic acids or nucleic acid analogs such as PNA as well as colour labels such as HRP and one or more fluorophores. Other linker derivatives can be prepared for conjugation to combinations of dextran, PNA, and antibodies. Linker derivatives with multiple conjugated atoms, groups, or molecules may be used to amplify signals in a variety of ways. For example, minute quantities of antibodies or antigens may be detected by attaching the antibody or antigen to a linker derivative comprising multiple fluorophores. Further, two potentially cross-reactive antigens may be distinguished by attaching the antigens to linker derivatives comprising different types of fluorophores. Multi-layer systems may also be constructed in which certain interacting atoms, groups, or molecules such as complementary nucleic acids or nucleic acid analogs or a protein and a ligand are placed in between another detectable label such as a colour label and a surface or molecule.

Enhancing the Solubility of Conjugated Substances

Another surprising feature of some of the instant linkers is a relatively high solubility despite the presence of relatively few polar or charged groups. Hence, linkers, for example, those comprising two or more L15 units in some derivatives, or four or more L15 units in other derivatives, can also be employed to enhance the solubility of an atom, group, or molecule in aqueous solution. For example, an acetyl-L-X group may be used to enhance the solubility of the atom, group, or molecule X. Surprisingly, PNA probes with multiple fluorophores spaced via at least four L15 units showed higher water solubility, as well as less aggregation and less non-specific binding, than those without conjugated linkers and with only one fluorophore. Further, poly-linker derivatives of the present invention conjugated to even 50 to 100 bases of PNA as well as to fluorophores did not aggregate and showed high water solubility.

Other Exemplary Uses of Linker Derivatives

In yet other embodiments, the instant linkers may be conjugated to a drug compound, for instance, to increase its retention, solubility, or to effectively link it to another group so as to target it to a particular area of the body. For example, in some embodiments, at least one linker of homogeneous molecular and structural formula is conjugated to at least one drug compound.

The instant linkers are also useful in a variety of biological and chemical assays. For instance, in capture assays, steric barriers may be relieved by in effect lifting a probe from a surface so that it is free in solution to recognize its target. If the rate of binding between the probe and target is slow relative to the rate of diffusion, a shorter linker length may be employed. However, when the rate of binding is rapid compared to the rate of diffusion in the system, a long linker may be advantageous. Because the instant linkers may be prepared at precise short or long lengths, as well as in mixtures of different lengths, depending on the synthesis method used, the instant linkers provide a uniform system around which such assays may be designed.

MHC I and MHC II Heavy and Light Chain Sequences

This is examples of amino acid sequences of full length and truncated MHC I and MHC II heavy and light chains:

```
Example MHC I heavy chain, HLA-A*0201, full length
                                          (SEQ ID NO: 1)
GSHSMRYFFTSVSRPGRGEPRFIAVGYVDDTQFVRFDSDAASQRMEPRAP

WIEQEGPEYWDGETRKVKAHSQTHRVDLGTLRGYYNQSEAGSHTVQRMYG

CDVGSDWRFLRGYHQYAYDGKDYIALKEDLRSWTAADMAAQTTKHKWEAA

HVAEQLRAYLEGTCVEWLRRYLENGKETLQRTDAPKTHMTHHAVSDHEAT

LRCWALSFYPAEITLTWQRDGEDQTQDTELVETRPAGDGTFQKWAAVVVP

SGQEQRYTCHVQHEGLPKPLTLRWEPSSQPTIPIVGIIAGLVLFGAVITG

AVVAAVMWRRKSSDRKGGSYSQAASSDSAQGSDVSLTACKV

Example MHC I heavy chain, HLA-A*0201, truncated
(-transmembrane and cytoplasnic domain)
                                          (SEQ ID NO: 2)
GSHSMRYFFTSVSRPGRGEPRFIAVGYVDDTQFVRFDSDAASQRMEPRAP

WIEQEGPEYWDGETRKVKAHSQTHRVDLGTLRGYYNQSEAGSHTVQRMYG

CDVGSDWRFLRGYHQYAYDGKDYIALKEDLRSWTAADMAAQTTKHKWEAA

HVAEQLRAYLEGTCVEWLRRYLENGKETLQRTDAPKTHMTHHAVSDHEAT

LRCWALSFYPAEITLTWQRDGEDQTQDTELVETRPAGDGTFQKWAAVVVP

SGQEQRYTCHVQHEGLPKPLTLRWE

Example MHC I light chain, β2m, full length
                                          (SEQ ID NO: 3)
MSRSVALAVLALLSLSGLEGIQRTPKIQVYSRHPAENGKSNFLNCYVSGF

HQSDIEVDLLKNGERIEKVEHSDLSFSKDWSFYLLYYTEFTPTEKDEYAC

RVNHVTLSQPKIVKWDRDM

Example MHC II α-chain, DRA*0101, full length
                                          (SEQ ID NO: 4)
IKEEHVIIQAEFYLNPDQSGEFMFDFDGDEIFHVDMAKKETVWRLEEFGR

FASFEAQGALANIAVDKANLEIMTKRSNYTPITNVPPEVTVLTNSPVELR

EPNVLICFIDKFTPPVVNVTWLRNGKPVTTGVSETVFLPREDHLFRKFHY

LPFLPSTEDVYDCRVEHWGLDEPLLKHWEFDAPSPLPETTENVVCALGLT

VGLVGIIIGTIFIIKGVRKSNAAERRGPL

Example MHC II α-chain, DRA*0101, truncated
(-transmembrane and cytoplasmic domain)
                                          (SEQ ID NO: 5)
IKEEHVIIQAEFYLNPDQSGEFMFDFDGDEIFHVDMAKKETVWRLEEFGR

FASFEAQGALANIAVDKANLEIMTKRSNYTPITNVPPEVTVLTNSPVELR
```

-continued
```
EPNVLICFIDKFTPPVVNVTWLRNGKPVTTGVSETVFLPREDHLFRKFHY

LPFLPSTEDVYDCRVEHWGLDEPLLKHWEFDAPSPLPETTE

Example MHC II β-chain, HLA-DRB1*0401, full length
                                        (SEQ ID NO: 6)
GDTRPRFLEQVKHECHFFNGTERVRFLDRYFYHQEEYVRFDSDVGEYRAV

TELGRPDAEYWNSQKDLLEQKRAAVDTYCRHNYGVGESFTVQRRVYPEVT

VYPAKTQPLQHHNLLVCSVNGFYPGSIEVRWFRNGQEEKTGVVSTGLIQN

GDWTFQTLVMLETVPRSGEVYTCQVEHPSLTSPLTVEWRARSESAQSKML

SGVGGFVLGLLFLGAGLFIYFRNQKGHSGLQPTGFLS

Example MHC II β-chain, HLA-DRB1*0401, truncated
(-transmembrane and cytoplasnic domain)
                                        (SEQ ID NO: 7)
GDTRPRFLEQVKHECHFFNGTERVRFLDRYFYHQEEYVRFDSDVGEYRAV

TELGRPDAEYWNSQKDLLEQKRAAVDTYCRHNYGVGESFTVQRRVYPEVT

VYPAKTQPLQHHNLLVCSVNGFYPGSIEVRWFRNGQEEKTGVVSTGLIQN

GDWTFQTLVMLETVPRSGEVYTCQVEHPSLTSPLTVEWRARSESAQSKM
```

The polypeptides a and b can include various polypeptide variants. Variant a and/or b polypeptides can include a and/or b polypeptides containing amino acid insertions, deletions or substitutions, as well as chemical modifications.

Amino acid substitutions can include conservative and non-conservative amino acid substitutions. Conservative amino acid substitutions replace an amino acid with an amino acid of the same class, whereas non-conservative amino acid substitutions replace an amino acid with an amino acid of a different class. Non-conservative substitutions result in a change in the hydrophobicity of the polypeptide or in the bulk of a residue side chain. In addition, non-conservative substitutions can make a substantial change in the charge of the polypeptide, such as reducing electropositive charges or introducing electronegative charges. Examples of non-conservative substitutions include a basic amino acid for a non-polar amino acid, or a polar amino acid for an acidic amino acid. Amino acid insertions, deletions and substitutions can be made using random mutagenesis, site-directed mutagenesis, or other recombinant techniques known in the art.

Variant a and/or b polypeptides can also be evaluated based on a predetermined number of conservative amino acid substitutions, as defined herein below. Conservative amino acid substitution as used herein relates to the substitution of one amino acid (within a predetermined group of amino acids) for another amino acid (within the same group), wherein the amino acids exhibit similar or substantially similar characteristics.

Within the meaning of the term "conservative amino acid substitution" as applied herein, one amino acid may be substituted for another within the groups of amino acids indicated herein below:

i) Amino acids having polar side chains (Asp, Glu, Lys, Arg, His, Asn, Gln, Ser, Thr, Tyr, and Cys,)
ii) Amino acids having non-polar side chains (Gly, Ala, Val, Leu, Ile, Phe, Trp, Pro, and Met)
iii) Amino acids having aliphatic side chains (Gly, Ala Val, Leu, Ile)
iv) Amino acids having cyclic side chains (Phe, Tyr, Trp, His, Pro)
v) Amino acids having aromatic side chains (Phe, Tyr, Trp)
vi) Amino acids having acidic side chains (Asp, Glu)

vii) Amino acids having basic side chains (Lys, Arg, His)
viii) Amino acids having amide side chains (Asn, Gln)
ix) Amino acids having hydroxy side chains (Ser, Thr)
x) Amino acids having sulphor-containing side chains (Cys, Met),
xi) Neutral, weakly hydrophobic amino acids (Pro, Ala, Gly, Ser, Thr)
xii) Hydrophilic, acidic amino acids (Gln, Asn, Glu, Asp), and
xiii) Hydrophobic amino acids (Leu, Ile, Val) Accordingly, a variant polypeptide, or a fragment thereof according to the present invention, can comprise, within the same variant of the sequence or fragments thereof, or among different variants of the sequence or fragments thereof, at least one substitution, such as a plurality of substitutions introduced independently of one another.

It is clear from the above outline that the same variant or fragment thereof can comprise more than one conservative amino acid substitution from more than one group of conservative amino acids as defined herein above.

Positive Control Experiments for the Use of MHC Multimers

When performing analysis of samples with MHC multimers using e.g. flow cytometry or other technologies/methods, it is important to include appropriate positive and negative controls. In addition to establishing proper conditions for the experiments, positive and negative control reagents can also be used to evaluate the quality (e.g. specificity and affinity) and stability (e.g. shelf life) of produced MHC multimers.

Positive control experiments may be performed as a control before analysis of a given sample, simultaneously with analysis of sample and/or after analysis of sample. The positive control experiment may be a control of the MHC multimer reagent itself, a control of the sample analysed or a control of the analysis method used.

Evaluating MHC Multimer Reagent

One preferred positive control experiment of the present invention includes analysis of the, quality, performance, specificity, stability and integrity of MHC multimer reagents. Principles and methods for performing this kind of experiments include but are not limited to:

Evaluation of MHC multimers ability to bind TCR. The quality of MHC multimer reagents can be evaluated by analysis of the ability of the MHC multimer reagent to bind specific TCR. The TCR have to be specific for one or more MHC-peptide complexes of the multimer and preferable not able to recognise other MHC-peptide complexes consisting of different MHC alleles and/or different peptide in the peptide binding cleft. However TCR's specific for more than one MHC-peptide complex can also be used.

In one preferred positive control experiment of the present invention MHC multimer binding to TCR's displayed on the surface of cells are analysed. In such experiments the positive control reagent is TCR expressing cells. That includes measurement of specific MHC multimer binding to specific cell lines (e.g. T-cell lines) displaying displaying TCRs with appropriate specificity and affinity for the MHC multimer in question. Example useful cell lines are natural T-cell lines, T-cell hybridomas, cells transfected/transformed with genes encoding specific TCR e.g. transfected mammalian cells, yeasT-cells, insecT-cells and bacterial cells and cell like structures displaying TCR including but not limited to liposomes and micelles.

Another positive control experiment of the present invention using TCR displayed on cell surface includes measurement of specific MHC multimer binding to cells in blood samples, preparations of purified lymphocytes (HPBMCs) as described elsewhere herein, CSF samples, samples of lymph, synovial fluid, semen, sputum or other bodily fluids that contain cells carrying TCR molecules specific for the MHC multimer in question.

Alternatively MHC multimer binding to immobilized specific T-cells can be measured e.g. measurement of MHC multimer binding to T-cells in solid tissue, in sections of solid tissue, in tissue or in organs inside body and to TCR expressing cells immobilised on solid support as described elsewhere herein.

In another positive control experiment of the present invention MHC multimer binding to TCR's immobilised on solid support are measured. In such experiments the positive control reagent is immobilized TCR or TCR in solution that later are immobilized on solid support. The TCR can be full-length (i.g. comprise the intracellular- and intra-membrane domains), or can be truncated (e.g. only comprise the extracellular domains or subunits of extracellular domains). The TCR may be natural in sequence e.g. identical in sequence to one or more naturally occurring TCR's, may be mutated in one or more positions or insertions/deletions of amino acids can be introduce. Likewise, the TCR can be chemically or enzymatically modified on one or more amino acids. The TCR may also be fused with one or more proteins or other molecules. Fusion with another protein can be made by genetically fusion of the gene encoding that protein with genes encoding one or both polypeptide chains of the TCR or encoding part of either chain. An example is fusion of genes encoding antibody or fragment of antibody e.g. the constant part with genes encoding TCR.

Protein or other molecules like carbohydrates, small organic molecules, DNA, RNA, PNA, lipids, polymers, metals can also be attached to the TCR by covalent or non-covalent interaction as described for multimerisation domains elsewhere herein.

The TCR's can be generated by elution from T-cells or other TCR expressing cells, generated by recombinant methods known by persons skilled in the art, by in vitro translation of mRNA obtained from cells expressing TCR or by chemically synthesis.

Useful solid supports for immobilisation of TCR include beads, particles, biodegradable particles, sheets, gels, filters, membranes (e. g. nylon membranes), fibres, capillaries, needles, microtitre strips, tubes, plates or wells, combs, pipette tips, micro arrays, chips, slides, any other solid support as described elsewhere herein or indeed any solid surface material.

TCR's can be attached to the solid support by covalent or non-covalent interaction as described elsewhere herein for attachment of MHC complexes to solid support or other multimerization domains.

MHC multimer binding to TCR or T-cell can be determined directly using labeled MHC multimer or a secondary labelling molecule specific for the MHC multimer or by measurement of effect of binding MHC multimer as described elsewhere herein.

Alternatively MHC multimer are first bound to TCR/T-cell, then eluted and subsequently detected through labelling molecule(s), secondary marker molecules with labels, by activity of eluted product or by determination of amount of eluted MHC multimer e.g. determination of protein concentration, measurement of amount of label (flourecense intensity, enzymatic activity, ect.) or amount of multimerisation domain (e.g. counting of cells if multimerisation domain is a cell ect.).

Another example includes measurement of functional MHC in an assay where the total protein concentration is measured before functional MHC is captured, by binding to e.g. immobilized TCR. Then non-binding MHC is removed by e.g. removing supernatant and concentration of non-bound protein are measured. If the dissociation constant for the interaction is known, the amount of total and the amount of non-bound protein can be determined. From these numbers, the fraction of functional MHC complex can be determined.

Useful methods and principles for measurement of MHC multimer binding to T-cell and/or TCR are described in the section "Technical applications for use of MHC multimers"

Evaluation of MHC multimers ability to bind TCR-like molecules is another type of positive control experiment. TCR-like molecules are molecules binding MHC multimers with same specificity as TCR, i.e. recognising the peptide binding grove part of the MHC-peptide complex. Examples of TCR-like molecules include but is not limited to antibodies, antibody fragments, antibody like scaffold proteins, aptamers or any other molecule able to bind MHC-peptide complexes in a peptide and MHC alle specific manner.

Binding of MHC multimers to TCR-like molecules follows the same methods and principles as described for binding to TCR above. Thus positive control reagents in such positive control experiments are cells or cell-like structures expressing TCR-like molecules, TCR-like molecules immobilised to solid support and/or TCR-like molecules in solution.

Analysis of conformation of MHC-peptide complex in MHC multimer. MHC-peptide complexes are only able to be recognised by specific T-cells if the MHC-peptide complex have the correct three-dimensional structure i.e. the correct fold and contains both MHC polypeptide chains and antigenic peptide. Therefore measurement of the conformation of MHC-peptide complexes in a MHC multimer are relevant positive control experiments.

One preferred analysis of conformational correct folded MHC-peptide complexes in MHC multimers includes use of antibodies or other molecules recognising structural correct MHC molecules and not unfolded molecules or MHC molecules that are fallen apart. The antibodies recognise one or more epitopes on the MHC-peptide complexes that are only present when the MHC-peptide complex is correct assembled. An example is the antibody clone W6/32 that recognise all human HLA I molecules but only when both heavy chain and $\beta$2m are assemblet (Parham et al. (1979). J. Immunol., vol 123, 342-349).

Molecules useful for this type of positive control experiment includes but is not limited to antibody, antibody fragment e.g. Fab, $(Fab)_2$ Fv, scFV, aptamers, antibody like molecules, scaffold proteins. Also included are cells and cell-like structures expressing any of the above described type of molecules and also viral particles expressing such molecules.

Antibodies and other molecules recognising a confor-
mational correct epitope on MHC-peptide com-
plexes can be generated and used in positive control
experiments as described for TCR above. Thus posi-
tive control reagents in such positive control experi-
ments are cells or cell-like structures expressing
molecules recognising conformational epitopes on
MHC molecules, molecules recognising conforma-
tional epitopes on MHC molecules in solution and/or
immobilised to solid support.

A preferred embodiment includes measurement of
MHC multimer binding to beads or other types of
solid support, to which antibodies or molecules that
recognize conformational epitopes on MHC-peptide
complexes have been immobilized. Bound MHC
multimer are then detected through a label on the
multimer or through a secondary labelled marker
molecule. An example is measurement of correctly
folded MHC in a quantitative ELISA, e.g. where the
MHC binds to immobilized molecules recognizing
the correctly folded complex.

Another preferred embodiment includes detection of
binding of MHC multimers to cells, cell-like struc-
tures, yeast or viral particles displaying antibodies or
other molecules able to recognise conformational
epitopes on MHC-peptide complexes.

Alternative methods to determine correct conformation
of MHC-peptide complexes in MHC multimers
include X-ray Crystallography, circular dichroism
and NMR spectroscopy.

During production of MHC multimers, it can also be
desirable to determine the degree of correctly folded
MHC. The fraction or amount of functional and/or
correctly folded MHC can be tested in a number of
different ways, using methods and principles as
described above.

Measurement of presence of components of MHC mul-
timer e.g. MHC-peptide complex, MHC polypeptide
chains, antigenic peptide and label is another way to
perform a positive control experiment. This type of
analysis does not tell if the MHC multimer is functional
but gives information of the intactness of the multimer.

The presence of MHC-peptide complex, MHC polypep-
tide chains, antigenic peptide and/or label on a multi-
mer may be determined by detection of binding of an
antibody or other molecule to one or more of the
components in the MHC multimer. Examples include
measurement of binding of antibodies to any epitope in
MHC-peptide complexes, in MHC I heavy chain, in
β2microglobulin, in MHC II α-chain or β-chain, in
antigenic peptide, in label, in multimerisation domain,
in the linker connecting MHC-peptide complexes and/
or label to multimerization domain or in tags or other
recognising binding any other part of MHC multimer.

Antibodies and other molecules recognising components
of MHC multimer can be generated and used in posi-
tive control experiments as described for the use of
TCR in positive control experiments above. Thus posi-
tive control reagents in such positive control experi-
ments are cells or cell-like structures expressing mol-
ecules recognising any part of MHC multimer, soluble
molecules recognising any part of MHC multimer
and/or such molecules to solid support.

A preferred embodiment includes measurement of MHC
multimer binding to beads or other types of solid
support, to which antibodies or molecules recognising
components of MHC multimer have been immobilized.

Bound MHC multimer are then detected through a label
on the multimer or through a secondary labelled marker
molecule.

Another preferred embodiment includes detection of
binding of MHC multimer to cells, cell-like structures,
yeast or viral particles displaying antibodies or other
molecules able to recognise components of MHC mul-
timer Alternatively the presence of MHC-peptide complex,
MHC polypeptide chains, antigenic peptide and/or
label in a MHC multimer can be measured using Mass
spectrometry (MS), HPLC, FPLC, SDS PAGE or other
methods that can visualize the individual components
of the MHC multimer due to their different size and/or
chemical and/or physical properties. Prior to analysis it
may be advantageous to split the MHC multimer into
its individual components by e.g. boiling, changeing
pH, using detergent ect.

Above principles for positive control experiments evalu-
ating MHC multimer reagents are given. However positive
control experiments determining the quality and stability of
individual components of the MHC multimer are also
important. Quality and stability of labelling molecules can
be evaluated using methods measuring their presences e.g.
by detection with antibodies or other molecules able to bind
the label or using MS, HPLC, FPLC or similar methods.
Alternatively the activity e.g. fluorescence or enzymatic
activity of the label can be measured.

The quality and stability of individual MHC-peptide
complexes can be determined using the same principles as
described above for MHC multimers but can also be deter-
mined by:

Measurement of MHC-peptide complex binding using
shift assays. Binding of specific MHC-peptide com-
plexes to soluble TCRs, antibodies, aptamers or other
soluble molecules recognising MHC-peptide com-
plexes can be measured in so called shift assay. A shift
assay is here an assay detecting a shift in size of a given
MHC-peptide complex. Upon binding another mol-
ecule the molecular weight of a MHC-peptide complex
will increase with the molecular weight of the molecule
bound and this increase in size can be measured using
methods able to separate molecules according to size
including but not limited to SDS PAGE, size exclusion
chromatography and density gradient centrifugation
(e.g. CsCl). Preferable soluble TCR, TCR-like mol-
ecules or molecules recognizing conformational
epitopes on the MHC-peptide complexes are used. A
shift in size of a preparation of MHC-peptide complex
upon addition of such molecules will then indicate that
the MHC-peptide complex is present in the sample and
correctly folded and is functional.

An example is measurement of functional MHC complex
using a non-denaturing SDS PAGE gel-shift assay,
where functional MHC complexes bind to soluble TCR
(or another molecule that recognize correctly folded
MHC complex), and thereby shifts the TCR to another
position in the gel.

Depending on the technical method employed for the
positive control experiment one or more of the above
described principles for measurement can be used. For
example for flow cytometry analysis cells, beads or particles
are preferred as positive control reagents since they can be
seen as individual populations during a flow cytometry
analysis.

When using beads or particles as positive controls they
are preferable such that they can be distinguished from T-cells in the sample e.g. due to different size, different scatter properties and/or different labelling or labelling intensity Preferable the beads or particles are small e.g. with a diameter between 0.1-100 um but can in principle be of any size useful in a flow cytometer analysis. The beads or particles may be fluorescent themselves or coupled to one or more fluorescent molecules as described elsewhere herein. In principle the same type and same principles of beads and particles can be used as what is described in relation to counting beads in flow cytometry experiments, detection of T-cells using beads with immobilised MHC multimers and bead-based MHC multimers elsewhere herein.

When performing positive control experiments using IHC as analysis method tissue sections or cells immobilized to e.g. glass plates are preferred as positive controls. Likewise when performing ELISA or ELISA-like control experiments TCR or T-cell's immobilized to wells of a microtiter plate or similar are preferred.

Evaluating Sample and Analysis

Another preferred type of positive control experiments include evaluation of sample and analysis method. Such experiments determine whether a sample is intact and useful and/or whether the analysis method is successful. Such positive controls are preferably analysed on same sample as used in the MHC multimer analysis in question. However, another sample from same individual, a similar sample from another individual or a complete different sample can also be used. In these latter cases only information of the quality of analysis methods are determined.

The positive control can be an internal control and added into the same sample for which it is a positive control together with MHC multimer reagent i.e. into same container or it can a natural part of sample. Alternatively the positive control reagents are added to a separate container containing the same or a different sample. In all cases the analysis method is the same as used for analysis of actual sample with MHC multimer.

Positive control experiments evaluating analysis method and or sample include but are not limited to:

Measurement of MHC multimer binding to beads or other solid supports with immobilised molecules specific for MHC-peptide complex e.g. specific TCR, TCR-like molecules, molecules recognizing conformational epitopes on MHC-peptide complexes, molecules recognizing any epitope on MHC-peptide complexes or molecules recognizing tag or other detectable components on the MHC multimer e.g. recognizing streptavidin or coiled-coil structure. Example of various MHC multimer tags are described elsewhere herein.

Principles and methods for measurement of MHC multimer binding to such beads or solid support are described above in the section "Evaluating MHC multimer reagent"

This type of control can be used to evaluate analysis method as well as MHC multimer reagent used.

Measurement of MHC multimer binding to Cells displaying TCR or other molecules specific for MHC-peptide complexes or other part of MHC multimer. Cells includes T-cells, T-cell lines, T-cell hybridomas, cells transfected/transformed with genes encoding TCR, cells transfected/transformed with genes encoding TCR-like molecules able to recognise MHC-peptide complexes, cells displaying other molecules specific for MHC-peptide complexes or any other part of MHC multimer or cell-like structures displaying TCR, TCR-like molecules or other molecules able to recognize MHC-peptide complexes or any other part of MHC multimer. Principles and methods for measurement of MHC multimer binding to such cells or cell-like structures are described above in the section "Evaluating MHC multimer reagent".

This type of control can be used to evaluate analysis method as well as MHC multimer reagent used Measurement of binding positive control MHC multimers to T-cells and/or TCR in sample. The positive control MHC multimer include MHC multimers comprising MHC molecule complexed with an appropriate peptide that allows the MHC multimer to interact specifically and efficiently with its cognate TCR.

The type MHC multimer can be identical to or different from the MHC multimer used in the analysis in question, e.g. comprice the same or different mulimerisation domain. Likewise, the positive MHC multimer can have the same specificity as the MHC multimer used in the analysis or it may have specificity for other T-cells in the sample analysed.

This type of control can be used to evaluate analysis method as well as the quality of sample.

Measurement of HLA-type of sample

T-cell from a given donor are "educated" to recognize only MHC allele's identical to MHC alleles expressed on cells of that donor, they are self-restricted. Therefore a given MHC multimer are only recognized by T-cells in a sample if that sample derive from a donor positive for the same MHC allele(s) as is in the MHC multimer and of cause if the MHC complexes of the MHC multimers presents the right peptide.

MHC multimers of the present invention may feature one or more different MHC allele's and one or more different MHC multimers may be applied for analysis of a given sample. In many aspect of the present invention it is therefore important that the sample derive from a donor that have MHC alleles corresponding to one or more MHC alleles of the MHC multimer(s) used for analysis. Positive control experiments determining whether the sample contains or derive from a donor with matching MHC allele type can therefore be important controls. MHC allele determination of a given sample are in the following called MHC allele typing and includes but is not limited to:

MHC allele typing using PCR. MHC allele typing can be determined by amplification of DNA fragments encoding MHC polypeptide chains by PCR using primers specific for all known MHC alleles or selected groups of alleles e.g. human alleles, sub groups of human alleles or few selected alleles. DNA fragments from a given donor can be obtained by lysing or otherwise disrupting cells from the sampe to be analysed or from another sample from that donor.

MHC allele typing using MHC allele specific antibodies or marker molecules. Expression of specific MHC alleles on the surface of a cell can be determined by measuring the binding of antibodies or other marker molecules specific for one or more MHC alleles. Binding of antibody or other marker molecules may be detected directly through a label on the antibody/marker molecule or through secondary labeled antibodies and marker molecules. In the following antibodies and other marker molecules are collectively called marker molecules.

In one preferred embodiment marker molecules with different specificity are labeled with same labeling molecule and thereby detected as a pool. In such a positive control experiment the presence of alleles recognized by any of the marker molecules used for analysis are determined and not the presence of individual alleles. The panel of marker molecules used is matching the MHC alleles in the MHC multimer preparation used for analysis of sample.

In another preferred embodiment each marker molecule is labeled with an individual label. In such a positive control experiment the presence of alleles recognized by any of the marker molecules used for analysis are determined and also the presence of individual alleles. The panel of marker molecules used is matching the MHC alleles in the MHC multimer preparation used for analysis of sample.

In another preferred embodiment of the present invention groups of marker molecules are labeled with same label and other groups of marker molecules are labeled with other labels. In such a positive control experiment the presence of alleles recognized by any of the marker molecules used for analysis are determined and not the presence of individual alleles. However the presences of subgroups of MHC alleles may be determined. The panel of marker molecules used is matching the MHC alleles in the MHC multimer preparation used for analysis of sample.

In another preferred embodiment of the present invention marker molecules specific for different alleles are labeled with same label thereby identifying subpopulations of MHC expressing cells for which one or more is positive for one ore more additional marker molecules labeled with another label. For example 6 different marker molecules (A, B, C, D, E, F) are labeled using 3 different labels (1, 2, 3) as follows: marker molecule A, B and E are labeled with label 1, marker molecule C, D and E are labeled with label 2 and marker molecule B, C and F are labeled with label 3. Thereby all 6 marker molecules can be distinguished from each other by one or more labels: marker molecule A is labeled with label 1, marker molecule B is labeled with label 1 and 3, marker molecule C is labeled with label 2 and 3, marker molecule D is labeled with label 2, marker molecule E is labeled with label 1 and 2 and marker molecule F is labeled with label 3. Using this form for labeling few types of labeling molecules may be used for labeling many different marker molecules.

MHC allele typing using MHC multimers. MHC multimers can also be used for determination of MHC allele occurrence in a sample. MHC multimers are good positive controls if they carry common antigenic peptides meaning antigenic peptides derived from antigenic proteins any donor have been in contact with and thereby have specific T-cells for. One preferred type of antigenic peptides are those derived from common pathogens that most of us have been infected with including but not limited to proteins from CMV, EBV, influenza and other common viruses and proteins from common bacteria.

Another preferred type of antigenic peptides is derived from self proteins, meaning proteins that we have naturally in our own body. An example of such self proteins is Melan-A/MART-1. Circulating Melan-A/MART-1 specific T-cells have been detected with MHC multimers in human healthy donors (Zippelius et al. (2002). J. Exp. med. Vol 195, 485-494).

Measurement of binding of MHC multimers carrying common antigenic epitopes to T-cells in the sample analysed can therefore be used for MHC allele typing of the sample. Binding of MHC multimer may be detected directly through a label on the MHC multimer or through secondary labelled marker molecules or as described elsewhere herein.

Preferred embodiments for labeling of MHC multimers used as positive controls are as described above for labeling antibodies and other marker molecules.

Minimization of Undesired Binding of the MHC Multimer

Identification of MHC-peptide specific T-cells can give rise to background signals due to unwanted binding to cells that do not carry TCRs. This undesired binding can result from binding to cells or other material, by various components of the MHC multimer, e.g. the dextran in a MHC dextramer construct, the labelling molecule (e.g. FITC), or surface regions of the MHC-peptide complex that do not include the peptide and the peptide-binding cleft.

MHC-peptide complexes bind to specific T-cells through interaction with at least two receptors in the cell membrane of the T-cell. These two receptors are the T-cell receptor (TCR) and CD8 for MHC I-peptide complexes and TCR and CD4 receptor protein for MHC II-peptide complexes. Therefore, a particularly interesting example of undesired binding of a MHC multimer is its binding to the CD8 or CD4 molecules of T-cells that do not carry a TCR specific for the actual MHC-peptide complex. The interaction of CD8 or CD4 molecules with the MHC is not very strong; however, because of the avidity gained from the binding of several MHC complexes of a MHC multimer, the interaction between the MHC multimer and several CD8 or CD4 receptors potentially can result in undesired but efficient binding of the MHC multimer to these T-cells. In an analytical experiment this would give rise to an unwanted background signal; in a cell sorting experiment undesired cells might become isolated. Other particular interesting examples of undesired binding is binding to lymphoid cells different from T-cells, e.g. NK-cells, B-cells, monocytes, dendritic cells, and granulocytes like eosinophils, neutrophils and basophiles.

Apart from the MHC complex, other components in the MHC multimer can give rise to unspecific binding. Of special interest are the multimerization domain, multimerization domain molecules, and labeling molecules.

One way to overcome the problem with unwanted binding is to include negative controls in the experiment and subtract this signal from signals derived from the analyzed sample, as described elsewhere in the invention.

Alternatively, unwanted binding could be minimized or eliminated during the experiment. Methods to minimize or eliminate background signals include:

Mutations in areas of the MHC complex responsible for binding to unwanted cells can be introduced. Mutations here mean substitution, insertion, and/or deletion of natural or non-natural amino acids. Sub-domains in the MHC complex can be responsible for unwanted binding of the MHC multimer to cells without a TCR specific for the MHC-peptide complex contained in the MHC multimer. One example of special interest of the present invention is a small region in the α3-domain of the α-chain of MHC I molecules that is responsible for binding to CD8 on all cytotoxic T-cells. Mutations in this area can alter or completely abolish the interaction between CD8 on cytotoxic T-cells and MHC multimer (Neveu et al. (2006) Int Immunol. 18, 1139-45). Similarly a sub domain in the β2 domain of the β-chain of MHC II molecules is responsible for binding CD4 molecules on all CD4 positive T-cells. Mutations in this sub domain can alter or completely abolish the interaction between MHC II and CD4. Another embodiment is to mutate other areas of MHC I/MHC II complexes that are involved in interactions with T-cell surface receptors different from TCR, CD8 and CD4, or that bind surface receptors on B-cells, NK cells, Eosiniophils, Neutrophils, Basophiles, Dendritic cells or monocytes.

Chemical alterations in areas of the MHC complex responsible for binding to unwanted cells can be employed in order to minimize unwanted binding of MHC multimer to irrelevanT-cells. Chemical alteration here means any chemical modification of one or more amino acids. Regions in MHC complexes that are of special interest are as mentioned above the α3 domain of the α-chain in MHC I molecules and β2 domains in the β-chain of MHC II molecules. Other regions in MHC I/MHC II molecules that can be chemically modified to decrease the extent of undesired binding are regions involved in interaction with T-cell surface receptors different from TCR, CD8 and CD4, or that bind surface receptors on B-cells, NK cells, Eosiniophils, Neutrophils, Basophiles, Dendritic cells or monocytes.

Another method to minimize undesired binding involves the addition of one or more components of a MHC multimer, predicted to be responsible for the unwanted binding. The added component is not labeled, or carries a label different from the label of the MHC multimer used for analysis. Of special interest is addition of MHC multimers that contain nonsense peptides, i.e. peptides that interact efficiently with the MHC protein, but that expectably do not support specific binding of the MHC multimer to the TCR in question. Another example of interest is addition of soluble MHC complexes not coupled to one or more multimerization domain(s), and with or without peptide bound in the peptide binding cleft. In another embodiment, individual components of the MHC complex can be added to the sample, e.g. I α-chain or subunits of MHC I α-chain either folded or unfolded, beta2microglobulin or subunits thereof either folded or unfolded, α/β-chain of MHC II or subunits thereof either folded or unfolded. Any of the above mentioned individual components can also be attached to one or more multimerization domain(s) identical or different from the one used in the MHC multimer employed in the analysis.

Of special interest is also addition of one or more multimerization domain similar or identical to the one or more multimerization domain used in the MHC multimer or individual components of the one or more multimerization domain.

Reagents able to identify specific cell types either by selection or exclusion can be included in the analysis to help identify the population of T-cells of interest, and in this way deselect the signal arising from binding of the MHC multimer to undesired cells.

Of special interest is the use of appropriate gating reagents in flow cytometry experiments. Thus, fluorescent antibodies directed against specific surface markers can be used for identification of specific subpopulations of cells, and in this way help to deselect signals resulting from MHC-multimers binding to undesired cells.

Gating reagents of special interest that helps identify the subset of T-cells of interest when using MHC I multimers are reagents binding to CD3 and CD8 identifying all cytotoxic T-cells. These reagents are preferably antibodies but can be any labeled molecule capable of binding CD3 or CD8. Gating reagents directed against CD3 and CD8 are preferably used together. As they stain overlapping cell populations they are preferably labeled with distinct fluorochromes. However, they can also be used individually in separate samples. In experiments with MHC II multimers reagents binding to CD3 and CD4 identifying T helper cells can be used. These reagents are preferably antibodies but can be any labeled molecule capable of binding CD3 or CD4. Gating reagents directed against CD3 and CD4 are preferable used together. As they stain overlapping cell populations they are preferably labeled with distinct fluorochromes. However, they can also be used individually in separate samples.

Other gating reagents of special interest in experiments with any MHC multimer are reagents binding to the cell surface markers CD2, CD27, CD28, CD45RA, CD45RO, CD62L and CCR7. These surface markers are unique to T-cells in various differentiation states. Co staining with either of these reagents or combinations thereof together with MHC multimers helps to select MHC multimer binding T-cells expressing a correct TCR. These reagents can also be combined with reagents directed against CD3, CD4 and/or CD8.

Another flow cytometric method of special interest to remove signals from MHC multimer stained cells not expressing the specific TCR, is to introduce an exclusion gate. Antibodies or other reagents specific for surface markers unique to the unwanted cells are labeled with a fluorochrome and added to the test sample together with the MHC multimer. The number of antibodies or surface marker specific reagents are not limited to one but can be two, three, four, five, six, seven, eight, nine, ten or more individual reagents recognizing different surface markers, all of which are unique to the unwanted cells. During or after collection of data all events representing cells labeled with these antibodies are dumped in the same gate and removed from the dataset. This is possible because all the antibodies/reagents that bind to the wrong cells are labeled with the same fluorochrome.

Reagents of special interest that exclude irrelevanT-cells include reagents against CD45 expressed on red blood cells, CD19 expressed on B-cells, CD56 expressed on NK cells, CD4 expressed on T helper cells and CD8 expressed on cytotoxic T-cells, CD14 expressed on monocytes and CD15 expressed on granulocytes and monocytes.

Negative Control Reagents and Negative Control Experiments for the Use of MHC Multimers in Flow Cytometry and Related Techniques Experiments with MHC multimers require a negative control in order to determine background staining with MHC multimer. Background staining can be due to unwanted binding of any of the individual components of the MHC multimer, e.g., MHC complex or individual components of the MHC complex, multimerization domain or label molecules. The unwanted binding can be to any surface or intracellular protein or other cellular structure of any cell in the test sample, e.g. undesired binding to B-cells, NK cells or T-cells. Unwanted binding to certain cells or certain components on cells can normally be corrected for during the analysis, by staining with antibodies that bind to unique surface markers of these specific cells, and thus identifies these as false positives, or alternatively, that binds to other components of the targeT-cells, and thus identifies these cells as true positives. A negative control reagent can be used in any experiment involving MHC multimers, e.g. flow cytometry analysis, other cytometric methods, immunohistochemistry (IHC) and ELISA. Negative control reagents include the following:

MHC complexes or MHC multimers comprising MHC complexes carrying nonsense peptides. A nonsense peptide is here to be understood as a peptide that binds the MHC protein efficiently, but that does not support binding of the resultant MHC-peptide complex to the desired TCR. An example nonsense peptide is a peptide with an amino acid sequence different from the linear sequence of any peptide derived from any known protein. When choosing an appropriate nonsense peptide the following points are taken into consideration. The peptide should ideally have appropriate amino acids at relevant positions that can anchor the peptide to the peptide-binding groove of the MHC. The remaining amino acids should ideally be chosen in such a way that possible binding to TCR (through interactions with the peptide or peptide-binding site of MHC) are minimized. The peptide should ideally be soluble in water to make proper folding with MHC alpha chain and β2m possible in aqueous buffer. The length of the peptide should ideally match the type and allele of MHC complex. The final peptide sequence should ideally be taken through a blast search or similar analysis, to ensure that it is not identical with any peptide sequence found in any known naturally occurring proteins.

MHC complexes or MHC multimers comprising MHC complexes carrying a chemically modified peptide in the peptide-binding groove. The modification should ideally allow proper conformation of the MHC-peptide structure, yet should not allow efficient interaction of the peptide or peptide-binding site of MHC with the TCR.

MHC complexes or MHC multimers comprising MHC complexes carrying a naturally occurring peptide different from the peptide used for analysis of specific T-cells in the sample. When choosing the appropriate natural peptide the following should be taken into consideration. The peptide in complex with the MHC protein should ideally not be likely to bind a TCR of any T-cell in the sample with such an affinity that it can be detected with the applied analysis method. The peptide should ideally be soluble in water to make proper folding with MHC alpha chain and β2m possible in aqueous buffer. The length of the peptide should match the type and allele of MHC complex.

Empty MHC complexes or MHC multimers comprising empty MHC complexes, meaning any correctly folded MHC complex without a peptide in the peptide-binding groove.

MHC heavy chain or MHC multimers comprising MHC heavy chain, where MHC heavy chain should be understood as full-length MHC I or MHC II heavy chain or any truncated version of MHC I or MHC II heavy chain. The MHC heavy chains can be either folded or unfolded. Of special interest is MHC I alpha chains comprising the α3 domain that binds CD8 molecules on cytotoxic T-cells. Another embodiment of special interest is MHC II β chains comprising the β2 domain that binds CD4 on the surface of helper T-cells.

Beta2microglobulin or subunits of beta2microglobulin, or MHC multimers comprising Beta2microglobulin or subunits of beta2microglobulin, folded or unfolded.

MHC-like complexes or MHC multimers comprising MHC-like complexes folded or unfolded. An example could be CD1 molecules that are able to bind peptides in a peptide-binding groove that can be recognized by T-cells (Russano et al. (2007). CD1-restricted recognition of exogenous and self-lipid antigens by duodenal gammadelta+T lymphocytes. J Immunol. 178(6):3620-6)

Multimerization domain(s) without MHC or MHC-like molecules, e.g. dextran, streptavidin, lgG, coiled-coil-domain liposomes.

Labels, e.g. FITC, PE, APC, pacific blue, cascade yellow or any other label listed elsewhere herein.

Negative controls 1-4 can provide information about potentially undesired binding of the MHC multimer, through interaction of a surface of the MHC-peptide complex different from the peptide-binding groove and its surroundings. Negative control 5 and 6 can provide information about binding through interactions through the MHC I or MHC II proteins (in the absence of peptide). Negative control 7 can provide information about binding through surfaces of the MHC complex that is not unique to the MHC complex. Negative controls 8 and 9 provide information about potential undesired interactions between non-MHC-peptide complex components of the MHC multimer and cell constituents.

Application of MHC Multimers in Immune Monitoring, Diagnostics, Prognostics, Therapy and Vaccines MHC multimers detect antigen specific T-cells of the various T-cell subsets. T-cells are pivotal for mounting an adaptive immune response. It is therefore of importance to be able to measure the number of specific T-cells when performing a monitoring of a given immune response. Typically, the adaptive immune response is monitored by measuring the specific antibody response, which is only one of the effector arms of the immune system. This can lead to miss-interpretation of the actual clinical immune status.

In many cases intruders of the organism can hide away inside the cells, which can not provoke a humoral response. In other cases, e.g. in the case of certain viruses the intruder mutates fast, particularly in the genes encoding the proteins that are targets for the humoral response. Examples include the influenza and HIV viruses. The high rate of mutagenesis renders the humoral response unable to cope with the infection. In these cases the immune system relies on the cellular immune response. When developing vaccines against such targets one needs to provoke the cellular response in order to get an efficient vaccine.

Developing vaccines that should give rise to lifelong protection is another case where the cellular immune system needs to be activated. Commonly, various childhood vaccines are expected to give lifelong protection but will only come to trial many years after the vaccination has been performed and then there is only to hope that it actually have created effective immunity.

Therapeutically cancer vaccines generally rely on cytotoxic effector T-cells and have short duration of function. Therefore, continuous monitoring is important. MHC multimers are therefore very important for immune monitoring of vaccine responses both during vaccine development, as a means to verify the obtained immunity for lifelong vaccines and to follow cancer patients under treatment with therapeutically cancer vaccines.

The number of antigen specific cytotoxic T-cells can be used as surrogate markers for the overall wellness of the immune system. The immune system can be compromised severely by natural causes such as HIV infections or big traumas or by immuno suppressive therapy in relation to transplantation. The efficacy of an anti HIV treatment can be evaluated by studying the number of common antigen-specific cytotoxic T-cells, specific against for example Cytomegalovirus (CMV) and Epstein-Barr virus. In this case the measured T-cells can be conceived as surrogate markers. The treatment can then be corrected accordingly and a prognosis can be made.

A similar situation is found for patients undergoing transplantation as they are severely immune compromised due to pharmaceutical immune suppression to avoid organ rejection. The suppression can lead to outbreak of opportunistic infections caused by reactivation of otherwise dormant viruses residing in the transplanted patients or the grafts. This can be the case for CMV and EBV viruses. Therefore measurement of the number of virus specific T-cells can be used to give a prognosis for the outcome of the transplantation and adjustment of the immune suppressive treatment. Similarly, the BK virus has been implied as a causative reagent for kidney rejection. Therefore measurement of BK-virus specific T-cells can have prognostic value.

In relation to transplantation, the presence of specific T-cells directed against minor histocompatibility antigens (mHAgs) is important as they can cause graft versus host reaction/disease that can develop to a fatal situation for the patient. Again, a well-adjusted immune suppressive treatment is important. A similar reaction denoted graft versus cancer is sometimes employed in the treatment of malignancies of the lymphoid system. It is evident that such treatment is balancing on the edge of a knife and will benefit of specific measurement of relevant effector T-cells.

Due to lack of organs, transplantations across greater mismatches are increasingly making harsher immune suppressive treatment more common. This calls for more efficient methods to monitor the immune status of the patient so that corrective measures in the treatment can be applied in due cause.

MHC multimers can be of importance in diagnosis of infections caused by bacteria, virus and parasites that hide away inside cells. Serum titers can be very low and direct measurement of the disease-causing organisms by PCR can be very difficult because the host cells are not identified or are inaccessible. Other clinical symptoms of a chronic infection can be unrecognizable in an otherwise healthy individuals, even though such persons still are disease-carriers and at risk of becoming spontaneously ill if being compromised by other diseases or stress. Likewise, cancers can also be diagnosed early in its development if increased numbers of cancer specific T-cells can be measured in circulation, even though the tumor is not yet localized.

Antigen-specific T helper cells and regulatory T-cells have been implicated in the development of autoimmune disorders. In most cases the timing of events leading to autoimmune disease is unknown and the exact role of the immune cells not clear. Use of MHC multimers to study these diseases will lead to greater understanding of the disease-causing scenario and make provisions for development of therapies and vaccines for these diseases.

Therapeutically use of MHC multimers can be possible, either directly or as part of therapeutically vaccines. When performing autologous cancer therapy it is often recognized that the in vitro amplified cancer-specific effector T-cells do not home effectively to the correct target sites but ends up in the lungs. If the molecules responsible for interaction with the correct homing receptor can be identified these can be added to the MHC multimer making a dual, triple or multiple molecular structure that are able to aid the antigen-specific T-cells home to the correct target, as the MHC complex will bind to the specific T-cell and the additional molecules will mediate binding to the targeT-cells.

In a preferable embodiment, MHC multimers bound to other functional molecules are employed to directly block, regulate or kill these cells. The MHC complexes specifically recognize the target T-cells and direct the action of the other molecules to the target. Derivatives of MHC multimers can be useful as vaccines, as vaccine components or as engineered intelligent adjuvant. The possibility of combining MHC complexes that specifically bind certain T-cells with molecules that trigger, e.g. the humoral response or the innate immune response, can accelerate vaccine development and improve the efficiency of vaccines.

In relation to the use and application of MHC multimers in immune monitoring, diagnostics, prognostics, therapy and vaccines several organisms and human proteins are of relevance, comprising but not limited to virus, bacteria, archaeo, fungi, parasites, allergens, minor histocompatibility antigens (mHAgs), auto antigens, cancer associated proteins and other disease associated proteins. Of special relevance are the following; Adenovirus (subgropus A-F), BK-virus, CMV (Cytomegalo virus, HHV-5), EBV (Epstein Barr Virus, HHV-4), HBV (Hepatitis B Virus), HCV (Hepatitis C virus), HHV-6a and b (Human Herpes Virus-6a and b), HHV-7, HHV-8, HSV-1 (Herpes simplex virus-1, HHV-1), HSV-2 (HHV-2), JC-virus, SV-40 (Simian virus 40), VZV (Varizella-Zoster-Virus, HHV-3), Parvovirus B19, *Haemophilus* influenza, HIV-1 (Human immunodeficiency Virus-1), HTLV-1 (Human T-lymphotrophic virus-1), HPV (Human Papillomavirus), *Mycobacterium tuberculosis, Mycobacterium bovis, Borrelia burgdorferi, Helicobacter pylori, Streptococcus pneumoniae, Listeria monocytogenes, Histoplasma capsulatum, Aspergillus fumigatus, Candida albicans, Cryptococcus neoformans, Pneumocystis carinii, Plasmodium falciparum, Plasmodium vivax, Plasmodium malariae, Schistosoma mansoni, Schistosoma japonicum, Schistosoma haematobium, Trypanosoma cruzi, Trypanosoma rhodesiense, Trypanosoma gambiense, Leishmania donovani, Leishmania tropica*, Birch, Hazel, Elm, Ragweed, Wormwood, Grass, Mould, Dust Mite, HA-1, HA-8, USP9Y, SMCY, TPR-protein, HB-1Y, GAD64, Collagen, Survivin, Survivin-2B, Livin/ML-IAP, Bcl-2, Mci-1, Bcl-X (L), Mucin-1, NY-ESO-1, Telomerase, CEA, MART-1, HER-2/neu, bcr-abl, PSA, PSCA, Tyrosinase, p53, hTRT, Leukocyte Proteinase-3, hTRT, gp100, MAGE antigens, GASC, JMJD2C, JARD2 (JMJ), JHDM3a, WT-1, CA 9, Protein kinases, Collagen, human cartilage glycoprotein 39, beta-amyloid, Abeta42, APP, Presenilin 1.

In Vivo Diagnostics

Antigen specific tumor infiltrating lymphocytes can be used to identify tumor lesions and metastases as the antigen specific T-cells will migrate/home to the tumor site to exert their help or immuno modulatory action (CD4+T helper cells) or cytotoxic killing of tumor cells expressing the tumor specific/tumor associated peptide MHC complex (CD8+ T-cells). Likewise identification of sites of infection tumor lesions can be identified as they typically attract antigen specific T-cells.

Localization of tumors and sites of infection can be carried out using antigen specific T-cells labelled with a paramagnetic isotope in conjunction with magnetic resonance imaging (MRI) or electron spin resonance (ESR). In general, any conventional method for diagnostic imaging visualization can be utilized. Usually gamma and positron emitting radioisotopes are used for camera and paramagnetic isotopes for MRI. For peripheral cancer lesion in skin (e.g. melanoma) fluorescently labelled antigen specific T-cells can be used likewise.

Therapy and Vaccines

Therapy and vaccine approaches for manipulation of immune responses Biological therapy (immunotherapy, biotherapy, or biological response modifier therapy) is a relatively new type of treatment and based on knowledge of cellular and molecular mechanism underlying activation of the human immune system. For example, the immune system can recognise the difference between healthy cells and cancer cells in the body and work to eliminate those that become cancerous. Biological therapies use the body's immune system, either directly or indirectly, to fight cancer or to lessen the side effects that can be caused by some cancer treatments. An important goal of such immunotherapy is boosting of killing power of immune system cells by stimulation of appropriate effector cells, such as T-cells.

Conventional vaccines for infectious diseases, such as measles, mumps, and tetanus, are effective because they expose the immune system to weakened versions of the disease. This exposure causes the immune system to respond by producing antibodies. Once the immune system has created antibodies, some of the activated immune cells remember the exposure. Therefore, the next time the same antigen enters the body, the immune system can respond more readily to destroy it.

For cancer treatment, researchers are developing vaccines that can encourage the immune system to recognise cancer cells. These vaccines can help the body reject tumours and prevent cancer from recurring. In contrast to vaccines against infectious diseases, cancer vaccines are designed to be injected after the disease is diagnosed, rather than before it develops. By example, it has been shown that immunisation with DCs loaded with appropriate peptides from tumour associated antigens (TAAs) stimulate "tumour specific" T-cells, which in some patients prevent further progression of the disease and eventually lead to regression of the disease. This approach takes advantage of the "professional pathway" of antigen processing/-presentation performed by DCs. In contrast, injection of soluble tumour TAAs or soluble MHC molecules comprising appropriate peptides from TAAs have only proven a limited or no effect, presumably due to low efficacy of antigen stimulation from soluble antigens. The low affinity as well as insufficient stimulation of specific T-cells can explain poor protection obtained by immunisation with soluble peptide/MHC molecule. Indeed, the low intrinsic affinity of essential ligand-receptor interactions has implied limited utilisation of soluble recombinant proteins for stimulation of specific T-cells.

As evident from the above, MHC molecules play a very important role, and thus detection of cells recognising MHC molecules is of major importance and value. Likewise, several attempts have been made to manipulate the immune system in a controllable, efficient and consistent way.

However, the success has been limited. Thus, finding substances for immunotherapy that actually works would be a major step forward for the fight against a number of serious diseases for which we do not at present have a cure.

The present invention is related to the major undertaking to generate compounds comprising MHC molecules to detect and analyse receptors on MHC recognising cells such as epitope specific T-cell clones or other immune competent effector cells. It is shown herein that the increased valences of compounds of the invention produce surprisingly higher avidity in comparison to oligo-valent complexes (tetramers) known from the prior art. This allows for quantitative analysis of even small cell populations by e. g. flow cytometry.

The potential and value of the present invention is obvious, as several reports have demonstrated lack of correlation between T-cell reactivity in peripheral blood and the course of neoplastic diseases. For instance, analysis of T-cell activity in tumour tissues as well as lymphatic tissues can provide better insights on immunity toward solid tumours.

Combining the growing genome databases of primary protein sequences of humans and parasites with the knowledge of how the immune system handles the molecular information provided by appropriate ligands will lead to new and powerful strategies for development of curative vaccines.

This in turn will improve the possibilities for directed and efficient immune manipulations against diseases caused by tumour genesis or infection by pathogenic agent like viruses and bacteria. HIV is an important example.

The ability to generate and ligate recombinant MHC molecules or a variety of mixed ligands to multimerization domain(s) as envisaged by the present invention, will enable a novel analytical tool for monitoring immune responses and contribute to a rational platform for novel therapy and "vaccine" applications. Therapeutic compositions ("vaccines") that stimulate specific T-cell proliferation by peptide-specific stimulation are indeed a possibility within the present invention. Thus, quantitative analysis and ligand-based detection of specific T-cells that proliferate by the peptide specific stimulation should be performed simultaneously to monitor the generated response. Effective methods to produce a variety of molecules from the group of highly polymorphic human HLA encoded proteins would lead to advanced analyses of complex immune responses, which can comprise a variety of peptide epitope specific T-cell clones. The high avidity-based flow cytometry and tissue-staining approaches from the state of art technology disclosed herein will add significantly to the development of such advanced analysis of T-cell responses.

Further Applications

The MHC multimers of the present invention have numerous uses and are a valuable and powerful tool e. g. in the fields of diagnosis, prognosis, monitoring, stratification, and determining the status of diseases or conditions as well as in therapy. Thus, the MHC multimer can be applied in the various methods involving the detection of MHC recognising cells. Furthermore, the present invention relates to compositions comprising the MHC multimers in a solubilising medium. The present invention also relates to compositions comprising the MHC multimers immobilised onto a solid or semi-solid support. The MHC multimers are very suitable as detection systems. Thus, the present invention relates to the use of the MHC multimers as defined herein as detection systems.

In another aspect, the present invention relates to the general use of MHC molecules and multimers of such MHC molecules in various sample-mounted methods. These methods include diagnostic methods, prognostic methods, methods for determining the progress and status of a disease or condition, and methods for the stratification of a patient.

The MHC multimers of the present invention are also of value in testing the expected efficacy of medicaments against or for the treatment of various diseases. Thus, the present invention relates to methods of testing the effect of medicaments or treatments, the methods comprising detecting the binding of the MHC multimers to MHC recognising cells and establishing the effectiveness of the medicament or the treatment in question based on the specificity of the MHC recognising cells. The present invention relates to therapeutic compositions comprising as active ingredients the MHC multimers as defined herein.

An important aspect of the present invention is therapeutic compositions comprising as active ingredients effective amounts of MHC recognising cells obtained using the MHC multimers as defined herein to isolate relevant MHC recognising cells, and expanding such cells to a clinically relevant number.

The present invention further relates to methods for treating, preventing or alleviating diseases, methods for inducing anergy of cells, as well as to methods for up-regulating, down-regulating, modulating, stimulating, inhibiting, restoring, enhancing and/or otherwise manipulating immune responses. The invention also relates to methods for obtaining MHC recognising cells using the MHC multimers as described herein.

Uses in which the MHC multimers of the invention can suitably be provided in solubilised form include radio immune assay (RIA), cell bound radioactive ligand assay, flow cytometry and ELISA. Such assays are readily known to the person skilled in the art as are the procedures, by which such are carried out.

Uses in which the MHC multimers of the invention can suitably be provided immobilised onto a solid or semi-solid support include flow cytometry, immunomagnetic separation techniques, ex vivo stimulation of cultured cells, aggregation techniques, lateral flow devices, ELISA, RIA and cell bound radio ligand assays.

Thus, the present invention relates in particular to MHC multimers as defined above for use in flow cytometric methods, histochemical methods, and cytochemical methods. Accordingly, the MHC multimers of the invention are suited as detection systems.

Methods employing the MHC multimers of the invention The MHC multimers of the invention are a powerful tool in a broad range of in vitro or ex vivo methods.

Thus, the present invention relates to methods for detecting the presence of MHC recognising cells in a sample comprising the steps of (a) providing a sample suspected of comprising MHC recognising cells, (b) contacting the sample with a MHC molecule construct as defined above, and (c) determining any binding of the MHC molecule construct, which binding indicates the presence of MHC recognising cells.

Such methods are a powerful tool in diagnosing various diseases. Establishing a diagnosis is important in several ways. A diagnosis gives information about the disease, thus the patient can be offered a suitable treatment regime. Also, establishing a more specific diagnosis can give important information about a subtype of a disease for which a particular treatment will be beneficial (i. e. various subtypes of diseases can involve display of different peptides which are recognised by MHC recognising cells, and thus treatment can be targeted effectively against a particular subtype). In this way, it can also be possible to gain information about aberrant cells, which emerge through the progress of the disease or condition, or to investigate whether and how T-cell specificity is affected. The binding of the MHC molecule construct makes possible these options, since the binding is indicative for the presence of the MHC recognising cells in the sample, and accordingly the presence of MHC molecules displaying the peptide. The present invention also relates to methods for monitoring MHC recognising cells comprising the steps of (a) providing a sample suspected of comprising MHC recognising cells, (b) contacting the sample with a MHC molecule construct as defined above, and (c) determining any binding of the MHC molecule construct, thereby monitoring MHC recognising cells.

Such methods are a powerful tool in monitoring the progress of a disease, e. g. to closely follow the effect of a treatment. The method can i. a. be used to manage or control the disease in a better way, to ensure the patient receives the optimum treatment regime, to adjust the treatment, to confirm remission or recurrence, and to ensure the patient is not treated with a medicament which does not cure or alleviate the disease. In this way, it can also be possible to monitor aberrant cells, which emerge through the progress of the disease or condition, or to investigate whether and how T-cell specificity is affected during treatment. The binding of the MHC molecule construct makes possible these options, since the binding is indicative for the presence of the MHC recognising cells in the sample, and accordingly the presence of MHC molecules displaying the peptide.

The present invention also relates to methods for establishing a prognosis of a disease involving MHC recognising cells comprising the steps of (a) providing a sample suspected of comprising MHC recognising cells, (b) contacting the sample with a MHC molecule construct as defined above, and (c) determining any binding of the MHC molecule construct, thereby establishing a prognosis of a disease involving MHC recognising cells.

Such methods are a valuable tool in order to manage diseases, i. a. to ensure the patient is not treated without effect, to ensure the disease is treated in the optimum way, and to predict the chances of survival or cure. In this way, it can also be possible to gain information about aberrant cells, which emerge through the progress of the disease or condition, or to investigate whether and how T-cell specificity is affected, thereby being able to establish a prognosis.

The binding of the MHC molecule construct makes possible these options, since the binding is indicative for the presence of the MHC recognising cells in the sample, and accordingly the presence of MHC molecules displaying the peptide.

The present invention also relates to methods for determining the status of a disease involving MHC recognising cells comprising the steps of (a) providing a sample suspected of comprising MHC recognising cells, (b) contacting the sample with a MHC molecule construct as defined above, and (c) determining any binding of the MHC molecule construct, thereby determining the status of a disease involving MHC recognising cells.

Such methods are a valuable tool in managing and controlling various diseases. A disease could, e. g. change from one stage to another, and thus it is important to be able to determine the disease status. In this way, it can also be possible to gain information about aberrant cells which emerge through the progress of the disease or condition, or to investigate whether and how T-cell specificity is affected, thereby determining the status of a disease or condition. The binding of the MHC molecule construct makes possible these options, since the binding is indicative for the presence of the MHC recognising cells in the sample, and accordingly the presence of MHC molecules displaying the peptide.

The present invention also relates to methods for the diagnosis of a disease involving MHC recognising cells comprising the steps of (a) providing a sample suspected of comprising MHC recognising cells, (b) contacting the sample with a MHC molecule construct as defined above, and (c) determining any binding of the MHC molecule construct, thereby diagnosing a disease involving MHC recognising cells.

Such diagnostic methods are a powerful tool in the diagnosis of various diseases. Establishing a diagnosis is important in several ways. A diagnosis gives information about the disease, thus the patient can be offered a suitable treatment regime. Also, establishing a more specific diagnosis can give important information about a subtype of a disease for which a particular treatment will be beneficial (i. e. various subtypes of diseases can involve display of different peptides which are recognised by MHC recognising cells, and thus treatment can be targeted effectively against a particular subtype). Valuable information can also be obtained about aberrant cells emerging through the progress of the disease or condition as well as whether and how T-cell specificity is affected. The binding of the MHC molecule construct makes possible these options, since the binding is indicative for the presence of the MHC recognising cells in the sample, and accordingly the presence of MHC molecules displaying the peptide.

The present invention also relates to methods of correlating cellular morphology with the presence of MHC recognising cells in a sample comprising the steps of (a) providing a sample suspected of comprising MHC recognising cells, (b) contacting the sample with a MHC molecule construct as defined above, and (c) determining any binding of the MHC molecule construct, thereby correlating the binding of the MHC molecule construct with the cellular morphology.

Such methods are especially valuable as applied in the field of histochemical methods, as the binding pattern and distribution of the MHC multimers can be observed directly. In such methods, the sample is treated so as to preserve the morphology of the individual cells of the sample. The information gained is important i. a. in diagnostic procedures as sites affected can be observed directly.

The present invention also relates to methods for determining the effectiveness of a medicament against a disease involving MHC recognising cells comprising the steps of (a) providing a sample from a subject receiving treatment with a medicament, (b) contacting the sample with a MHC molecule construct as defined herein, and (c) determining any binding of the MHC molecule construct, thereby determining the effectiveness of the medicament.

Such methods are a valuable tool in several ways. The methods can be used to determine whether a treatment is effectively combating the disease. The method can also provide information about aberrant cells which emerge through the progress of the disease or condition as well as whether and how T-cell specificity is affected, thereby providing information of the effectiveness of a medicament in question. The binding of the MHC molecule construct makes possible these options, since the binding is indicative for the presence of the MHC recognising cells in the sample, and accordingly the presence of MHC molecules displaying the peptide.

The present invention also relates to methods for manipulating MHC recognising cells populations comprising the steps of (a) providing a sample comprising MHC recognising cells, (b) contacting the sample with a MHC molecule construct immobilised onto a solid support as defined above, (c) isolating the relevant MHC recognising cells, and (d) expanding such cells to a clinically relevant number, with or without further manipulation.

Such ex vivo methods are a powerful tool to generate antigen-specific, long-lived human effector T-cell populations that, when re-introduced to the subject enable killing of targeT-cells and has a great potential for use in immunotherapy applications against various types of cancer and infectious diseases.

As used everywhere herein, the term "MHC recognising cells" are intended to mean such which are able to recognise and bind to MHC molecules. Such MHC recognising cells can also be called MHC recognising cell clones, targeT-cells, target MHC recognising cells, target MHC molecule recognising cells, MHC molecule receptors, MHC receptors, MHC peptide specific receptors, or peptide-specific cells. The term "MHC recognising cells" is intended to include all subsets of normal, abnormal and defecT-cells, which recognise and bind to the MHC molecule. Actually, it is the receptor on the MHC recognising cell that binds to the MHC molecule.

As described above, in diseases and various conditions, peptides are displayed by means of MHC molecules, which are recognised by the immune system, and cells targeting such MHC molecules are produced (MHC recognising cells).

Thus, the presence of such MHC protein recognising cells is a direct indication of the presence of MHC molecules displaying the peptides recognised by the MHC protein recognising cells. The peptides displayed are indicative and can be involved in various diseases and conditions.

For instance, such MHC recognising cells can be involved in diseases of inflammatory, auto-immune, allergic, viral, cancerous, infectious, allo- or xenogene (graft versus host and host versus graft) origin.

In particular, the MHC recognising cells can be involved in a chronic inflammatory bowel disease such as Crohn's disease or ulcerative colitis, sclerosis, type I diabetes, rheumatoid arthritis, psoriasis, atopic dermatitis, asthma, malignant melanoma, renal carcinoma, breast cancer, lung cancer, cancer of the uterus, cervical cancer, prostatic cancer, brain cancer, head and neck cancer, leukaemia, cutaneous lymphoma, hepatic carcinoma, colorectal cancer, bladder cancer, rejection-related disease, Graft-versus-host-related disease, or a viral disease associated with hepatitis, AIDS, measles, pox, chicken pox, rubella or herpes.

In one embodiment, the MHC recognising cells are selected from subpopulations of CD3+ T-cells, gamma, delta T-cells, alpha, beta T-cells, CD4+ T-cells, T helper cells, CD8+ T-cells, Suppressor T-cells, CD8+ cytotoxic T-cells, CTLs, NK cells, NKT-cells, LAK cells, and MAK.

In the above-described methods, the sample is preferably selected from histological material, cytological material, primary tumours, secondary organ metastasis, fine needle aspirates, spleen tissue, bone marrow specimens, cell smears, exfoliative cytological specimens, touch preparations, oral swabs, laryngeal swabs, vaginal swabs, bronchial lavage, gastric lavage, from the umbilical cord, and from body fluids such as blood (e. g. from a peripheral blood mononuclear cell (PBMC) population isolated from blood or from other blood-derived preparations such as leukopheresis products), from sputum samples, expectorates, and bronchial aspirates. Such samples can be used as they are, or they can be subjected to various purification, decontamination, filtration, or concentration methods, and/or methods to isolate parts of the sample like immunomagnetic separation. The sample or part thereof (sample constituents) can further be treated so as to preserve morphology or arrest the cells of the sample.

Such methods for sample treatment are readily known by the person skilled in the art.

The MHC molecule construct employed in the methods of the invention may, as mentioned above, be directly or indirectly labelled so as to facilitate observation of binding. Thus, the MHC molecule construct can suitably be labelled so as to enable observation by inspection in a microscope, by light, by fluorescence, by electron transmission, or by flow cytometry.

It is to be understood that one MHC molecule construct can be employed in the methods as well as several (a plurality of) MHC multimers (i. e. one or more), depending on the information desired. The total number of MHC multimers as well as actual combination of MHC molecules, peptides, optionally biologically active compounds, and optionally labelling compounds are in principle unlimited.

The methods of the invention described above can suitably be such, wherein the sample to be analysed is mounted on a support. The support can suitably be a solid or semi-solid surface. Suitable solid and semi-solid surfaces are readily known in the art, and include glass slides, beads, particles, membranes, filters, filter membranes, polymer slides, polymer membranes, chamber slides, backings, settings, dishes, and petridishes. In particular, the support can be a glass slide, a membrane, a filter, a polymer slide, a chamber slide, a dish, or a petridish. The sample or parts thereof can suitably be grown or cultured directly on the support prior to analysis.

However, the cells need not be grown or cultured prior to analysis. Often the sample will be analysed directly without culturing. It is to be understood that samples for direct analysis can undergo the processing procedures described above.

Thus, the sample may, either directly or after having undergone one or more processing steps, be analysed in primarily two major types of methods, in situ methods (in situ analyses) and in vitro methods (in vitro analyses).

In this context, in situ methods (in situ analyses) are to be understood as assays, in which the morphology of the sample cells is essentially preserved. By "essentially preserved" is meant that the overall morphology is preserved, making it possible to identify some or all of the structural compositions of the tissue or cells. Examples are analysis of smears, biopsies, touch preparations and spreading of the sample onto the support. Samples can be subjected to i. a. fixation, permeabilisation, or other processing steps prior to analysis.

In vitro methods are to be understood as methods, in which the overall morphology is not preserved. In the case of in vitro methods, the sample is subjected to a treatment, which disrupts the morphology of the cell structure. Such treatments are known to the person skilled in the art and include treatment with organic solvents, treatment with strong chaotropic reagents such as high concentrations of guanidine thiocyanate, enzyme treatment, detergent treatment, bead beating, heat treatment, sonication and/or application of a French press.

Histological and cytological materials include biopsies and other tissue samples. In general, cytology is the study of the structure of all normal and abnormal components of cells and the changes, movements, and transformations of such components. Cytology disciplines include cytogenics, cytochemistry, and microscopic anatomy. Cells are studied directly in the living state or are killed (fixed) and prepared by e. g. embedding, sectioning, or staining for investigation in bright field or electron microscopes.

One well-known cytology procedure is the Papanicolaou test medical procedure used to detect cancer of the uterine cervix. A scraping, brushing, or smear, is taken from the surface of the vagina or cervix and is prepared on a slide and stained for microscopic examination and cytological analy-sis. The appearance of the cells determines whether they are normal, suspicious, or cancerous.

By histology is generally understood the study of groups of specialised cells called tissues that are found in most multi-cellular plants and animals.

Histologists study the organisation of tissues at all levels, from the whole organ down to the molecular components of cells. Animal tissues are for example classified as epithelium, connective, muscle and nerve tissue. Blood and lymph are sometimes commonly classified separately as vascular tissue.

These tissue types are combined in different ways in the organism to form characteristic organs. The way cells are connected and organised is sometimes called the morphology of the tissue and gives valuable information about the state of the cells and the tissue.

A variety of techniques are used for histological studies, including tissue culture, use of various fixatives and stains, the use of a microtome for preparing thin sections, light microscopy, electron microscopy, and X-ray diffraction. The histology field also includes histochemistry, which is the study of the chemical composition of tissue structures.

Histological investigation includes study of tissue death and regeneration and the reaction of tissue to injury or invading organisms. Because normal tissue has a characteristic appearance, histologic examination is often utilised to identify diseased tissue.

There are in general, two categories of histological materials. The most common is a fixed, paraffin-embedded tissue specimen, often archive material. These specimens are fixed, usually using a formalin-based fixative, dehydrated to xylene, embedded in paraffin or plastic (e. g. Epon, Araldite, Lowicryl, LR White or polyacrylamide), sectioned onto a slide, deparaffinised or otherwise treated, re-hydrated, and stained.

The second category includes preparations, which are fresh tissues and/or cells, which generally are not fixed with aldehyde-based fixatives. Such specimens are either placed directly on a slide or cover slip, or frozen and sectioned onto slides. Such specimens are then fixed, usually with an alcohol- or acetone-based fixative, and stained. These specimens commonly include biopsy materials, which can be analysed while the surgical procedure is in progress (frozen sections), cytological preparations (including e. g. touch preparations and blood smears), and tissues, which are to be histochemically analysed.

The method of viewing the stained specimens includes bright field microscopes or scanners, fluorescent microscopes or scanners, transmission electron microscope (TEM) or scanning electron microscope (SEM).

Immunostaining requires a series of treatment steps conducted on a tissue section mounted on a slide to highlight by selective staining certain morphological indicators of disease states. Typical steps include pre-treatment of the tissue section to reduce non-specific binding, contacting with specific reagent, and various visualisation techniques, optionally separated by washing steps. Counterstaining with e. g. hematoxylin, Ehrlich staining, Sirius red, Methyl green, methylene blue, and the like, can also be applied. Incubations at room temperature or at slightly elevated temperatures, usually around 40° C., can be applied, and the tissue must be continuously protected from dehydration.

In the following, some of the individual steps in a staining procedure are described.

Fixatives are needed to preserve cells and tissues in a reproducible and life-like manner. To achieve this, tissue blocks, sections, or smears are immersed in a fixative fluid, or in the case of smears, are dried.

Fixatives stabilise cells and tissues thereby protecting them from the rigors of processing and staining techniques.

Types of fixative include formalin (aqueous formaldehyde) and neutral buffered formalin (NBF) is among the most commonly used. Other fixatives include glutaraldehyd, acrolein, carbodiimide, imidates, benzoequinone, osmic acid and osmium tetraoxide.

Fresh biopsy specimens, cytological preparations (including touch preparations and blood smears), frozen sections and tissues for immunohistochemical analysis are commonly fixed in organic solvents, including ethanol, methanol and/or acetone.

The methods for attaching or mounting sections to slides include using clean slides and relying on the capillary attraction and no adhesives. Other techniques include glues like egg-white glycerine, glycerine-gelatine mixtures, polyvinyl acetate glue, chrome-alum gelatine and poly lysine coating. Heating or "burning" of the section as a means of facilitating mounting of the section should be used with caution, as the tissue can be destroyed.

To facilitate the specific recognition in fixed tissue, it is often necessary to retrieve or unmask the targets through pre-treatment of the specimens to increase reactivity of the majority of targets.

Target retrieval includes a variety of methods by which the availability of the target for interaction with a specific detection reagent is maximised. The most common techniques are enzymatic digestion with a proteolytic enzyme (e. g. Protinease, pronase, pepsin, papain, trypsin or neuraminidase) in an appropriate buffer or heat induced epitope retrieval (HIER) using microwave irradiation, heating in a regular oven, autoclaving or pressure-cooking in an appropriately pH stabilised buffer, usually comprising EDTA, Tris-HCl, citrate, urea, glycin-HC1 or boric acid.

The penetration of reagents through the tissue section can be increased using detergents during pre-treatment of sections or cytological preparations, or as additives to dilution media and rinsing buffers.

Additionally, the signal-to-noise ratio can be increased by different physical methods, including application of vacuum and ultrasound, or freezing and thawing of the sections before or during incubation of the reagents.

Endogenous biotin binding sites or endogenous enzyme activity (e. g. phosphatase, catalase or peroxidase) can be removed as a step in the staining procedure.

Similarly, blocking of unspecific binding sites with inert proteins like, HSA, BSA, ovalbumine, fetal calf serum or other sera, or detergents like Tween20, Triton X-100, Saponin, BRIJ® or PLURONIC® s is widely used.

Blocking unspecific binding sites in the tissue or cells with unlabelled and target non-specific versions of the specific reagents.

The standard visualisation techniques utilised in immunocytochemistry can not be used directly for staining of the receptors, as the binding relies on the low binding strength of MHC molecules and not the high avidity antibodies or DNA probes normally used. Also, the polymorph and somewhat sensitive nature of the MHC molecule distinguishes it from e. g. the monoclonal antibodies used in immunocytochemistry. On the other hand, in order to be of practical use, specific receptor staining procedures and methods used should resemble current methods.

The present invention surprisingly makes it possible to stain specific receptors using a methodology which resembles routine immunocytochemistry procedures.

The most commonly used detection methods in immunohistochemistry are direct visualisation of fluorescence or gold particles and enzyme mediated colorimetric detection.

For direct fluorescent studies, the labels can e. g. be 5-(and 6)-carboxyFLUORESCEIN™, 5- or 6-carboxyFLUORESCEIN™, 6-(FLUORESCEIN™)-5-(and 6)-carboxamido hexanoic acid, FLUORESCEIN™ isothiocyanate (FITC), rhodamine, tetra-methylrhodamine, and dyes such as Cy2, Cy3, and CY5™, optionally substituted coumarin including AMCA, PerCP, phycobiliproteins including R-phycoerythrin (RPE) and allophycoerythrin (APC), Texas Red, Princeston Red, Green fluorescent protein (GFP) and analogues thereof, and conjugates of R-phycoerythrin or allophycoerythrin and e. g. CY5™ or Texas Red, and inorganic fluorescent labels based on semiconductor nanocrystals (like quantum dot and QDOT®TX nanocrystals), and time-resolved fluorescent labels based on lanthanides like $Eu3+$ and $Sm3+$.

Colloidal gold or silver can be used as direct labels for immunocytochemical studies for electron microscopy and light microscopy. Amplification of the signal can be obtained by further silver enhancement of the colloidal gold particles.

The general enzymatic methods use labelled avidin or streptavidin-biotin (LAB), avidin or streptavidin-biotin complex (ABC), enzyme anti-enzyme complex (e. g. PAP and APAAP), direct dextran polymer based antibody-enzyme complex (e. g. DAKO's EPOS); indirect dextran polymer based antibody-enzyme complex (e. g. DAKO's EnVision) or double bridge enzyme anti-enzyme complex.

The enzymatic staining uses enzymatic labels such as horse radish peroxidase (HRP), alkaline phosphatase (AP), beta-galactosidase (GAL), glucose-6-phosphate dehydrogenase, beta-N-acetylglucosaminidase, invertase, Xanthine Oxidase, firefly luciferase and glucose oxidase (GO).

Examples of commonly used substrates for horse radish peroxidase include 3,3'-diaminobenzidine (DAB), diaminobenzidine with nickel enhancement, 3-amino-9-ethylcarbazole (ABC), Benzidine dihydrochloride (BDHC), Hanker-Yates reagent (HYR), Indophane blue (IB), tetramethylbenzidine (TMB), 4-chloro-I-naphtol (CN), a-naphtol pyronin (a-NP), o-dianisidine (OD), 5-bromo-4-chloro-3-indolylphosphate (BCIP), Nitro blue tetrazolium (NBT), 2-(p-iodophenyl)-3-p-nitrophenyl-5-phenyl tetrazolium chloride (INT), tetranitro blue tetrazolium (TNBT), 5-bromo-4-chloro-3-indoxyl-beta-D-galactoside/ferro-ferricyanide (BCIG/FF).

Examples of commonly used substrates for Alkaline Phosphatase include Naphthol-AS-B1-phosphate/fast red TR (NABP/FR), Naphthol-AS-MX-phosphate/fast red TR (NAMP/FR), Naphthol-AS-BI-phosphate/fast red TR (NABP/FR), Naphthol-AS-MX-phosphate/fast red TR (NAMP/FR), Naphthol-AS-BI-phosphate/new fuschin (NABP/NF), bromochloroindolyl phosphate/nitroblue tetrazolium (BCIP/NBT), 5-Bromo-4-chloro-3-indolyl-b-d-galactopyranoside (BCIG).

One of the most potent detection systems is the catalysed reporter deposition (CARD); this amplification method is based on the deposition of labelled tyramide on tissue through the enzymatic action of HRP. After HRP-immunostaining, labelled tyramide is applied and bound near the site of HRP-activity. The bound and labelled tyramide is then visualised by traditional fluorescence or colorimetric enzyme mediated detection.

Automated staining systems have been introduced to reduce cost, increase uniformity of slide preparation, reduce laborious routine work and most significantly reduce procedural human errors.

The current automated systems can handle any immuno-chemical assay including assays relying on immunofluores-cence, indirect immunoassay procedures, enzyme or gold staining methods. They perform all steps of the immuno-histochemical assay irrespective of complexity or their order, at the prescribed time and temperature.

Immunocytochemistry techniques have traditionally used specific antibodies for identification and visualisation of specific antigens. The technique is complex, many steps and molecules with high affinities for specific staining are needed.

By the present invention, immunocytochemistry tech-niques have been improved to allow identification of the minute quantity of delicate receptors, which is not based on antibody-antigen interactions.

Staining of MHC peptide specific receptors in tissue mounted on e. g. slides will be a very potent diagnostic tool, enabling identification of MHC peptide specific receptors, optionally combined with morphological information, if desired.

By further combining morphological information with double staining of specific cells and specific receptors, additional useful diagnostic information can be obtained.

Flow cytometric method The MHC multimers of the invention are suitably used as labelled reagents to identify MHC recognising cells by flow cytometry. This further allows for the analysis of additional surface markers like e. g. antibody epitopes expressed by CD8, CD4, CD3, CD94/NKG2-A/C and KIRs.

A further advantage of the MHC multimers of the inven-tion is that by coupling flow cytometric analysis with high-speed cell sorting, functional assays can be performed on sorted cells without the need for in vitro expansion of the cells to be analysed.

In the flow cytometer, different cells can be identified by their distinct cell morphology like density, shape and size. Tissue morphology as such is not visible from the data obtained from flow cytometer as the cells are broken up.

Flow cytometry is a system for measuring cells, beads or particles as they move in a liquid stream, in the so-called flow cell, through a laser or light beam past a sensing area. The relative light scattering and colour discriminated fluo-rescence of the particles is measured.

A flow cytometer consists in general of a light source, flow cell, optics to focus light of different colours onto a detector, signal amplifier and processor and a computer to record and analyse data.

Lasers are used as the preferred light source in modern flow cytometers. The most common laser used is the argon-ion laser. This produces a major line at 488 nm, which gives a source of blue light for excitation of e. g. FLUORES-CEIN™ phycoerythrin, and tandem conjugates and for propidium iodide used in DNA measurements. In the flow cell, cells are aligned by hydrodynamic focusing, so that they pass through the laser beams one at a time.

Light scatter is utilised to identify the cell or particle population of interest, while the measurement of fluores-cence intensity provides specific information about indi-vidual cells.

Individual cells held in the stream of fluid are passed through one or more laser beams. The cells scatter the laser light, which at the same time make fluorescent dyes emit light at various frequencies. Photomultiplier tubes (PMT) convert light to electrical signals and cell data is collected.

What makes flow cytometry such a powerful technique is its ability to measure several parameters on many thousands of individual cells in a very short time, by measurement of their fluorescence and the way in which they scatter light. As an example, using blue light for excitation, it is possible to measure red, green and orange fluorescence and the amount of light scattered, both forward and at right angles to the beam, on each cell in a population of thousands.

Many instruments can measure at least five different parameters. As all the parameters cannot be combined for display simultaneously in a correlated fashion, a system called gating is employed. Regions of interest- or "Gates"—are defined, enabling selection of specific cell populations for display of further parameters. A flow cytometer can be used to analyse sub-populations of cells, which have been fluorescently labelled, with speed and accuracy. Sorting on the basis of other features, e. g. size, is also possible.

Flow cytometry instruments simultaneously generate three types of data: 1) Forward scatter (FSc) gives the approximate cell or particle size, 2) Side or Orthogonal scatter (SSc) gives the cell or particle complexity or granu-larity, and 3) fluorescent labelling is used to investigate e. g. cell structure and function.

Forward and side scatter are used for preliminary identi-fication of cells. In a peripheral blood sample, for example, lymphocyte, monocyte, and granulocyte populations can be defined on the basis of forward and side scatter. Forward and side scatter are used to exclude debris and dead cells. Particles, for example, can be identified by their size and/or their fluorescence.

Cell or particle populations can be represented on single or dual parameter histograms. Light scatter and fluorescence signals can be analysed after linear or logarithmic amplifi-cation. Once the population of cells or particles to be analysed has been identified, the fluorescence associated with bound antibodies or dyes is determined after the background fluorescence has been established.

Some flow cytometers are able to physically sort cells or particles into specific populations. This is most commonly done by electrostatic deflection of charged droplets com-prising a cell. The flow cell is vibrated and causes the liquid stream to break up into small droplets as it leaves the exit nozzle. At the moment a cell or particle of interest is inside the droplet currently being formed, the flow cell is charged-thus charging the droplet. The stream of droplets then passes through a pair of electrically charged plates, and droplets that are charged (comprising the cells or particles of interest) are deflected into a collection vessel.

The electric field created between the plates can direct the cells or particles towards one of several, user-specified collection receptacles. Uncharged droplets flow into a waste vessel.

Analysis of concentrations of cells or subsets of cells, often referred to as "absolute counting", can be of further interest for medical diagnostics or monitoring the status of cells in cell cultures or other biotechnological processes.

The flow cytometer is able to rapidly screen large num-bers of cells far beyond the capacity of traditional patho-logical or cytological methods. The information obtained aids in the diagnosis, classification, and prognosis of a variety of diseases.

The applications to which flow cytometry can be applied have expanded rapidly from cell sorting, to measurement of cell surface antigens, and analysis of DNA to aid the interpretation of malignant disorders.

Common uses for flow cytometry in the routine clinical laboratory include immunophenotyping of hematopoietic neoplasms, immune status evaluation, especially quantifica-tion of CD4+ T-cells in HIV positive patients, and DNA cell cycle analysis of solid tumours.

Different cell populations that compose the hematopoietic system express distinct different cell surface antigens at various stages of maturation. By detecting and measuring these expressed antigens, flow cytometry can aid in the classification of the cell lineage of leukaemia and lymphoma.

Although not intended to be an independent diagnostic modality, flow cytometry is often able to sub-classify haematopoietic malignancies beyond the capabilities of traditional morphologic and cytochemical techniques.

The most common routine uses of flow cytometry have been measurement of surface antigens (markers) by immuno-fluorescent labelling using monoclonal antibodies. The markers commonly used are total B-cells, total T-cells and subsets of T-cells. The markers for total T-cells, Helper T-cells and suppressor T-cells have been assigned the cluster differentiation (CD) categories of CD3, CD4, and CD8, respectively. This spectrum of markers, of which there are more than 45 in all, are used for clinical classification of immunodeficiency states, lymphoid leukaemias, autoimmune diseases and for monitoring their response to therapy.

For example, CD4 and CD8 measurements are especially useful to monitor the progression of AIDS, as the CD4+ cells are depleted by infection by HIV, whereas the CD8+ cells persist. The absolute number of CD4+ cells is also a marker of progression of HIV infection to more overt AIDS. The CD4/CD8 ratio can also be used to assess the success of immunosuppressive therapy with cyclosporin A in transplant patients.

For immune status evaluation, typically sub-populations of lymphocytes are identified and quantified by the flow cytometer by utilising monoclonal antibodies to various cell surface antigens. Patients with acquired or congenital immunodeficiency disease and patients on immunosuppressive drug therapy exhibit characteristic alterations in lymphocyte populations.

The typical direct staining procedure for flow cytometry can include one or several of the following steps besides washing and mixing steps: Fixation of the cells with e. g. buffered formaldehyde, permeabilisation, addition of fluorescently labelled target specific reagent, incubation, centrifugation, aspiration of the supernatant from the cell pellet, resuspension, dilution and analysis on flow cytometer.

Several examples on flow cytometry based detection and quantitative analysis of proliferating immune subpopulations of in vitro expanded T-cells in blood samples from patients have been reported. Well-known examples on antigenic TAA peptides recognised by T-cell that have been monitored in patients undergoing tumour specific immune therapy are MART-1 (27-35), gap100 (154-162), and NY-ESO (157-165). Other interesting MHC molecules include HLA A, HLA B, HLA C, H-2, DR-alleles and HLA E to detect a variety of receptors with low intrinsic affinities e. g. peptide specific TCRs and NK receptors like CD94/NKG2-A/C and KIRs.

The interaction between peptide/MHC molecule and the specific counter receptor is driven by a relatively high affinity, which is essential for the staining function.

The constructs of the invention are therefore in particular useful for flow cytometric analysis of even subtle subpopulations of MHC recognising cells. The increased binding avidity of MHC multimers of the invention allows detection of MHC recognising cells expressing low affinity receptors. The augmented interactions also allow detection of even very small MHC recognising cell populations in blood samples without the need for in vitro expansion. It is therefore envisioned that MHC multimers of the invention are useful for direct monitoring by flow cytometry of all types of MHC recognising cells in blood samples.

The poly-ligand MHC multimers of the invention also allow better separation of specific and unspecific MHC recognising cells and, thus, augment utilisation of fast flow cell sorting of antigen specific MHC recognising cells.

Other techniques Also, it is believed that the MHC multimers of the invention can suitably be applied in the so-call "free-floating" techniques.

In staining procedures using the so-called "free floating techniques", a tissue section is brought into contact with different reagents and wash buffers in suspension or freely floating in appropriate containers, e. g. micro centrifuge tubes.

The tissue sections can be transferred from tube to tube with different reagents and buffers during the staining procedure using e. g. a "fishing hook like" device, a spatula or a glass ring.

The different reagents and buffer can also be changed by gentle decantation or vacuum suction. Alternatively, containers with the tissue sections can be emptied into a special staining net, like the Corning "Netwells" and the tissue section washed before being transferred back into the tube for the next staining step.

All the individual staining procedure steps, including e. g. fixation, antigen retrieval, washing, incubation with blocking reagents, immuno-specific reagents and e. g. the enzymatic catalysed development of the coloured stains, are done while the tissue section is floating freely or withheld on nets. After development of the stain, the tissue section is mounted on slides, dried, before being counterstained and cover slipped before being analysed in e. g. a microscope.

Occasionally, the tissue section is mounted on slides following the critical incubation with the immuno-specific reagents. The rest of the staining process is then conducted on the slide mounted tissue sections.

The free-floating method has been used mainly on thick tissue sections. It is important that sections never dry out during the staining process.

Advantages of the free-floating method include even and good penetration of the immunohistochemical staining reagents. The free-floating method allows for high concentrations of reagents and good mixing.

Compositions comprising MHC multimers Compositions (kits) comprising MHC multimers are also an important embodiment of the present invention. Such compositions can be formulated in a way making them ready-to-use in hospitals and laboratories.

They can also be formulated so as to enable the user to modify or use as desired.

It is to be understood that the composition can include one MHC molecule construct or several MHC molecule constructs, depending on the intended use. The total number of MHC multimers as well as actual combination of MHC molecules and peptides are in principle unlimited.

Thus, the present invention relates to compositions comprising a MHC molecule construct as defined above and optionally other components such as buffers and/or visualisation means. The MHC molecules of the MHC molecule construct can be peptide filled or peptide free MHC molecules as defined above, or a mixture thereof. The MHC molecule construct and optionally other components can be provided in separate containers or in the same container.

In one embodiment, the composition of the invention comprises a MHC molecule construct as defined above in a solubilising medium. The composition can be such, wherein the MHC molecule construct comprises peptide filled MHC molecules, or such, wherein the MHC molecule construct comprises peptide free MHC molecules. In the latter case, the composition can be such, wherein peptides to fill the peptide free MHC molecules, and the MHC molecule construct comprising peptide free MHC molecules are provided separately.

In another embodiment, the composition of the invention comprises a MHC molecule construct as defined above, wherein the MHC molecule construct is immobilised onto a solid or semi-solid support. Suitable solid and semi-solid supports are indicated above. The composition can be such, wherein the MHC molecule construct comprises peptide filled MHC molecules, or such, wherein the MHC molecule construct comprises peptide free MHC molecules.

In the latter case, the composition can be such, wherein peptides to fill the peptide free MHC molecules are provided separately.

In particular, the MHC multimers can be provided in a form, wherein the MHC molecules are filled with low affinity peptides. Thus, it can be possible to exchange these low affinity peptides with higher affinity peptides for a particular use. This application can particularly be valuable when providing the compositions (kits). Filling the MHC molecules with low affinity peptides has the advantage of stabilising the MHC molecules, while providing the benefits of peptide free MHC molecules.

In the following, the production of MHC molecules, peptides, and MHC multimers is described.

Production of MHC molecules, peptides and MHC multimers Herein the production of MHC molecules and i. a. their usage for well-defined MHC molecules organised as poly-ligand compounds on one or more multimerization domain(s) (MHC molecule constructs) to achieve specific binding of the MHC molecule to immune competent targeT-cells (MHC recognising cells) expressing appropriate T-cell receptors and NK cell receptors are described.

Production of MHC molecule Some MHC molecules have proven very difficult to obtain from natural sources i. e. eukaryotic cells as they are contaminated or pre-occupied with undesired peptides during the cellular biosynthesis.

Recent technological progress allows production of peptide empty but functional MHC Class I as well as MHC Class II using appropriate cDNA ligated into a bacterial expression vector. In vitro folding procedure Oxidized Protein Folding (OPF) allows production of well-defined MHC Class I molecules. The method can be of use in any protein production scheme (be it in prokaryotes or eucaryotes) where the protein (e. g. inclusion bodies) at some point during the production is solvated in chaotrophic (e. g. urea) at conditions that do not disrupt established and appropriate disulphide bonds. Briefly, the OPF method takes advantage of pre-formed disulphide bonds that guide the denatured MHC molecule through an efficient and fast folding pathway in buffers with appropriate conditions (like pH, salinity). By example, peptide empty and relatively stable MHC Class I molecule is instantly formed by dilution of denatured heavy chain molecule with appropriate disulphide bonds in a buffer comprising excess of functional ß2m. This intermediate state of de novo folded MHC Class I heavy chain is strictly controlled by the presence of P2m. Subsequent addition of peptide induces molecular changes in the heavy chain molecule and lead to formation of stable and functional MHC Class I molecules. Thus, the OPF method allows production of MHC Class I molecule in two distinct forms, namely a) as a peptide filled molecule, which is extremely stable and T-cell binding, and b) as a partially mature, peptide free molecule ("empty" MHC molecules), which is reasonably stable and readily peptide receptive. In comparison, conventional folding of bacterial produced MHC molecule requires presence of both B12m and peptide and leads, consequently, only to stable peptide filled MHC molecules.

Oxidised states of e. g. MHC Class I subunits can, only, be obtained by biochemical purification, e. g. size exclusion and ion-exchange chromatography of individual subunits from urea solubilised bacterial inclusion bodies or from denatured MHC Class I molecules produced in eukaryotic cells e. g. CHO cells.

The MHC molecules can also be generated by recombinant technology to obtain well defined and highly purified components tagged with an appropriate moiety (e. g. a biotinylation site) for ligation to the one or more multimerization domain(s) via a binding entity, like e. g. streptavidin. MHC molecules and MHC-like molecules are only obtained with difficulty from natural sources, as they are loaded with many different peptides in intracellular compartments during biosynthesis. Efficient methods for production of MHC molecules are also prerequisites to overcome the extreme polymorphism of the MHC locus. In the human population more than 400 different HLA A, HLA B and HLA C alleles exist, and more that 200 HLA D alleles exist.

This molecular diversity has as stated above an immunological purpose, but is a practical obstacle to MHC production because many different MHC molecules need be generated and individually optimised, validated, characterised, stored etc. Recombinant MHC molecules that present well-defined peptides can, however, be obtained with high efficacy by in vitro folding of denatured and pre-oxidised subunits (i. e. heavy and light P2M of MHC Class I molecules, and a, B chains of MHC Class II molecules) from MHC molecules that have been produced in bacteria or eukaryotic cells.

MHC molecules can be obtained by cloning of cDNA encoding the various molecules of interest following standard procedures, e. g. as described in Molecular Cloning. Briefly, cDNA is synthesised from appropriate cell lines using commercial cDNA synthesis kits (in casu from Pharmacia). For instance, in the case of human cells, the cells can be derived from the panel of HLA expressing EBV transformed human B-cell lines from the 12 International Histocompatibility Workshop Cell Lines Panel Database ("HLA: Genetic diversity of HLA.

In the case of HLA A*0201, an appropriate cell line would be the IHW 9012. The nucleotide sequence corresponding to a desired MHC (HLA) molecule can be found at public available databases. Using the appropriate sequence information oligonucleotide primers can be designed to amplify by the PCR reaction the coding region encompassing of the relevant mature MHC (HLA) molecule from the appropriate cDNA.

The relevant forward and backward primer set for the purpose of amplifying is inserted into the NcoI and HindIII restriction sites of an appropriate expression vector. Suitable expression vectors are e. g. obtainable from Novagen (Novagen, Inc, Madison, WI, USA).

The peptides (or peptide antigens) to fill the MHC molecules can be any length. The peptides should be at least 8-10 amino acid residues long when associated to MHC Class I molecules. The length of the peptides associated to MHC Class II molecules are usually longer than the peptides associated to MHC Class I molecules and can be e. g. as much as 50 amino acid residues, however, usually less than about 20 amino acid residues such as less than about 17 amino acid residues. However, it is to be understood that the above-indicated lengths are by way of example, and should, thus, not be limiting.

Since antigenic molecules or tissues are known for a number of immunopathologies, suitable peptides can be selected using this information. By way of example, a panel of antigenic peptides from tumour-associated antigens recognised by specific cytotoxic T-cells has been identified.

The amino acid composition can also be obtained by iterative procedures or by molecular modelling. The rapid and reliable identification of MHC Class I- and Class II-restricted T-cell epitopes is essential in various fields of medical research including the definition of new tumour antigens, auto-antigens or with respect to infectious diseases. A prerequisite therefore is the exact knowledge about the molecular interactions within the MHC-peptide-TCR complex. By means of synthetic combinatorial peptide libraries a large number of MHC peptide binding motifs have been revealed with in the last ten years. A common feature of MHC peptide binding motifs is the presence of anchor residues of the peptide and pockets of the binding site, which control the strength of peptide binding to the MHC molecule. More than 500 different MHC molecules have been found, each of them comprising different peptide binding motifs. From existing biodatabases comprising information of binding motifs, a number of algorithms have developed to predict MHC binding motifs deduced from known sequences of antigens. One well-known example is the DATABASE OF MHC LIGANDS AND PEPTIDE MOTIFS "SYFPEITHI", a database comprising approximately 2000 peptide sequences known to bind Class I and Class II MHC molecules. The entries are compiled from published reports. The databases provide a strong tool for identification of MHC binding motifs in molecules involved in a variety of infections and cellular transformations. For example HIV/SIV antigens and tumour-associated antigens have been identified. From the known sequences of these antigens a number of MHC binding motifs have been predicted and subsequently verified by peptide binding analyses. Similar deductions of MHC binding peptides are available for a variety of disease-associated antigens in e. g. cancer, malaria and tuberculosis.

More recent approaches to improve prediction of suitable MHC Class I peptide epitopes are based on knowledge to digest patterns of proteosomes that generate the MHC Class I bound peptides in ER. By example, the NetChop WWW server produces neural network predictions for cleavage sites of the human proteasome (cbs. dtu. dk/-services/NetChop/). Since the proteasome structure is quite conserved, it is likely that the server is able to produce reliable predictions for at least the other mammalian proteasomes. A similar WWW server is available at uni-tuebingen. de/uni/kxi/.

Analysis by trained artificial networks enables identification of additional motifs and characteristics that promote or inhibit cleavage. The tools also enable, in combination with a predictor of MHC binding capacity, a more complete prediction of the generation and presentation of peptides on MHC Class I molecules.

Peptides can be obtained by solid phase synthesis methods. The first stage of the technique firstly introduced by Merrifield (refs. 14 and 15) consists of peptide chain assembly with protected amino acid derivatives on a polymeric support. The second stage of the technique is the cleavage of the peptide from the support with the concurrent cleavage of all side chain protecting groups to give the crude free peptide. To achieve larger peptides, these processes can be repeated sequentially.

For a review of this methodology, including the different chemical protection schemes and solid and soluble supports, see for example G. Barany and Fields (refs. 16 and 17).

A large number of peptides, so-called peptide libraries, can be obtained by combinatorial peptide synthesis; see e. g. Gordon et al., R. A. Houghten et al. and G. Jung et al. (refs. 18, 19 and 20). These collections of peptides can contain both natural, unnatural amino acids and amino acid mimics in the sequences. The libraries are useful for screening a large number of peptides.

Other methods for obtaining peptides include enzymatic fragment ligation, genetic engineering techniques as e. g. site-directed mutagenesis. Alternatively, the peptides can be obtained after isolation from natural sources.

By the present invention, it is possible to bind low affinity soluble MHC molecules stably to their specific counter receptors. The process making this possible is described in the following and comprises associating the MHC molecule to one or more multimerization domain(s) (which can be chosen to be soluble or non-soluble, depending on the intended use) to form the MHC molecule construct, which thus is a poly-ligand (i. e. poly-valent) compound.

The plurality of low affinity MHC molecules organised in this way as multi- or poly-valent molecular complexes compensates for intrinsic high off-rates related to binding of individual MHC molecules.

The MHC multimers of the present invention expressing multiple low affinity MHC molecules bind to specific receptors on MHC recognising cells with high avidity. For instance, the monomer form of soluble HLA Class I dissociates rapidly, whereas a MHC molecule construct of the invention comprising HLA Class I has proven far more stable.

Thus, the present invention further relates to a process for preparing a MHC molecule construct.

The process of the invention comprises the steps of (a) providing a MHC molecule or a MHC molecule subunit, and (b) associating the MHC molecule or the MHC molecule subunit to one or more suitable multimerization domain(s) as described herein, or a suitable multimerization domain(s) and a suitable binding entity as described herein, thereby obtaining a MHC molecule construct.

As mentioned, the multimerization domain(s) can be chosen so as to be soluble or non-soluble.

More specifically, the process of the present invention comprises the steps of (a) providing a prokaryotic or eukaryotic cell comprising one or more genes coding for a tagged or untagged MHC molecules or MHC molecule subunits, the gene or genes being expressible in said cell, (b) cultivating the cell under conditions where the gene is expressed, (c) isolating the MHC molecules or MHC subunits from the cell under conditions which allow subsequent purification of the MHC molecules or MHC molecule subunits generated by the cell, and (d) optionally subjecting the isolated MHC molecule subunits to a folding treatment prior to or during a process of association to one or more multimerization domain(s) as described herein, or a binding entity and one or more multimerization domain(s) as described herein, thereby obtaining the MHC molecule construct.

The MHC molecules can be generated in the same cell or in different cells. In the latter case, the MHC molecules (which can very well be two different kinds of molecules, e. g. a heavy chain of a MHC Class I molecule and a fm) can be combined prior to or during the time of association to the one or more multimerization domain(s) (with or without a binding entity).

HosT-cells comprising appropriate expression vectors can be prokaryotic or eukaryotic.

Particularly preferred for production of MHC molecules used herein is the versatile and high expressive bacterial expression. By way of example, an *E. coli* strain e. g. lysogene BL21 (DE3) can easily be transformed with a cDNA encoding expression vector of interest and induced to expression of large amounts of molecules.

The host cells comprising expression plasmids encoding the MHC molecules can be of prokaryotic origin (bacteria) or of eukaryotic origin (yeast, insect or mammalian cells).

A preferred bacterial production is such which yields high amounts of denatured subunit molecule e. g. heavy chain and p2m molecule. Functional MHC molecules can be obtained by in vitro folding following standard procedures known by persons skilled in the art. For example, a conventional method describes that denatured and fully reduced MHC Class I heavy chain molecule obtained from bacteria regenerates in presence of P2m and appropriate peptide at physical and chemical conditions that allow formation of disulphide bonds and establishment of secondary and tertiary formation of denatured polypeptide chains. Both peptide and p2m are added in excess in comparison to the amount of folding heavy chain to compensate for the low affinities of subunit molecules in the early folding phases. The peptide of interest should comprise appropriate anchor residues to ensure a sufficient loading into the peptide-binding site formed by the heavy chain.

A more recently developed and preferred method "Oxidised Folding Protein" (OPF) takes advantage of heavy chain molecules with pre-formed disulphide bonds, which direct a fast and more efficient folding of denatured molecules.

This method describes folding of MHC Class I heavy chains in presence of P2m alone. A peptide empty and bio-chemically stable MHC Class I molecule is formed by association of heavy- and light chain. Subsequent addition of peptides comprising appropriate anchor residues leads to fast formation of the functional and stable MHC-peptide complexes.

Well-defined MHC molecules or MHC molecule subunits can also be produced in cells encoding appropriate cDNAs.

Expression vectors comprising such cDNA can be introduced into host cells using any technique known in the art.

These techniques include electroporation, calcium-phosphate mediated transfection, transferrin-polycation mediated DNA transfer, transfection with naked or encapsulated nucleic acids, liposome mediated cellular fusion, intracellular transportation of DNA-coated latex beads, protoplast fusion and viral infection.

Therapy As mentioned above, the present invention relates in general to the field of therapy. MHC multimers of the invention are a powerful tool in various therapeutic applications. In particular, the MHC multimers of the invention are applicable in in vivo and ex vivo therapeutic applications as will be apparent from the following.

The present invention is also based on the recognition that it is possible to design a poly-ligand MHC molecule construct so as to (I) target specific MHC recognising cells, and (II) induce a response as desired, in specific target MHC recognising cells by addressing receptors on such cells. It was further recognised that with such design of MHC molecule/peptide complexes with a given specificity, it is possible to "add" other stimuli to the therapeutic composition by incorporating other molecules, which will affect the activity of the MHC recognising cells. Thus, it is possible to modulate the activity of specifically targeted MHC recognising cell clones, while leaving other MHC recognising cell clones unaffected.

Furthermore, it is also possible to specifically modulate the activity of more than one MHC recognising cell clone by choosing the before-mentioned other molecules appropriately. The inventions is further based on the recognition that it is possible to obtain specific MHC recognising cells using the MHC multimers described herein, to modulate such ex vivo, whereby such cells can be used for in vivo treatment.

Accordingly, the present invention provides for methods of up-regulating, down-regulating, modulate, restoring, enhancing, and/or stimulate the immune system, as well as methods of inducing anergy of cells. This can in accordance with the present invention in general be accomplished in two ways, namely in vivo or ex vivo. By "in vivo" is meant that an effective amount of an active substance or ingredient is administered to a subject by any suitable route, the active substance or ingredient exerting its effect in the subject. By "ex vivo" (can also be termed "in vitro") is meant thaT-cells withdrawn from a subject are in some way affected outside the subject, and then re-introduced to the subject, thereby achieving a desired response.

It is to be understood that the therapeutic compositions of the present invention can comprise one or more MHC multimers as defined above. As also described above, the MHC molecules of the construct can be peptide filled, peptide empty or mixtures thereof. The MHC molecules of each construct can be the same or different.

Likewise, the peptides of the MHC molecules can be the same or different. Likewise, the MHC molecule construct can comprise one or more biologically active molecules, which can be the same or different. These expressions are described in the foregoing.

In particular, the inclusion of biologically active molecules can be important to initiate a response as desired. As mentioned above, the immune system is dependent on several signalling pathways, and thus inclusion of biologically active molecules, either as part of the MHC construct or alone, can be an excellent way to control or guide the immune system.

Thus, the present invention relates generally to the MHC multimers per se as defined above for use as therapeutic compositions or medicaments. The present invention also relates to the MHC multimers as defined herein for use in in vivo therapy and for use in ex vivo therapy.

In one aspect, the present invention relates to therapeutic compositions comprising as an active ingredient a MHC molecule construct as defined herein.

In another aspect, the present invention relates to therapeutic compositions comprising as active ingredient an effective amount of MHC recognising cells, the MHC recognising cells being obtainable by bringing a sample from a subject comprising MHC recognising cells into contact with a MHC molecule construct as described herein, whereby the MHC recognising cells become bound to the MHC molecule construct, isolating the bound MHC molecule construct and the MHC recognising cells, and expanding such MHC recognising cells to a clinically relevant number.

The therapeutic compositions can suitably comprise one or more adjuvants and/or excipients.

As used herein, the term "adjuvant" refers to an immunological adjuvant. By this is meant a compound that is able to enhance or facilitate the immune system's response to the ingredient in question, thereby inducing an immune response or series of immune responses in the subject. The adjuvant can facilitate the effect of the therapeutic composition by forming depots (prolonging the half-life of the ingredient), provide additional T-cell help and stimulate cytokine production. Facilitation of antigen survival and unspecific stimulation by adjuvants may, in some cases, be required if MHC molecule epitopes are the only feature in the therapeutic composition recognised by the immune system.

Included in the term "immune response" is specific humoral, i. e. antibody, as well as cellular immune responses, the antibodies being serologic as well as secretory and pertaining to the subclasses IgM, IgD, IgG, IgA and IgE as well as all isotypes, allotypes, and subclasses thereof. The term is further intended to include other serum or tissue components. The cellular response includes Type-1 and Type-2 T-helper lymphocytes, cytotoxic T-cells as well NK cells.

Examples of suitable adjuvant are those mentioned above, i. e. saponins such as Quit. A and Qs-21, oil in water emulsions such as MF59, MPL, PLG, PLGA, aluminium salts calcium phosphate, water in oil emulsions such as IFA (Freund's incomplete adjuvant) and CFA (Freund's complete adjuvant), interleukins such as IL-1 (3, IL-2, IL-7, IL-12, and INFy, Adju-Phose, glucan, antigen formulation, biodegradable microparticles, Cholera Holotoxin, liposomes, DDE, DHEA, DMPC, DMPG, DOC/Alum Complex, Iscoms muramyl peptide, monophosphoryl lipid A, muramyl tripeptide, and phospatidylethanolamine In a preferred embodiment, the adjuvant is selected from saponins such as Quil A and Qs-21, MF59, MPL, PLG, PLGA, calcium phosphate, and aluminium salts. Examples of suitable excipients are those mentioned above, i. e. diluents, buffers, suspending agents, wetting agents, solubilising agents, pH-adjusting agents, dispersing agents, preserving agents, and/or colorants. In particular a PBS buffer without calcium ions and magnesium ions can be suited.

The therapeutic compositions of the invention can suitably be applied in the treatment, prevention, stabilisation, or alleviation of various diseases.

Diseases of relevance are those mentioned above, i. e. diseases of inflammatory, auto-immune, allergic, viral, cancerous, infectious, allo- or xenogene (graft versus host and host versus graft) origin. In particular, the disease can be a chronic inflammatory bowel disease such as Crohn's disease or ulcerative colitis, sclerosis, type I diabetes, rheumatoid arthritis, psoriasis, atopic dermatitis, asthma, malignant melanoma, renal carcinoma, breast cancer, lung cancer, cancer of the uterus, prostatic cancer, brain cancer, head and neck cancer, leukaemia, cutaneous lymphoma, hepatic carcinoma, colorectal cancer, bladder cancer, rejection-related disease, Graft-versus-host-related disease, or a viral disease associated with hepatitis, AIDS, measles, pox chicken pox, rubella or herpes.

More specifically, the disease can be of inflammatory/auto-immune origin, including asthma, hypersensitivity pneumonitis, interstitial lung disease, sarcoidosis, idiopathic pulmonary fibrosis, interstitial lung disease associated with Crohn s Disease or ulcerative colitis or Whipple's disease, interstitial lung disease associated with Wegeners granulomatosis or hypersensitivity vasculitis, vasculitis syndromes, Hennoch-Schonleins purpura, Goodpastures syndrome, Wegeners granulomatosis, renal diseases such as antibody mediated glomerulopathia as in acute glomerulonephritis, nephritis associated with systemic lupus erythematosus, nephritis associated with other systemic diseases such as Wegeners granulomatosis and Goodpastures syndrome and mixed connective tissue disease, chronic interstitial nephritis, chronic glomerulonephritis, gastrointestinal diseases such as Crohn s Disease, Ulcerative colitis, coeliac disease, Whipple's disease, collagenous colitis, eosinophillic colitis, lymphatic colitis, hepatobilliary diseases such as auto-immune hepatitis, alcohol induced hepatitis, periportal fibrosis, primary billiary cirrhosis, sclerosing colangitis, disorders of the central or peripheral nervous system such as demyelinating disease as multiple sclerosis, acute disseminated encephalomyelitis, sub-acute sclerosing panencephalitis, skin disease such as psoriasis, atopic dermatitis, eczema, allergic skin disease, progressive systemic sclerosis (scleroderma), exfoliating dermatitis, pemphigus vulgaris, joint diseases such as rheumatoid arthritis, ankylosing spondylitis, arthritis associated with psoriasis or inflammatory bowel disease, muscoloskelletal diseases such as myastenia gravis, polymyositis, endocrine diseases such as insulin dependent diabetes mellitus, auto-immune thyroiditis (Hashimoto), thyreotoxicosis, Graves, diseases of the hematopoetic system such as auto-immune anaemia, auto-immune thrombocytopenia, cardiovascular diseases such as cardiomyopathia, vasculitis, cardiovascular disease associated with systemic diseases as systemic lupus erythematosus, polyarthritis nodosa, rheumatoid arthritis, scleroderma, sarcoidosis, diseases of cancerous origin, including malignant melanoma, Sezary's syndrome, cutaneous T-cell lymphoma, renal cell carcinoma, colorectal cancer, breast cancer, ovarian cancer, cancer of the uterus, prostatic cancer, hepatic carcinoma, lung cancer, and sarcoma, diseases, disorders or conditions of allergic origin.

The most common allergens, to which allergic reactions occur, include. inhalation allergens originating i. a. from trees, grasses, herbs, fungi, house dust mites, storage mites, cockroaches and animal hair, feathers, and dandruff. Important pollen allergens from trees, grasses and herbs are such originating from the taxonomic orders of Fagales, Oleales and Pinales including i. a. birch (*Betula*), alder (*Alnus*), hazel (*Corylus*), hornbeam (*Carpinus*) and olive (*Olea*), the order of Poales including i. a. grasses of the genera *Lolium, Phleum, Poa, Cynodon, Dactylis* and *Secale*, the orders of Astrales and Urticales including i. a. herbs of the genera *Ambrosia* and *Artemisia*. *Important inhalation allergens from fungi are i. a. such originating from the genera Alternaria* and *Cladosporium*. Other important inhalation allergens are those from house dust mites of the genus *Dermatophagoides*, storage mites from the genus Lepidoglyphys destructor, those from cockroaches and those from mammals such as cat, dog, horse, cow, and bird. Also, allergic reactions towards stinging or biting insects such as those from the taxonomic order of Hymenoptera including bees, wasps, and ants are commonly observed. Specific allergen components are known to the person skilled in the art and include e. g. Bet v 1 (*B. verrucosa*, birch), Aln g 1 (*Alnus glutinosa*, alder), Cor a 1 (*Corylus* avelana, hazel) and Car b 1 (*Carpinus betulus*, hornbeam) of the Fagales order. Others are Cry j 1 (Pinales), Amb a 1 and 2, Art v 1 (Asterales), Par j 1 (Urticales), Ole e 1 (Oleaves), Ave e 1, Cyn d 1, Dac g 1, Fes p 1, Hol 11, Lol p 1 and 5, Pas n 1, Phl p 1 and 5, Poa p 1,2 and 5, Sec c 1 and 5, and Sor h 1 (various grass pollens), Alt a 1 and Cla h 1 (fungi), Der f 1 and 2, Der p 1 and 2 (house dust mites, *D. farinae* and *D. pteronyssinus*, respectively), Lep d 1, Bla g 1 and 2, Per a 1 (cockroaches, Blatella *germanica* and *Periplaneta americana*, respectively), Fel d 1 (cat), Can f 1 (dog), Equ c 1,2 and 3 (horse), Apis m 1 and 2 (honeybee), Ves g 1,2 and 5, Pol a 1,2 and 5 (all wasps) and Sol i 1, 2,3 and 4 (fire ant), to mention the most common.

The therapeutic compositions of the invention can be formulated in any suitable way, i. a. depending on the route of administration, and the amount of active ingredient to be administered. In particular, the therapeutic compositions of the invention can be formulated for parenteral administration, including intravenous, intramuscular, intraarticular, subcutaneous, intradermal, epicutantous/transdermal, and intra-peritoneal administration, for infusion, for oral administration, for nasal administration, for rectal administration, or for topic administration.

The MHC molecule construct can suitably be immobilised onto a solid or semi-solid support. Examples of solid and semi-solid support are those mentioned above, i. e. particles, beads, biodegradable particles, sheets, gels, filters, membranes, fibres, capillaries, needles, microtitre strips, tubes, plates or wells, combs, pipette tips, micro arrays, and chips. In particular, the solid support can be selected from particles and beads, preferably particles and beads, which are polymeric, magnetic or superparamagnetic. For in vivo therapy, biodegradable particles will be especially preferred, while for ex vivo therapy, biodegradable, polymeric, magnetic, paramagnetic or superparamagnetic particles will be especially preferred.

As mentioned, the MHC multimers used in the therapeutically compositions are very interesting molecule poly-ligand compounds possessing highly appropriate properties for modulation of MHC recognising cells both in vivo and ex vivo.

The poly-ligand MHC multimers can, due to the one or more multimerization domain(s), be loaded with a plurality of peptide-displaying MHC molecules to ensure high avidity binding to specific counter receptors.

It is to be understood that such responses include inducing anergy leading to apoptosis, up-regulating a response, down-regulating a response, stimulating a response, modulating a response, enhancing a response, inhibiting a response, and in any other way manipulating a response. In this connection, it should be understood that the MHC molecules/peptides of the construct can be chosen so as to induce a number of other responses, or activate signal pathways which results in the production of various signalling substances which can have a beneficial influence on the disease to be treated, prevented or alleviated.

To accomplish this, the MHC molecule construct used in the composition can suitably comprise heterogeneous or homogeneous MHC molecules (e. g. displaying different peptides) to elicit one or more or more functions in the target MHC recognising cells in vivo and ex vivo.

Furthermore, this desired effect of the MHC molecule construct can be enhanced, reduced, inhibited, stimulated or combined with other effects by the further attachment of biologically active compounds as described above, thereby addressing specific MHC recognising cell clones.

For this, a specific combination of MHC molecule and peptide can be selected. By way of example, loading co-stimulatory molecules e. g. B7.1 onto a poly-ligand MHC molecule construct thus leads to formation of a bi-functional poly-ligand MHC molecule construct, which (I) is directed to the peptide specific MHC recognising cell clones of interest and (II) facilitate appropriate stimulation implying two mandatory signals to initiate an immune response. Another example is compositions for the treatment of auto-immune diseases wherein a recombinant toxin, e. g. PE-38, is also attached to the MHC multimers used.

By this, it is possible to modulate the response in any way it would be desired. Therefore, the present invention also relates to a method of designing a MHC molecule/peptide combination, resulting in a desired targeT-cell response both in vivo and ex vivo.

A variety of diseases, including cancer cause immuno-suppression in the patients. Immunotherapy is an attempt to stimulate the patient's own immune system to recognise and destroy cancer cells. The tumour can exert its suppressive influence over the immune system through several different mechanisms. Although tumour cells can prime the immune system, tumour escape mechanisms can induce immuno-logical tolerance to the tumour. There are several known mechanisms of tumour escaping immune surveillance. For instance, tumour cells are often inefficient in presenting tumour antigens to effector T-cells. This can be the result of tumour cell down-regulation or mutation of MHC mol-ecules, or down-regulation of co-stimulatory molecules such as B7, or other molecules, such as TAP, that are important in the antigen presenting pathway.

Furthermore, tumour cells have been shown to induce tolerance in T-cells by down-regulating the expression of CD3-zeta chain in T-cells. Tumour cells can also suppress T-cell activation by release of inhibitory cytokines, and induce apoptosis in T-cells through Fas-Fas ligand interac-tion. Tumour cells also have the ability to suppress the immune system through release of cytokines such as IL-12 that inhibits the maturation of immature dendritic cells into fully mature antigen presenting cells. Inhibitory factors released by tumour cells have been shown to suppress granulocyte activation, thus avoiding the killing of tumour cells by activated granulocytes.

Common treatment regimes such as chemotherapy and radiation therapy also suppress immunity in a more general way.

A variety of different prior art strategies have been employed in an attempt to restore or enhance the patient's immune response to tumours, including treatment with monoclonal antibodies, cancer vaccines, cytokine therapy and adoptive cellular immunotherapy using dendritic cells or T-cells. Cellular immunotherapy involving T-cells include CD8+ cytotoxic effector cells that have the capacity to kill tumour cells. Furthermore, it has been shown that CD4+ cytokine producing T-cells also play an important role in maintaining a sustainable anti-tumour cell activity of cyto-toxic CD8 cells. The success, however, of the prior art methods have been limited.

In accordance with the above, interesting the MHC mul-timers of the therapeutic composition can be such, wherein at least two of the MHC molecules of the MHC molecule construct used are different, wherein the MHC molecules of the MHC molecule construct used are the same, wherein at least two of the peptides harboured by a plurality MHC molecules of the MHC molecule construct used are different, wherein the peptides harboured by the MHC molecules of the MHC molecule construct used are the same, wherein the peptides harboured by the MHC molecules of the MHC molecule construct used are chemically modified or synthe-sised to contain not natural amino acids, hydrophilic or hydrophobic groups, wherein the peptides harboured by the MHC Class I molecules of the MHC molecule construct used are linked to the MHC Class I heavy chain by a flexible linker, wherein the peptides harboured by the MHC Class I molecules of the MHC molecule construct used are linked to the MHC Class I light chain (ß12m) by a flexible linker, wherein the peptides are harboured by MHC Class I mol-ecules of the MHC molecule construct used comprising of MHC Class I heavy chain in association with a light chain (2m) by a flexible linker, wherein the peptide harboured by the MHC Class II molecules of the MHC molecule construct used are linked to the alfa-chain by a flexible linker, wherein the peptide harboured by the MHC Class II molecules of the MHC molecule construct used are linked to the 0-chain by a flexible linker, wherein the MHC Class I molecules of the MHC molecule construct used are mutated, wherein the MHC Class II molecules of the MHC molecule construct used are mutated, wherein the MHC molecules of the MHC molecule construct used are peptide free MHC molecules.

As mentioned above, the MHC molecule construct can comprise one or more biologically active molecules. Such are defined above. Particularly preferred biologically compounds will be selected from MIC A, MIC B, CDId, ULBP-1, ULBP-2, ULBP-3, CD2, CD3, CD4, CD5, CD8, CD9, CD27, CD28, CD30, CD69, CD134 (OX40), CD137 (4-1BB), CD147, CDw150 (SLAM), CD152 (CTLA-4), CD153 (CD30L), CD40L (CD154), NKG2D, ICOS, HVEM, HLA Class II, PD-1, Fas (CD95), FasL, CD40, CD48, CD58, CD70, CD72, B7.1 (CD80), B7.2 (CD86), B7RP-1, B7-H3, PD-L1, PD-L2, CD134L, CD137L, ICOSL, LIGHT, CD16, NKp30, NKp44, NKp46, NKp80, 2B4, KIR, LIR, CD94/NKG2A, and CD94/NKG2C.

As mentioned the present invention relates to methods for the treatment of an animal, including a human being, which methods comprise administering a therapeutic composition as described herein in an effective amount.

The treatment can be such which involves up-regulation, down-regulation, modulation, stimulation, inhibition, restoration, enhancement and/and otherwise manipulation of immune responses. This can indeed be accomplished by the compositions of the present invention. The present invention also relates to methods of inducing anergy in a cell, by which methods a therapeutic composition as described herein is administered.

In a further aspect, the present invention relates to methods of performing adoptive immunotherapy, which methods comprise administrating to an animal, including a human being, a therapeutic composition as described herein.

As mentioned above, the therapeutic composition of the invention is suited for in vivo therapy.

Therapeutic compositions for in vivo therapy can suitably comprise from 1 to 10 different MHC molecule constructs.

Thus, the inclusion of two, three, four, five, six or more different MHC multimers are contemplated and believed to be advantageous in some cases. Also, it can be advantageous to include a MHC molecule construct carrying MHC molecules harbouring different peptides. The amount of each MHC molecule construct depends on the MHC molecule construct or combination of MHC multimers in question. Furthermore, the affinity of the MHC molecule should be taken into consideration. High-affinity, as well as low affinity peptides can be harboured by the MHC molecules. This, however, is expected to affect the amount necessary to generate the desired response and the strength of the desired response. It is contemplated that the amount of MHC molecule construct required to induce a systemic immune response will typically be in the range of from 0.0001 to 10,000 µg/kg/dose, such as from 0.01 to 1000 µg/kg/dose, from 0.1 to 100 µg/kg/dose, or from 1 to 10 µg/kg/dose.

In general, the MHC molecules used should be synergenic with the receiving subject to avoid or minimise the risk of alloreactions.

The administration of the composition of the invention can be as single doses or as several doses. In certain cases, administration only once can be sufficient. In general, several doses should be given with intervals of a day, a week, two weeks, a month, or several months, etc. For example, a single dose can be given once, or a dose can be given as a primer, followed by one or more administration, or a continuous administration regime like up to four doses per week, followed by one month without administrations, followed by up to four doses per week (optionally with increasing amount of the MHC molecule construct), etc. Optionally different adjuvants or combinations of adjuvants can be used in the different administrations. These are all examples, and the optimal administration regime depends on the MHC molecule construct in question and several other factors. The person skilled in the art will readily know how to optimise this.

Of course, other medicaments can be administered simultaneously in order to enhance or support the treatment.

In particular, one or more MHC multimers without MHC molecules attached, but with biologically active molecules attached can be administered together with the MHC molecule construct to stimulate, up-regulate, down-regulate, inhibit or enhance other MHC recognising cell clones than the MHC recognising cell clones addressed by the MHC molecule construct of the composition. Such can also be added to promote response to the cell clone addressed. In particular, such biologically active molecules can be part of the MHC molecule construct as described in the foregoing.

Containers for mixing and storage of the therapeutic composition of the invention can be made of glass or various polymeric materials. The containers chosen should not adsorb the product stored. The containers can suitably be ampoules or capped vials for mono- or multidosage.

The invention further relates to methods for producing the therapeutic compositions of the invention, which methods comprise providing a MHC molecule construct as described herein, and solubilising or dispersing the MHC molecule construct in a medium suitable for therapeutic substances, and optionally adding other adjuvants and/or excipients.

As mentioned above, the compositions of the present invention are suited for ex vivo therapy.

Thus, the present invention relates in particular to therapeutic compositions comprising as an active ingredient an effective amount of MHC recognising cells, the MHC recognising cells being obtained by isolating from a subject MHC recognising cells using a MHC molecule construct as defined herein, and expanding such MHC recognising cells to a clinically relevant number.

Once the MHC recognising cells have been isolated they may, if needed, be genetical or in any other appropraite way modified or manipulated before they are expanded.

The MHC recognising cells can be isolated in a number of ways, which are described in more detail in the following.

In particular: 1) One or more MHC multimers as defined herein can be brought into contact with a sample from a subject, whereby the MHC multimers are allowed to bind to MHC recognising cells in the sample. The MHC multimers can then be recovered from the sample, whereafter the MHC recognising cells can be liberated from the MHC multimers and subsequently expanded.

2) One or more MHC multimers as defined herein can be brought into contact with a sample from a subject, whereby the MHC multimers are allowed to bind to MHC recognising cells in the sample. The MHC multimers can then be recovered from the sample, whereafter the MHC recognising cells can be liberated from the MHC molecule construct and subsequently expanded in the presence of one or more other MHC molecule constructs.

3) One or more MHC multimers as defined herein immobilised onto a solid or semi-support as defined herein can be brought into contact with a sample from a subject, whereby the MHC multimers are allowed to bind to MHC recognising cells in the sample. The MHC multimers can then be recovered from the sample, whereafter the MHC recognising cells can be liberated from the MHC multimers and subsequently expanded.

4) One or more MHC multimers as defined herein immobilised onto a solid or semi-support as defined herein can be brought into contact with a sample from a subject, whereby the MHC multimers are allowed to bind to MHC recognising cells in the sample. The MHC multimers can then be recovered from the sample, whereafter the MHC recognising cells can be liberated from the MHC multimers and subsequently expanded in the presence of one or more other MHC molecule constructs.

5) One or more labelled MHC multimers as defined herein immobilised onto a solid or semi-support as defined herein can be brought into contact with a sample from a subject, whereby the MHC multimers are allowed to bind to MHC recognising cells in the sample. The MHC multimers can then be recovered from the sample, whereafter the MHC recognising cells can be liberated from the MHC multimers and subsequently expanded.

6) One or more labelled MHC multimers as defined herein immobilised onto a solid or semi-support as defined herein can be brought into contact with a sample from a subject, whereby the MHC multimers are allowed to bind to MHC recognising cells in the sample. The MHC multimers can then be recovered from the sample, whereafter the MHC recognising cells can be liberated from the MHC multimers and subsequently expanded in the presence of one or more other MHC molecule constructs.

7) One or more MHC multimers as defined herein can be brought into contact with a sample from a subject, whereby the MHC multimers are allowed to bind to MHC recognising cells in the sample. Then the sample comprising the MHC recognising cells bound MHC multimers can be brought into contact with a solid or semi-solid support as defined herein having immobilised thereon one or more molecules which are able to bind to the any part of the MHC recognising cells or MHC molecule construct, whereby the MHC molecule construct with the bound MHC recognising cells will become bound to the support. The thus bound MHC multimers with MHC recognising cells can then be recovered from the sample, whereafter the MHC recognising cells can be liberated from the MHC multimers and subsequently expanded.

8) One or more labelled MHC multimers as defined herein can be brought into contact with a sample from a subject, whereby the MHC multimers are allowed to bind to MHC recognising cells in the sample.

Then the sample comprising the MHC recognising cells bound MHC multimers can be brought into contact with a solid or semi-solid support as defined herein having immobilised thereon one or more molecules which are able to bind to the any part of the MHC recognising cells or MHC molecule construct, whereby the MHC molecule construct with the bound MHC recognising cells will become bound to the support. The thus bound MHC multimers with MHC recognising cells can then be recovered from the sample, whereafter the MHC recognising cells can be liberated from the MHC multimers and subsequently expanded in the presence of one or more other MHC molecule constructs.

The above list is not exhaustive in any way.

It is to be understood that the time of contact between the MHC multimers and the sample will depend on several factors, i. a. the MHC multimers in question and the conditions under which the contacting take place. The contact time will be any such sufficiently to enable binding to the MHC recognising cells to the MHC molecule construct. The person skilled in the art will readily know how to optimise this. In general, the sample can and the MHC molecule construct can be brought into contact for 10 minutes to 2 hours, such as from 20-45 minutes, at a temperature of from 4° C. to 20° C.

It is to be understood that the MHC recognising cells are those indicated above.

It is to be understood that "sample" has the meaning defined above. In particular, the sample can be peripheral blood mononuclear cells (PBMC) or other blood-derived preparations such as leukopheresis products, or bone marrow, spleen or umbilical cord. Samples can be used as they are, or they can be subjected to various purification, decontamination, filtration, or concentration methods, and/or methods to isolate or remove parts of the sample like immunomagnetic separation.

The MHC molecule construct with bound MHC recognising cells can suitably be isolated by use of a magnetic field (if the support are magnetic particles or beads) (i. e. an immunomagnetic separation technique), or by use of a cell sorter device such as a flow cytometer. For the latter isolation procedure, the MHC multimers can suitably be labelled. If the immobilisation to the solid or semi-solid support is carried out following contact between the MHC molecule construct and sample, it is to be understood that the MHC molecule construct with the MHC recognising cells can be immobilised using a compound capable of binding thereto. Such, which are suitable, are indicated above. For immunomagnetic isolation of MHC recognising cells from larger sample volumes, disposable blood bags can be applied. Examples of equipment suited for such purpose are the Isolex®300i or MAXSEP™ (D equipment from Baxter Healthcare Corp, or the CliniMACS from Miltenyi Biotech. The MHC recognising cells can be liberated from the MHC molecule construct by procedures such as DNA-linker digested by DNase, temperature-sensitive Elastin-linker detaching antibodies, release by incubation and other release mechanisms known to persons skilled in the art.

The MHC molecule construct can in accordance with the definitions above comprise one or more biologically active molecules. Such can be included e. g in order to attract the MHC recognising cells desired, and to lower or prevent potential induction of apoptosis resulting from the isolation procedure.

It is to be understood that the expansion of the cells can be carried out in the presence of one or more MHC multimers as defined above. Such used MHC multimers can be the same as used for capturing the MHC recognising cells or can be different. Such can in accordance with the definitions above comprise one or more biologically active molecules. Such biologically active molecules will further facilitate multiple interactions with the TCR and co-stimulatory molecules on MHC recognising cells and produce efficient ex vivo stimulation of MHC recognising cells. The binding affinity of e. g. co-stimulatory molecules and their ligands is in the same range as the binding affinity of MHC molecule-peptide complexes and the TCR (10 uM range).

The inclusion of such biologically active molecules facilitates the use of natural molecules as a replacement for stimulatory antibodies during expansion, since they compensate for low affinity by introducing multiple binding interactions. In particular, the MHC recognising cells can be expanded in the presence of one or more MHC multimers without MHC molecules attached, but with biologically active molecules attached to stimulate, up-regulate, down-regulate, inhibit or enhance 1) other MHC recognising cell clones than the MHC recognising cell clones of interest as well as 2) the MHC recognising cell clones of interest. The expansion can further be carried out in the presence of feeder cells such as dendritic cells or stroma cells.

It is to be understood that the expansion of the cells can additionally be carried out in the presence of further compounds, e. g. such which promote or stimulate expansion of the cells, inhibit growth of non-relevanT-cells, or select for the desired cells. Such can e. g. be one or more biologically active molecules as described above. Such further compounds can also be selected from cytokines such as lymphokines, interferons, interleukins, growth factors, and colony-stimulating factors. For example, 11-2 can be added to enhance proliferation of cells, and other cytokines can be added to induce particular differentiation patterns, if required. For example, IL-4 triggers differentiation of T-cell populations into the Th2 subpopulation, and INF-gamma triggers differentiation into the Thi subpopulation. Of course a suitable culturing medium and suitable conditions have to be used to expand and maintain cells.

Expansion time is usually between 3 and 10 days, but can be as long as 14 to 20 days, or even longer providing viability and continued proliferation of cells are maintained.

In a special aspect, the present invention relates to methods of obtaining MHC recognising cells comprising, which methods comprise bringing into contact a MHC molecule construct as described herein and a sample suspected of comprising MHC recognising cells under conditions whereby the MHC recognising cells bind to the MHC molecule construct, and isolating the bound MHC molecule construct and MHC recognising cells.

Such methods are e. g. suited for the obtaining the MHC recognising cells of therapeutic compositions of the invention. Such methods are further believed to be of value for identifying new disease-associated peptides, in that random peptides can be applied as part of the MHC molecule construct, and their binding effect to MHC recognising cells can be tested. The methods can suitably be carried out by immunomagnetic separation techniques or by flow cytometry.

The invention further relates to methods for producing the therapeutic compositions of the invention, which methods comprise obtaining MHC recognising cells using a MHC molecule construct as described herein, expanding such MHC recognising cells to a clinically relevant number, formulating the obtained cells in a medium suitable for administration, and optionally adding adjuvants and/or excipients.

The invention further relates to kits for obtaining the MHC recognising cells. In one embodiment, such kits comprise one or more MHC protein constructs as defined herein, optionally immobilised on to a solid or semi-solid support as defined herein. In another embodiment, such kits comprise one or more MHC protein constructs as defined herein and means for immobilisation of the MHC multimers (s) prior to or following binding to the MHC recognising cells.

The invention further in general relates to the use of the MHC molecule construct described herein for ex vivo expansion of MHC recognising cells. For such ex vivo expansion of cells, the MHC molecule construct can be provided in soluble form. The MHC molecule construct can also be provided immobilised onto a solid or semi-solid support. The solid and semi-solid supports are those mentioned above. Beads and particles are especially preferred, in particular polymeric, magnetic or superparamagnetic particles or beads. In particular, the MHC molecule construct can comprise one or more of the biologically active compounds as described above.

In the following, more specific procedures are described in the context of cancerous diseases, but the procedures apply equally well to other diseases.

It is believed that one strategy to overcome the suppressive effect of e. g. tumour cells on the immune system would be to remove the immune relevanT-cells from a subject through standard apheresis procedures, and to expand and modify these immune cells ex vivo before re-infusion to the patients. This would not only remove the suppressive pressure of tumour cells, but also allow for the rescue of immunocompetenT-cells prior to immunosuppressive treatment regimens including chemotherapy and radiation therapy.

Pheripheral blood T-cells can be removed from a subject, and placed into culture under conditions that allow the T-cells to proliferate. Such conditions include growing T-cells with mitogens or antigens in the presence of cytokines (IL-2) and dendritic cells as antigen presenting cells. Antigen can be introduced in the cultures either as protein extracts from tumours, defined protein antigens or peptides, or as tumour mRNA or DNA transfected into the dendritic cells. Alternatively, T-cell expansion protocols have been developed that include the use of stimulatory antibodies such as anti-CD3 and anti-CD28 antibodies, either in soluble form or coupled to a solid phase. The advantage of such antibody-based expansion protocols is that they circumvent the need for feeder cells and tumour antigens that can not be readily available. Following ex vivo T-cell-expansion, often in the order of 100-1000 fold, the T-cells are re-infused to the patients in order to restore or enhance the immune function towards the tumour.

It is well known that T-cells of the immune system express a multitude of specificities, and only a limited number of the available T-cell clones express specificities that are relevant for the recognition and killing of the tumour cells.

Most prior art protocols for T-cell expansion do not take into consideration the antigen specificity of the T-cells for tumour antigens, and result in a polyclonal expansion of T-cells which include a multitude of irrelevant T-cell specificities. Although the expanded T-cells would help restore the immune function of the patients through production of cytokines, it is expected that only a fraction of the re-infused T-cells can recognise and kill tumour cells directly. In addition, polyclonal expansion of T-cells increases the risk of expanding T-cell clones with autoimmune specificities.

The present invention relates in particular to adoptive immunotherapy using T-cells with known specificities for tumour antigens. In this aspect of immunotherapy, CD4 and CD8 T-cells specific for pre-determined tumour antigens can be isolated from peripheral blood, apheresis products, bone marrow, lymph nodes, primary tumours, secondary organ metastasis and other tissues by an immunomagnetic separation procedure or by a flow cytometric procedure. After optional purification, the cells can be expanded ex vivo and re-infused to the patients. Such expanded antigen specific T-cells will have the ability to target tumour cells directly, and thus be more efficient than polyclonally expanded T-cells. In addition, the use of antigen specific T-cells would decrease the potential danger of re-infusing T-cells clones with autoimmune specificities.

By the present invention, a support as defined above, preferably in the form of beads or particles as defined above, having MHC multimers as defined herein immobilised thereon, can be applied to aid manipulation and separation of relevanT-cells from a sample. Thus, a support comprising magnetic particles can readily be removed by magnetic aggregation, which provides a quick, simple and efficient way of ex vivo separating bound cells.

The magnetic particles or beads with the specific T-cells attached can be removed ex vivo from a sample onto a suitable solid or semi-solid support by application of a magnetic field e. g. using a permanent magnet. It is usually sufficient to apply a magnet to the side of the vessel comprising the sample mixture to aggregate the particles to the wall of the vessel and to pour away the remainder of the sample.

Especially preferred are superparamagnetic particles, as magnetic aggregation and clumping of the particles during reaction can be avoided. DYNABEADS® (Dynal Biotech ASA, Oslo, Norway) are one particularly suited example.

In a convenient embodiment, the MHC multimers can be attached to the support, prior to contact with the sample. Such attachment can readily be achieved by methods (e. g. coupling chemistries) well known in the art, and conveniently the MHC multimers are bound directly to the solid support, for example by coating. However, the MHC multimers can also be attached via a spacer, a linker, or an antibody as described above. The MHC multimers can be covalently or reversibly attached according to choice.

Alternatively, as mentioned above, the MHC multimers can first be brought into contact with the sample, to bind to the T-cells before being attached to the solid support. In this case, the solid support can conveniently carry or be provided with a molecule as described above capable of binding to the MHC molecule construct thereby capturing the MHC molecule construct.

Non-limiting examples include antibodies against the binding entity, antibodies against the one or more multimerization domain(s), streptavidin or derivatives thereof for use with biotinylated multimerization domain(s), and anti-leucocyte antibodies.

Where more than one type of MHC molecule construct is used they can be attached to the same or different solid supports. Such a system using different solid supports is applicable particularly in the case of a particulate support such as beads or particles. Thus, different MHC multimers can be attached to different beads or particles. Such beads or particles can suitably have difference sizes or properties, which thus enable separation according to the different MHC molecule constructs.

In an embodiment where more than one different type of MHC molecule construct is used, appropriate amounts or ratios at which the different types of MHC multimers can be used will be readily determined by a person skilled in the art.

As mentioned above, cell separation techniques based on solid phase affinity binding (e. g. immunomagnetic separation (IMS)) are well known in the art and conditions to achieve this can readily be determined by the skilled worker in this field. Thus, for example a solid support carrying anti-leukocyte antibodies can be brought into contact with the sample. A particulate solid support may, for example, be added to the sample contained (e. g. suspended) in an appropriate medium (e. g. a buffer). The support can then be left in contact with the sample (e. g. incubated) for a length of time to enable binding to the cells to occur. Conditions during the step are not critical, and the sample-support mixture can be incubated at e. g. 4° C. to 20° C. for 10 minutes to 2 hours e. g. 20-45 minutes.

Antigen specific T-cells usually occur at very low frequencies. The low frequency of antigen specific T-cells makes these cells difficult targets for immunomagnetic iso-lation. In addition, the binding affinity between MHC-peptide complexes and the TCR is relatively low (in the order of 10 uM) compared to the binding affinity of antibodies and their target molecules (in the range of 10-0.1 nM). The low binding affinity of the MHC-peptide complexes can be compensated by introducing multiple binding sites between the solid phase used for cell isolation and the TCR on the T-cell surface. In the present invention, this is achieved by conjugating multiple MHC-peptide complexes to poly-ligand molecules. By coupling multiple such poly-ligand molecules to the solid phase, the avidity of binding to T-cells is increased to facilitate efficient isolation of the target T-cells.

Efficient isolation of antigen specific T-cells can be achieved by coupling the MHC-conjugated polymer molecules to the beads or particles prior to the cell isolation step, or indirectly by mixing soluble MHC multimers with the sample, before introducing beads or particles which have a binding affinity for the a part of the MHC molecule construct.

Following isolation, the T-cells can be cultivated under conditions that facilitate proliferation and expansion.

T-cell activation and proliferation depends, as described above, on two different signals delivered by antigen presenting cells. The first signal is the antigen specific signal delivered by MHC-peptide complexes to the TCR. The second signal is an antigen unspecific signal delivered by co-stimulatory molecules on the antigen presenting cells. Such co-stimulatory molecules include B7-1 and B7-2 which interact with interact with the CD28 molecule on T-cells, and other co-stimulatory molecules such as LFA-3, CD3, CD40, ICOS, NKG2D, OX40 and CD137.

As mentioned above, administration of the expanded cells can be by any convenient route. Typically, the number of cell for each administration should be about 109-10 cells. The cells can suitably be administered in a volume of from about 50 ml to about 1 litre, such as about 50 ml to about 500 ml, about 50 ml to about 250 ml, about 50 ml to about 150 ml, or about 50 ml to about 100 ml, depending on the route of administration and the disease to be treated. The cells can be administered in a single dose or as several doses. In certain cases, administration only once can be sufficient. In general, several doses should be given with intervals of a day, a week, two weeks, a month, or several months, etc. For example, a single dose can be given once, or a dose can be given as a primer, followed by one or more administration, or a continuous administration regime like up to four doses per week, followed by one month without administrations, followed by up to four doses per week (sometimes with increasing or decreasing amount of the cells), etc. Optionally different adjuvants or combinations of adjuvants can be used in the different administrations. These are all examples, and the optimal administration regime depends on the cells in question and several other factors. The person skilled in the art will readily know how to optimise this. Of course, other medicaments can be administered simultaneously in order to enhance or support the treatment.

In particular, a MHC molecule construct as defined herein, or one or more MHC multimers without MHC molecules attached, but with biologically active molecules attached can be administered together with the therapeutic composition to stimulate, up-regulate, down-regulate, inhibit or enhance other MHC recognising cell clones than the MHC recognising cell clones addressed by the MHC molecule construct of the composition. Such constructs can optionally be immobilised onto biodegradable particles.

Containers for mixing and storage of the therapeutic composition of the invention can be made of glass or various polymeric materials. The containers chosen should essentially not affect the product stored. The containers can suitably be ampoules or capped vials for mono- or multi-dosage.

In a special aspect, the present invention relates to uses of MHC molecules in histological methods, and uses of MHC molecules in cytological methods.

Such methods are sample-mounted methods.

This aspect of the invention is based on the surprising recognition that although MHC molecules or multimers of MHC molecules per se can not be very suited for some applications due to low intrinsic affinity, they perform unexpectedly well in sample-mounted applications.

Thus, in one embodiment, the present invention relates to the use of MHC molecules in a method for determining the presence of MHC recognising cells in a sample, wherein the MHC recognising cells of the sample are mounted on a support.

Such methods are a powerful tool in diagnosing various diseases. Establishing a diagnosis is important in several ways. A diagnosis gives information about the disease, thus the patient can be offered suitable treatment. Also, establishing a more specific diagnosis can give important information about a subtype of a disease for which a particular treatment will be beneficial (i. e. various subtypes of diseases can involve display of different peptides which are recognised by MHC recognising cells, and thus treatment can be targeted effectively against a particular subtype). In this way, it can also be possible to gain information about aberrant cells, which emerge through the progress of the disease or condition, or to investigate whether and how cell specificity is affected. The binding of the MHC molecule makes possible these options, since the binding is indicative for the presence of the MHC recognising cells in the sample, and accordingly the presence of MHC molecules displaying the peptide.

In another embodiment, the present invention relates to the use of a MHC molecule in a method for monitoring the presence of MHC recognising cells in a sample, wherein the MHC recognising cells of the sample are mounted on a support.

Such methods are a powerful tool in monitoring the progress of a disease, e. g. to closely follow the effect of a treatment. The method can i. a. be used to manage or control the disease in a better way, to ensure the patient receives the optimum treatment, to adjust the treatment, to confirm remission or recurrence, and to ensure the patient is not treated with a medicament which does not cure or alleviate the disease. In this way, it can also be possible to monitor aberrant cells which emerge through the progress of the disease or condition, or to investigate whether and how T-cell specificity is affected. The binding of the MHC molecule makes possible these options, since the binding is indicative for the presence of the MHC recognising cells in the sample, and accordingly the presence of MHC molecules displaying the peptide.

In yet another embodiment, the present invention relates to the use of a MHC molecule in a method for determining the status of a disease involving MHC recognising cells, in which method the MHC recognising cells of the sample are mounted on a support.

Such methods are a valuable tool in managing and controlling various diseases. A disease could, e. g. change from stage to another, and thus it is important to be able to determine the disease status. In this way, it can also be possible to gain information about aberrant cells which emerge through the progress of the disease or condition, or to investigate whether and how cell specificity is affected, thereby determining the status of a disease or condition. The binding of the MHC molecule makes possible these options, since the binding is indicative for the presence of the MHC recognising cells in the sample, and accordingly the presence of MHC molecules displaying the peptide.

In still another embodiment, the present invention relates to the use of a MHC molecule in a method for establishing a prognosis of a disease involving MHC recognising cells, in which method the MHC recognising cells of the sample are mounted on a support.

Such methods are a valuable tool in order to manage diseases, i. a. to ensure the patient is not treated without effect, to ensure the disease is treated in the optimum way, and to predict the chances of survival or cure. In this way, it can also be possible to gain information about aberrant cells, which emerge through the progress of the disease or condition, or to investigate whether and how T-cell specificity is affected, thereby being able to establish a prognosis.

The binding of the MHC molecule makes possible these options, since the binding is indicative for the presence of the MHC recognising cells in the sample, and accordingly the presence of MHC molecules displaying the peptide.

The present invention also relates to the use of a MHC molecule in methods for the diagnosis of a disease involving MHC recognising cells, in which method the MHC recognising cells of the sample are mounted on a support.

Such diagnostic methods are a powerful tool in the diagnosis of various diseases. Establishing a diagnosis is important in several ways. A diagnosis gives information about the disease, thus the patient can be offered suitable treatment. Also, establishing a more specific diagnosis can give important information about a subtype of a disease for which a particular treatment will be beneficial (i. e. various subtypes of diseases can involve display of different peptides which are recognised by MHC recognising cells, and thus treatment can be targeted effectively against a particular subtype). Valuable information can also be obtained about aberrant cells emerging through the progress of the disease or condition as well as whether and how T-cell specificity is affected. The binding of the MHC molecule makes possible these options, since the binding is indicative for the presence of the MHC recognising cells in the sample, and accordingly the presence of MHC molecules displaying the peptide.

The present invention also relates to the use of a MHC molecule in methods of correlating cellular morphology with the presence of MHC recognising cells in a sample.

Such methods are especially valuable as applied in the field of histological methods, as the binding pattern and distribution of the MHC multimers can be observed directly. In such methods, the sample is treated so as to preserve the morphology of the individual cells of the sample. The information gained is important i. a. in diagnostic procedures as sited affected can be viewed directly.

As mentioned above, the use of the MHC molecule is in sample-mounted methods. Thus, the sample is mounted on a support. The support is selected from a solid or semi-solid surface. In particular, the support is selected from glass slides, membranes, filters, polymer slides, chamber slides, dishes, and petridishes.

The sample can suitably be selected from histological material, cytological material, primary tumours, secondary organ metastasis, fine needle aspirates, spleen tissue, bone marrow specimens, cell smears, exfoliative cytological specimens, touch preparations, oral swabs, laryngeal swabs, vaginal swabs, bronchial lavage, gastric lavage, from the umbilical cord, and from body fluids such as blood (e. g. from a peripheral blood mononuclear cell (PBMC) population isolated from blood or from other blood-derived preparations such as leukopheresis products), from sputum samples, expectorates, and bronchial aspirates. Such can be subjected to various treatments.

The MHC molecule to be used can be a MHC Class I molecule selected from the group consisting of a heavy chain, a heavy chain combined with a ß2m, a heavy chain combined with a peptide, and a heavy chains dimer with a peptide; or a MHC Class II molecule selected from the group consisting of an a/p dimer, an a/dimer with a peptide, oc/ß dimer combined through an affinity tag and a oc/ß dimer combined through an affinity tag with a peptide; or a MHC Class I like molecule or a MHC Class II like molecule.

The MHC molecule can suitably be a vertebrate MHC molecule such as a human, a murine, a rat, a porcine, a bovine or an avian molecule. The explanation to these molecules given above also applies here.

In particular, the MHC molecule to be used can be a human MHC molecule.

The MHC molecule to be used can be a peptide free MHC molecule, or a peptide filled MHC molecule.

The MHC molecule to be used can suitably be attached to a binding entity. Suitable binding entities are those described above, including streptavidin (SA) and avidin and derivatives thereof, biotin, immunoglobulins, antibodies (monoclonal, polyclonal, and recombinant), antibody fragments and derivatives thereof, leucine zipper domain of AP-1 (jun and fos), hexa-his (metal chelate moiety), hexa-hat GST (glutathione S-tranferase) glutathione affinity, Calmodulin-binding peptide (CBP), STREP-TAG®, Cellulose Binding Domain, Maltose Binding Protein, S-Peptide Tag, Chitin Binding Tag, Immuno-reactive Epitopes, Epitope Tags, E2Tag, HA Epitope Tag, Myc Epitope, FLAG Epitope, AU1 and AU5 Epitopes, Glu-Glu Epitope, KT3 Epitope, IRS Epitope, Btag Epitope, Protein Kinase-C Epitope, VSV Epitope, lectins that mediate binding to a diversity of compounds, including carbohydrates, lipids and proteins, e. g. Con A (Canavalia *ensiformis*) or WGA (wheat germ agglutinin) and tetranectin or Protein A or G' (antibody affinity). It is to be understood that the binding entity can be a combination of those mentioned above.

For enabling detection of the MHC molecule, the MHC molecule can further comprise a labelling compound. The labelling compound is suitably such which is directly or indirectly detectable. Thus, the labelling compound can be a fluorescent label, an enzyme label, a radioisotope, a chemiluminescent label, a bioluminescent label, a polymer, a metal particle, a hapten, an antibody, or a dye. In particular, the labelling compound can be selected from 5-(and 6)-carboxyFLUORESCEIN™, 5- or 6-carboxyFLUORESCEIN™, 6-(FLUORESCEIN™)-5-(and 6)-carboxamido hexanoic acid, FLUORESCEIN™ isothiocyanate (FITC), rhodamine, tetrameth-ylrhodamine, and dyes such as Cy2, Cy3, and CY5™, optionally substituted coumarin including AMCA, PerCP, phycobiliproteins including R-phycoerythrin (RPE) and allophycoerythrin (APC), Texas Red, Princeston Red, Green fluorescent protein (GFP) and analogues thereof, and conjugates of R-phycoerythrin or allophycoerythrin and e. g. CY5™ or Texas Red, and inorganic fluorescent labels based on semiconductor nanocrystals (like quantum dot and QDOT®^nanocrystals), and time-resolved fluorescent labels based on lanthanides like Eu3+ and Sm3+, from haptens such as DNP, biotin, and digoxiginin, or is selected from enzymatic labels such as horse radish peroxidase (HRP), alkaline phosphatase (AP), beta-galactosidase (GAL), glucose-6-phosphate dehydrogenase, beta-N-acetyl-glucosaminidase, ß-glucuronidase, invertase, Xanthine Oxidase, firefly luciferase and glucose oxidase (GO), or is selected from luminiscence labels such as luminol, isoluminol, acridinium esters, 1,2-dioxetanes and pyridopyridazines, or is selected from radioactivity labels such as incorporated isotopes of iodide, cobalt, selenium, tritium, and phosphor.

A labelling compound can be attached to the MHC molecule, the binding entity, or both to the MHC molecule and the binding entity.

Thus, the present invention relates to methods for detecting the presence of MHC recognising cells in a sample comprising the steps of (a) providing a sample suspected of comprising MHC recognising cells mounted on a support, (b) contacting the sample with a MHC molecule as described herein, and (c) determining any binding of the MHC molecule, which binding indicates the presence of MHC recognising cells.

The invention further relates to methods for monitoring MHC recognising cells comprising the steps of (a) providing a sample suspected comprising MHC recognising cells mounted on a support, (b) contacting the sample with a MHC molecule as described herein, and (c) determining any binding of the MHC molecule, thereby monitoring MHC recognising cells.

The invention also relates to methods for establishing a prognosis of a disease involving MHC recognising cells comprising the steps of (a) providing a sample suspected comprising MHC recognising cells mounted on a support, (b) contacting the sample with a MHC molecule as described herein, and (c) determining any binding of the MHC molecule, thereby establishing a prognosis of a disease involving MHC recognising cells.

Furthermore, the invention relates to methods for determining the status of a disease involving MHC recognising cells comprising the steps of (a) providing a sample suspected comprising MHC recognising cells mounted on a support, (b) contacting the sample with a MHC molecule as described herein, and (c) determining any binding of the MHC molecule, thereby determining the status of a disease involving molecule recognising cells.

The present invention also relates to methods of correlating cellular morphology with the presence of MHC recognising cells in a sample comprising the steps of (a) providing a sample suspected of comprising MHC recognising cells mounted on a support, (b) contacting the sample with a MHC molecule as described herein, and (c) determining any binding of the MHC molecule, thereby correlating the binding of the MHC molecule construct with the cellular morphology.

Also comprised by this invention are methods for diagnosing a disease involving MHC recognising cells, comprising the steps of (a) providing a sample suspected comprising MHC recognising cells mounted on a support, (b) contacting the sample with a MHC molecule as described herein, and (c) determining any binding of the MHC molecule, thereby diagnosing a disease involving MHC recognising cells.

The invention also relates to methods for determining the effectiveness of a medicament against a disease involving MHC recognising cells comprising the steps of (a) providing a sample from a subject receiving treatment with a medicament mounted on a support, (b) contacting the sample with a MHC molecule as described herein, and (c) determining any binding of the MHC molecule, thereby determining the effectiveness of the medicament.

The disease can be of inflammatory, auto-immune, allergic, viral, cancerous, infectious, allo- or xenogene (graft-versus-host and host-versus-graft) origin. In particular, the disease can be a chronic inflammatory bowel disease such as Crohn's disease or ulcerative colitis, sclerosis, type I diabetes, rheumatoid arthritis, psoriasis, atopic dermatitis, asthma, malignant melanoma, renal carcinoma, breast cancer, lung cancer, cancer of the uterus, cervical cancer, prostatic cancer, brain cancer, head and neck cancer, leukaemia, cutaneous lymphoma, hepatic carcinoma, colorectal cancer, bladder cancer, rejection-related disease, Graft-versus-host-related disease, or a viral disease associated with hepatitis, AIDS, measles, pox, chicken pox, rubella or herpes.

The sample to be subjected to the methods of the invention can suitably be selected from histological material, cytological material, primary tumours, secondary organ metastasis, fine needle aspirates, spleen tissue, bone marrow specimens, cell smears, exfoliative cytological specimens, touch preparations, oral swabs, laryngeal swabs, vaginal swabs, bronchial lavage, gastric lavage, from the umbilical cord, and from body fluids such as blood (e. g. from a peripheral blood mononuclear cell (PBMC) population isolated from blood or from other blood-derived preparations such as leukopheresis products), from sputum samples, expectorates, and bronchial aspirates. Such can be subjected to various treatments.

Definitions

As used everywhere herein, the term "a", "an" or "the" is meant to be one or more, i. e. at least one.

Adjuvant: adjuvants are drugs that have few or no pharmacological effects by themselves, but can increase the efficacy or potency of other drugs when given at the same time. In another embodiment, an adjuvant is an agent which, while not having any specific antigenic effect in itself, can stimulate the immune system, increasing the response to a vaccine.

Agonist: agonist as used herein is a substance that binds to a specific receptor and triggers a response in the cell. It mimics the action of an endogenous ligand that binds to the same receptor.

Antagonist: antagonist as used herein is a substance that binds to a specific receptor and blocks the response in the cell. It blocks the action of an endogenous ligand that binds to the same receptor.

Antibodies: As used herein, the term "antibody" means an isolated or recombinant binding agent that comprises the necessary variable region sequences to specifically bind an antigenic epitope. Therefore, an antibody is any form of antibody or fragment thereof that exhibits the desired biological activity, e.g., binding the specific target antigen. Antibodies can derive from multiple species. For example, antibodies include rodent (such as mouse and rat), rabbit, sheep, camel, and human antibodies. Antibodies can also include chimeric antibodies, which join variable regions from one species to constant regions from another species. Likewise, antibodies can be humanized, that is constructed by recombinant DNA technology to produce immunoglobulins which have human framework regions from one species combined with complementarity determining regions (CDR's) from a another species' immunoglobulin. The antibody can be monoclonal or polyclonal. Antibodies can be divided into isotypes (IgA, IgG, IgM, IgD, IgE, IgG1, IgG2, IgG3, IgG4, IgA1, IgA2, IgM1, IgM2)

Antibodies: In another embodiment the term "antibody" refers to an intact antibody, or a fragment of an antibody that competes with the intact antibody for antigen binding. In certain embodiments, antibody fragments are produced by recombinant DNA techniques. In certain embodiments, antibody fragments are produced by enzymatic or chemical cleavage of intact antibodies. Exemplary antibody fragments include, but are not limited to, Fab, Fab', F(ab')2, Fv, and scFv. Exemplary antibody fragments also include, but are not limited to, domain antibodies, nanobodies, minibodies ((scFv-CHs)l), maxibodies ((scFv-CH$_2$—CH$_3$)$_2$), diabodies (noncovalent dimer of scFv).

Antigen presenting cell: An antigen-presenting cell (APC) as used herein is a cell that displays foreign antigen complexed with MHC on its surface.

Antigenic peptide: Any peptide molecule that is bound to or able to bind into the binding groove of either MHC I or MHC II molecules.

Aptamer: the term aptamer as used herein is defined as oligonucleic acid or peptide molecules that bind a specific target molecule. Aptamers are usually created by selecting them from a large random sequence pool, but natural aptamers also exist. Aptamers can be divided into DNA aptamers, RNA aptamers and peptide aptamers.

Avidin: Avidin as used herein is a glycoprotein found in the egg white and tissues of birds, reptiles and amphibians. It contains four identical subunits having a combined mass of 67,000-68,000 daltons. Each subunit consists of 128 amino acids and binds one molecule of biotin.

Biologically active molecule: A biologically active molecule is a molecule having itself a biological activity/effect or is able to induce a biological activity/effect when administered to a biological system. Biologically active molecules include adjuvants, immune targets (e.g. antigens), enzymes, regulators of receptor activity, receptor ligands, immune potentiators, drugs, toxins, cytotoxic molecules, co-receptors, proteins and peptides in general, sugar moieties, lipid groups, nucleic acids including siRNA, nanoparticles, small molecules.

Bioluminescent: Bioluminescence, as used herein, is the production and emission of light by a living organism as the result of a chemical reaction during which chemical energy is converted to light energy.

Biotin: Biotin, as used herein, is also known as vitamin H or B$_7$. Biotin has the chemical formula $C_{10}H_{16}N_2O_3S$.

Bispecific antibodies: The term bispecific antibodies as used herein is defined as monoclonal, preferably but not limited to human or humanized, antibodies that have binding specificities for at least two different antigens. The antibody can also be trispecific or multispecific.

Carrier: A carrier as used herein can be any type of molecule that is directly or indirectly associated with the MHC peptide complex.

Chelating chemical compound: Chelating chemical compound, as used herein, is the process of reversible binding of a ligand to a metal ion, forming a metal complex.

Chemiluminescent: Chemiluminescence, as used herein, is the emission of light (luminescence) without emission of heat as the result of a chemical reaction.

Chromophore: A chromophore, as used herein, is the part of a visibly coloured molecule responsible for light absorption over a range of wavelengths thus giving rise to the colour. By extension the term can be applied to UV or IR absorbing parts of molecules.

CMV: Cytomegalo Virus

CMV pp65: cytomegalovirus (CMV) internal matrix protein pp65

Coiled-coil polypeptide: the term coiled-coil polypeptide as used herein is a structural motif in proteins, in which 2-7 alpha-helices are coiled together like the strands of a rope Counting beads: Beads or particles that can be used as internal control beads enabling absolute cell count in a sample.

Covalent binding: The term covalent binding is used herein to describe a form of chemical bonding that is characterized by the sharing of pairs of electrons between atoms. Attraction-to-repulsion stability that forms between atoms when they share electrons is known as covalent bonding.

Crosslinking is the process of chemically joining two or more molecules by a covalent bond. Crosslinking reagents contain reactive ends to specific functional groups (primary amines, sulfhydryls, etc.) on proteins or other molecules.

Dendritic cell: The term dendritic cell as used herein is a type of immune cells. Their main function is to process antigen material and present it on the surface to other cells of the immune system, thus functioning as antigen-presenting cells.

Detection: In this invention detection means any method capable of measuring one molecule bound to another molecule. The molecules are typically proteins but can be any type of molecule.

Detection molecule: A molecule or a complex comprising a marker molecule and a labeling molecule. A detection molecule can be both in one molecule.

Dextran: the term dextran as used herein is is a complex, branched polysaccharide made of many glucose molecules joined into chains of varying lengths. The straight chain consists of $\alpha 1 \rightarrow 6$ glycosidic linkages between glucose molecules, while branches begin from $\alpha 1 \rightarrow 3$ linkages (and in some cases, $\alpha 1 \rightarrow 2$ and $\alpha 1 \rightarrow 4$ linkages as well).

Diabodies: The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites.

DNA: The term DNA (Deoxyribonucleic acid) duplex as used herein is a polymer of simple units called nucleotides, with a backbone made of sugars and phosphate atoms joined by ester bonds. Attached to each sugar is one of four types of molecules called bases.

DNA duplex: In living organisms, DNA does not usually exist as a single molecule, but instead as a tightly-associated pair of molecules. These two long strands entwine like vines, in the shape of a double helix.

Electrophilic: electrophile, as used herein, is a reagent attracted to electrons that participates in a chemical reaction by accepting an electron pair in order to bond to a nucleophile.

Enzyme label: enzyme labelling, as used herein, involves a detection method comprising a reaction catalysed by an enzyme.

Epitope-focused antibody: Antibodies also include epitope-focused antibodies, which have at least one minimal essential binding specificity determinant from a heavy chain or light chain CDR3 from a reference antibody, methods for making such epitope-focused antibodies are described in U.S. patent application Ser. No. 11/040,159, which is incorporated herein by reference in its entirety.

Fluorescent: the term fluorescent as used herein is to have the ability to emit light of a certain wavelength when activated by light of another wavelength.

Fluorochromes: fluorochrome, as used herein, is any fluorescent compound used as a dye to mark e.g. protein with a fluorescent label.

Fluorophore: A fluorophore, as used herein, is a component of a molecule which causes a molecule to be fluorescent.

Folding: In this invention folding means in vitro or in vivo folding of proteins in a tertiary structure.

Fusion antibody: As used herein, the term "fusion antibody" refers to a molecule in which an antibody is fused to a non-antibody polypeptide at the N- or C-terminus of the antibody polypeptide.

Glycosylated: Glycosylation, as used herein, is the process or result of addition of saccharides to proteins and lipids.

Hapten: A residue on a molecule for which there is a specific molecule that can bind, e.g. an antibody.

Heteroconjugate antibodies are composed of two covalently joined antibodies. Such antibodies have, for example, been proposed to target immune system cells to unwanted cells.

IgG: IgG as used herein is a monomeric immunoglobulin, built of two heavy chains and two light chains. Each molecule has two antigen binding sites.

Isolated antibody: The term "isolated" antibody as used herein is an antibody which has been identified and separated and/or recovered from a component of its natural environment.

Immuno active molecule: By the term "immuno active molecule" is meant any compound that as an active part of a MHC multimer, a solution containing MHC multimers, a therapeutics or a vaccines is modulating the immuno-activity of the MHC multimer/the solution of MHC multimer/the therapeutic and/or the vaccine itself or is modulating the immune system as such. Included in Immuno active molecules are Biological active molecules.

Immunoconjugates: The invention also pertains to immunoconjugates comprising an antibody conjugated to a cytotoxic agent such as a chemotherapeutic agent, toxin (e.g., an enzymatically active toxin of bacterial, fungal, plant, or animal origin, or fragments thereof), or a radioactive isotope (i.e., a radioconjugate). Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. A variety of radionuclides are available for the production of radioconjugated antibodies. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene).

Influenza MP1: influenza A matrix protein 1

Ionophore: ionophore, as used herein, is a lipid-soluble molecule usually synthesized by microorganisms capable of transporting ions.

Label: Label herein is used interchangeable with labeling molecule. Label as described herein is an identifiable substance that is detectable in an assay and that can be attached to a molecule creating a labeled molecule. The behavior of the labeled molecule can then be studied.

Labelling: Labelling herein means attachment of a label to a molecule.

Lanthanide: lanthanide, as used herein, series comprises the 15 elements with atomic numbers 57 through 71, from lanthanum to lutetium.

Linker molecule: Linker molecule and linker is used interchangeable herein. A linker molecule is a molecule that covalently or non-covalently connects two or more molecules, thereby creating a larger complex consisting of all molecules including the linker molecule.

Liposomes: The term liposome as used herein is defined as a spherical vesicle with a membrane composed of a phospholipid and cholesterol bilayer. Liposomes, usually but not by definition, contain a core of aqueous solution; lipid spheres that contain no aqueous material are called micelles.

Immunoliposomes: The antibodies disclosed herein can also be formulated as immunoliposomes. Liposomes comprising the antibody are prepared by methods known in the art, such as described in Epstein et al., Proc. Natl. Acad. Sci. USA 82: 3688 (1985); Hwang et al., Proc. Natl. Acad. Sci. USA 77: 4030 (1980); and U.S. Pat. Nos. 4,485,045 and 4,544,545. Particularly useful liposomes can be generated by the reverse-phase evaporation method with a lipid composition comprising phosphatidylcholine, cholesterol, and PEG-derivatized phosphatidylethanolamine (PEG-PE).

Marker: Marker is used interchangeably with marker molecule herein. A marker is molecule that specifically associates covalently or non-covalently with a molecule belonging to or associated with an entity.

MHC: Denotes the major histocompatibility complex.

A "MHC Class I molecule" as used everywhere herein is defined as a molecule which comprises 1-3 subunits, including a heavy chain, a heavy chain combined with a light chain (beta$_2$m), a heavy chain combined with a light chain (beta$_2$m) through a flexible linker, a heavy chain combined with a peptide, a heavy chain combined with a peptide through a flexible linker, a heavy chain/beta$_2$m dimer combined with a peptide, and a heavy chain/beta$_2$m dimer with a peptide through a flexible linker to the heavy or light chain. The MHC molecule chain can be changed by substitution of single or by cohorts of native amino acids or by inserts, or deletions to enhance or impair the functions attributed to said molecule. By example, it has been shown that substitution of XX with YY in position nn of human beta$_2$m enhance the biochemical stability of MHC Class I molecule complexes and thus can lead to more efficient antigen presentation of subdominant peptide epitopes.

MHC complex: MHC complex is herein used interchangeably with MHC-peptide complex, unless it is specified that the MHC complex is empty, i.e. is not complexed with peptide.

MHC Class I like molecules (including non-classical MHC Class I molecules) include CD1d, HLA E, HLA G, HLA F, HLA H, MICA, MIC B, ULBP-1, ULBP-2, and ULBP-3.

A "MHC Class II molecule" as used everywhere herein is defined as a molecule which comprises 2-3 subunits including an alpha-chain and a beta-chain (alpha/beta-dimer), an alpha/beta dimer with a peptide, and an alpha/beta dimer combined with a peptide through a flexible linker to the alpha or beta chain, an alpha/beta dimer combined through an interaction by affinity tags e.g. jun-fos, an alpha/beta dimer combined through an interaction by affinity tags e.g. jun-fos and further combined with a peptide through a flexible linker to the alpha or beta chain. The MHC molecule chains can be changed by substitution of single or by cohorts of native amino acids or by inserts, or deletions to enhance or impair the functions attributed to said molecule. Under circumstances where the alpha-chain and beta-chain have been fused, to form one subunit, the "MHC Class II molecule" can comprise only 1 subunit.

MHC Class II like molecules (including non-classical MHC Class II molecules) include HLA DM, HLA DO, I-A beta2, and I-E beta2.

"MHC complexes" and "MHC constructs" are used interchangably herein.

"MHC protein" and "MHC molecule" are used interchangably herein. Accordingly, a functional MHC peptide complex comprises a MHC protein or MHC molecule associated with a peptide to be presented for cells or binding partners having an affinity for said peptide.

By the terms "MHC complexes" and "MHC multimers" as used herein are meant such complexes and multimers thereof, which are capable of performing at least one of the functions attributed to said complex or multimer. The terms include both classical and non-classical MHC complexes. The meaning of "classical" and "non-classical" in connection with MHC complexes is well known to the person skilled in the art. Non-classical MHC complexes are subgroups of MHC-like complexes. The term "MHC complex" includes MHC Class I molecules, MHC Class II molecules, as well as MHC-like molecules (both Class I and Class II), including the subgroup non-classical MHC Class I and Class II molecules.

The MHC molecule can suitably be a vertebrate MHC molecule such as a human, a mouse, a rat, a porcine, a bovine or an avian MHC molecule. Such MHC complexes from different species have different names. E.g. in humans, MHC complexes are denoted HLA. The person skilled in the art will readily know the name of the MHC complexes from various species.

MHC multimer: The terms MHC multimer, MHCmer and MHC'mer herein are used interchangeably, to denote a complex comprising more than one MHC-peptide complexes, held together by covalent or non-covalent bonds.

MHC molecule: Herein denotes the empty MHC protein, i.e. MHC protein not complexed with antigenic peptide.

MHC multimer: The terms MHC multimer, MHCmer and MHC'mer herein are used interchangeably, to denote a complex comprising more than one MHC-peptide complexes, held together by covalent or non-covalent bonds.

Monoclonal antibodies: Monoclonal antibodies, as used herein, are antibodies that are identical because they were produced by one type of immune cell and are all clones of a single parenT-cell.

Monovalent antibodies: The antibodies in the present invention can be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking. In vitro methods are also suitable for preparing monovalent antibodies. Digestion of antibodies to produce fragments thereof, particularly, Fab fragments, can be accomplished using routine techniques known in the art.

Multimerization domain: A multimerization domain is a molecule, a complex of molecules, or a solid support, to which one or more MHC or MHC-peptide complexes can be attached. Multimerization domains thus include IgG, streptavidin, micelles, cells, polymers, beads and other types of solid support, and small organic molecules carrying reactive groups or carrying chemical motifs that can bind MHC complexes.

Nanobodies: Nanobodies as used herein is a type of antibodies derived from camels, and are much smaller than traditional antibodies.

Neutralizing antibodies: neutralizing antibodies as used herein is an antibody which, on mixture with the homologous infectious agent, reduces the infectious titer NMR: NMR (Nuclear magnetic resonance), as used herein, is a physical phenomenon based upon the quantum mechanical magnetic properties of an atom's nucleus. NMR refers to a family of scientific methods that exploit nuclear magnetic resonance to study molecules.

Non-covalent: The term noncovalent bond as used herein is a type of chemical bond, that does not involve the sharing of pairs of electrons, but rather involves more dispersed variations of electromagnetic interactions.

Nucleic acid duplex: A nucleic acid is a complex, high-molecular-weight biochemical macromolecule composed of nucleotide chains that convey genetic information. The most common nucleic acids are deoxyribonucleic acid (DNA) and ribonucleic acid (RNA).

Nucleophilic: a nucleophile, as used herein, is a reagent that forms a chemical bond to its reaction partner (the electrophile) by donating both bonding electrons.

"One or more" as used everywhere herein is intended to include one and a plurality.

A "peptide free MHC Class I molecule" as used everywhere herein is meant to be a MHC Class I molecule as defined above with no peptide.

A "peptide free MHC Class II molecule" as used everywhere herein is meant to be a MHC Class II molecule as defined above with no peptide.

Such peptide free MHC Class I and II molecules are also called "empty" MHC Class I and II molecules.

Pegylated: pegylated, as used herein, is conjugation of Polyethylene glycol (PEG) to proteins.

Phosphorylated; phosphorylated, as used herein, is is the addition of a phosphate ($PO_4$) group to a protein molecule or a small molecule.

"A plurality" as used everywhere herein should be interpreted as two or more.

PNA: PNA (Peptide nucleic acid) as used herein is a chemical similar to DNA or RNA. PNA is not known to occur naturally in existing life on Earth but is artificially synthesized and used in some biological research and medical treatments. DNA and RNA have a deoxyribose and ribose sugar backbone, respectively, whereas PNA's backbone is composed of repeating N-(2-aminoethyl)-glycine units linked by peptide bonds. The various purine and pyrimidine bases are linked to the backbone by methylene carbonyl bonds. PNAs are depicted like peptides, with the N-terminus at the first (left) position and the C-terminus at the right.

Polyclonal antibodies: a polyclonal antibody as used herein is an antibody that is derived from different B-cell lines. They are a mixture of immunoglobulin molecules secreted against a specific antigen, each recognising a different epitope.

Polymer: the term polymer as used herein is defined as a compound composed of repeating structural units, or monomers, connected by covalent chemical bonds.

Polypeptide: Peptides are the family of short molecules formed from the linking, in a defined order, of various α-amino acids. The link between one amino acid residue and the next is an amide bond and is sometimes referred to as a peptide bond. Longer peptides are referred to as proteins or polypeptide.

Polysaccharide: The term polysaccharide as used herein is defined as polymers made up of many monosaccharides joined together by glycosidic linkages.

Radicals: radicals, as used herein, are atomic or molecular species with unpaired electrons on an otherwise open shell configuration. These unpaired electrons are usually highly reactive, so radicals are likely to take part in chemical reactions.

Radioactivity: Radioactive decay is the process in which an unstable atomic nucleus loses energy by emitting radiation in the form of particles or electromagnetic waves.

RNA: RNA (Ribonucleic acid) as used herein is a nucleic acid polymer consisting of nucleotide monomers that plays several important roles in the processes that translate genetic information from deoxyribonucleic acid (DNA) into protein products Scaffold: A scaffold is typically an organic molecule carrying reactive groups, capable of reacting with reactive groups on a MHC-peptide complex. Particularly small organic molecules of cyclic structure (e.g. functionalized cycloalkanes or functionalized aromatic ring structures) are termed scaffolds.

Shift assay: an assay detecting a shift in size of a given molecule upon binding another molecule.

Staining: In this invention staining means specific or unspecific labelling of cells by binding labeled molecules to defined proteins or other structures on the surface of cells or inside cells. The cells are either in suspension or part of a tissue. The labeled molecules can be MHC multimers, antibodies or similar molecules capable of binding specific structures on the surface of cells.

Streptavidin: Streptavidin as used herein is a tetrameric protein purified from the bacterium *Streptomyces avidinii*. Streptavidin is widely use in molecular biology through its extraordinarily strong affinity for biotin.

Sugar: Sugars as used herein include monosaccharides, disaccharides, trisaccharides and the oligosaccharides— comprising 1, 2, 3, and 4 or more monosaccharide units respectively.

EXAMPLES

Example 1

This example describes how to make a MHC class I complex with a peptide in the peptide binding-groove. The MHC-complex in this example consisted of light chain β2m, the MHC class I Heavy Chain allele HLA-A*0201 (a truncated version in which the intracellular and transmembrane domains have been deleted) and the peptide QLFEELQEL (SEQ ID NO:8).

MHC I-complexes consists of 3 components; Light Chain (β2m), Heavy Chain and a peptide of typically 8-10 amino acids. In this example MHC-complexes was generated by in vitro refolding of heavy chain, β2m and peptide in a buffer comprising reduced and oxidized glutathione. By incubation in this buffer a non-covalent complex between Heavy Chain, β2m and peptide was formed. Heavy chain and β2m was expressed as inclusion bodies in *E. coli* prior to in vitro refolding following standard procedures as described in Garboczi et al., (1996), Nature 384, 134-141. Following refolding the MHC complexes was biotinylated using BirA enzyme able to biotinylate a specific amino acid residue in a recognition sequence fused to the C-terminal of the Heavy Chain by genetic fusion. Monomer MHC complexes was then purified by size exclusion chromatography.

1. 200 ml of refolding buffer (100 mM Tris, 400 mM L-arginin-HCL, 2 mM NaEDTA, 0.5 mM oxidized Gluthathione, 5 mM reduced Glutathione, pH 8.0) was supplied with protease inhibitors PMSF (phenylmethylsulphonyl fluoride), Pepstatin A and Leupeptin (to a final concentration of 1 mM, 1 mg/l and 1 mg/l, respectively). The refolding buffer was placed at 10° C. on a stirrer.

2. 12 mg of peptide QLFEELQEL (SEQ ID NO:8) was dissolved in DMSO or another suitable solvent (300-500 µl), and added drop-wise to the refolding buffer at vigorous stirring.

3. 4.4 mg of human Light Chain β2m was added drop-wise to the refolding buffer at vigorous stirring.

4. 6.2 mg of Heavy Chain HLA-A*0201 (supplied with DTT to a concentration of 0.1 mM) was added drop-wise to the refolding buffer at vigorous stirring.

5. The folding reaction was placed at 10° C. at slow stirring for 4-8 hours.

6. After 4-8 hours, step 3 and 4 was repeated and the folding reaction is placed at 10° C. at slow stirring O/N.

7. Step 3 and 4 was repeated, and the folding reaction is placed at 10° C. at slow stirring for 6-8 hours.

Optionally, steps 5-7 can be done in less time, e.g. a total of 0.5-5 hours.

8. After 6-8 hours the folding reaction was filtrated through a 0.2 m filter to remove aggregates.

9. The folding reaction was concentrated O/N at 10° C. shaking gently in a suitable concentrator with a 5000 mw cut-off filter. The folding reaction was concentrated to approximately 5-10 ml. (Optionally the filtrate can be stored at 4° C. and reused for another folding with the same peptide and heavy chain.)

10. The concentrated folding reaction was buffer-exchanged at least 8 times, into a MHC-buffer (20 mM Tris-HCl, 50 mM NaCl, pH 8.0) and concentrated (at 10° C. in a suitable concentrator with a 5000 mw cut-off filter) down to approximately 1 ml.

11. The heavy chain part of the MHC-complex was biotinylated by mixing the following components: approximately 1000 µl folded MHC-complex, 100 µl each of Biomix-A, Biomix-B and d-Biotin (all 3 from Biotin Protein Ligase Kit from Avidity, 10 µl birA enzyme (3 mg/ml, from Biotin Protein Ligase Kit from Avidity, 0.5 µl Pepstatin A (2 mg/ml) and 0.5 µl Leupeptin (2 mg/ml). The above was gently mixed and incubated O/N at room temperature.

12. The biotinylated and folded MHC-complex solution was centrifuged for 5 min. at 1700×g, room temperature.

13. Correctly folded MHC-complex was separated and purified from excess biotin, excess β2m, excess heavy chain and aggregates thereof, by size exclusion chromatography on a column that separates proteins in the 10-100 kDa range. Correctly folded monomer MHC-complex was eluted with a MHC-buffer (20 mM Tris-HCl, 50 mM NaCl, pH 8.0). The elution profile consisted of 4 peaks, corresponding to aggregated Heavy Chain, correctly folded monomer MHC-complex, β2m and excess biotin and peptide (See FIG. 3).

14. Fractions comprising the folded MHC-complex were pooled and concentrated to approximately 1 ml in a suitable concentrator with a 5000 mw cut-off filter. The protein-concentration was estimated from its absorption at 280 nm.

15. Folded MHC-complex can optionally be stored at −170° C. before further use.

16. The grade of biotinylation was analyzed by a SDS PAGE SHIFT-assay with Streptavidin (FIG. 4) and correct folding was confirmed by ELISA, using the antibody W6/32 that recognizes correctly folded MHC-peptide complex as described elsewhere herein.

The above procedure can be used for folding any MHC I complexes consisting of any β2m, any heavy chain and any peptide approx. 8-11 amino acids long. Either of the components can be truncated or otherwise modified. The above procedure can also be used for generation of "empty" MHC I complexes consisting of β2m and heavy chain without peptide.

Example 2

This example describes how to generate soluble biotinylated MHC II complexes using a baculovirus expression system, where the MHC II complex was DR4 consisting of the α-chain DRA1*0101 and the β-chain DRB1*0401 as described by Svendsen et al., (2004), J. Immunol. 173(11): 7037-45. Briefly, The hydrophobic transmembrane regions of the DRα and DRβ chains of DR4 were replaced by leucine zipper dimerization domains from the transcription factors Fos and Jun to promote DR α/β assembly. This was done by ligating cytoplasmic cDNA sequences of DRA1*0101 and DRB1*0401 to fos- and jun-encoding sequences. A birA site GLNDIFEAQKIEWH (SEQ ID NO:20) was added to the 3' end of the DRA1*0101-fos template. Covalently bound peptide AGFKGEQGPKGEP (SEQ ID NO:21) derived from collagen II amino acid 261-273 were genetically attached by a flexible linker peptide to the N terminus of the DRβ-chain. Finally, the modified DRA1*0101 and DRB1*0401 inserts were cloned into the expression vector pAcAb3. The pAcAB3-DRA1*0101/DRB1*0401 µlasmids were cotransfected with linearized baculovirus DNA (BD Pharmingen; BaculoGold kit) into Sf9 insecT-cells, according to the manufacturer's instructions. Following two rounds of plaque purification, clonal virus isolates were further amplified three times before preparation of high-titervirus ($10^8$-$10^{10}$/ml). These stocks were used to infect High Five or serum-free Sf21 insecT-cells (Invitrogen Life Technologies, Carlsbad, CA) for protein production. Spinner cultures (2-3×$10^6$ cells/ml) were infected at a multiplicity of infection of 1-3 in a volume of 150 ml per 2 L spinner flask. Supernatants were harvested and proteinase inhibitor tablets (Roche, Basel, Switzerland) were added before affinity purification on MiniLeak-Low columns (Kem-En-Tec) coupled with the anti-HLA-DR monoclonal antibody L243. HLA-DR4 complexes were eluted with diethylamine (pH 11) into neutralization buffer (2 M Tris, pH 6.5) and immediately buffer exchanged and concentrated in PBS, 0.01% NaN₃, using Millipore (Bedford, MA) concentrators. The purity of protein was confirmed by SDS-PAGE. The purified DR4 complexes were biotinylated in vitro as described for MHC I complexes elsewhere herein. These complexes can now be used for coupling to any dimerization domain, e.g. divynylsulfone activated dextran 270coupled with SA and a fluorochrome.

Example 3

This example describes how to generate empty biotinylated MHC II complexes using a baculovirus expression system, where the MHC II complex consists of any α-chain and any β-chain, including truncated and otherwise modified versions of the two. Briefly, The hydrophobic transmembrane regions of the DRα and DRβ chains of MHC II are replaced by leucine zipper dimerization domains from the transcription factors Fos and Jun to promote DR α/β assembly. This is done by ligating cytoplasmic cDNA sequences of DRα and DRβ to fos- and jun-encoding sequences. A birA site GLNDIFEAQKIEWH (SEQ ID NO:20) is added to the 3' end of either the DRa-fosl DRα-jun or the DRp-jun/DRβ-fos template. The modified DRα and DRβ inserts is cloned into the expression vector pAcAb3 and cotransfected with linearized baculovirus DNA into Sf9 insecT-cells, according to the manufacturer's instructions. Following rounds of plaque purification, clonal virus isolates is further amplified before preparation of high-titer virus. These stocks are used to infect High Five or serum-free Sf21 insecT-cells (Invitrogen Life Technologies, Carlsbad, CA) for protein production, e.g. as Spinner cultures. Supernatants are harvested and proteinase inhibitors added before affinity purification, e.g. using MiniLeak-Low columns (Kem-En-Tec) coupled with anti-MHC II antibody. The purified MHC II complexes is biotinylated in vitro as described for MHC I complexes elsewhere herein. These biotinylated MHC II complexes can now be used for coupling to any dimerization domain, e.g. divinylsulfone activated dextran 270coupled with SA and a fluorochrome.

Example 4

This example describes how to generate biotinylated MHC II complexes using a cell based protein expression system, where the MHC II complex consist of any α-chain and any β-chain, including truncated and otherwise modified versions of the two. The MHC II complex can also have a peptide bound in the peptide binding cleft.

The hydrophobic transmembrane regions of the MHC II α-chain and MHC II β-chain are replaced by leucine zipper dimerization domains from the transcription factors Fos and Jun to promote α/β chain assembly. This is done by ligating cytoplasmic cDNA sequences of α-chain and β-chain to fos- and jun-encoding sequences. A birA site GLNDIFEAQK-IEWH (SEQ ID NO:20) is added to the 3' end of the DRα-fos template. Optionally covalently bound peptide is genetically attached by a flexible linker peptide to the N terminus of the DRβ-chain. The modified DRα and DRβ inserts is cloned into a suitable expression vector and transfected into a cell line capable of protein expression, e.g. insecT-cells, CHO cells or similar. Transfected cells are grown in culture, supernatants are harvested and proteinase inhibitors added before affinity purification, e.g. using a MiniLeak-Low columns (Kem-En-Tec) coupled with anti-MHC II antibody. Alternatively the expressed MHC II complexes can be purified by anion- or cation-exchange chromatography. The purified MHC II complexes is biotinylated in vitro as described for MHC I complexes elsewhere herein. These biotinylated MHC II complexes can now be used for coupling to any dimerization domain, e.g. divynylsulfone activated dextran 270coupled with SA and a fluorochrome.

Example 5

This example describes how an activated divinylsylfone-dextran (270 kDa)(VS-dex270) was coupled with streptavidin (SA) and Allophycocyanin (APC).
1. Streptavidin (approx. 100 mg SA/ml in 10 mM HEPES, 0,1M NaCl, pH 7.85) was dialysed with gentle stirring for 2 days against 10 mM HEPES, 0.1M NaCl, pH 7.85 (20 fold excess volume) at 2-8° C. with 1 buffer change/day.
2. 5 ml of APC from a homogen suspension (approx. 10 mg/ml) was centrifuged 40 min. at 3000 rpm. The supernatant was discharged and the precipitate dissolved in 5 ml of 10 mM HEPES, 0,1M NaCl, pH 7.85. This APC solution was dialysed with gentle stirring in the dark for 2 days against 10 mM HEPES, 0.1M NaCl, pH 7.85 (20 fold excess volume) at 2-8° C. with 1 buffer change/day.
3. The APC-solution was concentrated to 1 ml and the concentration measured to 47 g/L at UV 650 nm. The A650/A278-ratio was measured to 4.2.
4. The SA-solution was filtrated through a 0.45 m filter and the protein concentration was measured to 61.8 g SA/L at UV 278 nm.
5. Conjugation: The reagents was mixed to a total volume of 500 μl in the following order with 8.1 mol SA/mol Dex and 27 mol APC/mol Dex.:
   a) 90 μl water
   b) 160 μl activated VS-dex270
   c) 23 μl SA (61.8 g/L)~8.1 equivalents,
   d) 177 μl APC (47 g/L)~27 equivalents,
   e) 50 μl of 100 mM HEPES, 1M NaCl, pH 8
   The reaction was placed in a water bath with stirring at 30° C. in the dark for 18 hours.
6. The coupling was stopped by adding 50 μl 0.1M ethanolamine, pH 8.0.
7. The conjugate was purified on a Sephacryl S-200 column with 10 mM HEPES, 0.1M NaCl buffer, pH 7.2.
8. 3 peaks were collected (peak 1: APC-SA-dex270; peak 2: Free APC; peak 3: Free SA). Volume, UV A650 and UV A278 were measured.
9. The concentration of dextran270, APC/Dex and SA/Dex were calculated to $22.4 \times 10^{-8}$ M; 3.48 and 9.54 respectively.
10. The conjugate were added $NaN_3$ and BSA to a final concentration of 15 mM and 1% respectively. The volume was adjusted with 10 mM HEPES, 0.1M NaCl, pH 7.2 to a final concentration of $16 \times 10^{-8}$ M Dex270.
11. The conjugate were kept at 2-8° C. in dark until further use.

Example 6

This example describes how an activated divinylsylfone-dextran(270 kDa)(VS-dex270) was coupled with streptavidin (SA) and R-phycoerythrin (RPE).

The coupling procedure described for coupling of SA and APC to VS-dex270 (as described elsewhere herein) were followed with the exception that APC were replaced with RPE.

Example 7

This example describes how to couple an empty MHC or a MHC-complex to a dextran multimerization domain, to generate a MHC-dextramer. The MHC-dextramer in this example consisted of APC-streptavidin (APC-SA)-conjugated 270kDA dextran and a biotinylated, folded MHC-complex composed of β2m, HLA-A*0201 heavy chain and the peptide NLVPMVATV (SEQ ID NO:9).

The APC-SA conjugated 270kDA dextran contained 3,7 molecules of SA per dextran (each SA can bind 3 MHC-complexes) and the concentration was $16 \times 10^{-8}$ M. The concentration of the HLA-A*0201/NLVPMVATV (SEQ ID NO:9)-complex was 4 mg/ml (1 μg=20,663 μmol). The molecular concentration of the MHC-complex was $8,27 \times 10^{-5}$M.

The MHC-complex was attached to the dextran by a non-covalent Biotin-Streptavidin interaction between the biotinylated Heavy Chain part of the MHC-complex and the SA, conjugated to dextran.

Here follows a protocol for how to produce 1000 μl of a MHC-dextramer solution with a final concentration of approximately $32 \times 10^{-9}$M:

1. 200 μL 270 kDA vinylsulfone-activated dextran, corresponding to $3,2 \times 10^{-11}$ mol, and 4 μl MHC-complex, corresponding to $3,55 \times 10^{-10}$ mol was mixed and incubated at room temperature in the dark for 30 min.
2. A buffer of 0,05M Tris-HCl, 15 mM NaN₃, 1% BSA, pH 7,2 was added to a total volume of 1000 μl.
3. The resulting MHC-dextramer preparation can now be used in flow cytometry experiments.

Example 8

This example describes how the quality of a MHC multimer can be tested. The MHC multimer is in this example a MHC-dextramer, and the test involves specific binding of the MHC-dextramer to TCRs immobilized on beads.

Recombinant TCRs (CMV3 TCRs; Soluble CMVpp65 (NLVPMVATV (SEQ ID NO:9))-specific TCR protein) specific for the MHC-peptide complex HLA-A*0201(NLVPMVATV (SEQ ID NO:9)), where the letters in parenthesis denote the peptide complexed to the MHC-allele HLA-A*0201, were obtained from Altor Biosciences. The TCRs were dimers linked together via an IgG framework.

The purity of the TCRs were verified by SDS PAGE and was between 95-100% pure. The quality of the TCRs were verified by their ability to recognize the relevant MHC-dextramer and not irrelevant MHC dextramers in ELISA experiments (data not shown).

Carboxylate-modified beads were coupled with dimeric TCR (CMV3 TCRs; Soluble CMVpp65(NLVPMVATV)-specific TCR protein), incubated with fluorescently labeled MHC-dextramers and the extend of cell staining analysed by flow cytometry, as follows:

Immobilization of TCR on carboxylate beads:

1. $3 \times 10^9$ Carboxylate-modified beads, Duke Scientific Corporation, XPR-1536, 4 μm, lot:4394 were washed in 2×500 μl Wash buffer 1 (0,05% TETRONIC®1307, 0,1M MES-buffer (2-[N-morpholino]ethanesulfonic acid), pH 6,0), centrifuged 4 min at 15000 g, and the supernatant was discarded.
2. 125 μl EDAC/Sulfo-NHS (50 mM EDAC (1-ethyl-3-(3-dimethylaminopropyl) carbodiimide), 50 mM Sulfo-NHS, in Wash buffer 1) was added to the beads, and the suspension incubated at room temperature for 20 min.
3. Beads were washed in 2×250 μl Wash buffer 1 and centrifuged 2 min at 15000 g, and the supernatant was discarded.

4. TCR was added in various concentrations from 0 μg to 20 μg, and incubated with slow shaking overnight at 4° C.
5. Beads were centrifuged 4 min at 15000 g, and the supernatant discarded.
6. Beads were washed in 2×500 μl Wash buffer 1 and centrifuged 4 min at 1500 g, and the supernatant was discarded.
7. 125 μl 20 mM Glycin in Wash buffer 1 was added, and resuspended beads incubated for 1 hour at room temperature.
8. Beads were washed in 2×500 μl phosphate-buffered saline (PBS) pH 7.2, 0.5% TETRONIC®1307, and centrifuged 2 min at 15000 g, and the supernatant was discarded.
9. Beads were resuspended in 250 μl PBS pH 7.2, 0.05% TETRONIC®1307.

Bead concentration after resuspension was $1,2 \times 10^7$ beads/μl. Beads coated with TCR were stored at 2-8° C. until further use.

Flow cytometry analysis:

1. 20 μl beads ($1,2 \times 10^7$ beads/μl) coated with 0-20 μg TCRs, as described above were washed in 200 μl Wash buffer 2 (5% FCS, PBS, pH 7.4).
2. Beads were centrifuged 3 min at 12000 g, and the supernatant was discarded, and beads resuspended in 50 μl Wash buffer 2.
3. 10 μl MHC-dextramers were added, and samples were incubated 15 min. at room temperature in the dark.
4. Samples were washed in 1 ml Wash buffer 2, centrifuged at 300 g for 5 min. The supernatant was discarded, and pellet resuspended in 0.4 ml PBS pH 7.4, and kept at 4° C. in the dark until analysis on flow cytometer.
5. Samples were analysed by flow cytometry on a CYAN instrument.

The results are shown in FIG. 6. Beads coated with 2-20 μg TCR all showed positive staining with the specific HLA-A*0201(NLVPMVATV (SEQ ID NO:9))/RPE and not with an irrelevant HLA-A*0201(ILKEPVHGV (SEQ ID NO:10))/RPE dextramer. It can be concluded that carboxylate beads coated with dimeric TCRs can be used to test the quality of the MHC-dextramers.

Example 9

This example describes how the quality of a MHC multimer can be tested. The MHC multimer was in this example a MHC-dextramer, and the test involved specific binding of the MHC-dextramer to monomeric and dimeric TCRs immobilized to different kinds of beads.

Binding of MHC-dextramer to carboxylated beads coated with monomeric TCR:

Recombinant monomeric TCRs (CMV3 TCRs; Soluble CMVpp65(NLVPMVATV (SEQ ID NO:9))-specific TCR protein) specific for the MHC-peptide complex HLA-A*0201(NLVPMVATV (SEQ ID NO:9)), were obtained from Altor Biosciences.

The purity of the TCRs were verified by SDS PAGE. The quality of the TCRs were verified by their ability to recognize the relevant MHC-dextramer and not irrelevant MHC dextramers in ELISA experiments (data not shown).

Carboxylate modified beads were coupled with monomeric TCR (CMV3 TCRs; Soluble CMVpp65(NLVPMVATV (SEQ ID NO:9))-specific TCR protein), incubated with fluorescently labeled MHC-dextramers and the extend of cell staining analysed by flow cytometry, as described in Example 8. 0-20 g of monomeric TCRs were coupled to Carboxylate modified beads.

Flow cytometry analysis of beads coupled with 0-20 μg of monomeric TCRs showed a slightly stronger signal when stained with the relevant HLA-A*0201(NLVPMVATV (SEQ ID NO:9)) dextramer than with an irrelevant MHC-dextramer (data not shown). It might be desirable to coat the beads with larger amounts of monomeric TCRs in order to increase the signal difference between relevant and irrelevant MHC-dextramer.

Beads couples with 0 μg of monomeric TCRs showed identical signal when stained with relevant and irrelevant MHC-dextramers.

We conclude that the monomeric TCRs coupled to Carboxylate modified beads can be used as positive control for the MHC-dextramer.

Binding of MHC-dextramer to streptavidin beads coupled with biotinylated monomeric TCR: Recombinant monomeric, biotinylated TCRs (CMV3 TCRs; Soluble CMVpp65 (NLVPMVATV (SEQ ID NO:9))-specific TCR protein) specific for the MHC-peptide complex HLA-A*0201 (NLVPMVATV (SEQ ID NO:9)), were obtained from Altor Biosciences.

The purity of the TCRs were verified by SDS PAGE. The quality of the TCRs were verified by their ability to recognize the relevant MHC-dextramer and not irrelevant MHC dextramers in ELISA experiments (data not shown).

Streptavidin beads were coupled with monomeric biotinylated TCR (CMV3 TCRs; Soluble CMVpp65 (NLVPMVATV (SEQ ID NO:9))-specific TCR protein), incubated with fluorescently labeled MHC-dextramers and the extend of cell staining analysed by flow cytometry.

Immobilization of TCR on streptavidin beads:

1. $2 \times 10^6$ Streptavidin Coated Compel Magnetic beads, Bangs laboratories, CM01N, lot: 6998, were washed in $2 \times 500$ I phosphate-buffered saline (PBS) pH 7.2 centrifuged 5 min at 15000 g, and then the supernatant was discarded.
2. Beads were resuspended in 50 μl PBS pH 7.2.
3. 0-4 μg TCRs was added. Incubated at room temperature for 30 min.
4. Beads were washed in $2 \times 500$ μl PBS, pH 7.2. Centrifuged 5 min at 15000 g, and the supernatant was discarded.
5. Beads were resuspended in 100 μl PBS pH 7.2.

Bead concentration after resuspension was $2 \times 10^4$ beads/μl. Beads coated with TCRs were stored at 2-8° C. until further use.

Flow cytometry analysis:

1. 50 μl streptavidin beads (~$1 \times 10^6$ beads) coated with 0-4 μg TCRs were added 10 μl MHC-dextramers, and samples were incubated at 4° C. for 1 hour.
2. $2 \times 500$ μl PBS pH 7.2 was added, and samples were centrifuged for 5 min at 15000 g, and supernatant discarded.
3. Beads were resuspended in 500 μl PBS pH 7.2 and kept at 4° C. in the dark until analysis on a flow cytometer.
4. Samples were analysed by flow cytometry on a CYAN instrument.

Beads were stained with HLA-A*0201(NLVPMVATV (SEQ ID NO:9))-dextramers specific for the TCR and with irrelevant MHC-dextramers not able to bind the TCR. Flow cytometry analysis of beads coupled with >0 μg TCRs showed a slightly stronger signal when stained with the relevant MHC-dextramer than with the irrelevant MHC-dextramer (data not shown). The staining intensity was identical when beads conjugated with 0 μg TCR were stained with either specific or non-specific MHC-dextramers. We conclude that the monomeric biotinylated TCRs bound to streptavidin coated beads can be used as positive control for the MHC-dextramer.

Binding of MHC-dextramers toamine-modified beads coupled with monomeric or dimeric TCRs:

Recombinant monomeric or dimeric TCRs (CMV3 TCRs; Soluble

CMVpp65(NLVPMVATV (SEQ ID NO:9))-specific TCR protein) specific for the MHC-peptide complex HLA-A*0201(NLVPMVATV (SEQ ID NO:9)), were obtained from Altor Biosciences.

The purity of the TCRs were verified by SDS PAGE. The quality of the TCRs were verified by their ability to recognize the relevant MHC-dextramer and not irrelevant MHC dextramers in ELISA experiments (data not shown).

Amine-modified beads were coupled with dimeric TCR (CMV3 TCRs; Soluble CMVpp65(NLVPMVATV (SEQ ID NO:9))-specific TCR protein).

Immobilization of TCR on amine modified beads:

1. $3 \times 10^9$ Amine modified beads, Duke Scientific XPR-1536, 4 μm, lot:4393 were washed in $2 \times 500$ I phosphate-buffered saline (PBS) pH 7.5 centrifuged 4 min at 15000 g, and then the supernatant was discarded.
2. Resuspend beads in 0.3 ml PBS pH 7.5
3. 25 μl 20 mM solution of SPDP (N-Succinimidyl 3-(2-pyridyldithio) propionate) in DMSO was added to the beads, and the suspension incubated at room temperature for 30 min.
4. Beads were washed in $2 \times 1$ ml PBS comprising 1 mM EDTA, pH 7,5. Centrifuged 4 min at 15000 g, and the supernatant was discarded.
5. Resuspend beads in 0.3 ml PBS comprising 1 mM EDTA, pH 7.5.
6. 10 mg dithiothritol (DTT) was added, and suspension incubated at room temperature for 30 min.
7. Beads were washed in $2 \times 1$ ml PBS, pH 7.5. Centrifuged 4 min at 15000 g, and the supernatant was discarded.
8. Sedimented beads, were added a freshly prepared SPDP-derivatized protein prepared according to the following outlines (step 14-15):
9. Treat protein (in this example dimeric TCR) 2-5 mg/ml, in 0.1 ml carbonate buffer, pH 8 with 10 μl 20 mM solution of SPDP in DMSO at room temperature for 30 min.
10. Remove excess reagent by passing through a small desalting column in PBS pH 7.5, or by rapid dialyse against PBS pH 7.5.
11. Add >1 mg SPDS-protein per 109 beads, to the SPDP derivatized and reduced bead preparation from paragraph 13. 0-1 mg of SPDS-protein per 109 beads might be desirable.
12. Resuspend beads in the SPDP-protein solution. Incubate with slow shaking overnight at 4° C.
13. Beads were washed in $2 \times 1$ ml PBS pH 7.5. Centrifuged 4 min at 15000 g, and the supernatant was discarded.
14. Resuspend beads in 250 I PBS pH 7.5.

Bead concentration after resuspension was $1.2 \times 10^7$ beads/μl. Beads coated with TCRs were stored at 2-8° C. The quality of MHC-dextramer can now be analysed by examining the degree of binding of specific MHC-dextramer to the TCR-coated beads, versus the binding of irrelevant MHC-dextramer to the TCR coated beads.

Various reaction conditions (e.g various protein:bead ratios) and assay for optimal coupling yield can be explored. The latter can be done by using an ELISA technique (incubate protein/bead conjugated with an appropriate anti-protein enzyme conjugated (e.g. HRP Peroxidase) followed by washing and colour development with a suitable substrate (e.g. TMB/Peroxide)) or by flow cytometry (e.g. a fluorescence labelled anti-protein (in this example MHC multimer HLA-A*0201(NLVPMVATV (SEQ ID NO:9))) to assess level of covalently bound protein to amine-modified beads.

We conclude that the TCRs coupled to amine-modified beads coupled can be used as positive controls for the MHC Dextramer as described in Example 8 and 9.

Example 10

This example describes how TCR-coated beads can be used as internal, positive controls when analysing suspensions of Human Peripheral Blood Mononuclear Cells (HPBMCs), whole blood samples or any other cell sample of interest. The MHC multimer employed in this example is a MHC-dextramer.

In this example TCR-coated carboxylated beads generated as described in Example 8 were added to a sample comprising either HPBMCs or whole peripheral blood.

HPBMCs and TCR-beads were incubated with fluorescently labelled MHC-dextramers and the extent of cell staining analysed by flow cytometry according to this general staining procedure:

1. Transfer $1\text{-}3\times10^6$ µlymphoid cells (PBMC or splenocytes) to a 12×75 mm polystyrene test tube. Other cells of interest can be used. Allocate only $2\text{-}5\times10^5$ cells per tube when staining T-cell clones or cell lines due to the high frequency of antigen-specific T-cells
2. Add 2 ml 0.01 mol/L PBS comprising 5% fetal calf serum and centrifuge at 300×g for 5 minutes. Remove supernatant and resuspend cells in remaining liquid.
3. Add 10 I of MHC Dextramer and mix gently with a vortex mixer. Incubate in the dark at room temperature for 10 minutes.
4. Add an optimally titrated amount of anti-CD8 antibody conjugated with a relevant flourochrome (e.g. Dako clone DK25 for human lymphocytes or clone YTS169.4/KT15 for mouse lymphocytes). Incubate in the dark at 2-8° C. for 20 min.
5. Add 2 ml of 0.01 mol/L PBS comprising 5% fetal calf serum and centrifuge at 300× g for 5 minutes.
6. Resuspend pellet in an appropriate fluid for flow cytometry, e.g. 0.4 ml PBS. Analyse on a flow cytometer or store at 2-8° C. in the dark until analysis. Do not store longer than 2 hours before analysis.

Human peripheral whole blood and TCR-beads were incubated with fluorescently labelled MHC-dextramers and the extent of cell staining analysed by flow cytometry as follows:

1. Transfer 100 µL whole blood to a 12×75 mm polystyrene test tube.
2. Add 10 µl of MHC Dextramer and mix with a vortex mixer. Incubate in the dark at room temperature for 10 minutes.
3. Add an optimally titrated amount of anti-CD8 antibody (e.g. Dako clone DK25) conjugated with a relevant fluorochromes and mix well. Continue incubation at 2-8° C. in the dark for 20 minutes.
4. Add 2 mL EasyLyse™ working solution (Code No. S2364) and incubate for 10 minutes.

5. Centrifuge for 5 minutes at 300× g and aspirate supernatant.
6. Add 2 mL 0.01 mol/L PBS and centrifuge for 5 minutes at 300× g and aspirate supernatant.
7. Resuspend pellet in an appropriate fluid for flow cytometry, e.g. 0.4 mL PBS, and analyze on a flow cytometer or store at 2-8° C. in the dark until analysis. Do not store longer than 2 hours before analysis.

FIG. 7 shows examples of TCR-beads added into whole blood or HPBMC samples.

In both experiments it is possible, by forward- vs. side-scatter measurements, to distinguish TCR-beads from cell populations in the sample. Region R1 is TCR-beads, and region R2 is lymphocyte cell population of interest in the analysis of MHC positive T-cells.

The size and conditions of coating of beads might be optimized. The size of beads or labeling of beads (e.g. fluorescent labeling) can be optimized to allow separation of cells of interest in the sample. In this example the forward- vs. side-scatter dot plot has been used for gating of cell populations of interest. Other parameters (e.g. fluorescence intensity) for cell populations of interest can be used.

Human peripheral whole blood and other cells (e.g. HPBMCs) can be stained with MHC Dextramers simultaneously with immuno-phenotyping of relevant antigens. The staining procedure describes the use of labelled CD8 antibody together with MHC dextramers; additional antibodies for detection of other extracellular antigens can be added. Likewise, detection of intracellular antigens can be performed simultaneously with MHC-detection (for protocol, see IntraStain procedure, cat no. K2311, Dako. Additional washing step prior to IntraStain Reagent A is essential for good results using MHC Dextramers together with this IntraStain procedure).

Example 11

This example describes how TCR-coated beads can be used as internal, positive controls when analysing suspensions of Human Peripheral Blood Mononuclear Cells (HPBMCs), whole blood samples or any cell sample of interest. The MHC multimer employed in this example is a MHC-tetramer.

In this example TCR-coated beads as described in Example 8 and 9 are added to a sample comprising either HPBMCs or whole peripheral blood.

HPBMCs/whole peripheral blood and TCR-beads are incubated with fluorescently labelled MHC-tetramers and the extent of cell staining is analysed by flow cytometry according to staining procedures as described for Tetramers in the product insert by Beckman Coulter.

Results can be analysed as in Example 10, and it will be possible, by forward- vs. side-scatter measurements, to distinguish TCR-beads from cell populations in the sample.

Example 12

This example describes how TCR-coated beads can be used as internal, positive controls when analysing suspensions of Human Peripheral Blood Mononuclear Cells (HPBMCs), blood samples (red blood cell depleted) or any cell sample of interest. The MHC multimer employed in this example is a MHC-pentamer.

In this example TCR-coated beads as described in Example 8 and 9 are added to a sample comprising either HPBMCs or blood.

HPBMCs/blood sample and TCR-beads are incubated with fluorescently labelled MHC-pentamers and the extent of cell staining is analysed by flow cytometry according to staining procedures as described for Petramers in the product insert by ProImmune. Results can be analysed as in Example 10 and it will be possible, by forward- vs. side-scatter measurements, to distinguish TCR-beads from cell populations in the sample.

Example 13

This example describes how it can be examined whether a MHC multimer is correctly folded. The MHC multimer is in this example a MHC-dextramer, and the test involves specific binding of the MHC-dextramer to antibodies immobilized on beads.

Beads were coated with the antibody clone W6/32. W6/32 is an antibody recognizing all human MHC I HLA-A, B and, C alleles but only when they are in the correct conformation and properly loaded with antigenic peptide. The protocol for immobilization of proteins on carboxylate beads described in example 8 was followed. In the following these W6/32 antibody coated carboxylated beads are referred to as W/32-beads.

W6/32-beads were incubated with fluorescently labeled MHC-dextramers and the extent of cell staining analyzed by flow cytometry. The staining procedure described in example 8 was followed.

W6/32-beads incubated with correctly folded MHC-dextramers showed efficient staining. Experiments with W6/32-beads incubated with unfolded heavy chain attached to fluorescently labelled dextran, or a fluorescently labelled dextran without MHC complex attached, showed less fluorescence intensity compared to W6/32-beads incubated with correct folded MHC-dextramer.

We conclude that beads coupled with the antibody clone W6/32 can be used as positive control for all MHC alleles recognized by this antibody.

Other antibodies, or other types of molecules such as DNA aptamers recognizing correctly folded MHCs or parts of MHC could be used in similar experiments.

Example 14

This example describes how the quality of the MHC multimer can be tested. The MHC multimer in this example is a MHC-dextramer, and the test involves specific binding of the MHC-dextramer to TCRs or other MHC-recognizing molecules.

Experiments can be performed with any kind of TCRs or MHC-recognizing molecules immobilized on a bead or other solid support.

Procedures as described in examples elsewhere herein can be used, depending on the chemistry of the MHC recognizing molecules and type of solid support. Procedures for coupling of molecules and type of solid support can be chosen and optimized according to the chemistry of the molecules and solid support. Alternatively, the experiments could be performed without including solid supports, e.g. by performing immunoprecipitation of formed MHC multimer-TCR complexes.

Example 15

This example describes how the quality of a MHC multimer can be tested. The MHC multimer in this example is a MHC-dextramer, and the test involves specific binding of the MHC-dextramer to a cell line that expresses specific TCRs and display these on the cell surface.

A transfected Jurkat T-cell line (JT3A) from Altor Biosciences specific for the MHC complex HLA-A*0201 (NLVPMVATV (SEQ ID NO:9)) was evaluated as positive control for the MHC-dextramer HLA-A*0201(NLVPM-VATV (SEQ ID NO:9)). The cells were cultured and treated to express TCR just before evaluation. Under the conditions used, 20-50% of the cells were expected to express and display TCR. After stimulation the cells were incubated with fluorescently labeled MHC-dextramers and the extent of cell staining analyzed by flow cytometry, as follows:

1. JT3A cells growing in log phase were incubated at room temperature for 2-3 hours to express TCRs (The TCRs are not stable expressed at 37° C.).
2. After 3 hours cells were centrifuged for 5 min at 400 g, and the supernatant was discarded.
3. Cells were washed in PBS pH 7.4+5% FCS, and centrifuged for 5 min at 400 g. The supernatant was discarded, and cells resuspended in proper volume PBS pH 7.4+5% FCS for counting in a Burker chamber.
4. $1 \times 10^6$ cells per sample in 100 µl PBS pH 7.4+5% FCS were added to each sample tube.
5. 10 µl MHC-dextramers were added. Incubation for 30 min at 4° C. in the dark.
6. 5 µl anti-CD3 was added to each sample. Further incubation for 30 min at 4° C. in the dark.
7. Samples were washed in 2 ml PBS, centrifuged for 5 min at 300 g. Supernatant discarded and sample resuspended in 0.4 ml PBS pH 7.4.
8. Samples were kept at 2-8° C. in the dark until analysis on flow cytometer.
9. Samples were analyzed by flow cytometry on a CYAN instrument.

Data were analyzed by the Summit software. Stimulated JT3A cells were stained with the specific MHC-dextramer HLA-A*0201(NLVPMVATV (SEQ ID NO:9)) and anti-CD3. Another sample of cells were stained with the irrelevant MHC-dextramer HLA-A*0201(GILGFVFTL (SEQ ID NO:22)) and anti-CD3. The cells stained with HLA-A*0201(GILGFVFTL (SEQ ID NO:22)) had weak signals (low fluorescent intensity), and therefore regarded as the negative population. A boundary was introduced in the dot plot, to mark the negative population. Cells with fluorescence higher than the negative boundary were hereafter regarded positive. 19% and 0.25% of the cells were regarded positive when stained with the relevant and irrelevant MHC-dextramer, respectively. See table below.

| MHC-complex | Percentage of positive cells |
|---|---|
| HLA-A*0201(NLVPMVATV (SEQ ID NO: 9)) | 19% |
| HLA-A*0201(GILGFVFTL (SEQ ID NO: 22)) | 0.25% |

The results thus correlate well with the expected 20-50% HLA-A*0201 (NLVPMVATV (SEQ ID NO:9)) positive JT3A cells after stimulation. We conclude that the transfected JurkaT-cell line (JT3A) can be used as positive control for the MHC-dextramer.

Example 16

This example describes how the quality of a MHC multimer can be tested. The MHC multimer in this example is a MHC-dextramer, and the test involves specific binding of the MHC-dextramer to cell preparations expressing TCRs.

Three different peptide specific T-cell preparations of Human cytotoxic T lymphocyte lines specific for a viral peptide were incubated with fluorescently labeled MHC-dextramers and the extent of cell staining analyzed by flow cytometry. The following T-cell preparations were examined: (NLV) specific for MHC-dextramer HLA-A*0201 (NLVPMVATV (SEQ ID NO:9)), (IPSI) specific for MHC-dextramer B*3501(IPSINVHHY (SEQ ID NO:23)) and (GLC) specific for MHC-dextramer A*0201(GLCLVALM (SEQ ID NO:24)).

1. Cells were added 1 ml RPMI and then transfer to a tube with 9 ml RPMI. Cells were centrifuged for 5 min at 300 g, and the supernatant was discarded.
2. Cells were washed in 10 ml PBS pH 7.4+5% FCS, and centrifuged for 5 min at 300 g, and the supernatant was discarded.
3. $1 \times 10^6$ cells per sample in 100 µl PBS pH 7.4+5% FCS were added to sample tubes.
4. 10 µl MHC Dextramers were added, and incubated at room temperature in the dark for 10 min.
5. 5 µl anti-CD3 and anti-CD8 were added to each sample. Further incubation for 20 min at 4° C. in the dark.
6. Samples were washed in 2 ml PBS pH 7.4+5% FCS and centrifuged for 5 min at 300 g, and the supernatant was discarded.
7. Pellets were resuspended in 0.4 ml PBS pH 7.4.
8. Samples were kept in the dark at 2-8° C. until analysis on a flow cytometer.
9. Samples were analyzed by flow cytometry on a CYAN instrument.

Data were analyzed by the Summit software. The cell preparations were stained with anti-CD3, anti-CD8, the respective specific MHC-dextramer, or an irrelevant MHC-dextramer. Anti-CD3 positive cells were positively gated and anti-CD8 vs. MHC-dextramer were depicted in a dot plot. The main population of anti-CD8 positive cells stained with the irrelevant MHC-dextramer was regarded as negative, and a boundary was introduced in the dot plot to mark the negative population. Anti-CD8 positive cells with fluorescence higher than the negative boundary were regarded positive. In the NLV and IPSI cell preparations, approximately 95% of the CD8$^+$ cells were positive for the relevant MHC dextramer. 45% of the CD8$^+$ GLC cells were positive for relevant MHC Dextramers, see table below. Cell preparations were not stained by the irrelevant MHC-dextramer.

We conclude that the different peptide specific T-cell preparations can be used as positive controls for the relevant MHC-dextramer.

| Cell preparation | MHC-complex | Percentage of positive cells |
|---|---|---|
| NLV | HLA-A*0201(NLVPMVATV) (SEQ ID NO: 9)) | 97% |
| | HLA-B*3501(IPSINVHHY (SEQ ID NO: 23)) | 0.02% |
| IPSI | HLA-B*3501(IPSINVHHY (SEQ ID NO: 23)) | 95% |
| | HLA-A*0201(NLVPMVATV (SEQ ID NO: 9)) | 0.01% |

-continued

| Cell preparation | MHC-complex | Percentage of positive cells |
|---|---|---|
| GLC | HLA-A*0201(GLCLVALM (SEQ ID NO: 24)) | 45% |
| | HLA-A*0201(ILKEPVHGV (SEQ ID NO: 10)) | 0.1% |

Example 17

This example describes how the quality of the MHC multimer can be tested. The MHC multimer in this example is a MHC-dextramer, and the test involves specific binding of the MHC-dextramer to cell lines or other preparations expressing TCRs or MHC-recognizing molecules.

Experiments can be performed with any kind of TCRs or MHC-recognizing molecules displayed on cells (e.g. a cell line or a cell preparation).

Procedures as described in Example 15 and 16 can be used with any kind of TCRs or MHC-recognizing molecules displayed on cells. Stimulation of cells has to be optimized for the specific experiments (e.g. stimulation with chemicals and/or temperature to express the TCR prior to analysis).

Results can be analyzed as in Example 15 and 16 and cell preparations stained with relevant MHC-dextramers will extent higher signal intensity than when stained with irrelevant MHC-dextramers.

Example 18

This example describes how the quality of the MHC multimer can be tested. The MHC multimer in this example is a MHC-dextramer, and the test involves specific binding of the MHC-dextramer to TCRs or MHC recognizing motifs immobilized or expressed on molecules detectable in flow cytometry.

The experiments can be performed with any kind of molecule detectable in flow cytometry. MHC-recognizing molecules can be displayed on beads, cells, or other entities that are amenable to flow cytometry analysis.

MHC-recognizing molecules can be displayed on entities amenable in flow cytometry either naturally or artificially (e.g. chemical coupling). Procedures as described in the above examples can be applied, depending on the nature of the molecules. Alternatively procedures optimized for the specific molecule can be applied.

Molecules can be stained with fluorescently labeled MHC-dextramers and the extent of cell staining can be analyzed by flow cytometry. Molecules stained with relevant MHC-dextramers will extent higher signal intensity than when stained with irrelevant MHC-dextramers.

Example 19

This example describes how the quantity of correctly folded MHC can be determined by ELISA assay. The test involves specific binding of the MHC to anti-HLA-ABC antibody, clone W6/32. W6/32 is an antibody recognizing all human MHC I HLA-A, B and C alleles but only when they are in the correct conformation and properly loaded with antigenic peptide.

The ELISA can be carried out as follows. A preparation of MHC complexes is incubated in wells of a microtiter plate pre-coated with W6/32 antibody following standard ELISA procedure regarding washes, blocking ect. A secondary antibody recognizing MHC (e.g. anti-$\beta_2$m) is used for visualization. The secondary antibody can be labelled, e.g. with Horse radish Peroxidase or it can be unlabelled, and a labeled compound specific for the secondary antibody is then employed (e.g. EnVision System) before visualization. A compound for visualization is added, e.g. TMB One-Substrate System when Peroxidase enzyme is the label. The chromogenic intensity is measured and the result from the ELISA assay is evaluated. In parallel a standard curve of is generated, e.g. consisting of various concentrations of correctly folded MHC complexes. The chromogenic intensity of the tested MHC sample can now be converted to actual concentrations of correctly folded MHC using the standard curve. We conclude that the ELISA assay together with a standard curve can be used to quantify correctly folded MHC.

Example 20

This example describes how the quantity of correctly folded MHC can be determined by ELISA assay. The test involves specific binding of MHC complexes to a molecule recognizing correctly folded MHC (e.g. antibody, TCR, aptamers, or other MHC-peptide complex binding molecules).

As described elsewhere the quantity of correctly folded MHC can be measured in an ELISA assay using a molecule specific for correctly folded MHC complexes either for catching of the testet MHC complex preparation or for detection of it. The result obtained from bound MHC complex in the sample tested is correlated to a standard curve for determination of concentration. The ELISA assay can be conducted and optimized by various measures depending on the reagent and enzyme used.

Example 21

This example describes how the quantity of correctly folded MHC can be determined by competitive ELISA assay. The test involves specific binding of MHC complexes to a molecule recognizing correctly folded MHC (e.g. antibody, TCR, aptamers, or other MHC-peptide complex binding molecules). The analysis is carried out as follows. A preparation of correctly folded MHC of known concentration is immobilized in wells of a microtiter plate. A mixture of a molecule recognizing correctly folded MHC (e.g. the antibody W6/32) and soluble MHC complex, comprising a mixture of correctly and non-correctly folded MHC, is added to the microtiter plate. The molecules recognizing correctly folded MHC will now attach to either the immobilized MHC or the correctly folded MHC in the soluble fraction. The amount of molecules recognizing correctly folded MHC bound to the immobilized MHC in the microtiter plate is measured, e.g. by addition of a secondary labeled or unlabeled antibody specific for the molecule recognizing correctly folded MHC. Depending on the characteristic of the secondary antibody visualization is performed. The result of the ELISA assay is evaluated. The amount of bound molecules specific for correctly folded MHC complexs is inversely proportional to the quantity of correctly folded MHC in the soluble fraction. The quantity of correctly folded MHC in the soluble fraction can be measured using a standard curve, obtained using known amounts of a pure preparation of MHC complexes and constant amount of molecules recognizing correctly folded MHC.

We conclude that an indirect competitive ELISA can be used to quantify correctly folded MHC.

Example 22

This example describes how the quantity of correctly folded MHC can be determined by competitive ELISA assay. The test involves specific binding of MHC complexes to a molecule recognizing correctly folded MHC (e.g. antibody, TCR, aptamers, or other MHC-peptide complex binding molecules).

The analysis is carried out as follows. Molecules recognizing correctly folded MHC are immobilized in wells of a microtiter plate. A preparation of in vitro folded MHC complexes is mixed with a known amount of labeled correctly folded MHC and the mixture added to the microtiter plate. The correctly folded MHC in the mixture will now compete for binding to the molecules recognizing correctly folded MHC immobilized in the microtiter plate. The amount of bound labeled MHC can now be visualized and measured. The result is inversely proportional to the quantity of correctly folded MHC in the mixture. The quantity of correctly folded MHC in the mixture can be measured using a standard curve, obtained using known amounts of a pure preparation of MHC mixed with a constant amount of labeled MHC.

Example 23

This example describes how the quantity of correctly folded MHC can be determined by competitive ELISA assay. The test involves specific binding of the MHC to a molecule recognizing correctly folded MHC (e.g. antibody, TCR, aptamers, or other MHC-peptide complex binding molecules) or to molecules recognizing MHC, correctly as well as non-correctly folded (e.g. antibody, TCR, aptamers, or other MHC-peptide complex binding molecules).

1. A preparation of MHC complexes are immobilized in a microtiter plate and incubated with a labeled molecule recognizing MHC, correctly as well as non-correctly folded (in the following referred to as recognizing all MHC complexes).
2. Then an unlabeled molecule recognizing correctly folded MHC is added in major excess. These molecules will displace all the MHC recognizing molecules added in step 1 that binds correctly folded MHC complexes.
3. The amount of bound labeled molecule recognizing all MHC can now be visualized and measured.
4. The result is inversely proportional to the quantity of correctly folded MHC. The quantity of correctly folded MHC can be measured using a standard curve, obtained using known amounts of a MHC incubated with labeled molecule recognizing all MHC.

Example 24

This example describes how the quantity of correctly folded MHC can be determined. The test involves specific binding of MHC complexes to anti-HLA-ABC antibody, clone W6/32. In this example W6/32 antibody is immobilized on magnetic beads.

1. The protein concentration in a purified preparation of MHC complexes is determined by spectofotometric measurement of $OD_{280}$. Other techniques can be used as well, e.g. BCA (bicinchoninic acid) assay or SDS-PAGE gel.

2. To measure the proportion of correctly folded MHC, a sample of the MHC complex preparation is incubated with W6/32 antibody coated magnetic beads.

3. After incubation the beads are sedimented or captured by a magnet and excess supernatant is withdrawn.

4. The concentration of protein in the supernatant is measured as in step 1.

5. The proportion of correctly folded MHC complex is calculated as follows:

X: Total protein concentration (step 1)

Y: Protein concentration after capture of correctly folded MHC (step 4)

% of correct folded MHC=$(1-(Y/X))*100$%

Ex. X=10 mg/ml
   Y=2 mg/ml

% of correct folded MHC=$(1-(2 \text{ mg/ml}/10 \text{ mg/ml}))*100$%=80%

The proportion of correctly folded MHC can be used as quality parameter, to measure the variation from production to production of a specific MHC-peptide complex.

Example 25

This example describes how the quantity of correctly folded MHC can be determined. The test involves specific binding of MHC complexes to a molecule recognizing correctly folded MHC (e.g. antibody, TCR, aptamers, or other MHC-peptide complex binding molecules). The MHC recognizing molecules can be immobilized to a solid support (e.g. beads, microtiter plate or gel material).

1. The protein concentration in a purified preparation of MHC complexes is determined by spectofotometric measurement of $OD_{280}$. Other techniques can be used as well, e.g. BCA (bicinchoninic acid) assay or SDS-PAGE gel.

2. To measure the proportion of correctly folded MHC, a sample of the MHC complex preparation is incubated with a molecule recognizing correctly folded MHC complex immobilized to a solid support.

3. After incubation supernatant is withdrawn.

4. The concentration of protein in the supernatant is measured as in step 1.

5. The proportion of correctly folded MHC complex is calculated as follows:

X: Total protein concentration (step 1)

Y: Protein concentration after capture of correctly folded MHC (step 4)

% of correct folded MHC=$(1-(Y/X))*100$%

Ex. X=10 mg/ml
Y=2 mg/ml

% of correct folded MHC=$(1-(2 \text{ mg/ml}/10 \text{ mg/ml}))*100$%=80%

The proportion of correctly folded MHC can be used as quality parameter, to measure the variation from production to production of a specific MHC-peptide complex.

Example 26

This example describes how the quantity of correctly folded MHC can be determined. The test involves specific binding of MHC complexes to anti-HLA-ABC antibody, clone W6/32. In this example W6/32 antibody is immobilized on magnetic beads.

1. A preparation of MHC complexes is incubated with W6/32 antibody coated magnetic beads and all correctly folded MHCs are thereby captured.

2. After incubation the beads are sedimented or captured by magnet, the supernatant withdrawn and the amount of non-bound MHC complex (equal to not correctly folded MHC complex) is determined by ELISA.

3. To measure the quantity of MHC complexes in solution before and after incubation with W6/32 antibody coated magnetic beads an ELISA assay is applied. A microtiter plate is coated with an antibody recognizing all MHC complexes correct as well as non-correct folded.

4. Samples of MHC complex before and after incubation with W6/32 antibody coated magnetic beads are added to the coated microtiter plate.

5. A labeled secondary antibody recognizing MHC (e.g. anti-$\beta_2$m) is used for visualization. Alternatively the secondary antibody is unlabelled, and a labeled molecule specific for the secondary antibody is employed (e.g. EnVision System) before visualization.

6. The proportion between results from the sample after incubation with W6/32 antibody coated magnetic beads and the sample before incubation with W6/32 antibody coated magnetic beads is a measure of the amount of non correct folded MHC complex and thereby an indirect measure of the amount of correct folded MHC complex. To obtain exact values for the amount of MHC complex in each sample a standard curve can be generated.

Example 27

This example describes how the quantity of correctly folded MHC in a sample can be determined. The test involves specific binding of MHC complexes to a molecule recognizing correctly folded MHC complex (e.g. antibody, TCR, aptamers, or other MHC-peptide complex binding molecules). The MHC recognizing molecules can be immobilized to any solid support (e.g. beads, microtiter plate or gel material). Correctly folded MHC complex in a sample is captured by addition of the sample to the immobilized MHC-binding molecule, and then non-bound MHC-complex (equal to not correctly folded MHC complex) is removed. The proportion of MHC complex in the two fractions (before and after incubation with immobilized MHC-specific molecule) can be evaluated by any method capable of determination of the total amount of MHC complex (folded or undfodled)

Example 28

This example describes how the quantity of correctly folded MHC in a sample can be determined. The test involves specific binding of MHC complex to a molecule recognizing correctly folded MHC (e.g. antibody, TCR, aptamers, or other MHC-peptide complex binding molecules). The specific binding is evaluated by native protein gel electrophoresis.

A preparation of in vitro folded and purified MHC complex is incubated with a molecule recognizing correctly folded MHC, e.g. the antibody W6/32.

The product is analysed by native protein gel electrophoresis (lane 1) together with a sample of in vitro folded and purified MHC complex not incubated with MHC recognizing molecule (lane 2), and a sample of the molecule recognizing correctly folded MHC (lane 3). In the protein gel the different proteins are separated according to size. The various protein products are visualized in the gel e.g. by Comassie blue staining, isotope or chemiluminiscence. In the sample with MHC complex and MHC-binding molecule correctly folded MHC complex will bind the MHC-binding molecule and appear in the protein gel as one or more large bands in the top of the gel. In contrast non-correctly folded MHC complex will appear as monomer lower in the gel. The fraction of not correctly folded MHC (lane 1) can now be compared with the total amount of MHC in the sample (lane 2) and the difference between the two correlates with the amount of correctly folded MHC complex in the sample. The results can be evaluated in different manners to determine the quantity of correctly folded MHC, e.g. comparison of intensity to the intensity of products of known concentration.

Example 29

This example describes how to verify that a MHC-complex is correctly folded by a sandwich-ELISA assay. W6/32 mouse-anti-HLA-ABC antibody (Dako M0736), that recognizes a conformational epitope on correctly folded MHC-complex, was used as coating-antibody. HRP-conjugated rabbit anti-β2m (Dako P0174) was used for visualization.

1. Wells of a microtiter plate was pre-coated with W6/32 antibody (Dako M0736, 5 μg/ml in 0.1M NaHCO₃, 1 mM MgCl₂, pH 9.8, 50 μl/well) following a standard ELISA procedure regarding washes and blocking ect.
2. After addition of 50 I of 0.5M Tris-HCl, 0.1 M NaCl, 0.1% Tween 20, 0.01% Bronidox, pH 7.2 to each well, 50 I of a sample of purified folded MHC-complex (in a concentration of approx. 0.4 mg/ml) was added to two wells in to columns in the microtiter plate, diluted 2-fold down the column and incubated 2 hours at 4° C. Light chain β2m (0.15 mg/ml in 0.5M Tris-HCl, 0.1 M NaCl, 0.1% Tween 20, 0.01% Bronidox, pH 7.2) was used as a negative control and the cell-line KG-1a, expressing HLA-A*30, HLA-A*31 and HLA-B*35 heavy chains, was used as positive control (10⁶ cells/well).
3. After a standard ELISA wash, 50 I of the detecting antibody; HRP-conjugated rabbit anti-β2m (Dako P0174), diluted 1:2500 in 1% Skimmed Milk in 0.5M Tris-HCl, 0.1 M NaCl, 0.1% Tween 20, 0.01% Bronidox, pH 7.2 was added to each well. The plate was incubated 1 hour at 4° C.
4. After a standard ELISA wash, 50 I of an amplifying antibody; HRP-Dextran500-conjugated goat anti-rabbit (Dako DM0106), diluted 1:2000 in 1% Skimmed Milk in 0.5M Tris-HCl, 0.1 M NaCl, 0.1% Tween 20, 0.01% Bronidox, 1% mouse serum (Dako X0190) pH 7.2 was added. The plate was incubated 30 min. at 20° C.
5. After a standard ELISA wash, 50 I of Dako S1599 (TMB+Substrat Chromogen) was added to each well for visualization.
6. After 10 min. the visualization reaction was stopped with 50 μl 0.5M H₂SO₄/well.
7. The chromogenic intensity was measured at OD₄₅₀ and the result from the ELISA assay evaluated.

As shown in FIG. 5 the OD₄₅₀ values from wells with MHC complex was more than 6 times higher than OD₄₅₀ values from wells with the negative control β2m. This ELISA procedure can be used to verify the presence of correctly folded MHC-peptide complexes in a preparation of MHC complexes.

Example 30

This example describes the generation and application of negative controls, where the MHC complex is HLA-A*0201 loaded with either of the nonsense peptides GLAGDVSAV (SEQ ID NO:11) or ALIAPVHAV (SEQ ID NO:12) and these MHC complexes are coupled to a 270 kDa dextran multimerization domain. The nonsense peptides have an amino acid sequence different from the linear sequence of any peptide derived from any known naturally occurring protein. This was analyzed by a blast search. The amino acids at position 2 and 9 can serve as anchor residues when binding to HLA-A*0201 molecules.

Purified MHC (peptide) molecules consisting of the allele HLA-A*0201, human beta2microglobulin and peptide was generated by in vitro refolding, purified and biotinylated as described elsewhere herein. Biotinylated HLA-A*0201 (peptide) was mixed with APC-SA-conjugated 270 kDa dextran in an amount corresponding to a ratio of 5 biotinylated HLA-A*0201(peptide) molecules per SA molecule and incubated for 30 minutes in the dark at room temperature. The APC-SA-conjugated 270 kDa dextran contained 9 molecules APC and 3,7 molecules SA per dextran molecule. Following incubation the mixture was diluted into a buffer comprising 0,05M Tris/HCl, 15 nM NaN₃ and 1% BSA to a final concentration of 3,8×10⁻⁸ M dextran. By this procedure the following MHC multimer constructs were made:

1) A negative control construct comprising APC-SA-conjugated 270 kDa dextran and biotinylated HLA-A*0201 in complex with beta2microglobulin and the nonsense peptide GLAGDVSAV (SEQ ID NO:11) (nonsense peptide 1).
2) A negative control construct comprising APC-SA-conjugated 270 kDa dextran and biotinylated HLA-A*0201 in complex with beta2microglobulin and the nonsense peptide ALIAPVHAV (SEQ ID NO:12) (nonsense peptide 2).
3) A construct comprising APC-SA-conjugated 270 kDa dextran and biotinylated HLA-A*0201 in complex with beta2microglobulin and the peptide NLVPMVATV (SEQ ID NO:9) derived from pp65 protein from human cytomegalovirus (HCMV).
4) A construct comprising APC-SA-conjugated 270 kDa dextran and biotinylated HLA-A*0201 in complex with beta2microglobulin and the peptide GLCTLVAML (SEQ ID NO:13) derived from BMLF-1 protein from Epstein Barr virus (EBV).
5) A construct comprising APC-SA-conjugated 270 kDa dextran and biotinylated HLA-A*0201 in complex with beta2microglobulin and the peptide ILKEPVHGV (SEQ ID NO:10) Reverse Transcriptase from Human Immunodeficiency Virus (HIV).

The binding of the HLA-A*0201(peptide)/APC dextran constructs to Human Peripheral Blood Mononuclear Cells (HPBMC) from various donors was analyzed by flow cytometry following a standard flow cytometry protocol. Briefly, HPBMC from the blood of 9 individual donors were isolated, by a standard protocol using FICOLL®-Hypaque. 1×10⁶ purified HPBMC at a concentration of 2×10⁷ cells/ml were incubated with 10 I of one of the HLA-A*0201 (peptide)/APC dextran constructs described above for 10 minutes in the dark at room temperature. 10 μl of each of the antibodies mouse-anti-human CD3/PE (clone UCHT1 from Dako) and mouse-anti-human CD8/PB (clone DK25 from Dako) were added and the incubation continued for another 20 minutes at 4° C. in the dark. The samples were then washed by adding 2 ml PBS; pH=7.2 followed by centrifugation for 5 minutes at 200×g and the supernatant removed. The cells were then resuspended in 400-500 µl PBS; pH=7.2 and analyzed on a CYAN ADP flowcytometer.

Donor 1-5 were known to have detectable T-cells specific for HLA-A*0201(NLVPMVATV (SEQ ID NO:9)) and no detectable T-cells specific for HLA-A*0201(ILKEPVHGV (SEQ ID NO:10)) while donor 6 were known not to have detectable specific T-cells for either HLA-A*0201(NLVPM-VATV (SEQ ID NO:9)) nor HLA-A*0201(ILKEPVHGV (SEQ ID NO:10)). Lymphocytes from these 6 donors were stained with MHC multimer construct 1, 2, 3, and 5. Donor 1-5 showed positive staining with MHC multimer construct 3 as expected while no staining was observed with the either of the negative control MHC complex constructs 1 and 2 or with MHC complex construct 5. An example showing the staining patterns for donor 2 is shown in FIG. 8. No specific staining was observed of lymphocytes from donor 6 with either of the MHC multimer constructs.

Donor 7-8 known to have detectable T-cells specific for HLA-A*0201(GLCTLVAML (SEQ ID NO:13)) and no detectable T-cells recognizing HLA-A*0201(ILKEPVHGV (SEQ ID NO:10)) and donor 9 having no detectable T-cells specific for either HLA-A*0201(GLCTLVAML (SEQ ID NO:13)) nor HLA-A*0201(ILKEPVHGV (SEQ ID NO:10)) were all stained with MHC multimer construct 1, 2, 4, and 5. Donor 7 and 8 demonstrated efficient staining with MHC multimer construct 4 as expected while no staining was observed with the other MHC multimer constructs tested. No staining was observed of lymphocytes from donor 9 with either of the MHC multimer constructs tested. A summary of the results is shown in FIG. 9.

In conclusion this experiment demonstrates that the negative MHC multimer constructs 1 and 2 did not stain any specific T-cells in lymphocyte preparations from 10 different donors. Donors known to have specific T-cells for either HLA-A*0201(GLCTLVAML (SEQ ID NO:13)) or HLA-A*0201(NLVPMVATV (SEQ ID NO:9)) also demonstrated positive staining with the corresponding MHC multimer constructs 3 and 4. None of the 10 donors were infected with HIV and as expected did not appear to have T-cells specific for HLA-A*0201 in complex with the HIV derived peptide ILKEPVHGV (SEQ ID NO:10), and as expected none of these donors showed staining with MHC multimer construct 5. MHC multimer construct 1 and 2 are therefore suitable negative controls when using HLA-A*0201(peptide) multimers for detection of specific T-cells in Flow Cytometry.

Example 31

This is an example of how to generate and use negative controls, where the MHC complex is any MHC I or MHC II complex of human, mouse, rabbit, rat, swine or monkey origin loaded with a nonsense peptide. A nonsense peptide is here to be understood as a peptide having an amino acid sequence different from any peptide derived from any known naturally occurring protein, and preferably is not recognized by any T-cell when presented by a MHC complex. The nonsense peptide has amino acid residues at relevant positions that anchor the peptide to the peptide-binding groove of the MHC complex. The MHC (nonsense peptide) complex is coupled to a 270 kDa dextran multimerization domain.

Purified MHC (peptide) molecules consisting of the alpha chain, human beta2microglobulin and peptide is generated by in vitro refolding, purified and biotinylated as described elsewhere. Biotinylated MHC (peptide) is mixed with APC-SA-conjugated 270 kDa dextran in amounts corresponding to a ratio of three biotinylated MHC (peptide) molecules per SA molecule and incubated for 30 minutes in the dark at room temperature. The APC-SA-conjugated 270 kDa dextran contains 9 molecules APC and 3,7 molecules SA per dextran molecule. Following incubation the mixture is diluted into a buffer comprising 0,05M Tris/HCl, 15 nM NaN$_3$ and 1% BSA to a final concentration of $3,8×10^{-8}$ M dextran.

By this procedure the following MHC complex constructs are made:
1. A negative control construct comprising APC-SA-conjugated 270 kDa dextran and biotinylated alpha chain in complex with beta2microglobulin and a corresponding nonsense peptide. A nonsense peptide is here to be understood as a peptide with an amino acid sequence different from any peptide derived from any known naturally occurring protein and the nonsense peptide is not recognized by any T-cell when presented by a MHC complex.
2. A construct comprising APC-SA-conjugated 270 kDa dextran and biotinylated alpha chain in complex with beta2microglobulin and a peptide derived from a known protein.

The binding of the MHC (peptide)/APC dextran constructs to Human Peripheral Blood Mononuclear Cells (HPBMC) from various donors is analyzed by flow cytometry following a standard flow cytometry protocol. Briefly, HPBMC from the blood of 9 individual donors are isolated by a standard protocol using FICOLL®-Hypaque. $1×10^6$ purified HPBMC at a concentration of $2×10^7$ cells/ml is incubated with 10 µl of one of the MHC (peptide)/APC dextran constructs described above for 10 minutes in the dark at room temperature. 10 µl of each of each of the antibodies mouse-anti-human CD3/PE (clone UCHT1 from Dako) and mouse-anti-human CD8/PB (clone DK25 from Dako) are added and the incubation continued for another 20 minutes at 4° C. in the dark. The samples are then washed by adding 2 ml PBS; pH=7.2 followed by centrifugation for 5 minutes at 200×g and the supernatant removed. The washed cells are resuspended in 400-500 µl PBS; pH=7.2 and analyzed on a CYAN ADP flowcytometer.

The staining patterns of flow cytometry analysis with the two MHC (peptide)/APC constructs 1 and 2 are compared. There will be no staining observed with construct 1.

Example 32

This is an example of how to generate negative controls, where the MHC complexes is any MHC I or MHC II molecule of human, mouse, rabbit, rat, swine, monkey or any other origin loaded with a nonsense peptide and where the MHC (nonsense peptide) complexes are coupled to any multimerization domain. A nonsense peptide is here to be understood as a peptide that have an amino acid sequence different from any peptide derived from any known naturally occurring protein and cannot be recognized by any T-cell when presented by a MHC complex. The nonsense peptide carries amino acid residues at relevant positions that anchor the peptide to the peptide-binding groove of the MHC complex.

The MHC (nonsense peptide) complex can be made as described elsewhere herein, and can then be coupled to one or more relevant multimerization domain(s). The labeling of the one or more multimerization domain(s) can be optimized depending on later use of the negative control e.g. in flow cytometry analysis, IHC, ELISA or similar.

Example 33

This example describes the generation of a negative control, where the MHC complex is HLA-A*0201 coupled to a 270 kDa dextran, and where the MHC is loaded with the peptide ILAKFLHWL (SEQ ID NO:25) that have pivaloyl coupled to Lysine at position 4. ILAKFLHWL (SEQ ID NO:25) is a peptide derived from telomerase and is known to bind HLA-A*0201. Pivaloyl is a small molecule that confers high sterical hindrance. Because pivaloyl is placed at a central position in the peptide it is likely to inhibit or completely abrogate the interaction with a specific TCR, because TCR-recognition is normally directed to the middle of the peptide when bound in the peptide-binding cleft. In the following the pivaloyl-modified peptide will be designated ILAK$^P$FLHWL (SEQ ID NO:35).

Purified HLA-A*0201(ILAK$^P$FLHWL (SEQ ID NO:35)) molecules consisting of the HLA-A*0201 heavy chain, human beta2microglobulin and ILAK$^P$FLHWL (SEQ ID NO:35) peptide is generated by in vitro refolding, purified and biotinylated as described elsewhere herein. Biotinylated HLA-A*0201(ILAK$^P$FLHWL (SEQ ID NO:35)) molecules are mixed with fluorochrome-SA-conjugated 270 kDa dextran molecules. The resulting HLA-A*0201(ILAK$^P$FLHWL (SEQ ID NO:35))/fluorochrome-carrying dextran molecules can be used as negative controls in e.g. flow cytometric analysis.

Example 34

This example describes the generation of a negative control, where the MHC complex is any MHC I or MHC II molecule of human, mouse, rabbit, rat, swine, monkey or any other origin loaded with the peptide ILAK$^P$FLHWL (SEQ ID NO:35) and coupled to any multimerization domain labeled with fluorochrome, HRP or any other label. Purified MHC (ILAK$^P$FLHWL (SEQ ID NO:35)) complexes consisting of the heavy chain, human beta2microglobulin and ILAK$^P$FLHWL (SEQ ID NO:35) peptide is generated by in vitro refolding, purified and biotinylated as described elsewhere herein. Biotinylated MHC (ILAK$^P$FLHWL (SEQ ID NO:35)) complexes are mixed with labeled multimerization domain, thereby generating MHC (ILAK$^P$FLHWL (SEQ ID NO:35)) multimers. The MHC (ILAK$^P$FLHWL (SEQ ID NO:35)) multimers may be used as negative controls in e.g. flow cytometric analysis, IHC, ELISA or similar.

Example 35

This example describes the generation of a negative control where the MHC is HLA-A*0201 loaded with the peptide ILKEPVHGV (SEQ ID NO:10) and coupled to a 270 kDa dextran multimerization domain. The peptide ILKEPVHGV (SEQ ID NO:10) is derived from HIV. HLA-A*0201(ILKEPVHGV (SEQ ID NO:10)) complexes are generated, biotinylated and coupled with a labeled dextran multimerization domain as described elsewhere herein. Then these HLA-A*0201(ILKEPVHGV (SEQ ID NO:10))-dextran conjugates are used as negative controls in experiments with samples from humans that are HLA-A*0201 positive and not infected by HIV, because it is not likely that they have T-cell's with a TCR specific for HLA-A*0201 (ILKEPVHGV (SEQ ID NO:10)) in amounts that can be detected by MHC multimer reagents. The conjugates can also be used as negative control in samples from humans that are HLA-A*0201 negative or in samples from other species.

Example 36

This example describes the generation of a negative control. CD8 molecules on the surface of cytotoxic T-cells bind MHC I complexes by interaction with amino acids in the α3 domain of the heavy chain. When using MHC multimers this interaction can result in MHC multimer binding to CD8 positive T-cells that are not restricted by the MHC (peptide) complex in the MHC multimer. In this example a proper negative control showing these false positive cells is described. Such a negative control can consist of MHC I heavy chain or truncated versions of MHC I heavy chain bound to any multimerization domain. The heavy chain can be folded or unfolded, and can have a peptide bound in the peptide binding groove but does not have to comprise a peptide. A MHC I heavy chain-multimerization domain can be made in a way similar to what is described for the generation of MHC I-multimerization domains. Briefly, purified MHC I heavy chain is expressed as inclusion bodies in E. coli and purified by general procedures. The heavy chain is refolded in vitro, purified and biotinylated, or the heavy chain can be biotinylated directly without refolding. Biotinylated heavy chain is coupled to any multimerization domain. The multimerization domain can be labeled with any suitable label or can be unlabeled depending on later use. Such a negative control can be used in experiments with MHC I multimers, e.g. in flow cytometry analysis, IHC, or ELISA.

Example 37

This example describes how to identify specific T-cells in a blood sample with MHC multimers using flow cytometry analysis without lysis of red blood cells and without washing the cells after staining. MHC complexes in this example consisted of HLA-A*0201 heavy chain, human beta2microglobulin and different peptides, and the MHC complexes were coupled to a 270 kDa dextran multimerization domain. Purified MHC-peptide complexes consisting of human heavy chain, human beta2microglobulin and peptide were generated by in vitro refolding, purified and biotinylated as described elsewhere herein. Biotinylated MHC-peptide complexes were then coupled to a 270 kDa dextran multimerization domain labelled with PE by interaction with streptavidin (SA) on the dextran multimerization domain. The SA-PE-dextran was made as described elsewhere herein. MHC-peptide complexes were added in an amount corresponding to a ratio of three MHC-peptide molecules per SA molecule and each molecule dextran contained 6.1 SA molecule and 3.9 molecules PE. The final concentration of dextran was $3.8\times10e-8$ M. The following constructs were made:

1. PE conjugated 270 kDa dextran coupled with HLA-A*0101 in complex with beta2microglobulin and the peptide VTEHDTLLY (SEQ ID NO:14) derived from Human Cytomegalo Virus (HCMV).
2. PE conjugated 270 kDa dextran coupled with HLA-A*0101 in complex with beta2microglobulin and the peptide IVDCLTEMY (SEQ ID NO:15) derived from ubiquitin specific peptidase 9 (USP9).

3. PE conjugated 270 kDa dextran coupled with HLA-A*0201 in complex with beta2microglobulin and the peptide NLVPMVATV (SEQ ID NO:9) derived from Human Cytomegalo Virus (HCMV).

4. PE conjugated 270 kDa dextran coupled with HLA-A*0201 in complex with beta2microglobulin and the peptide ILKEPVHGV (SEQ ID NO:10) derived from Human Immunodeficiency Virus (HIV).

5. PE/SA conjugated 270 kDa dextran coupled with HLA-B*0207 in complex with beta2microglobulin and the peptide TPRVTGGGAM (SEQ ID NO:16) derived from Human Cytomegalo Virus (HCMV).

6. PE conjugated 270 kDa dextran coupled with HLA-B*0207 in complex with beta2microglobulin and the peptide RPHERNGFTVL (SEQ ID NO:17) derived from Human Cytomegalo Virus (HCMV).

7. PE conjugated 270 kDa dextran coupled with HLA-B*0207 in complex with beta2microglobulin and the peptide TPGPGVRYPL (SEQ ID NO:18) derived from Human Immunodeficiency Virus (HIV).

These seven MHC multimer constructs were used for detection of specific T-cells in flow cytometry analysis using a no-lyse no-wash procedure. Blood samples from three individual donors were analyzed. The donors had previously been screened for the presence of specific T-cells using a general staining procedure including lysis and wash of the cell sample, and donor one turned out to be positive for HLA*0201 in complex with the peptide NLVPMVATV (SEQ ID NO:9), donor two were positive for HLA*0101 in complex with the peptide VTEHDTLLY (SEQ ID NO:14) and donor three were positive for HLA-B*0207 in complex with the peptides TPRVTGGGAM (SEQ ID NO:16) and RPHERNGFTVL (SEQ ID NO:17). In this experiment blood from each donor were analyzed with the MHC multimer construct they were supposed to have specific T-cells restricted for and with MHC multimers of same haplotype but carrying a negative control peptide. The negative control peptides were either derived from HIV or the self-protein USP 9. Self-protein here means a naturally occurring protein in normal cells of a human individual. Normal healthy donors not infected with HIV are not expected to have specific T-cells recognizing HIV derived peptides or peptides derived from self-proteins in complex with any HLA molecule in an amount detectable with this analysis method.

The blood was stained as follows: 100 µl EDTA stabilized blood were incubated with 5 µl MHC (peptide)/PE dextran for 5 minutes at room temperature. Anti-CD45/PB, anti-CD3/FITC and anti-CD8/APC antibody in an amount of 0.4-1.2 g/sample was added to each tube and the incubation continued for another 15 minutes. 850 I PBS; pH=7.2 was added and the sample analyzed on a CYAN ADP flowcytometry instrument with a speed of 150 I/minute. A total of 20.000 CD8 positive cells were acquired. During analysis CD45/PB antibody was used to set a trigger discriminator to allow the flow cytometer to distinguish between red blood cells and stained white blood cells (see FIG. 10A). Furthermore CD3/FITC antibody was used to select CD3 positive cells in a second gating strategy (see FIG. 10B).

Blood from donor one showed specific staining with HLA-A*0201(NLVPMVATV (SEQ ID NO:9)) multimer (construct 3) while no staining of specific T-cells was observed with the negative control HLA-A*0201 (ILKEPVHGV (SEQ ID NO:10)) multimer (construct 4). Donor two showed specific staining with HLA-A*0101 (VTEHDTLLY (SEQ ID NO:14)) multimer (construct 1) and no staining was observed with the negative control HLA-A*0101(IVDCLTEMY (SEQ ID NO:15)) multimer (construct 2). In blood from donor three a population of T-cells were stained with HLA-B*0207(TPRVTGGGAM (SEQ ID NO:16)) multimer (construct 5) and another population with HLA-B*0207(RPHERNGFTVL (SEQ ID NO:17)) multimer (construct 6) while no specific staining was observed with the negative control HLA-B*0207 (TPGPGVRYPL (SEQ ID NO:18)) multimer (construct 7). The results are shown in FIG. 11.

We have shown that MHC multimers of three different haplotypes can be used to identify specific T-cells in blood samples from three different donors using an approach without lysing red blood cells and without wash following staining with MHC multimer. This method is simple, fast and interfere as little as possible with cells in the blood sample.

Example 38

This example describes how to identify specific T-cells in a blood sample with MHC multimers using flow cytometry analysis without lysis of red blood cells and without washing cells upon staining. The MHC complex is here any MHC I or MHC II molecule of human, rodent, bovine, monkey or any other origin loaded with any peptide able to bind the peptide-binding cleft of the MHC complex and where the MHC-peptide complexes are coupled to any multimerization domain.

Purified MHC-peptide complexes is generated as described elsewhere herein and coupled to any multimerization domain labelled with a fluorescent dye, preferable FITC, PE, APC, pacific blue, cascade yellow or any other flour chrome. These MHC multimers are used for detection of specific T-cells by flow cytometry using the following procedure:

EDTA stabilized blood are incubated with MHC multimer at room temperature. The amount of blood analyzed is preferable 50-150 µl but could be any volume ranging from 1-1000 µl. The amount of MHC multimer depends on the multimer construct and the volume of blood and should be determined by titration prior to this type of experiment. The incubation time with MHC multimer is preferably 5-20 minutes but could be anything between 0 minutes and 1 hour. Then anti-CD45/CY, anti-CD3/APC and anti-CD8/PB antibody is added and the incubation continued. The incubation time is preferably 5-20 minutes but can be anything between 1 minute and 1 hour. The amount of antibody is preferable 0.4-1.2 µg/100 µl blood but these limits can be extended and should be determined by titration prior to this kind of experiments. The antibodies can be labelled with any fluorochrome as long as the fluorochrome is different from the fluorochrome on the MHC multimer. Next PBS; pH=7.0-8.0 is added and the sample analyzed by a flowcytometer. The amount of PBS added is preferable 500-1000 I but can also be more than 1000 µl and less than 500 µl. During analysis anti-CD45 antibody is used to set a trigger discriminator to allow the flow cytometer to distinguish between red blood cells and stained white blood cells. Different gating strategies can then be applied to analyse data. Preferably cells are first gated on CD3 positive cells and then for CD8 positive cells, but can also be gated only for CD8 positive cells of only for CD3 positive cells. Alternatively "dump" gates can be applied excluding unwanted cells, e.g. B-cells, CD4-positive cells, NK-cells.

In the above example MHC multimers are added prior to antibodies but MHC multimers and antibodies can also be added simultaneously to the blood sample and incubated for preferably 5-30 minutes but the incubation time can be anything between 1 minute and 2 hours.

This method can be used to identify specific T-cells in blood samples from different donors using an approach without lysing red blood cells and without wash following staining with MHC multimer. This method is simple, fast and interfere as little as possible with cells in the blood sample

Example 39

This example illustrates how MHC multimers together with counting beads was used for exact numeration of MHC-peptide specific T-cells in a flow cytometry analysis whit no lyses of red blood cells and no washing steps during or after staining. Counting beads in this example was CytoCount™, Count Control Beads from Dako that are polystyrene Fluorospheres with a diameter of 5.2 µm. The MHC multimer consisted of HLA-A*0101 heavy chain complexed with human beta2microglobulin and a peptide and the MHC-peptide complexes were coupled to a 270 kDa dextran multimerization domain labelled with PE. MHC multimers were generated as described elsewhere herein and the following two constructs were made:

1) PE conjugated 270 kDa dextran coupled with HLA-A*0101 in complex with beta2microglobulin and the peptide VTEHDTLLY (SEQ ID NO:14) derived from Human Cytomegalo Virus (HCMV).

2) PE conjugated 270 kDa dextran coupled with HLA-A*0101 in complex with beta2microglobulin and the peptide IVDCLTEMY (SEQ ID NO:15) derived from ubiquitin specific peptidase 9 (USP9).

Construct 2 is a negative control for construct 1 in this example and both were used for detection of specific T-cells by flow cytometry using a no-lyse no-wash procedure: 100 µl of EDTA stabilized blood from a donor positive for HLA*0101 in complex with the peptide VTEHDLLY (SEQ ID NO:14) were incubated with 5 µl MHC multimer for 5 minutes at room temperature. Anti-CD45/CY, anti-CD3/PB and anti-CD8/APC antibody in an amount of 0.4-1.2 µg/sample was added and the incubation continued for another 15 minutes. 850 µl PBS; pH=7.2 was added together with precise 50 µl CytoCount beads 1028 bead/µl and the sample analyzed on a CYAN ADP flowcytometry instrument with a speed of 150 I/minute. A total of 20.000 CD8 positive cells were acquired. During analysis CD45/CY antibody was used to set a trigger discriminator to allow the flow cytometer to distinguish between red blood cells and stained white blood cells.

A dot plot was made for each sample showing MHC multimer vs CD8 positive events (se FIGS. 12 A and B). Based on the negative control a gate comprising events representing CD8 positive T-cells specific for MHC multimer was defined. Similarly histogram plots for each sample was made showing FITC signal vs counts (FIGS. 12 C and D). In these histograms the amount of beads in the analyzed sample were identified since the beads in contrast to the cells emit light in the FITC channel. In principle the beads could be visualized in any fluorochrome channel because they emit light in all channels but it was important to visualize the beads in a channel where there was no interfering signal from labelled cells.

The concentration of T-cells specific for HLA-A*0101 (VTEHDTLLY (SEQ ID NO:14)) multimer (construct 1) in the blood sample were determined using the counting beads as an internal standard. Events obtained from staining with the negative control MHC multimer, construct 2, were defined as background signals and subtracted from the result obtained from staining with construct 1.

Concentration of HLA-A*0101(VTEHDTLLY (SEQ ID NO:14)) specific T-cells in the blood sample=((Count of MHC multimer+CD8+ positive cells, construct 1× concentration of beads×dilution factor of beads)/counted beads))-((Counted MHC multimer+CD8+ cells, construct 2× concentration of beads×dilution factor of beads)/counted beads) =992,6 cells/ml. (For details se FIG. 12).

This experiment demonstrated how CytoCount™ counting beads together with MHC multimers could be used to determine the exact concentration of MHC-peptide specific T-cells in a blood sample using a no-lyse no-wash method.

Example 40

This example describes an analysis of specific T-cells in blood using MHC multimers where MHC multimers together with antibodies are pre-mixed and embedded in a matrix material to retain and immobilize the reagents prior to use. In this example the matrix was composed of Trehalose and Fructose and the MHC complex consisted of HLA-A*0101 heavy chain complexed with human beta2microglobulin and peptide. The MHC-peptide complexes were coupled to a 270 kDa dextran multimerization domain.

Purified MHC-peptide complexes consisting of heavy chain, human beta2microglobulin and peptide were generated by in vitro refolding, purified and biotinylated as described elsewhere herein. Biotinylated MHC (peptide) complexes were coupled to a 270 kDa dextran multimerization domain labelled with PE, thereby generating PE labelled MHC multimers. The following MHC multimer constructs were made:

1) PE conjugated 270 kDa dextran coupled with HLA-A*0101 in complex with beta2microglobulin and the peptide VTEHDTLLY (SEQ ID NO:14) derived from Human Cytomegalo Virus (HCMV).

2) PE conjugated 270 kDa dextran coupled with HLA-A*0101 in complex with beta2microglobulin and the negative control peptide IVDCLTEMY (SEQ ID NO:15) derived from ubiquitin specific peptidase 9 (USP9).

Tubes with a matrix material to retain and immobilize the above described MHC multimer constructs together with antibodies relevant for later flow cytometer analysis were made. The matrix material was made to retain MHC multimer and antibody in the container when dry but release them into the sample medium when a sample comprising cells of interest was added to the tube.

Experimentally, solutions of 20% Fructose in water and 20% Trehalose in water were made and mixed in a 1:1 ratio. 15 µl of this mixture were transferred to two 5 ml Falcon tubes. A premix of antibodies were made consisting of 40 µl anti-CD8 Alexa700 labelled antibody in a concentration of 25 g/ml+40 µl anti-CD3 Pacific Blue labelled antibody in a concentration of 100 µg/ml+160 µl anti-CD45 Cascade Yellow labelled antibody in a concentration of 200 µg/ml. 12 µl of this mixture were added to each Falcon tube together with 3 µl of either of the two MHC multimer constructs. 100 µl butylated hydroxytoluen (BHT) with a concentration of 99 mg/L were added. The mixtures were dried under vacuum a 2-8° C. over night. 100 µl EDTA stabilized blood from a donor with T-cells specific for HLA-A*0101 complexed with the peptide VTEHDTLLY (SEQ ID NO:14) were added to each of the two tubes. As a control experiment 6 µl of the antibody premix described above were transferred to two empty 5 ml Falcon tubes together with 3 μl of either of the MHC multimer constructs and 100 I blood from the same donor. All four tubes were incubated for 15 minutes at room temperature. Then 900 μl PBS; pH=7.2 was added and the sample analyzed on a CYAN ADP flowcytometer instrument.

A total of 20.000 CD8 positive cells were acquired for each sample. During analysis CD45/CY antibody was used to set a trigger discriminator to allow the flow cytometer to distinguish between red blood cells and stained white blood cells.

As expected and shown in FIG. 13 a population of CD8 positive and HLA-A*0101(VTEHDTLLY (SEQ ID NO:14)) multimer positive cells were observed in the two samples stained with construct 1. The amount of specific T-cells detected in the matrix sample was comparable to the amount of specific T-cells detected in the control sample without matrix material. No HLA-A*0101(IVDCLTEMY (SEQ ID NO:15)) multimer specific CD8 positive cells were observed in the two samples stained with the negative control MHC multimer construct 2.

This experiment demonstrates that the MHC multimer constructs used in this experiment can be embedded in a sugar matrix and later used for analysis of specific T-cells in a blood sample and that this method gives results comparable to results obtained from a no-lyse no-wash staining procedure.

Example 41

This example describes an analysis of specific T-cells in blood or other samples with cells in solution using MHC multimers where MHC multimers together with antibodies are pre-mixed and embedded in a matrix material to retain and immobilize the reagents prior to use. In this example the matrix is composed of Trehalose and Fructose and the MHC multimer is any MHC I, MHC II or MHC like molecule.

Tubes with a matrix material to retain and immobilize MHC multimer constructs together with antibodies relevant for later flow cytometer analysis are made. The matrix material is made to retain MHC multimer and antibody in the container when dry but release them into the sample medium when a sample comprising cells of interest is added to the tube. The matrix is preferable water-soluble sugar mixtures but can be any contiguous mass releasing its components upon addition of aqueous solution. The matrix embedding medium can comprise one or more compounds including carbohydrates, polymers, small proteins etc. Examples of carbohydrates for use in the matrix include saccharose, arabinose, ribulose, fructose, sorbose, glucose, mannose, gulose, galactose, sucrose, lactose, maltose, trehalose, raffinose and melizitose. Examples of suitable polymers for use in matrix include polyvinyl alcohols, polyethylene glycols, polyethylene imines, polyacryl amides, polyaziridines, glycols, polyacrylic acids, esters or derivatives thereof. Examples of small proteins include BSA, other albumins or protein fragments.

The matrix-embedding medium is transferred to tubes preferable 5 ml tubes or other tubes usable in flow cytometry. Fluorochrome antibodies are added and here means any antibody useable for gating when analysing samples with T lymphocytes. Preferable antibodies are directed against CD8, CD4, CD3, CD45, CD27, CD28, CD45RA, CD45RO and CD62L. Then MHC multimer constructs are added but can also be added simultaneously with the antibodies or before the antibodies. Addition of MHC multimer is not restricted to one type of MHC multimer but several different MHC multimers can be added to the same tube and thereby embedded in the same matrix sample. Optionally scavengers for oxygen-derived radicals can be added. Examples of such radical scavengers are ascorbic acid, beta-carotene, bilirubin, butylated hydroxytoluene, butylated hydroxyanisol, tert-butylhydroquinone, d-alpha-tocopherol, trolox and hydroxyanisol. The matrix mixtures are then dried under vacuum a 2-8° C. over night.

Cell samples in solution are added to the dry or semidry matrix tubes. Cell samples here means any sample comprising specific T-cells. That is preferable whole blood, homogenized spleen, lymph nodes, tumors or similar or purified lymphocytes from any of the above. The samples are incubated at room temperature for 1 minute to 2 hours, preferable 10-30 minutes. They can also be incubated at 4° C. or 37° C. or any temperature in between those two. The samples are analyzed on a flowcytometry instrument.

As an alternative to the above described method MHC multimers can be added to the sample after addition of cell sample thereby only embedding antibodies and not MHC multimer in the matrix. Similarly only MHC multimer are embedded in the matrix and antibodies added after addition of cell sample.

For enumeration of specific T-cells in the samples counting beads can be embedded in the matrix medium. The beads are then added before, together with or after adding antibodies and MHC multimer. Alternatively counting beads added following incubation with cell sample. The exact amount of specific T-cells are determined as described elsewhere herein.

Example 42

This is an example of how to make and use MHC multimers consisting of a streptavidin multimerization domain with 3 biotinylated MHC complexes and 1 fluorophore molecule attached to the biotin binding pockets of streptavidin.

MHC complexes consisting of HLA-A*0201 heavy chain, beta2microglobulin and NLVPMVATV peptide or the negative control peptide GLAGDVSAV (SEQ ID NO:11) were generated as described elsewhere herein. The fluorophore in this example was FLUORESCEIN™-linker molecules as shown in FIG. 14. Each of these molecules consist of a linker-biotin molecule mounted with 4 trippel FLUORESCEIN™-linker molecules. The linker-biotin molecule was here H-L30-Lys($NH_2$)-L30-Lys($NH_2$)-L30-Lys($NH_2$) L300Lys(caproylamidobiotin)-$NH_2$ where L30 was a 30 atom large linker and L300 was a 300 atom large linker. Both L30 and L300 was composed of multiple L15 linkers with the structure shown in FIG. 14B. Linker-biotin molecules were generated as follows: Downloaded Boc-L300-Lys(Fmoc) resin (100 mg) was deprotected and subjected to coupling with Boc-Lys(2CIZ)—OH, Boc-L30-OH, Boc-Lys (2CIZ)—OH, Boc-L30-OH, Boc-Lys(2CIZ)—OH then Boc-L30-OH. The resin was Fmoc deprotected and reacted twice (2×2 h) with caproylamido biotin NHS ester (25 mg in 0.5 mL NMP+25 microL DIPEA). The resin was washed with TFA and the product cleaved off with TFA:TFMSA: mCresol:thioanisol (6:2:1:1), 1 mL, precipitated with diethyl ether and purified by RP-HPLC. MS calculated for $C_{300}H_{544}N_{64}O_{137}S$ is 7272.009 Da, found 7271.19 Da.

Alternatively linker-biotin molecule was H-L60-Lys ($NH_2$)-L60-Lys($NH_2$)-L60-Lys($NH_2$)L300Lys(caproylami-dobiotin)-NH2 and made from downloaded Boc-L300-Lys (Fmoc) resin (100 mg), and then prepared analogously to H-L30-Lys($NH_2$)-L30-Lys($NH_2$)-L30-Lys($NH_2$)L300Lys (caproylamidobiotin)-NH$_2$. MS calculated for C$_{360}$H$_{652}$N$_{76}$O$_{167}$S is 8749.5848 Da and was found to be 7271.19 Da. Yield 3 mg.

The trippel FLUORESCEIN™-linker molecules was here betaalanin-L90-Lys(Flu)-L90-Lys(Flu)-L90-Lys(Flu)-NH$_2$ where Lys=Lysine, Flu=FLUORESCEIN™ and L90 is a 90 atom linker (se FIG. 14 for further details). The trippel-FLUORESCEIN™-linker molecule was generated as follows: Downloaded Boc-Lys(Fmoc) resin, 2 g, was Boc deprotected and subjected to 3× coupling with Boc-L30-OH, Boc-Lys(Fmoc)-OH, 3× Boc-L30-OH, Boc-Lys(Fmoc)-OH, 3× Boc-L30-OH. The three Fmoc groups were removed and carboxyFLUORESCEIN™, 301 mg, activated with HATU, 274 mg, and DIPEA, 139 µL, in 8 mL NMP, was added to the resin twice for 30 min. The resin was Boc deprotected and subjected to 2×30 min coupling with beta-alanine-N,N-diacetic acid benzyl ester, followed by 5 min treatment with 20% piperidine in NMP. The resin was washed with DCM, then TFA and the product was cleaved off the resin, precipitated with diethyl ether and purified by RP-HPLC. Yield was 621 mg. MS calculated for C268H402N44O116 is 6096.384 Da, while MS found was 6096 Da.

Biotin-linker molecule were coupled together with 4 trippel FLUORESCEIN™-linker molecules as follows: (500 nmol) was dissolved in 88 microliter NMP+2 µl pyridine and activated for 10 min at room temperature (conversion to cyclic anhydride) by addition of 10 µl N,N' diisopropylcarbodiimide. Following activation the trippel FLUORESCEIN™-linker was precipitated with diethyl ether and redissolved in 100 microliter NMP comprising 10 nmol biotin-linker. Once dissolved the coupling was initiated by addition of 5 0 diisopropyl ethyl amine, and was complete after 30 min.

Streptavidin and FLUORESCEIN™-linker molecules are then mixed in a molar ration of 1:1 and incubated for ½ hour. Then MHC complexes are added in 3-fold molar excess in respect to streptavidin and incubated for another ½ hour. Alternatively, MHC complexes are added first, then FLUORESCEIN™-linker molecules or MHC complexes are mixed with FLUORESCEIN™-linker molecules before addition to Streptavidin.

These MHC multimers are then used to stain CMV specific T-cells in a flow Cytometry experiment. 1×10$^6$ purified HPBMC from a donor with T-cells specific for HLA-A*0201(NLVPMVATV (SEQ ID NO:9)) are incubated with 10 I of each of the two HLA-A*0201(peptide)/FLUORESCEIN™ constructs described above for 10 minutes in the dark at room temperature with a cell concentration of 2×10$^7$ cells/ml. 10 I of mouse-anti-human CD8/PB (clone DK25 from Dako) are added and the incubation continued for another 20 minutes at 4° C. in the dark. The samples are then washed by adding 2 ml PBS; pH=7.2 followed by centrifugation for 5 minutes at 200×g and the supernatant removed. The cells are resuspended in 400-500 I PBS; pH=7.2 and analyzed on a flowcytometer.

In the above described example the FLUORESCEIN™-linker is as shown in FIG. 14 but the linker molecule can be any linker molecule as described in patent application WO 2007/015168 A2 (Lohse (2007)) or alternatively chemical biotinylated fluorochrome can be used instead of FLUORESCEIN™-linker molecules. The MHC complexes described in this example is a MHC I molecule composed of HLA-A*0201 heavy chain, beta2microglobulin and NLVPMVATV (SEQ ID NO:9) peptide but can in principle be any MHC complex or MHC like molecule as described elsewhere herein.

Example 43

This is an example of how to make MHC multimers consisting of a streptavidin multimerization domain with 3 biotinylated MHC complexes attached to the biotin binding pockets of streptavidin and how to use such trimer MHC complexes to stain specific T-cells in a flow cytometry experiment by addition of a biotinylated fluorophore molecule. In this example the fluorophore is FLUORESCEIN™ linker molecules constructed as described elsewhere herein.

MHC complexes consisting of HLA-A*0201 heavy chain, beta2microglobulin and peptide are generated as described elsewhere. MHC complexes are incubated with streptavidin in a molar ratio of 3:1 for ½ hour.

These trimer MHC multimers are then used to stain CMV specific T-cells in a flow Cytometry experiment. 1×10$^6$ purified HPBMC from a donor with T-cells specific for HLA-A*0201(NLVPMVATV (SEQ ID NO:9)) are incubated with 10 µl HLA-A*0201(peptide) multimer construct for 10 minutes in the dark at room temperature with a cell concentration of 2×10$^7$ cells/ml. Then FLUORESCEIN™ linker molecules (as described in Example 42) are added and incubation continued for 5 minutes. 10 I mouse-anti-human CD8/PB antibody (clone DK25 from Dako) is added and the incubation continued for another 20 minutes at 4° C. in the dark. The samples are then washed by addition of 2 ml PBS; pH=7.2 followed by centrifugation for 5 minutes at 200×g and the supernatant removed. Cells are resuspended in 400-500 I PBS; pH=7.2 and analyzed on a flowcytometer.

In this example the FLUORESCEIN™-linker is as shown in FIG. 14 but the linker molecule can be any linker molecule as described in Lohse, Jesper, (2007), WO 2007/015168 A2 or alternative chemically biotinylated fluorochrome can be used. The MHC complexes described in this example is a MHC I molecule composed of HLA-A*0201 heavy chain, beta2microglobulin and NLVPMVATV (SEQ ID NO:9) peptide but can in principle be any MHC complex or MHC like molecule as described elsewhere herein.

Example 44

This is an example of how to make MHC multimers where the multimerization domain is dextran and the MHC complexes are chemically conjugated to the dextran multimerization domain.

MHC complexes consisting of HLA-A*0201 heavy chain, beta2microglobulin and NLVPMVATV (SEQ ID NO:9) peptide or the negative control peptide GLAGDVSAV (SEQ ID NO: 11) are generated as described elsewhere herein. Dextran with a molecular weight of 270 kDa is activated with divinylsulfone. Activated Dextran is then incubated with MHC and RPE in a 0.05 M NaCHO$_3$ buffer; pH=9.5 with a molar ratio between MHC and Dextran of 30-60 and a molar ratio between RPE and dextran of 3-7:1 The mixture is placed in a water bath at 30° C. for 16 hours. Excess flourochrome, MHC and dextran are removed by FPLC using a sephacryl S-300 column.

These MHC/RPE dextramers are then used to stain CMV specific T-cells in a flow Cytometry experiment. Briefly, 1×10$^6$ purified HPBMC from a donor with T-cells specific for HLA-A*0201(NLVPMVATV (SEQ ID NO:9)) are incubated with 10 µl of each of the two HLA-A*0201(peptide)/RPE constructs described above for 10 minutes in the dark at room temperature with a cell concentration of 2×10$^7$ cells/ml. 10 µl mouse-anti-human CD8/PB antibody (clone DK25 from Dako) are added and the incubation continued for another 20 minutes at 4° C. in the dark. The samples are then washed by adding 2 ml PBS; pH=7.2 followed by centrifugation for 5 minutes at 200×g and the supernatant removed. The cells are then resuspended in 400-500 µl PBS; pH=7.2 and analyzed on a flow cytometer.

Example 45

This is an example of how to make MHC multimers where the multimerization domain is dextran and MHC complexes are MHC I molecules chemically conjugated to dextran multimerization domain and the dextran multimerization domain also have fluorochrome chemically coupled.

Human beta2microglobulin is coupled to dextran as follows. Dextran with a molecular weight of 270 kDa is activated with divinylsulfone. Activated dextran is incubated with human beta2microglobulin and RPE in a 0.05 M $NaCHO_3$ buffer; pH=9.5 with a molar ratio between beta2microglobulin and Dextran of 30-60 and a molar ratio between RPE and dextran of 3-7:1. The molar ratio of the final product is preferable 4-6 RPE and 15-24 beta2microglobulin per dextran. The mixture is placed in a water bath at 30° C. for 16 hours. Excess fluorochrome, beta2microglobulin and dextran are removed by FPLC using a Sephacryl S-300 column. The beta2microglobulin-RPE-dextran construct is then refolded in vitro together with heavy chain and peptide using the following procedure. 200 ml refolding buffer (100 mM Tris, 400 mM L-arginin-HCL, 2 mM NaEDTA, 0.5 mM oxidized Gluthathione, 5 mM reduced Glutathione, pH 8.0) supplied with protease inhibitors PMSF, Pepstatin A and Leupeptin (to a final concentration of 1 mM, 1 mg/l and 1 mg/l, respectively) is made and cooled to 10° C. 12 mg NLVPMVATV (SEQ ID NO:9) peptide is dissolved in DMSO and added to the refolding buffer together with 20-30 mg beta2microglobulin-RPE-dex and 6 mg HLA-A*0201 heavy chain. Incubation at 10° C. for 4-8 hours, then 20-30 mg beta2microglobulin-RPE-dex and 6 mg HLA-A*0201 heavy chain is added and incubation continued for 4-8 hours. Another 20-30 mg beta2microglobulin-RPE-dex and 6 mg HLA-A*0201 heavy chain is added and incubation continued for 6-8 hours. The folding reaction is filtrated through a 0.2 µm filter to remove larger aggregates and then buffer exchanged into a buffer comprising 20 mM Tris-HCl, 50 nM NaCl; pH=8.0 followed by concentration to 1-2 ml sample. Dextran-RPE-MHC complexes are then separated from excess heavy chain and peptide by size exclusion chromatography using a Sephacryl S-300, S-400 or Sephacryl S-500 column.

These MHC/RPE dextramers can be used to stain CMV specific T-cells in a flow Cytometry experiment. Briefly, 1×10⁶ purified HPBMC from a donor with T-cells specific for HLA-A*0201(NLVPMVATV (SEQ ID NO:9)) are incubated with 10 I of each of the two HLA-A*0201(peptide)/RPE constructs described above for 10 minutes in the dark at room temperature with a cell concentration of 2×10⁷ cells/ml. 10 I of mouse-anti-human CD8/PB antibody (clone DK25 from Dako) are added and the incubation continued for another 20 minutes at 4° C. in the dark. The samples are then washed by adding 2 ml PBS; pH=7.2 followed by centrifugation for 5 minutes at 200×g and the supernatant removed. The cells are then resuspended in 400-500 µl PBS; pH=7.2 and analyzed on a flowcytometer.

Example 46

This is an example of how to make and use MHC multimers where the multimerisation domain is dextran coupled with Streptavidin and fluorochrome and where the MHC-peptide complex is chemically biotinylated.

Purified MHC-peptide complexes consisting of HLA-A*0201 heavy chain, human beta2microglobulin and either the peptides NLVPMVATV (SEQ ID NO:9) or GLAGDVSAV (SEQ ID NO:11) are generated as described elsewhere herein. Briefly, HLA-A*0201 heavy chain and human beta2microglobulin is expressed separately as inclusion bodies in *E. coli* and is then refolded in vitro together with peptide following standard procedures as described by Garboczi et al., (1996), Nature 384, 134-141. Following refolding the MHC-peptide complexes are purified according to size on a SEPHADEX®75 column and buffer exchanged to a buffer containing 100 mm Carbonate, pH=8.0. The MHC-peptide complexes are incubated with 40-80 g Biotinamidohexanoic acid N-hydroxysuccinimide ester (dissolved in DMSO) per milligram MHC-peptide complex and are incubated at room temperature for 4 hours, end-over-end. Excess biotin is removed using PD-10 columns (Amersham) and the buffer is changed to a buffer containing 20 mM Tris, 50 mM NaCl, pH=8.0. Biotinylated MHC-peptide complexes are then coupled to 270 kDa dextran multimerization domains containing Streptavidin (SA) and APC by interaction with SA on the dextran multimerization domains. The SA-APC-dextran is made as described elsewhere herein. MHC-peptide complexes are added in an amount corresponding to a ratio of three MHC-peptide molecules per SA molecule and each molecule dextran contains 3 SA molecules and 12 molecules APC. The final concentration of dextran is 3.8×10e-8 M.

The binding of HLA-A*0201(NLVPMVATV (SEQ ID NO:9))/APC and the HLA-A*0201(GLAGDVSAV (SEQ ID NO:11))/APC dextran constructs to Human Peripheral Blood Mononuclear Cells (HPBMC) from two donors is analyzed by flow cytometry following a standard flow cytometry protocol. Donor 1 is positive for T-cell's directed against HLA-A*0201(NLVPMVATV (SEQ ID NO:9)) complexes and negative for T-cells with specificity for HLA-A*0201(GLAGDVSAV (SEQ ID NO: 11)) complexes while donor 2 do not have T-cells specific either MHC-peptide complex. Briefly, HPBMC from the blood of two human donors are isolated, by a standard protocol using FICOLL®-Hypaque. 1×10⁶ purified HPBMC from each donor at a concentration of 2×10⁷ cells/ml are incubated with 10 I of each of the two MHC multimer constructs described above for 10 minutes in the dark at room temperature. 10 I of each of the antibodies mouse-anti-human CD3/PE (clone UCHT1 from Dako) and mouse-anti-human CD8/PB (clone DK25 from Dako) is added and the incubation continued for another 20 minutes at 4° C. in the dark. The samples are then washed by adding 2 ml PBS; pH=7.2 followed by centrifugation for 5 minutes at 200×g and the supernatant removed. The cells are resuspended in 400-500 I PBS; pH=7.2 and analyzed on a flowcytometer. Samples from donor 1 will show positive staining with HLA-A*0201(NLVPMVATV (SEQ ID NO:9))/APC dextran constructs (positive staining here means a distinguishable group of cells binding anti-CD3/PE, anti-CD8/PB antibodies and HLA-A*0201 (NLVPMVATV (SEQ ID NO:9))/APC multimers) while no staining will be observed with A*0201(GLAGDVSAV (SEQ ID NO:11))/APC dextran multimers. Donor 2 will be negatively stained with both MHC multimers.

Example 47

This is an example of how a MHC class 1 complex with a peptide in the peptide binding-groove was chemically biotinylated, coupled to a dextran multimerization domain containing Streptavidin (SA) and APC and then used to detect specific T-cells in a flow cytometry analysis.

MHC class 1 complexes consisting of light chain human beta2microglobulin, heavy chain HLA-A0201 and the peptide NLVPMVATV (SEQ ID NO:9) was generated as described next:

1. 200 ml of refolding buffer (100 mM Tris, 400 mM L-arginin-HCL, 2 mM NaEDTA, 0.5 mM oxidized Gluthathione, 5 mM reduced Glutathione, pH 8.0) was supplied with protease inhibitors PMSF (phenylmethylsulphonyl fluoride), Pepstatin A and Leupeptin (to a final concentration of 1 mM, 1 mg/l and 1 mg/l, respectively). The refolding buffer was placed at 10° C. on a stirrer.

2. 12.3 mg of peptide NLVPMVATV (SEQ ID NO:9) was dissolved in 400 I DMSO and added drop-wise to the refolding buffer at vigorous stirring.

3. 4.4 mg of human Light Chain β2m was added drop-wise to the refolding buffer at vigorous stirring.

4. 6.2 mg of Heavy Chain HLA-A*0201 (supplied with DTT to a concentration of 0.1 mM) was added drop-wise to the refolding buffer at vigorous stirring.

5. The folding reaction was placed at 10° C. at slow stirring for approx. 8 hours.

6. After approx. 8 hours, step 3 and 4 was repeated and the folding reaction was placed at 10° C. at slow stirring O/N.

7. Step 3 and 4 was repeated, and the folding reaction is placed at 10° C. at slow stirring for approx 6 hours.

8. After approx. 6 hours the folding reaction was filtrated through a 0.2 μm filter to remove aggregates.

9. The folding reaction was concentrated O/N at 10° C. shaking gently in a Vivacell 250 concentrator with a 5000 MWCO PES-filter. The folding reaction was concentrated to approx. 1.5 ml.

10. Correctly folded MHC-complex was separated and purified from excess β2m, excess heavy chain and aggregates thereof, by size exclusion chromatography on a 120 ml SUPERDEX 75 column. Correctly folded monomer MHC-complex was eluted with a buffer containing 100 mM Carbonat-buffer, pH 8.0

11. Fractions comprising the folded MHC-complex were pooled and concentrated to 3.24 mg/ml by centrifugation in a Vivaspin6 concentrator with a 5000 MWCO PES-filter. The protein-concentration was estimated from its absorption at 280 nm.

12. Folded MHC-complex was stored at −170° C. before further use.

The above MHC class 1 complex was chemically biotinylated as described next:

13. 100 μg of the folded MHC-complex (a buffer containing 100 mM Carbonat-buffer, pH 8.0) and 4 μg (40 μg biotin/mg MHC complex) Sulfo-NHS-LC-Biotin (sulfosuccinimidyl-6-[biotinamido]hexanoate, PIERCE 21335) dissolved to 1 mg/ml in water, was incubated at room temperature for 2.5 hours, end over end.

14. Excess biotin was removed using PD-10 columns (Amersham) and the buffer is changed to a buffer containing 20 mM Tris, 50 mM NaCl, pH=8.0.

15. The chemically biotinylated MHC-complex was concentrated by centrifugation in Vivaspin6 concentrator with a 5000 MWCO PES-filter and the protein-concentration was estimated from its absorption at 280 nm. 10 vol % of a buffer containing 0.05M Tris/HCl, 15 mM NaN3, 10% BSA, pH 7.2 was added and the final concentration of MHC-complex was calculated to 0.575 mg/ml.

The chemically biotinyaleted MHC class 1 complex was attached to a 270 kDa dextran multimerization domains containing Streptavidin (SA) and APC by a non-covalent interaction Biotin_Streptavidin interaction between the chemically biotinylated MHC complex and the SA on the dextran multimerization domains. The SA-APC-dextran is made as described elsewhere herein.

100 μl of a MHC-dextramer solution with a final concentration of $32 \times 10^{-9}$M was produced as follows:

16. 20 μl 270 kDa Vinylsulfone-activated dextran (each molecule dextran contains 3,7 SA molecules and 9 APC molecules), corresponding to $3,2 \times 10^{-12}$ mol, and 5,98 μl of the above described MHC-complex, corresponding to $7,1 \times 10^{-11}$ mol (6 mol MHC-complex/mol SA), was mixed and incubated at room temperature in the dark for 30 min.

17. A buffer of 0,05M Tris-HCl, 15 mM $NaN_3$, 1% BSA, pH 7.2 was added to a final volume of 100 μl.

18. The resulting MHC-dextramer preparation was then used in flow cytometry experiments.

The binding of the above MHC class 1 complex coupled to an APC dextran construct to Human Peripheral Blood Mononuclear Cells (HPBMC) from one donor were analyzed by flow cytometry following a standard flow cytometry protocol. As a negative control a MHC class 1 complex consisting of beta2microglobulin, heavy chain HLA-A0201 and the peptide GLAGDVSAV (SEQ ID NO: 11), produced by the same procedure as described above, were used.

Briefly, HPBMC from the blood of a human donors were isolated, by a standard protocol using FICOLL®-Hypaque. $1 \times 10^6$ purified HPBMC at a concentration of $2 \times 10^7$ cells/ml were incubated with 10 μl of each of the two MHC multimer constructs described above for 10 minutes in the dark at room temperature. 10 I of each of the antibodies mouse-anti-human CD3/PE, mouse-anti-human CD8/PB and mouse-anti-human CD4/FITC was added and the incubation continued for another 30 minutes at 4° C. in the dark. The samples are then washed by adding 2 ml PBS; pH=7.2 followed by centrifugation for 5 minutes at 200×g and the supernatant removed. The cells was resuspended in 400 I PBS; pH=7.2 and analyzed on a flowcytometer. Samples from the donor showed positive staining with HLA-A*0201 (NLVPMVATV (SEQ ID NO:9))/APC dextran constructs (positive staining here means a distinguishable group of cells binding anti-CD3/PE, anti-CD8/PB antibodies and HLA-A*0201(NLVPMVATV (SEQ ID NO:9))/APC multimers) while no staining was observed with A*0201 (GLAGDVSAV (SEQ ID NO:11))/APC dextran multimers. The result is shown in FIG. 15.

Example 48

This example describes how to make MHC multimers where the MHC complexes are attached to the mulitmerization domain by interaction of two alpha-helices and a disulfide bond between the adjacent cysteine residues.

The MHC-complex in this example consisted of light chain β2m, the MHC class I Heavy Chain allele HLA-B*0801 (a truncated version in which the intracellular and transmembrane domains have been deleted) fused to alphahelic and cysteine by genetic fusion, and the peptide RAKFKQLL (SEQ ID NO:19).

An alpha-helic sequence AQLEKELQALEKE-NAQLEWELQALEKELAQGGCGGSCG (SEQ ID

NO:26) comprising a C-terminal cysteine residue is fused to MHC class I Heavy Chain allele HLA-B*0801 modified as described elsewhere herein (deletion of intracellular and transmembran domains and introduction of recognition site for BirA enzyme) by genetic fusion. This is done by ligating cytoplasmatic cDNA sequence of the modified HLA-B*0801 to the alpha-helic encoding sequence. The HLA-B*0801-Coil sequence is cloned into the expression vector pGarboczi and expressed as inclusion bodies in *E. coli* prior to in vitro refolding together with β2m and peptide as described elsewhere herein. Following refolding the monomer MHC complexes is purified by size exclusion chromatography as described elsewhere herein.

The multimerization domain in this example is divinylsulfone activated dextran 270 (VS-dex270) decorated with peptides comprising an alpha-helic structure and a cysteine residue for dislulfid bond, and flourochromes.

A peptide comprising alpha-helic coil structure, cysteine residue for disulfide bond, and C-terminal cysteine for thiol reaction with reactive vinyl groups on dextran is synthesised; AQLEKELQALEKE-NAQLEWELQALEKELAQGG(C(tButhio))GGSC (SEQ ID NO:36). The internal cysteine is protected to direct reaction of C-terminal thiol to reactive vinyl on dextran.

VS-dex 270 and peptide is mixed under natural conditions to promote thiol reaction of the peptide to divinylsulfone on dextran. Afterwards fluorochrome of choice (e.g. R-phycoerythrine (RPE)) is added and pH is raised to favour reaction of amines of the fluorochrome to dextran. The reaction is stopped by adding nucleophilic reagent such as ethanolamine. The conjugate is purified by size exclusion chromatography. The internal cysteine is deprotected. In this example the protection group is tert-Butylthio, which is deprotected by reducing agents such as DTT. Immediately prior to assembling to MHC complexes, the reducing reagent is replaced by a non-reducing reagent, e.g. by buffer exchange on a spin-column.

MHC complexes are attached to the mulitmerization domain through interaction of the two alpha-helices and a disulfide bond between the adjacent cysteine residues.

Dextran decorated with deprotected alpha-helic peptides is mixed, in various molar ratios, with MHC complexes under oxidative conditions allowing the two alpha-helices to form coiled-coil structure, and the two adjacent —SH groups of cysteine residues to form disulfide bonds. Optionally the product is purified by size exclusion chromatography before use. The product can be used to stain specific T cells as described elsewhere herein for staining specific T cells with MHC dextramers.

Example 49

This example describes how to make MHC multimers where the MHC complexes are attached to the multimerization domain by interaction of two alpha-helices and a disulfide bond between the adjacent cysteine residues.

The MHC-complex in this example consisted of light chain β2m, the MHC class I Heavy Chain allele HLA-B*0801 (a truncated version in which the intracellular and transmembrane domains have been deleted) fused to alpha-helic and cysteine by genetic fusion, and the peptide RAKFKQLL.

An alpha-helic sequence AQLEKELQALEKE-NAQLEWELQALEKELAQGGCGGSCG (SEQ ID NO:26) comprising a C-terminal cysteine residue is fused to MHC class I Heavy Chain allele HLA-B*0801 modified as described elsewhere herein (deletion of intracellular and transmembran domains and introduction of recognition site for BirA enzyme) by genetic fusion. This is done by ligating cytoplasmatic cDNA sequence of the modified HLA-B*0801 to the alpha-helic encoding sequence. The HLA-B*0801-Coil sequence is cloned into the expression vector pGarboczi and expressed as inclusion bodies in *E. coli* prior to in vitro refolding together with β2m and peptide as described elsewhere herein. Following refolding the Monomer MHC complexes is purified by size exclusion chromatography as described elsewhere herein.

The multimerization domain in this example is divinylsulfone activated dextran 270 (VS-dex270) decorated with peptides comprising an alpha-helic structure and a cysteine residue for disulfide bond, and fluorochromes.

A peptide comprising alpha-helic coil structure, cysteine residue for disulfide bond, and C-terminal cysteine for thiol reaction with reactive vinyl groups on dextran is synthesised; AQLEKELQALEKE-NAQLEWELQALEKELAQGG(C(tButhio))GGSC (SEQ ID NO:36). The internal cysteine is protected to direct reaction of C-terminal thiol to reactive vinyl on dextran.

Peptide and VS-dex 270 is mixed in molar ratios 10-50:1 in 10 mM HEPES, 0.1 M NaCl, pH 7 to react thiol of peptide to divinylsulfone on dextran. Excess of peptide is removed by FPLC using a sepharyl S-300 column.

VS-dex 270 decorated with peptides is mixed to fluorochrome RPE in molar ratio 1:18 in 10 mM HEPES, 0.1 M NaCl, pH 8. The reaction is stopped by adding 0,1M ethanolamine, pH 8. The conjugate is purified by size exclusion chromatography using a Sephacryl S-300 column in 10 mM HEPES, 0.1 M NaCl, pH 7,2. The internal cysteine is deprotected. In this example the protection group is tert-Butylthio, which is deprotected by reducing agents such as 0.1 M DTT. Immediately prior to assembling to MHC complexes, the reducing reagent is replaced by 10 mM HEPES, 0.1 M NaCl, 15 mM NaN$_3$, 1% BSA, pH 7,2 by buffer exchange on a spin-column.

MHC complexes are attached to the mulitmerization domain through interaction of the two alpha-helices and a disulfide bond between the adjacent cysteine residues.

Dextran decorated with deprotected alpha-helic peptides is mixed with MHC complexes in molar ratios 1: 10-50 in 0.05 M Tris-HCl, 15 mM NaN$_3$, 1% BSA, pH 7,2 allowing the two alpha-helices to form coiled-coil structure, and the two adjacent —SH groups of cysteine residues to form disulfide bonds. Optionally the product is purified by size exclusion chromatography before use. The product can be used to stain specific T cells as described elsewhere herein for staining specific T cells with MHC dextramers.

Example 50

This example describes how to make MHC multimers where the MHC complexes are attached to the mulitmerization domain by interaction of two alpha-helices and a disulfide bond between the adjacent cysteine residues.

The MHC-complex in this example consisted of light chain β2m, the MHC class I Heavy Chain allele HLA-B*0801 (a truncated version in which the intracellular and transmembrane domains have been deleted) fused to alpha-helic and cysteine by genetic fusion, and the peptide RAKFKQLL.

An alpha-helic sequence AQLEKELQALEKE-NAQLEWELQALEKELAQGGCGGSCG (SEQ ID NO:26) comprising a C-terminal cysteine residue is fused to MHC class I Heavy Chain allele HLA-B*0801 modified as described elsewhere herein (deletion of intracellular and transmembrane domains and introduction of recognition site for BirA enzyme) by genetic fusion. This is done by ligating cytoplasmatic cDNA sequence of the modified HLA-B*0801 to the alpha-helic encoding sequence. The HLA-B*0801-Coil sequence is cloned into the expression vector pGarboczi and expressed as inclusion bodies in *E. coli* prior to in vitro refolding together with β2m and peptide as described elsewhere herein. Following refolding the Mono-mer MHC complexes is purified by size exclusion chroma-tography as described elsewhere herein.

The multimerization domain in this example is divi-nylsulfone activated dextran 270 (VS-dex270) decorated with peptides comprising a alpha-helic structure and a cysteine residue for disulfide bond, and fluorochromes.

A peptide comprising alpha-helic coil structure, cysteine residue for disulfide bond, and C-terminal cysteine for thiol reaction with reactive vinyl groups on dextran is synthe-sised; AQLEKELQALEKE-NAQLEWELQALEKELAQGG(C(tButhio))GGSC (SEQ ID NO:36). The internal cysteine is protected to direct reaction of C-terminal thiol to reactive vinyl on dextran.

VS-dex 270, peptide and fluorochrome is mixed under natural conditions to promote reaction of the peptide and fluorochrome (e.g. allophycocyanin, APC) to divinylsulfone on dextran. The reaction is stopped by adding nucleophilic reagent such as ethanolamine. The conjugate is purified by size exclusion chromatography. The internal cysteine is deprotected. In this example the protection group is tert-Butylthio, which is deprotected by reducing agents such as DTT. Immediately prior to assembling to MHC complexes, the reducing reagent is replaced by a non-reducing reagent, e.g. by buffer exchange on a spin-column.

MHC complexes are attached to the multimerization domain through interaction of the two alpha-helices and a disulfide bond between the adjacent cysteine residues. Dex-tran decorated with deprotected alpha-helic peptides is mixed, in various molar ratios, with MHC complexes under oxidative conditions allowing the two alpha-helices to form coiled-coil structure, and the two adjacent —SH groups of cysteine residues to form disulfide bonds. The product might be purified by size exclusion chromatography before used to stain specific T cells as described elsewhere herein.

Example 51

This example describes how to make MHC multimers where the MHC complexes are chemically conjugated to the multimerization domain by reaction of C-terminal cysteine to divinylsulfone on dextran.

The MHC-complex in this example consisted of light chain β2m, the MHC class I Heavy Chain allele HLA-B*0801 (a truncated version in which the intracellular and transmembrane domains have been deleted) fused cysteine by genetic fusion, and the peptide RAKFKQLL (SEQ ID NO:19).

A cysteine and glycine (Cys-Gly) residue is added to the C-terminal of MHC class I Heavy Chain allele HLA-B*0801 modified as described elsewhere herein (deletion of intracellular and transmembran domains and introduction of recognition site for BirA enzyme) by site-directed mutagen-esis. The HLA-B*0801-Cys sequence is cloned into the expression vector pGarboczi and expressed as inclusion bodies in *E. coli* prior to in vitro refolding together with β2m and peptide as described elsewhere herein. Following refolding the Monomer MHC complexes is purified by size exclusion chromatography as described elsewhere herein.

The multimerization domain in this example is divi-nylsulfone activated dextran 270 (VS-dex270) as described elsewhere herein.

VS-dex 270 and MHC complexes are mixed under natural conditions to promote thiol reaction of the C-terminal cys-teine to divinylsulfone on dextran. Afterwards fluorochrome of choice (e.g. RPE) is added and pH is raised to favour reaction of amines of the fluorochrome to dextran. The reaction is stopped by adding nucleophilic reagent such as ethanolamine. The conjugate is purified by size exclusion chromatography before used to stain specific T cells as described elsewhere herein.

Example 52

This example describes how to make MHC multimers where the MHC complexes are chemically conjugated to the multimerization domain by reaction of C-terminal cysteine to divinylsulfone on dextran.

The MHC-complex in this example consisted of light chain β2m, the MHC class I Heavy Chain allele HLA-B*0801 (a truncated version in which the intracellular and transmembrane domains have been deleted) fused cysteine by genetic fusion, and the peptide RAKFKQLL (SEQ ID NO:19).

A cysteine and glycine (Cys-Gly) residue is added to the C-terminal of MHC class I Heavy Chain allele HLA-B*0801 modified as described elsewhere herein (deletion of intracellular and transmembran domains and introduction of recognition site for BirA enzyme) by site-directed mutagen-esis. The HLA-B*0801-Cys sequence is cloned into the expression vector pGarboczi and expressed as inclusion bodies in *E. coli* prior to in vitro refolding together with β2m and peptide as described elsewhere herein. Following refolding the Monomer MHC complexes is purified by size exclusion chromatography as described elsewhere herein.

The multimerization domain in this example is divi-nylsulfone activated dextran 270 (VS-dex270) as described elsewhere herein.

VS-dex 270, MHC complexes and fluorochrome (e.g. APC) are mixed under natural conditions to promote reac-tion of the C-terminal cysteine of the MHC compels and the fluorochrome to divinylsulfone on dextran. The reaction is stopped by adding nucleophilic reagent such as etha-nolamine. The conjugate is purified by size exclusion chro-matography before used to stain specific T cells as described elsewhere herein.

Example 53

This example describes how to make MHC multimers where the MHC complexes are attached to the multimeriza-tion domain by streptavidin-biotin interaction. The MHC-multimer in this example consist of APC-streptavidin (APC-SA)-conjugated 270 kDa dextran and a biotinylated, folded MHC-complex composed of β2m, HLA-B*0801 Heavy Chain and the peptide RAKFKQLL (SEQ ID NO:19).

In this example the HLA-B*0801 contains a C-terminal cystein, generated as described elsewhere herein (example 51 and 52). After refolding in vitro of β2m, HLA-B*0801 Heavy Chain and the peptide RAKFKQLL (SEQ ID NO:19), and size exclusion chromatography, the MHC com-plex is treated with a —SH specific biotinylating reagent, e.g. 1-Biotinamido-4-[4'(maleimidomethyl)-clyco-hexan-ecarboxamido]-butane (biotin-BMCC). The biotinylated MHC complexes are separated from excess of biotin by size exclusion chromatography.

The biotinylated MHC complexes can be assembled to APC-SA-conjugated dextran or other SA-conjugated dextrans as described elsewhere herein, and used to stain specific T cells.

Example 54

This example describes how to make MHC multimers where the MHC complexes are attached to the multimerization domain by streptavidin-biotin interaction. The MHC-multimer in this example consist of APC-streptavidin (APC-SA)-conjugated 270 kDa dextran and a biotinylated, folded MHC-complex composed of β2m, HLA-B*0801 Heavy Chain and the peptide RAKFKQLL (SEQ ID NO:19).

In this example the β2m contains an N-terminal cystein. A N-terminal cystein residue is introduced to the β2m by site-directed mutagenesis. The β2m-Cys is cloned into a vector and expressed in *E. coli* prior to in vitro refolding together with Heavy Chain HLA-B*0801 and peptide as described elsewhere herein. The MHC complexes are separated by size exclusion chromatography and treated with a —SH specific biotinylating reagent, e.g. 1-Biotinamido-4-[4'(maleimidomethyl)-clyco-hexanecarboxamido]-butane (biotin-BMCC). The biotinylated MHC complexes are separated from excess of biotin by size exclusion chromatography.

The biotinylated MHC complexes can be assembled to APC-SA-conjugated dextran or other SA-conjugated dextrans as described elsewhere herein, and used to stain specific T cells.

Example 55

This is an example of how MHC multimers may be used for the detection of antigen specific T-cells simultaneously with activation of T cells. This example is a combination of i) direct detection of TCR, using MHC complexes coupled to any multimerisation as described elsewhere herein to stain antigen specific T cells, and ii) detection of induced intracellular cytokine production by addition of fluorophor-labelled anti-cytokine antibodies by flow cytometry.

Multicolor immunofluorescent staining with antibodies against intracellular cytokines and cell surface markers provides a high resolution method to identify the nature and frequency of cells which express a particular cytokine(s). In addition to enabling highly specific and sensitive measurements of several parameters for individual cells simultaneously, this method has the capacity for rapid analysis of large numbers of cells which are required for making statistically significant measurements.

Production of cytokines plays an important role in the immune response. Examples include the induction of many antiviral proteins by IFN-γ, the induction of T cell proliferation by IL-2 and the inhibition of viral gene expression and replication by TNF-α. Cytokines are not preformed factors; instead they are rapidly produced upon relevant stimulation. Intracellular cytokine staining relies upon the stimulation of T cells in the presence of an inhibitor of protein transport thus retaining the cytokines inside the cell.

Cellular activation to trigger cytokine production generally results in down-regulation of the T cell receptor. For this reason, MHC multimer staining is carried out prior to activation to ensure a good level of staining. The MHC multimers may be internalized with the T cell receptor during this period, but can still be detected in permeabilized cells. To analyze the effector function of antigen-specific T cells, the cells are first stained with MHC multimers, and then stimulated with antigen. This is followed by staining with antibodies specific for extracellular epitopes (such as CD8), then by membrane permeabilization and intracellular cytokine staining. The following protocol is an example of MHC multimer co-staining with anti-IFN-γ, TNF-α, MIP-1b, or IL-2.

Protocol applicable for intracellular staining of IFNg, TNFa, MIP-1b, or IL-2:

1. Prepare peripheral blood cells in phosphate buffered saline (PBS) at a cell concentration of $2\times10^7$ cells/ml.
2. Transfer the cell suspension to individual tubes in 50 μl aliquots.
3. Add relevant titrated fluorescently-labeled MHC multimers to the desired tubes, and incubate for 10 min at 22° C. (nonstimulated single-color controls should not be stained at this stage). Add 10 μl PBS to remaining tubes.
4. Add 500 μl PBS to each tube. Centrifuge at 450× g for 5 minutes at 10° C.
5. Aspirate supernatant. Agitate to disrupt cell pellets and resuspend in 200 μl complete RPMI.
6. Dilute peptide/antigen stock 1:50 in complete RPMI. Add 2 μl of this (10 μg/ml (investigate the effect on cytokine response of titrating your peptide)) to each desired tube. If using Leukocyte Activation cocktail (LAC) as a control, rapidly thaw this at 37° C. in a water bath and add 0.33 μl of this to each desired tube.
7. Place the tubes at 37° C. in a humidified $CO_2$ incubator for 15 minutes to 1 hour.
8. Add Brefeldin A (10 μg/ml final) to the desired tubes (n.b. LAC contains Brefeldin A) and return to the incubator. Incubate for 15 hours (the optimal incubation time is variable and must be determined).
9. Remove tubes from the incubator. Centrifuge at 450× g for 5 minutes at 10° C.
10. Aspirate supernatant. Resuspend desired cell pellets in 50 μl PBS containing an optimally titrated amount of anti-CD8 antibody. Add 50 μl PBS to remaining tubes.
Note: Single-color controls should be stained at this stage. If additional phenotyping of samples is desired, antibodies to other cell surface receptors may also be added at this time.
11. Incubate for 20 minutes on ice.
12. Add 500 μl PBS to each tube. Centrifuge at 450× g for 5 minutes at 10° C.
13. Aspirate supernatant. Agitate to disrupt cell pellets.
14. Add 200 μl 4% paraformaldehyde to each sample tube. Vortex tubes. Incubate for 20 minutes on ice. This step will fix the cell morphology of the activated cells.
Note: The procedure can be stopped at this point. Repeat steps 12 and 13. Resuspend the cells in 100 μl/tube PBS. Cover and store the cells at 4° C. for up to 3 days. To proceed, repeat steps 12 and 13. Resuspend the cells in 100 μl/tube permeabilization buffer and proceed to step 16.
15. Add 200 μl permeabilization buffer to each tube.
16. Centrifuge at 450× g for 5 minutes at 10° C. Aspirate supernatant.
17. Add 100 μl permeabilization buffer to the sample tubes that are to be stained with anti-cytokine antibody. Add 100 μl PBS to the remaining tubes (i.e. Single-color controls).
18. Incubate for 5 minutes at room temperature.
19. Add an optimally titrated amount of conjugated anti-cytokine antibody to the desired sample tubes and mix.

20. Incubate for 20 minutes at room temperature.

21. Add 200 µl permeabilization buffer to each tube and centrifuge at 450× g for 5 minutes at 10° C. Aspirate supernatant and agitate tubes to disrupt the cell pellets.

22. Resuspend the cells in 200 µl fix solution. Vortex tubes. It is important to vortex well when adding this fixative so that cells do not clump.

23. The samples are now ready for data acquisition and analysis on a flow cytometer but may be stored overnight at 4° C. in the dark prior to analysis.

We conclude that the MHC multimer constructs can be used to detect the presence of specific T cells in the blood simultaneously with activation and intracellular staining of cytokines.

Example 56

This is an example of how MHC multimers may be used for the detection of antigen specific T-cells simultaneously with activation of T cells. This example is a combination of i) direct detection of TCR, using MHC complexes coupled as pentamers to stain antigen specific T cells, and ii) detection of induced intracellular cytokine production by addition of fluorophor-labelled anti-cytokine antibodies by flow cytometry. The antigenic origin is Epstein-Barr Virus (EBV), thus, immune monitoring of EBV infection PBMCs were incubated with either a negative control (non-specific) Pentamer (A*0201/EBV (GLCTLVAML (SEQ ID NO:13))) or a Pentamer specific for the cells of interest (B*0801/EBV (RAKFKQLL (SEQ ID NO:19))), then stimulated with LAC (non-specific activation) or B*0801/EBV peptide (specific peptide activation) for 15 hours in the presence of Brefeldin A. Fixation, permeabilization and staining for IFN-γ were carried out exactly as detailed in the protocol outlined in the example above.

FIG. 16 illustrates Pentamer (specific or non-specific) versus intracellular IFN-γ staining after activation with specific or non-specific antigen.

This example shows that the MHC multimer constructs can be used to detect the presence of EBV specific T cells in the blood simultaneously with activation and intracellular staining of cytokines.

Example 57

This is an example of how MHC multimers may be used for the detection of antigen specific T-cells simultaneously with activation of T cells. This example is a combination of i) direct detection of TCR, using MHC complexes coupled as any multimerisation as described elsewhere herein to stain antigen specific T cells, and ii) indirect detection of TCR, by detection of induced intracellular cytokine production by addition of fluorophor-labelled anti-cytokine antibodies by flow cytometry. The antigenic origin is Rheumatoid arthritis (RA), thus, immune monitoring of RA.

PBMCs are incubated with either a negative control (non-specific) MHC multimer (HLA-DR4/nonsense) or a MHC multimer specific for the cells of interest (HLA-DR4/CII(261-273)), then stimulated with LAC (non-specific activation) or DR4/CII (261-273) peptide (specific peptide activation) for an optimal period of time in the presence of Brefeldin A. Fixation, permeabilization and staining for IFN-γ are carried out exactly as detailed in the protocol outlined in the example above.

We conclude that the MHC multimer constructs can be used to detect the presence of Rheumatoid arthritis specific T cells in the blood simultaneously with activation and intracellular staining of cytokines.

Example 58

This is an example of indirect detection of activation of T cells, by detection of intracellular cytokine production by addition of fluorophor-labelled anti-cytokine antibodies by flow cytometry. The MHC multimer used MHC complexes coupled as any multimerisation as described elsewhere herein. The antigenic origin is Rheumatoid arthritis (RA), thus, immune monitoring of RA.

PBMCs stimulated with LAC (non-specific activation) or DR4/CII(261-273) peptide (specific peptide activation) for an optimal period of time in the presence of Brefeldin A. Fixation, permeabilization and staining for IFN-γ are carried out as detailed in the protocol outlined in the example above. The initial MHC multimer staining in step 3-5 in the protocol is omitted in this experiment.

We conclude that the MHC multimer constructs can be used to activate Rheumatoid arthritis specific T cells in the blood.

Example 59

This is an example of how MHC multimers may be used for the detection of antigen specific T-cells and activation of T cells This example is a combination of i) direct detection of TCR, using MHC complexes coupled as any multimerisation as described elsewhere herein to stain antigen specific T cells, and ii) indirect detection of TCR, by detection of induced intracellular cytokine production by addition of fluorophor-labelled anti-cytokine antibodies by flow cytometry.

PBMCs are stimulated with either a negative control (non-specific) MHC multimer or a MHC multimer specific for the cells of interest (specific peptide activation) for an optimal period of time in the presence of Brefeldin A. Fixation, permeabilization and staining for IFN-γ are carried out as detailed in the protocol outlined in the example above.

We conclude that the MHC multimer constructs can activate T cells. The cytokine production is detected by intracellular staining in flow cytometric analysis.

Example 60

This is an example of how MHC multimers may be used for diagnosis of Lyme Disease in blood samples from humans infected with *Borrelia* bacteria.

In this example the MHC multimer used are MHC complexes coupled to fluorophor-labelled dextran (Dextramers). The dextramers are used for direct detection of TCR in flow Cytometry. The antigen origin is *Borrelia*, thus, immune monitoring of a *Borrelia* infection.

Lyme disease is caused by infection by *Borrelia* bacteria. During acute infection *Borrelia* specific activated T cells will be present in increased amounts in an activated state compared to healthy individuals. The presences of an increased amount of activated *Borrelia* specific T cells may thereby act as a surrogate marker for infection with *Borrelia* bacterium. MHC multimers carrying *borrelia* specific peptides is in this example used to detect the presence of *Borrelia* specific T cells in the blood of patients infected with *Borrelia*.

Purified MHC-peptide complexes consisting of HLA-A*0201 heavy chain, human beta2microglobulin and peptide derived from regions in Outer surface protein A or Flagellin B conserved among the three species *Borrelia Burgdorferi, Borrelia Garinii* and *Borrelia Afzelii* or a negative control peptide are generated by in vitro refolding, purified and biotinylated as described elsewhere herein. Biotinylated MHC-peptide complexes are then coupled to a 270 kDa dextran multimerization domain labelled with APC by interaction with streptavidin (SA) on the dextran multimerization domain. The dextran-APC-SA multimerization domain is generated as described elsewhere herein. MHC-peptide complexes are added in an amount corresponding to a ratio of three MHC-peptide molecules per SA molecule and each molecule dextran contains 3.7 SA molecule and 8.95 molecules APC. The final concentration of dextran is 3.8×10e-8 M. The following MHC (peptide)/APC dextran constructs are made:

1. APC-SA conjugated 270 kDa dextran coupled with HLA-A*0201 in complex with beta2microglobulin and the peptide ALIACKQNV (SEQ ID NO:27) derived from OspA.
2. APC-SA conjugated 270 kDa dextran coupled with HLA-A*0201 in complex with beta2microglobulin and the peptide FTKEDTIT (SEQ ID NO:28) derived from OspA.
3. APC-SA conjugated 270 kDa dextran coupled with HLA-A*0201 in complex with beta2microglobulin and the peptide SIQIEIEQL (SEQ ID NO:29) derived from Fla B
4. APC-SA conjugated 270 kDa dextran coupled with HLA-A*0201 in complex with beta2microglobulin and the peptide NLNEVEKVL (SEQ ID NO:30) derived from Fla B
5. APC-SA conjugated 270 kDa dextran coupled with HLA-A*0201 in complex with beta2microglobulin and the peptide SLAKIENAI (SEQ ID NO:31) derived from Fla B
6. APC-SA conjugated 270 kDa dextran coupled with HLA-A*0201 in complex with beta2microglobulin and the non-sense peptide GLAGDVSAV (SEQ ID NO:11)

The binding of the above described MHC (peptide)/APC dextran is used to determine the presence of Osp A or Fla B specific T cells in the blood from *Borrelia* infected individuals by flow cytometry following a standard flow cytometry protocol.

Blood from a patient with Lyme disease is isolated and 100 ul of this blood is incubated with 10 μl of each of the MHC (peptide)/APC dextran constructs described above for 10 minutes in the dark at room temperature. 5 μl of each of each of the antibodies mouse-anti-human CD3/PB (clone UCHT1 from Dako), mouse-anti-human CD4/FITC (clone MT310 from Dako) and mouse-anti-human CD8/PE (clone DK25 from Dako) are added and the incubation continues for another 20 minutes at 4° C. in the dark. The samples are then washed by adding 2 ml PBS; pH=7.2 followed by centrifugation for 5 minutes at 300×g and the supernatant removed. The washing step is repeated twice. The washed cells are resuspended in 400-500 μl PBS+1% BSA; pH=7.2 and analyzed on flowcytometer.

The presence of cells labeled with anti-CD3/PB, anti-CD8/PE and the MHC (peptide)/APC dextran constructs 1, 2, 3, 4 and 5 described above and thereby the presence of *Borrelia* specific T cells indicate that the patient are infected with *Borrelia* bacteria. Blood analysed with MHC (peptide)/APC dextran construct 6 show no staining of CD3 and CD8 positive cells with this MHC (peptide)/APC dextran construct. Results are shown in FIG. 17.

The sensitivity of the above described diagnostic test may be enhanced by addition of labeled antibodies specific for activation markers expressed in or on the surface of the *Borrelia* specific T cells.

This example shows that MHC (peptide)/APC dextran constructs can be used to detect the presence of *Borrelia* specific T cells in the blood of patients infected with *Borrelia*.

Example 61

The preparation of a Pentamer is described in e.g. (United States Patent application 20040209295). Briefly, the following steps lead to a fluorescent Pentamer reagent:

The following is a detailed example for cloning, expressing, and purifying a pentameric class I MHC complex, which comprises a chimeric fusion of .beta.2m with COMP. The chimeric .beta.2m-COMP protein is expressed in insoluble inclusion bodies in *E. coli* and subsequently assembled as pentameric .beta.2m-COMP in vitro. The pentameric class I MHC peptide complex is then formed in a second refolding reaction by combining .beta.2m-COMP pentamers and the human MHC class I alpha. molecule known as HLA-A*0201, in the presence of an appropriate synthetic binding peptide representing the T cell antigen. In this example, a well characterized antigen derived from Epstein-Barr virus BMLF1 protein, GLCTLVAML (SEQ ID NO:13) (a.a. 289-297), is used. The resultant complex is labelled with a fluorescent entity and used as a staining reagent for detecting antigen-specific T cells from a mixed lymphocyte population, in a flow cytometry application.

The strategy involves the sequential cloning into pET-24c vector of .beta.2m, yielding a construct referred to as pETBMC01, followed by the insertion of the oligomerisation domain of cartilage oligomeric matrix protein (COMP) with a biotin acceptor sequence (BP) for site-specific biotinylation with the biotin-protein ligase BirA, yielding a construct referred to as pETBMC02. Thirdly a polyglycine linker is cloned in between .beta.2m and COMP, yielding a construct referred to as pETBMC03, and finally, a serine-residue is removed by site-directed mutagenesis, which serine residue precedes the poly-glycine linker, to give the final .beta.2m-COMP/pET-24c construct, referred to as pETBMC04. Removal of the serine residue is carried out to avoid steric hindrance when the .beta.2m molecule is associated with the MHC class I chain protein.

The extracellular portion of .beta.2m comprises of 99 amino acids (equivalent to Ile1-Met99 of the mature protein) encoded by 74 bp-370 bp of the DNA sequence. This region of the .beta.2m sequence is amplified from a normal human lymphocyte cDNA library, by polymerase chain reaction (PCR) beta2m PCR product is purified from the above reaction mix using a QIAQUICK® PCR purification kit according to the manufacturer's instructions (Qiagen). 200 ng of purified PCR product and 1 .mu.g pET-24c vector (Novagen) are each digested with BamH I (10 U) and Nde I (10 U) restriction enzymes (New England Biolabs, NEB) for 4 h at 37 .degree. C., in accordance with the manufacturer's instructions, and purified.

The gel-purified insert and vector DNA are ligated at a 1:3 molar ratio (vector:insert, 50 ng: 7.5 ng) using T4 DNA ligase (5 U; Bioline), in T4 DNA ligase buffer (as supplied) for 16 hrs at 16 .degree. C.

The ligation mixtures and appropriate controls are subsequently transformed into XL1-Blue strain competent *E. coli* cells, according to the manufacturer's instructions (Stratagene). Successful transformants are selected by plating the cells on Luria-Bertani (LB) agar plates containing 30 .mu.g/ml kanamycin, and incubating overnight at 37 .degree. C.

A selection of single colonies from the bacterial transformation plates are screened by PCR with T7 promoter (1 .mu.M) and T7 terminator (1 .mu.M) primers (Sigma Genosys, see Appendix I for primer sequences), which are complementary to regions of the pET vector flanking the cloning site. Amplification is carried out using Taq DNA polymerase (1 U, Bioline) in Taq reaction buffer (as supplied), supplemented with 2 mM MgSO.sub.4 and 0.2 mM dNTPs, using 25 thermal-cycling reactions as detailed above. Successful transformants generated a DNA fragment of approximately 500 bp, ascertained by 1.5% agarose gel electrophoresis.

Bacterial transformants that generated the correct size of PCR products are inoculated into 6 ml of sterile LB-kanamycin medium and incubated overnight at 37 .degree. C. with 200 rpm shaking. pETBMC01 µlasmid DNA is recovered from the bacterial cultures using a QIAprep® Spin Mini-prep kit according to the manufacturer's instructions (Qiagen). The presence of the .beta.2m fragment in these plasmids is further verified by automated DNA sequencing.

The sequence of the oligomerisation domain of COMP is obtained from the Genbank database (accession #1705995) and a region encoding the coiled-coil domain (amino acids 21-85) is selected based on self-association experiments of COMP (Efinov et al., FEBS Letters 341:54-58 (1994)). A biotin acceptor sequence 'BP': SLNDIFEAQKIEWHE (SEQ ID NO:32) is incorporated at the C terminus and an additional 14 amino acid linker, PQPQPKPQPKPEPET (SEQ ID NO:33) is included to provide a physical separation between the COMP oligomerising domain and BP.

The whole region is synthesized using the overlapping complementary oligonucleotides, and purified COMP-BP and 1 .mu.g pETBMC01 vector are digested for 4 hrs at 37 .degree. C. using Hind III (10 U) and Xho I (10 U) restriction enzymes (NEB), as described in Section 1.1. The digestion products are purified, ligated, transformed and PCR screened as in Section 1.1. Plasmids positive from the screen are purified and sequenced as described in Section 1.1.

The poly-glycine linker is synthesized by annealing overlapping oligonucleotides. Since the nucleotide sequence of the polyGlycine linker only incorporates the 5' overhang of the cut BamH I restriction site, and the 3' overhang of the cut Hind III nucleotide recognition motifs, there is no need to digest the annealed product to produce the complementary single-stranded overhangs suitable for subsequent ligation. The oligonucleotides are phosphorylated and annealed as described in Section 1.2.

pETBMC02 is digested with BamH I (10 U) and Hind III (10 U). Ligation of the annealed poly-glycine linker into pETBMC02 was as described previously (Section 1.1), assuming 96 fmoles of annealed oligonucleotide/.mu.I. The transformation and PCR-screening reactions are as described in Section 1.1, but in addition, the presence of an inserted linker is verified by a restriction enzyme digestion of the PCR screen product to ascertain the presence or absence of a Sal I restriction site. Successful transformants are not susceptible to Sal I digestion, given the removal of the site from the plasmid vector backbone. Purification of pETBMC03 and automated sequencing is as described elsewhere herein.

Analysis of X-ray crystallography models of MHC class I molecules reveal that the C terminus of .beta.2m closely abuts the .alpha.3 domain of the alpha. chain. It is therefore desirable to achieve maximum flexibility at the start of the poly-glycine linker.

The extracellular portion of HLA-A*0201 alpha. chain (EMBL M84379) comprises of 276 amino acids (equivalent to Gly1-Pro276 of the mature protein) encoded by bases 73-900 of the messenger RNA sequence. This region of the A*0201 sequence is amplified from a normal human lymphocyte cDNA library by PCR, using the primers A2S #1 and A2S #2 which incorporated NcoI and BamHI restriction sites respectively. The procedure for cloning the A*0201 insert into Nco I/BamH I-digested pET-11 d vector (Novagen) is essentially as described for .beta.2m in Section 1.1.

An identical procedure is carried out to produce either .beta.2m-COMP or A*0201 .alpha. chain proteins. Plasmid DNA is transformed into an E. coli expression host strain in preparation for a large scale bacterial prep. Protein is produced as insoluble inclusion bodies within the bacterial cells, and is recovered by sonication. Purified inclusion bodies are solubilised in denaturing buffer and stored at −80 .degree. C. until required.

Purified plasmid DNA is transformed into the BL21(DE3) pLysS E. coli strain, which carries a chromosomal copy of the T7 RNA polymerase required to drive protein expression from pET-based constructs. Transformations into BL21 (DE3)pLysS competent cells (Stratagene) are carried out with appropriate controls.

A single bacterial transformant colony is innoculated into 60 ml sterile LB medium, containing appropriate antibiotics for selection, and left to stand overnight in a warm room (.about.24 .degree. C.) The resulting overnight culture is added to 6 litres of LB and grown at 37 .degree. C. with shaking (.about.240 rpm), up to mid-log phase (OD-.sub.600=0.3-0.4). Protein expression is induced at this stage by addition of 1.0 ml of 1M IPTG to each flask. The cultures are left for a further 4 h at 37 .degree. C. with shaking, after which the cells are harvested by centrifugation and the supernatant discarded.

The bacterial cell pellet is resuspended in ice-cold balanced salt solution and sonicated (XL series sonicator; Misonix Inc., USA) in a small glass beaker on ice in order to lyse the cells and release the protein inclusion bodies. Once the cells are completely lysed the inclusion bodies are spun down in 50 ml polycarbonate Oak Ridge centrifuge tubes in a Beckman high-speed centrifuge (J2 series) at 15,000 rpm for 10 min. The inclusion bodies are then washed three times in chilled Triton® wash This is followed by a final wash in detergent-free wash buffer.

The resultant purified protein preparation is solubilised in 20-50 ml of 8 M urea buffer, containing 50 mM MES, pH 6.5, 0.1 mM EDTA and 1 mM DTT, and left on an end-over-end rotator overnight at 4 .degree. C. Insoluble particles are removed by centrifugation and the protein yield is determined using Bradford's protein assay reagent (Bio-Rad Laboratories) and by comparison with known standards. Urea-solubilised protein is dispensed in 10 mg aliquots and stored at −80 .degree. C. for future use.

Assembly of .beta.2m-COMP from the urea-solubilised inclusion bodies is performed by diluting the protein into 20 mM CAPS buffer, pH 11.0, containing 0.2 M sodium chloride and 1 mM EDTA, to give a final protein concentration of 1.5 mg/ml. The protein is oxidised at room temperature by addition of oxidised and reduced glutathione to final concentrations of 20 mM and 2 mM, respectively. Following an overnight incubation, disulphide bond formation is analysed by non-reducing SDS-PAGE on 10% bis-tricine gels (Invitrogen).

The protein mixture is subsequently buffer exchanged into 20 mM Tris, pH 8.0, 50 mM sodium chloride ('S200 buffer'), and concentrated to a final volume of 4.5 ml, in preparation for enzymatic biotinylation with BirA (Affinity, Denver, Colo.). 0.5 ml of 10 .times. BirA reaction buffer (as supplied) is added, and recombinant BirA enzyme at 10 .mu.M final concentration, supplemented with 10 mM ATP, pH 7.0. A selection of protease inhibitors is also used to preserve the proteins: 0.2 mM PMSF, 2 .mu.g/ml pepstatin and 2 .mu.g/ml leupeptin. The reaction is left for 4 hours at room temperature.

Biotinylated .beta.2m-COMP is purified by size exclusion chromatography (SEC) on a SUPERDEX®200 HR 26/60 column (Amersham Biosciences), running S200 buffer.

500 ml of refolding buffer is prepared as follows: 100 mM Tris, pH 8.0, 400 mM Larginine hydrochloride, 2 mM EDTA, 5 mM reduced glutathione and 0.5 mM oxidised glutathione, dissolved in deionised water and left stirring at 4 .degree. C. 15 mg of lyophilised synthetic peptide GLCTLVAML (SEQ ID NO:13) is dissolved in 0.5 ml dimethylsulfoxide and added to the refolding buffer whilst stirring. 50 mg of biotinylated pentameric .beta.2m-COMP and 30 mg of A*0201 alpha. chain is added sequentially, injected through a 23gauge hypodermic needle directly into the vigorously-stirred buffer, to ensure adequate dispersion. The refolding mixture is then left stirring gently for 16 hours at 4 .degree. C.

The protein refolding mixture is subsequently concentrated from 500 ml to 20 ml using a MiniKros hollow fibre ultrafiltration cartridge (Spectrum Labs, Rancho Dominguez, Calif.) with a 30 kD molecular weight cutoff. Further concentration of the complex from 20 ml to 5 ml is carried out in Centricon Plus-20 centrifugal concentrators (30 kD molecular weight cut-off) according to the manufacturers instructions, followed by buffer exchange into S200 buffer using disposable PD10 desalting columns (Amersham Biosciences), according to the manufacturer's instructions. Final volume is 7.5 ml. The concentrated protein refold mixture is first purified by SEC on a SUPER-DEX® 200 HR 26/60 gel filtration chromatography column, as in Section 4.2. Fractions containing protein complexes in the region of 310 kD is collected.

Fractions collected from SEC are pooled and subjected to further purification by anion exchange chromatography on a MONOQ® HR 5/5 column (Amersham Biosciences), running a salt gradient from 0-0.5 M sodium chloride in 20 mM Tris over 15 column volumes. The dominant peak is collected. Protein recovery is determined using the Bradford assay.

Since each streptavidin molecule is able to bind up to 4 biotin entities, final labelling with phycoerythrin (PE)-conjugated streptavidin is carried out in a molar ratio of 1:0.8, streptavidin to biotinylated pentamer complex respectively, taking into account the initial biotinylation efficiency measurement made for .beta.2m-COMP in Section 4.2. The total required amount of pentamer complex is subdivided (e.g. into 5 equal amounts) and titrated successively into strepta-vidin-PE. The concentration of A*0201 pentamer-streptavidin complex is adjusted to 1 mg/ml with phosphate buffered saline (PBS), supplemented with 0.01% azide and 1% BSA.

This resultant fluorescent Pentamer reagent is stored at 4 .degree. C.

Example 62

This an example of a positive control experiment determining whether a sample contains or derives from a donor with certain MHC allele types.

In the present example the sample is analysed for the presences of T cells recognizing common pathogen antigens when bound to the MHC alleles HLA-A*0101, HLA-A*0201 and HLA-B*0702, thereby indirectly typing the sample for these three MHC alleles.

$10^6$ HBPMC are stained with a mix of 9 MHC-Dextramers (3-10 µl of each), carrying antigenic peptides derived from the antigenic proteins Influenza MP1, EBV BMLF-1 and CMV pp65. 3 different HLA alleles are used HLA-A*0101, HLA-A*0201 and HLA-B*0702 each carrying peptides derived from the 3 antigenic proteins. All MHC-Dextramers are all labeled with APC.

The sample is incubated for 10 min, where after the sample is stained with 5 µl of each of the antibodies; CD14/FITC, CD19/FITC, CD3/RPE and CD8/RPE for 20 min. Subsequently, the sample is washed and applied to flow cytometry analysis.

The sample is analyzed by sequential gating; the lymphocytes are identified using the scatter parameters, followed by applying an exclusion gate defined by the CD14/FITC, CD19/FITC positive cells. In the remaining cell populations the cytotoxic T cell population is defined by being RPE positive (CD3 and CD8 positive).

It is now analyzed if there is one or more population(s) of APC positive cells. If a population of cells is identified we can conclude that the donor has one or more of the tissue types HLA-A*0101, HLA-A*0201 and HLA-B*0702. If no population is formed we can conclude that either the tissue type is diverging from those in the test reagent, or the donor has no antigen specific cytotoxic T cells against the Flue-MP1, EBV-BMLF-1, CMV-pp65 antigens.

Example 63

This an example of a positive control experiment determining whether a sample contains or derive from a donor with certain MHC allele types.

In the present example the sample is analysed for the presences of T cells recognizing epitopes from the self protein MART-1 when the epitopes are bound to any MHC allele, thereby indirectly typing the sample for the applied MHC alleles.

$10^6$ HBPMC are stained with a mix of MHC-Dextramers (3-10 µl of each), carrying antigenic peptides derived from MART-1. All MHC-Dextramers are all labeled with APC.

The sample is incubated for 10 min, where after the sample is stained with 5 µl of each of the antibodies; CD14/FITC, CD19/FITC, CD3/RPE and CD8/RPE for 20 min.

Subsequently, the sample is washed and applied to flow cytometry analysis.

The sample is analyzed by sequential gating; the lymphocytes are identified using the scatter parameters, followed by applying an exclusion gate defined by the CD14/FITC, CD19/FITC positive cells. In the remaining cell populations the cytotoxic T cell population is defined by being RPE positive (CD3 and CD8 positive).

It is now analyzed if there is one or more population(s) of APC positive cells. If a population of cells is identified we can conclude that the donor has one or more of the HLA-types used in the analysis. If no population is formed we can conclude that either the tissue type is diverging from those in the test reagent, or the donor has no antigen specific cytotoxic T cells against the MART-1 epitopes tested.

Example 64

This an example of a positive control experiment determining whether a sample contains or derives from a donor with certain MHC allele types.

In the present example the sample is analysed for the presences of T cells recognizing epitopes from an antigen from a common pathogen when bound to the MHC alleles HLA-A*0201, HLA-A*2402 and HLA-B*0702, thereby indirectly typing the sample for these three MHC alleles.

The following MHC dextramer constructs were made:

1. APC-SA conjugated 270 kDa dextran coupled with HLA-A*0201 in complex with beta2microglobulin and the peptide NLVPMVATV (SEQ ID NO:9) derived from CMV pp65.

2. APC-SA conjugated 270 kDa dextran coupled with HLA-A*2402 in complex with beta2microglobulin and the peptide QYDPVAALF (SEQ ID NO:34) derived from CMV pp65.

3. APC-SA conjugated 270 kDa dextran coupled with HLA-B*0702 in complex with beta2microglobulin and the peptide TPRVTGGGAM (SEQ ID NO:16) derived from CMV pp65

$10^6$ HBPMC are stained with a mix of the 3 MHC-Dextramers constructs 1, 2, 3 described above (3-10 µl of each).

The sample is incubated for 10 min, where after the sample is stained with 5 µl of each of the antibodies; CD14/FITC, CD19/FITC, CD3/RPE and CD8/RPE for 20 min.

Subsequently, the sample is washed and applied to flow cytometry analysis.

The sample is analyzed by sequential gating; the lymphocytes are identified using the scatter parameters, followed by applying an exclusion gate defined by the CD14/FITC, CD19/FITC positive cells. In the remaining cell populations the cytotoxic T cell population is defined by being RPE positive (CD3 and CD8 positive).

It is now analyzed if there is one or more population(s) of APC positive cells. If a population of cells is identified we can conclude that the donor has one or more of the tissue types HLA-A*0201, HLA-A*2402 or HLA-B*0702. If no population is formed we can conclude that either the tissue type is diverging from those in the test reagent, or the donor has no antigen specific cytotoxic T cells against the, CMV-pp65 antigen.

Example 65

This is an example of how to type a sample for the presence of certain MHC alleles using MHC allele specific antibodies.

HPBMC from the blood of two donors, donor 1 and 2 were isolated by a standard protocol using FICOLL®-Hypaque. A fraction of the cells from each sample was transferred to two new tube making a total of 4 tubes. 10 µl PE-labeled antibody specific for the MHC alleles HLA-A*02 (clone BB7.2 from BD) was added to one tube for each sample and biotinylated antibody specific for HLA-A*03 (ab31572 from abcam) was added to the second tube of each sample. Samples were incubated at 4° C. for 10 minutes in the dark. Then 10 µl SA/PE (R0438 from Dako) was added to tubes with anti-HLA-A*03 antibody and incubation continued for another 30 minutes.

Cells were washed in 2 ml PBS, centrifuged and supernatant removed. Cells were resuspended I PBS and samples analysed on a CYAN flow cytometer. As a control unstained cell samples from each donor was also analysed.

Cells were gated using a lymphocyte gate in a FCS/SSC plot and the presence of PE positive staining was determined in each sample.

Donor 1 was positive for HLA-A*02 and negative for HLA-A*03 and donor 2 was negative for HLA-A*02 and positive for HLA-A*03. Results are shown in FIG. 18.

The results was confirmed in a PCR test using probes specific for HLA-A*02 and HLA-A*03 (data not shown).

This example demonstrates that antibodies specific for a specific HLA allele can be used to determine the HLA type of cells in a given sample.

The content of the XML file of the sequence listing named "Substitute-Sequence-Listing-30Jan2024-ST-26-12266-0203.xml", having a size of 36,061 bytes and a creation date of 30 Jan. 2024, and electronically submitted via Patent Center on 30 Jan. 2024, is incorporated herein by reference in its entirety.

---

The invention claimed is:

1. A composition comprising a plurality of MHC multimers and a carrier, wherein each MHC multimer comprises (a-b-P)$_n$, wherein n>1, wherein a and b together form a functional MHC protein capable of binding the peptide P, when P is present;

wherein (a-b-P) is the MHC-peptide complex formed when the peptide P binds to the functional MHC protein;

wherein each MHC protein or MHC-peptide complex is associated with one or more multimerization domains;

wherein said MHC multimer comprises one or more labels;

wherein the composition comprises groups of MHC multimers, wherein MHC multimers of some of said groups comprise one or more same labels within the group and MHC multimers of others of said groups each comprise two or more different labels within the group, wherein each group of MHC multimers presents a different peptide compared to other groups;

wherein the MHC multimers of each group are labelled with said one or more same labels or said two or more different labels;

wherein the composition is made by a process comprising providing a plurality of said MHC-peptide complexes and associating them with said one or more multimerization domains.

2. The composition according to claim 1, wherein said labels are selected from the group consisting of fluorophores, chromophores, electrochemiluminescent labels, bioluminescent labels, polymers, polymer particles, bead or other solid surfaces, metal particles, spin labels, radioisotopes, enzyme substrates, haptens, antigens, quantum dots, aminohexyl, pyrene, nucleic acids or nucleic acid analogs, peptide ligands or substrates, enzymes, antibodies and antibody fragments.

3. The composition according to claim 1, wherein said labels are fluorescent labels.

4. The composition according to claim 1, wherein the labels are attached directly to the MHC multimer, or wherein the labels are attached indirectly to the MHC multimer.

5. The composition according to claim 4, wherein the labels are attached indirectly via one or more marker molecules carrying one or more labels.

6. The composition according to claim 1, wherein the labels are covalently attached to the MHC multimer; or wherein the labels are non-covalently attached to the MHC multimer.

7. The composition according to claim 1, wherein one or more MHC-peptide complexes are covalently linked to the one or more multimerization domains.

* * * * *